US011739342B2

(12) United States Patent
Christensen et al.

(10) Patent No.: US 11,739,342 B2
(45) Date of Patent: Aug. 29, 2023

(54) NUCLEOTIDE SEQUENCES AND POLYPEPTIDES ENCODED THEREBY USEFUL FOR MODIFYING PLANT CHARACTERISTICS

(71) Applicant: CERES, INC., Thousand Oaks, CA (US)

(72) Inventors: Cory Christensen, Zionsville, IN (US); Nestor Apuya, Culver City, CA (US); Kenneth A. Feldmann, Tucson, AZ (US)

(73) Assignee: Ceres, Inc., Thousand Oaks, CA (US)

(*) Notice: Subject to any disclaimer, the term of this patent is extended or adjusted under 35 U.S.C. 154(b) by 0 days.

(21) Appl. No.: 17/402,195

(22) Filed: Aug. 13, 2021

(65) Prior Publication Data

US 2022/0042032 A1 Feb. 10, 2022

Related U.S. Application Data

(60) Division of application No. 16/793,481, filed on Feb. 18, 2020, now Pat. No. 11,142,773, which is a division of application No. 15/953,264, filed on Apr. 13, 2018, now Pat. No. 10,655,139, which is a continuation of application No. 14/565,186, filed on Dec. 9, 2014, now Pat. No. 9,957,521, which is a division of application No. 13/184,361, filed on Jul. 15, 2011, now Pat. No. 8,962,921, which is a division of application No. 11/140,450, filed on May 27, 2005, now Pat. No. 8,022,273.

(60) Provisional application No. 60/575,253, filed on May 27, 2004.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8242* (2013.01); *C12N 15/8261* (2013.01); *C12N 15/8271* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 8,022,273 B2 | 9/2011 | Christensen et al. | |
| 8,962,921 B2 | 2/2015 | Christensen et al. | |
| 9,957,521 B2 | 5/2018 | Christensen et al. | |
| 10,655,139 B2 | 5/2020 | Christensen et al. | |
| 11,136,590 B2 | 10/2021 | Christensen et al. | |
| 11,142,773 B2 | 10/2021 | Christensen et al. | |
| 2013/0042367 A1* | 2/2013 | Nadzan | C12N 15/8261 536/23.6 |
| 2020/0239902 A1 | 7/2020 | Christensen et al. | |
| 2021/0324399 A1 | 10/2021 | Christensen et al. | |
| 2022/0049267 A1 | 2/2022 | Christensen et al. | |

FOREIGN PATENT DOCUMENTS

| | | |
|---|---|---|
| EP | 1033405 A2 | 6/2000 |
| WO | 2002/016655 | 2/2002 |
| WO | 2003/081988 | 10/2003 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Kasuga et al. (Nature Biotechnology, vol. 17, pp. 287-291, Mar. 1999).
Thornton et al. (Nature structural Biology, structural genomics supplement, pp. 991-994; Nov. 2000).
Office Action dated Nov. 22, 2011 in Australian Application No. 2005250447.
Office Action dated Mar. 22, 2013 in Canadian Patent Application 2,568,367.
GenBank Accession No. AY084231, dated Jun. 13, 2002.
GenBank Accession No. AY084504, dated Jun. 13, 2002.
GenBank Accession No. AY084803, dated Jun. 13, 2002.
GenBank Accession No. AY085031, dated Jun. 13, 2002.
GenBank Accession No. AY085703, dated Jun. 13, 2002.
GenBank Accession No. AY086590, dated Jun. 13, 2002.
GenBank Accession No. NM_104688, dated Jan. 29, 2002.
GenBank Accession No. NM_106061, dated Jan. 29, 2002.
USPTO: Non-Final Office Action regarding U.S. Appl. No. 16/793,520, dated Apr. 15, 2021.
USPTO: Response to Non-Final Office Action regarding U.S. Appl. No. 16/793,520, filed May 24, 2021.
USPTO: Supplemental Response to Non-Final Office Action regarding U.S. Appl. No. 16/793,520, filed Jun. 2, 2021.
USPTO: Notice of Allowance regarding U.S. Appl. No. 16/793,520, dated Jun. 10, 2021.
U.S. Appl. No. 17/402,225, filed Aug. 13, 2021, Christensen et al.
Dai et al., The Rice YABBY1 Gene Is Involved in the Feedback Regulation of Gibberellin Metabolism, Plant Physiol. 144:121-133, 2007.
GenBank Accession No. AB011485, dated Feb. 14, 2004.
Sivamani et al., Improved biomass productivity and water use efficiency under water deficit conditions in transgenic wheat constitutively expressing the barley HVA1 gene, Plant Science 155:1-9, 2000.

* cited by examiner

*Primary Examiner* — Vinod Kumar
(74) *Attorney, Agent, or Firm* — DENTONS US LLP

(57) ABSTRACT

Isolated polynucleotides and polypeptides encoded thereby are described, together with the use of those products for making transgenic plants with increased tolerance to abiotic stress (e.g., high or low temperature, drought, flood).

11 Claims, 31 Drawing Sheets

Specification includes a Sequence Listing.

```
CeresClone:584111   ----MFRSMTTR  R-------GYER  LGKESATTAL  LHEGFRRSTS  LPSMGSNSSR----   43
Lead-clone:35743    MQMLRNLSTR    TRSRRGGYER    V-SDDSTFSL  GAKLRRSTS   VPYYAPS-------   46
gi|38603980         MQMLRNLSTR    TRSRRGGYER    V-SDDSTFSL  GAKLRRSTS   VPYYAPS-------   46
CeresClone:963524   MQMLRSFSTR    TRSRRGGYER    V-TDDSTFSL  GAKLRRSTS   VPYYAPS-------   46

Consensus           MQMLR-LSTR    TRSRRGGYER    V-SDDSIFSL  LGAKLRRSTS  VPYYAPS           50

CeresClone:584111   KMALGSLYGE    NLKRNPTKK     GNNN---SDNK SHPLLSFLAL  ----PRKKTT----   88
Lead-clone:35743    -RLGLGDFP     VILEKLPRQK    PTKTVVTSKL  SHPIFSLFDG  YRRRSKKKKAT       94
gi|38603980         -RLGLGDFP     VILEKLPRQK    PTKTVVTSKL  SHPIFSLFDG  VRRFNKKKKAT       94
CeresClone:963524   KLGAGGVP      LLEELPRQK     SKGWKPLSKF  SHPIFSFLNE  ---VKKSKT-        92

Consensus           -RLG-GDFP     VILEKLPRQK    PTKTVVISKL  SHPIFS--DG  YRRR-KKK-T       100

CeresClone:584111   ARPEFARYLE    YLKEGGMWDF    NSNKPVMYYE                                118
Lead-clone:35743    AKPEFSRYHE    YLKESGMWDL    PSNSPVIYFK                                124
gi|38603980         AKPEFSRYHE    MLKESGMWDL    RSNSPVIYFK                                124
CeresClone:963524   RKPEFSRYLE    MLKEGGMWDA    RINTPV-----                               118

Consensus           AKPEFSRY-E    YLKE-GMWDL    RSNSPVIYFK                                130
```

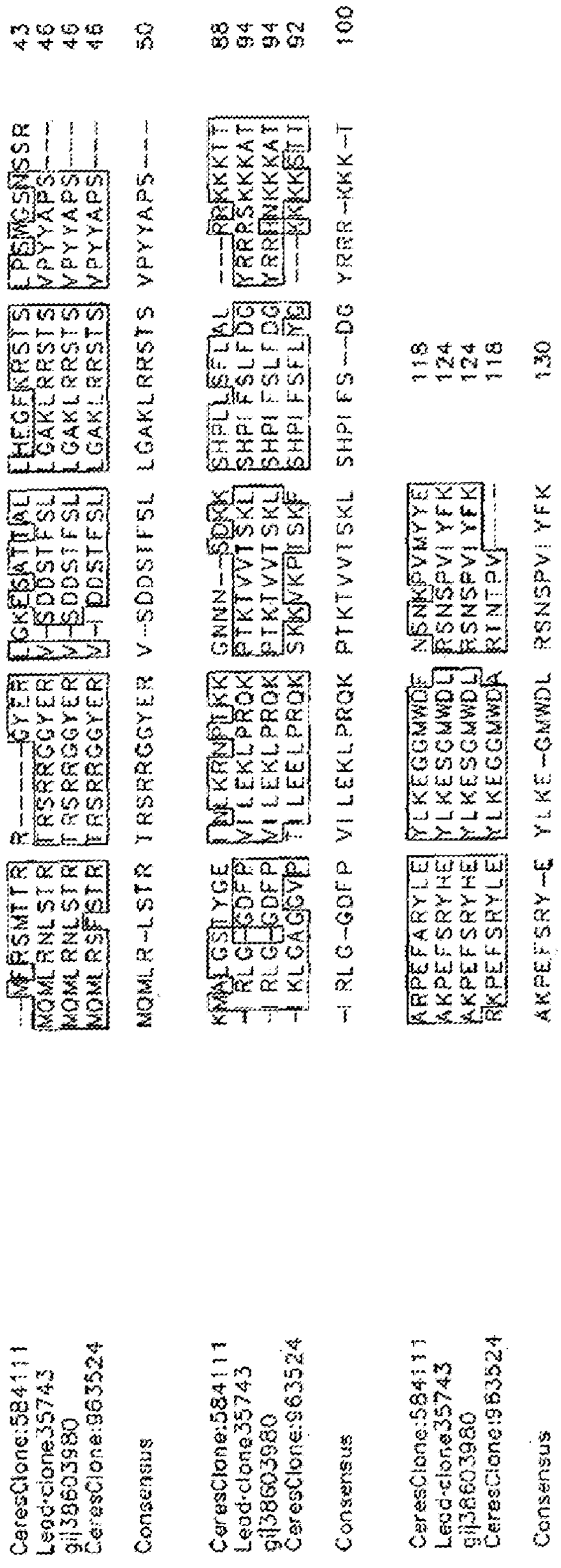

FIG. 2

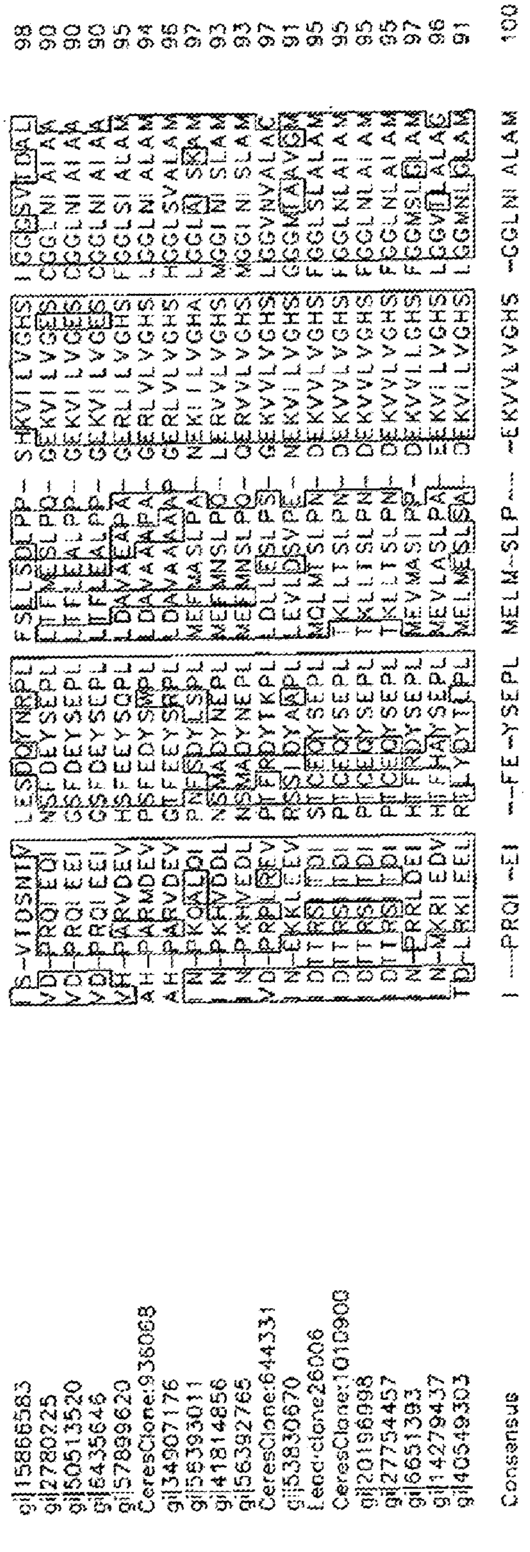
FIG. 3, continued

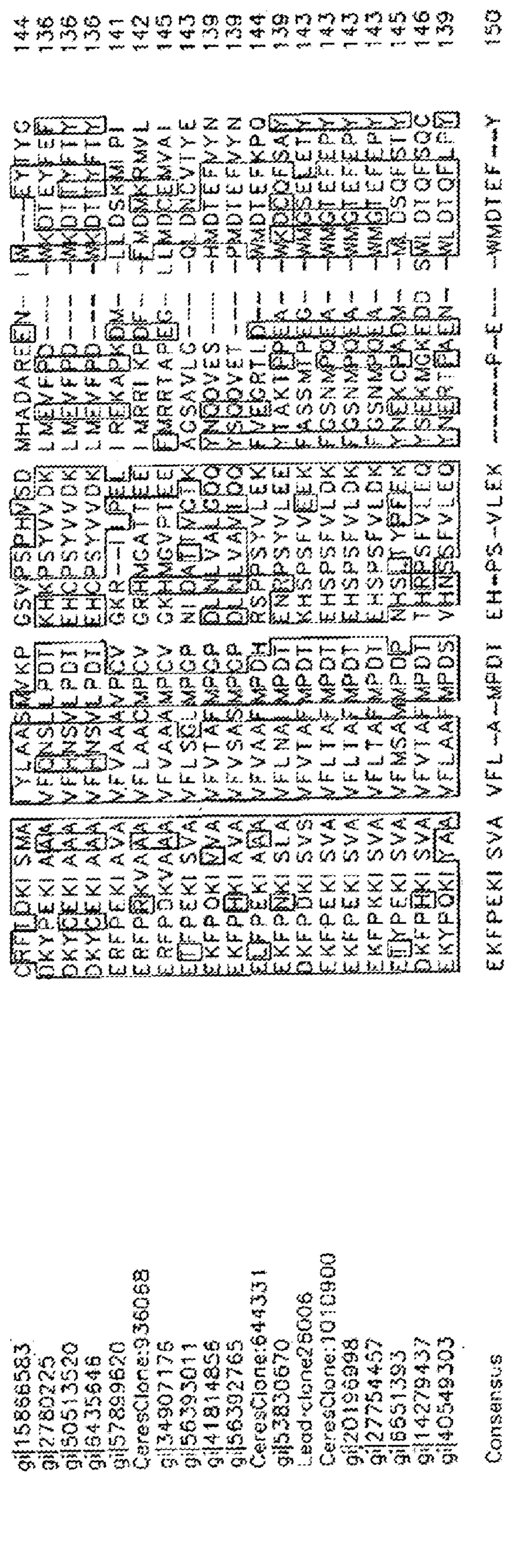
FIG. 3, continued

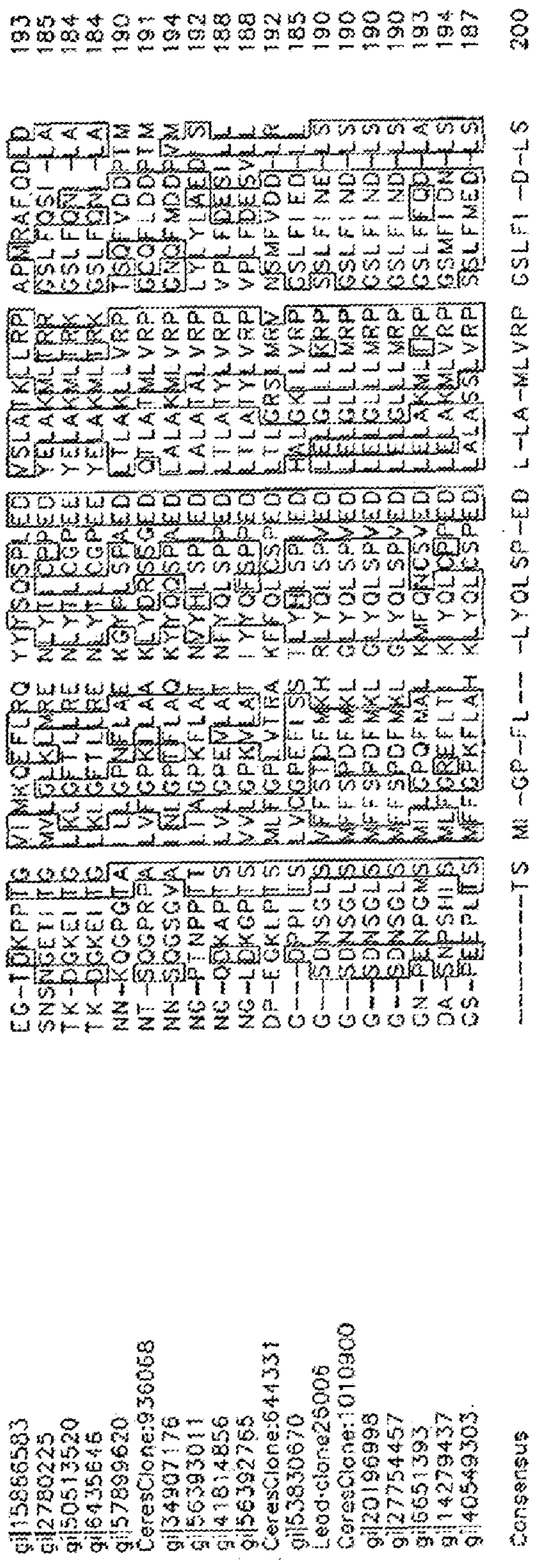
FIG. 3, continued

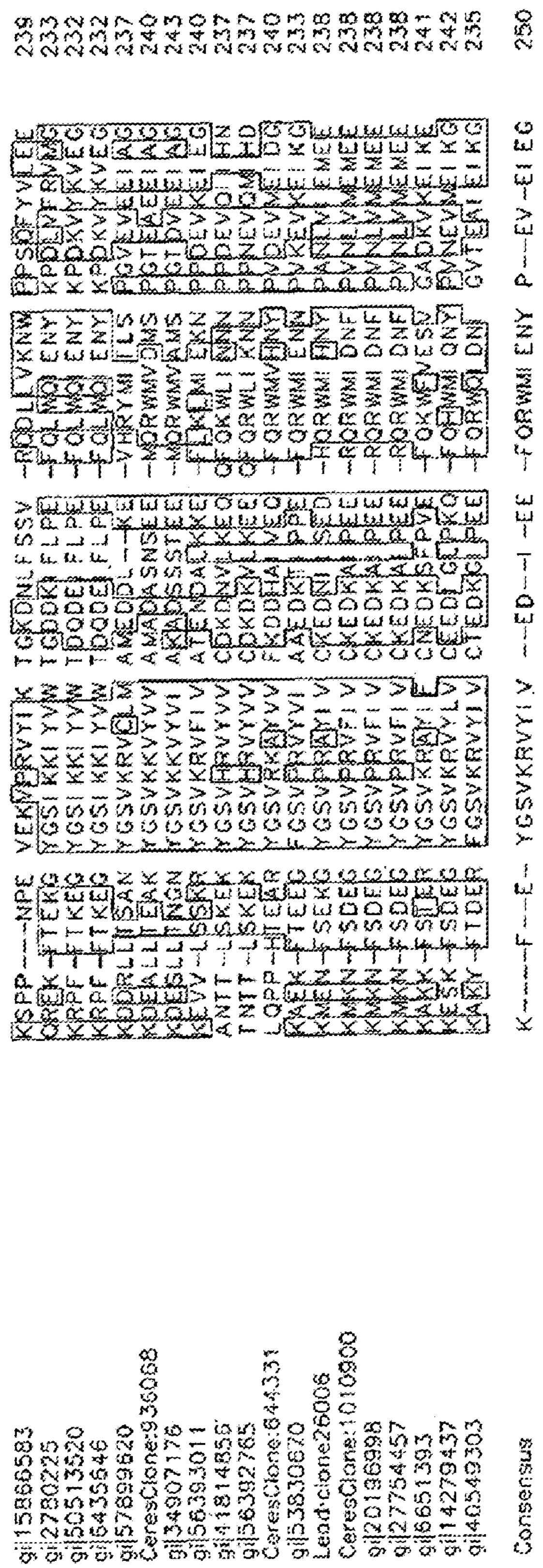
FIG. 3, continued

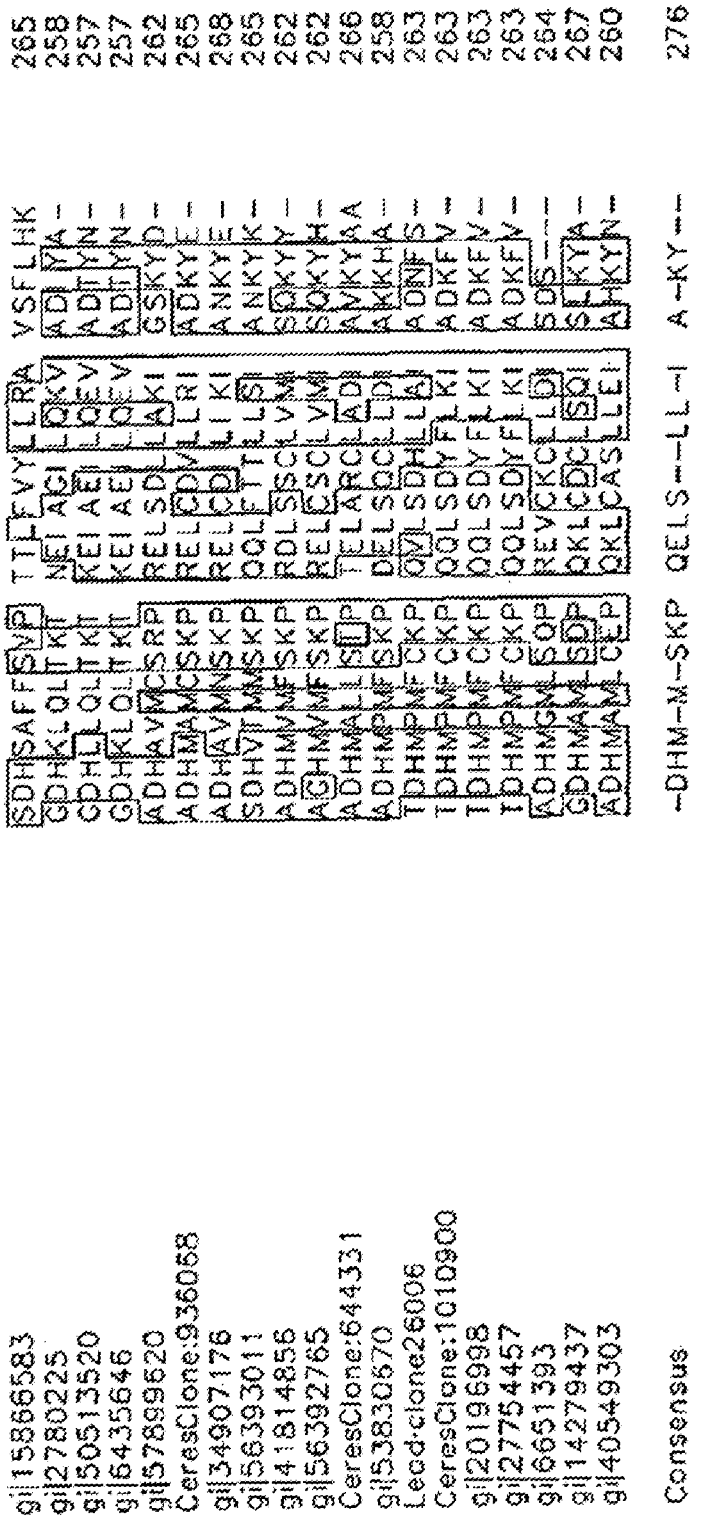
FIG. 3, continued

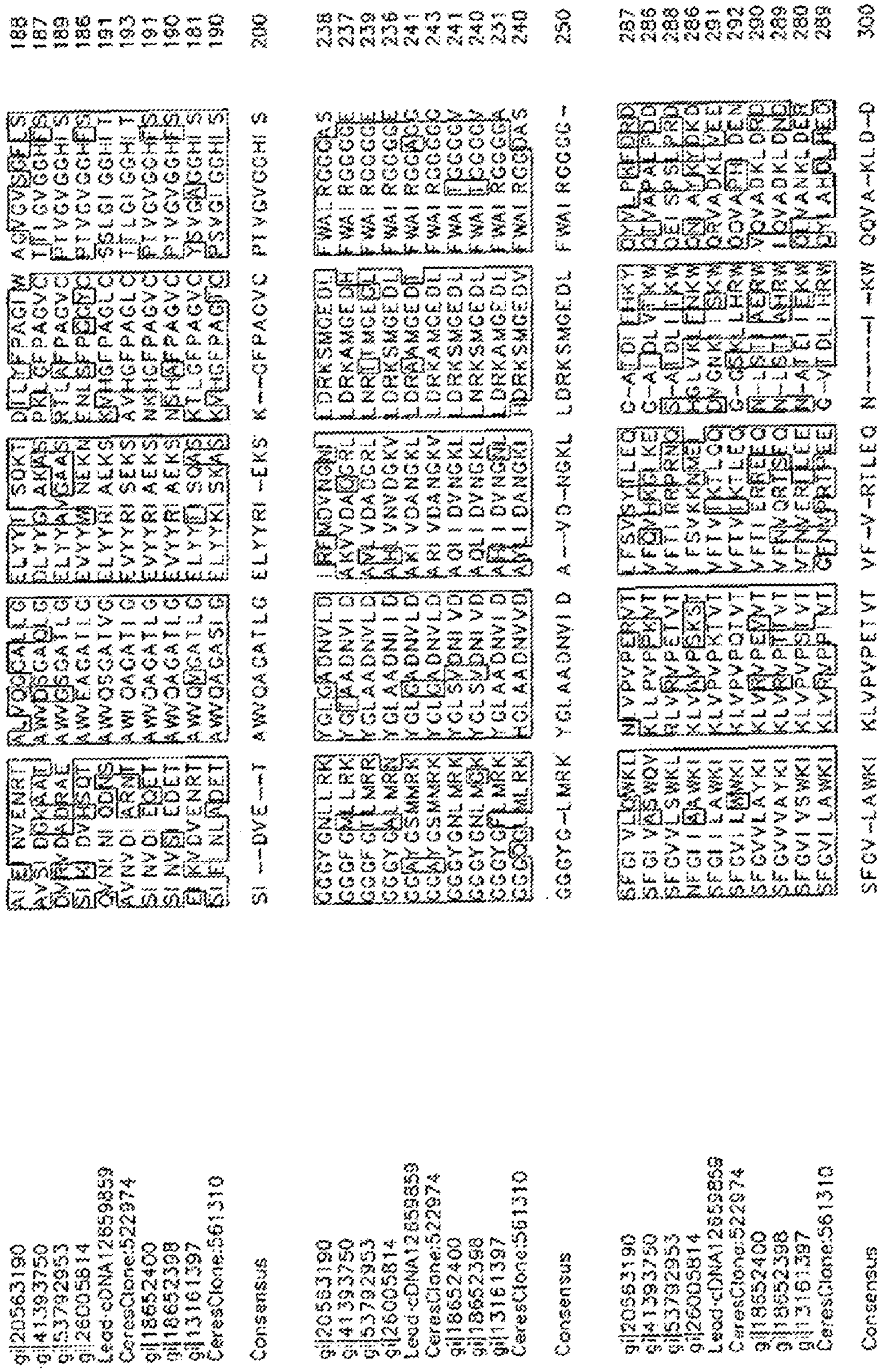
FIG 4, continued

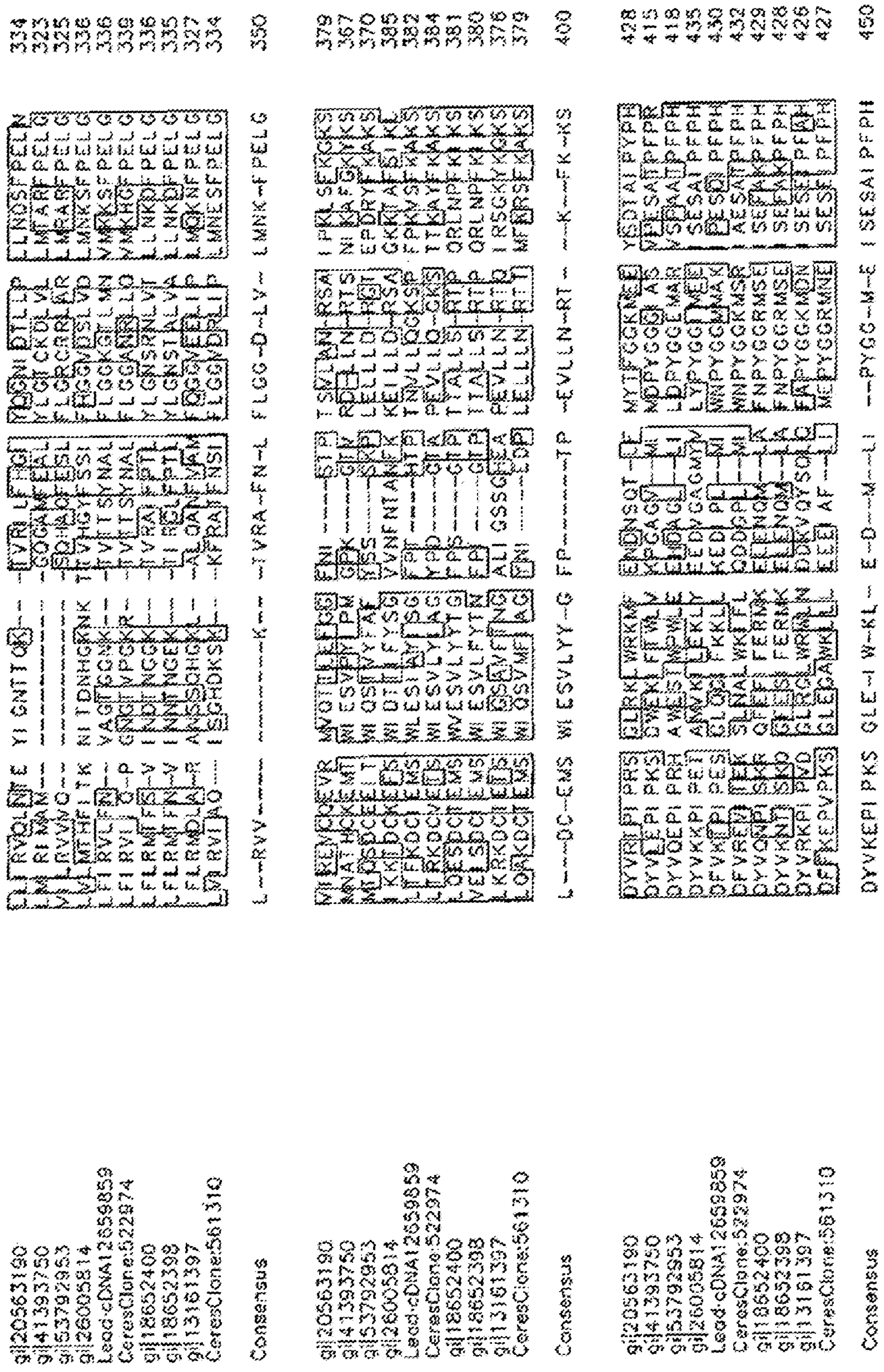
FIG. 4, continued

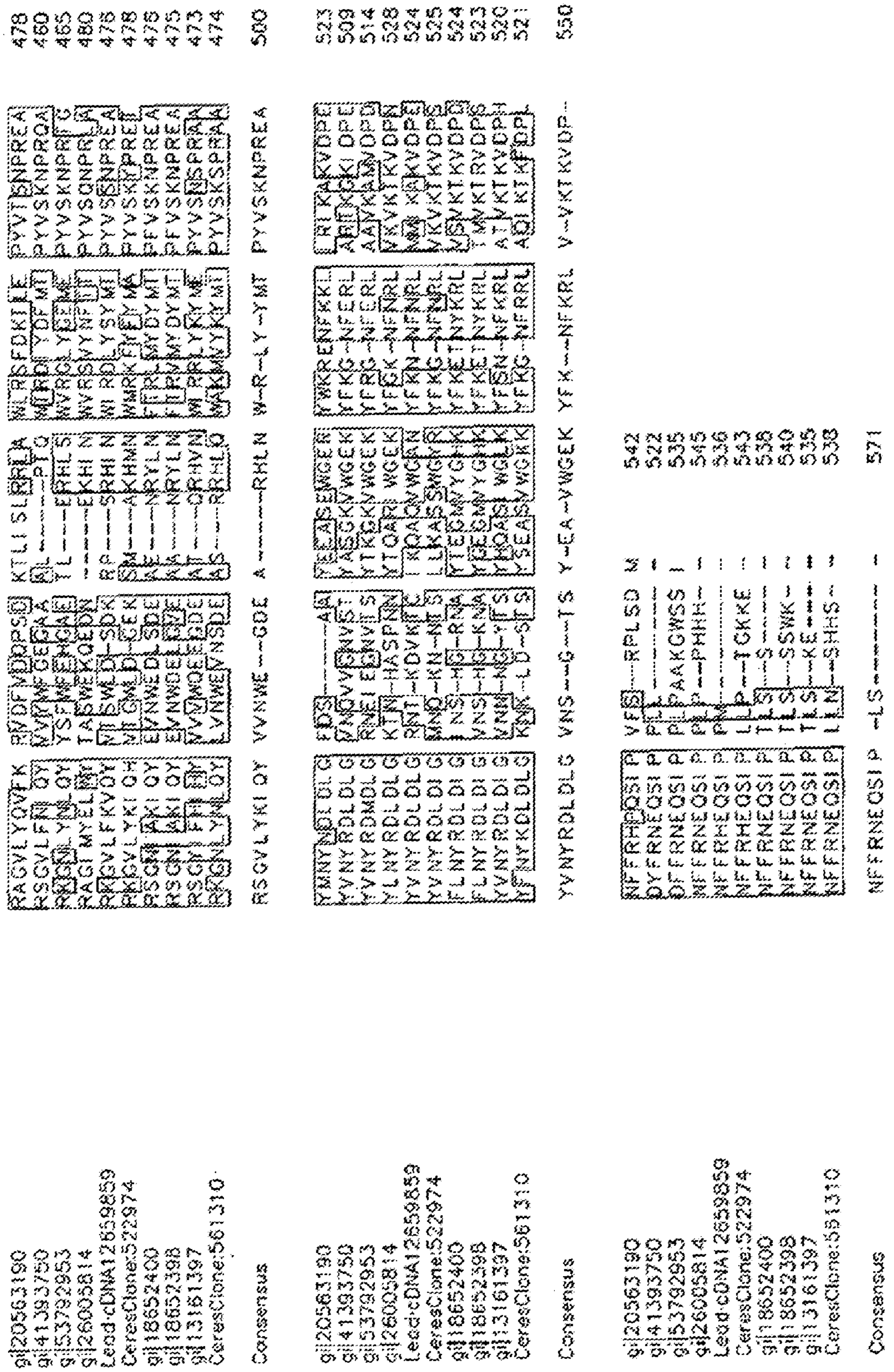
FIG. 4, continued

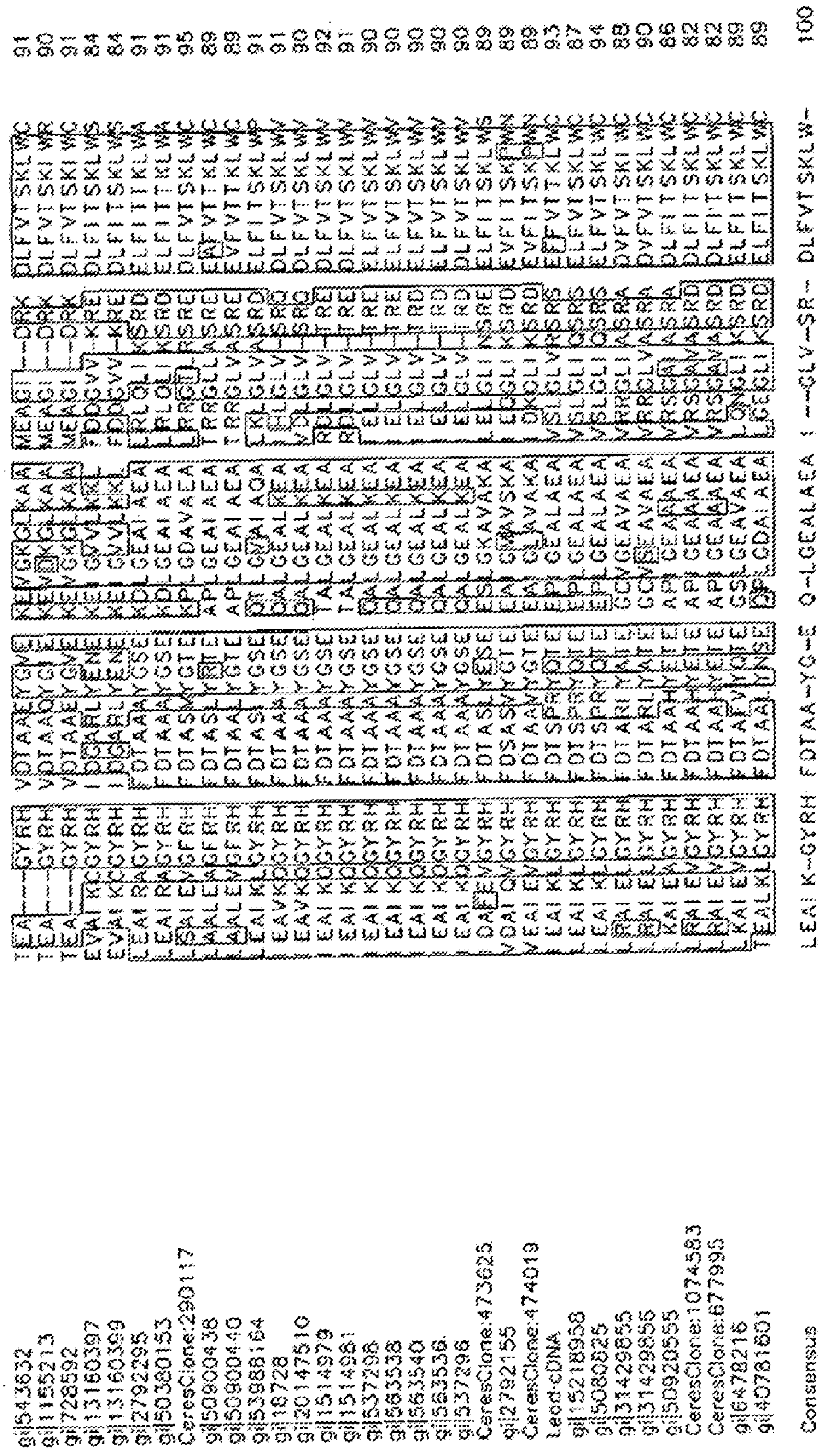
FIG. 5, continued

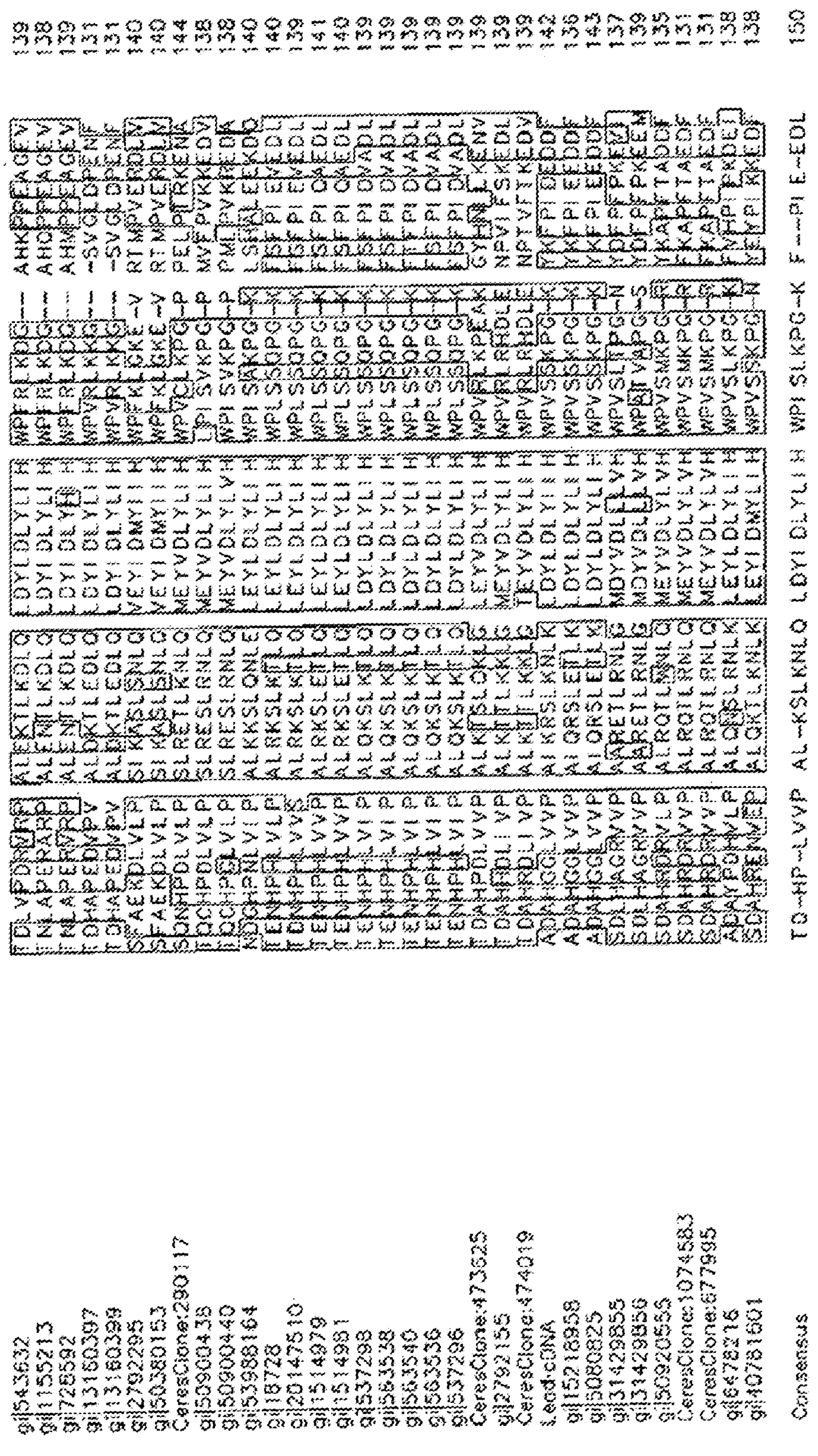
FIG. 5, continued

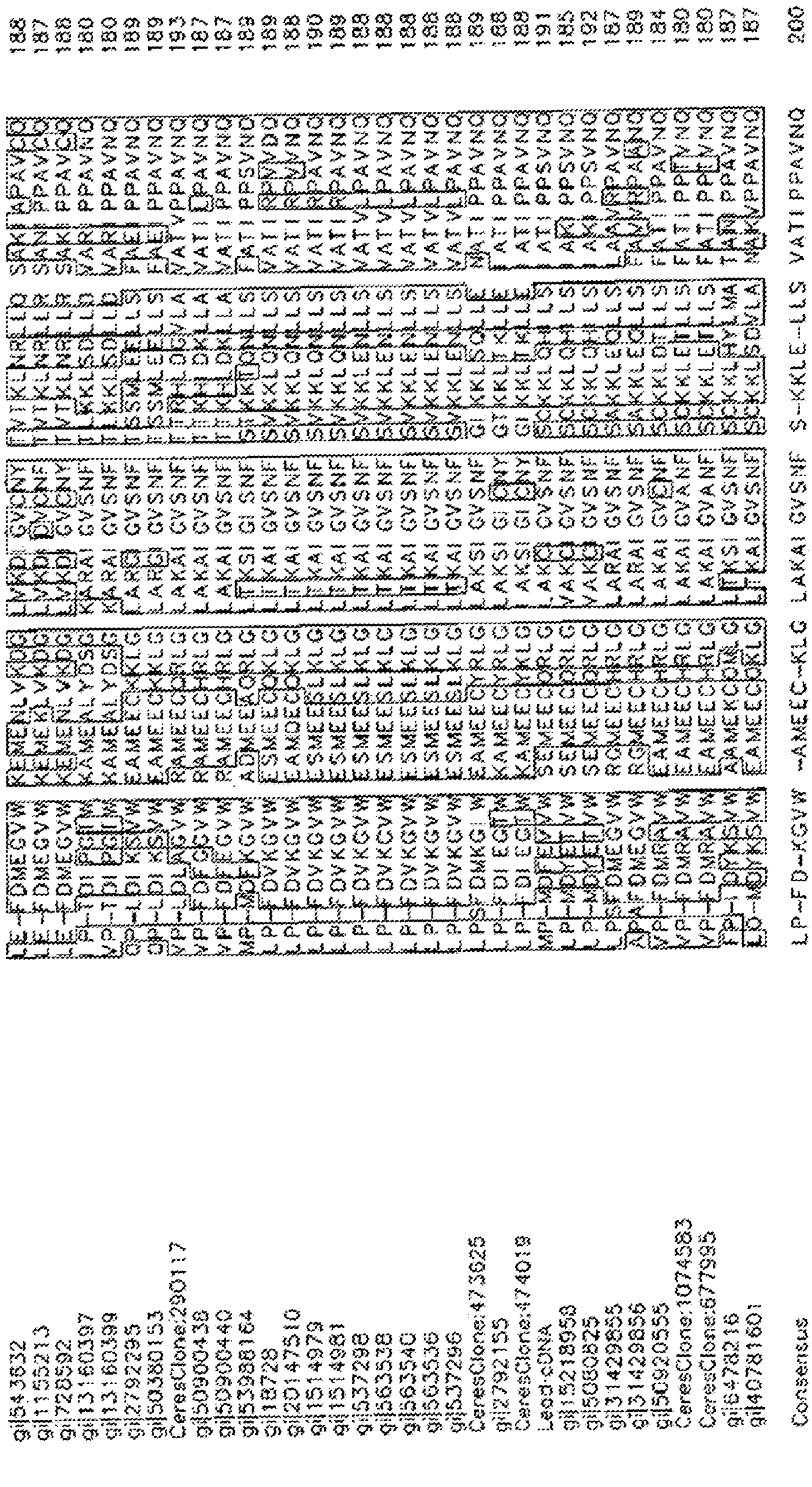
FIG. 5, continued

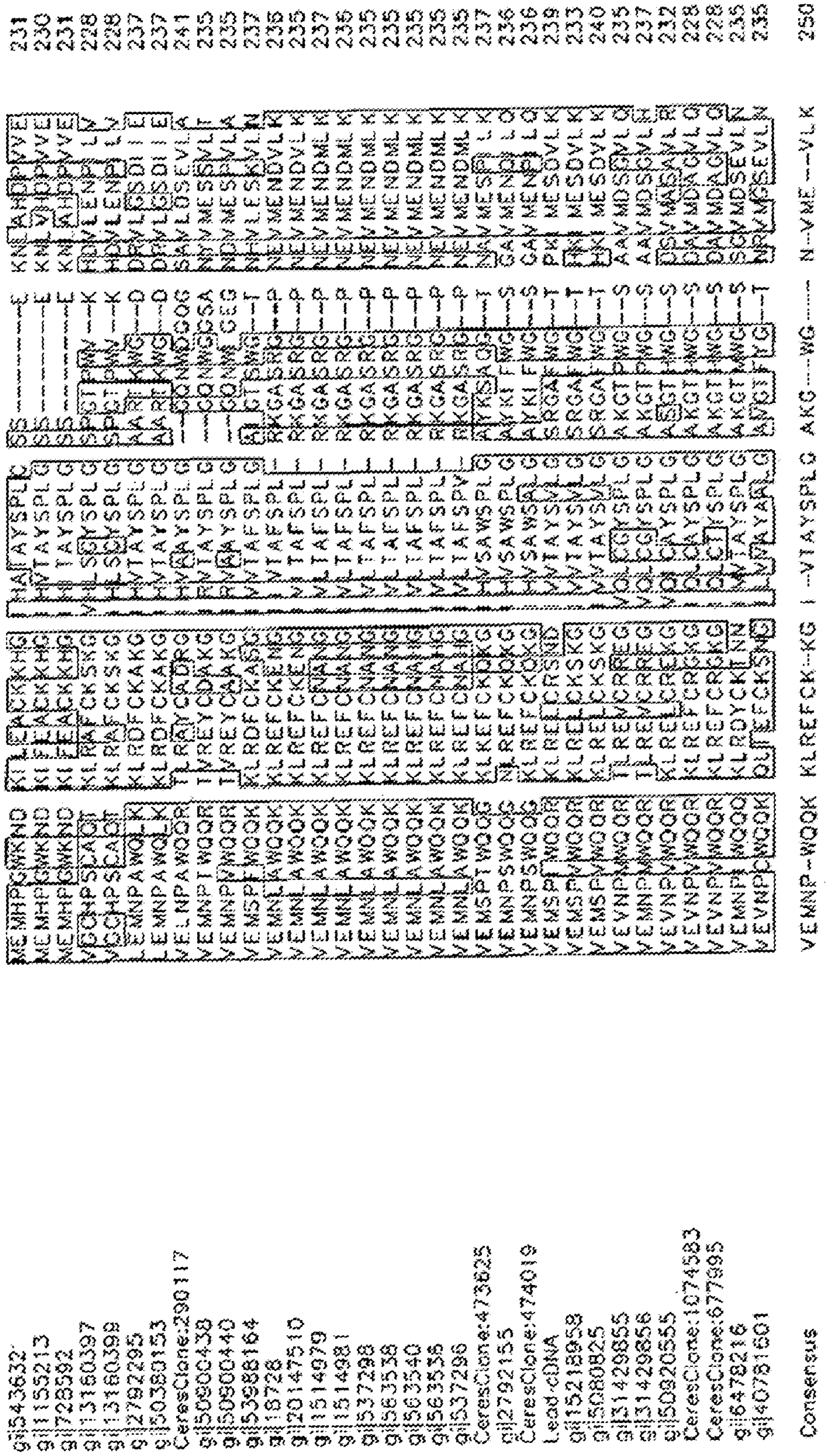
FIG 5, continued

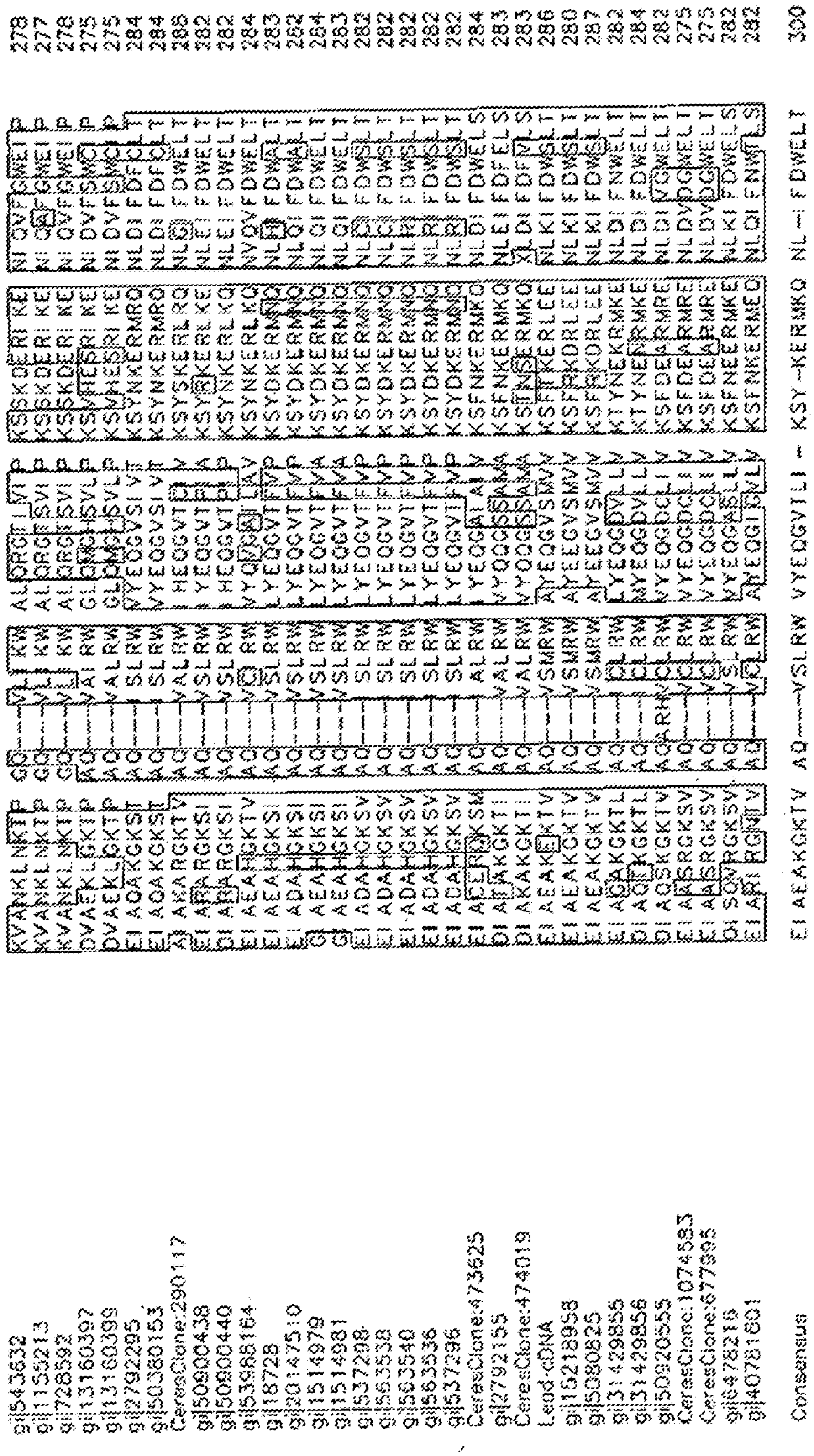
FIG. 5, continued

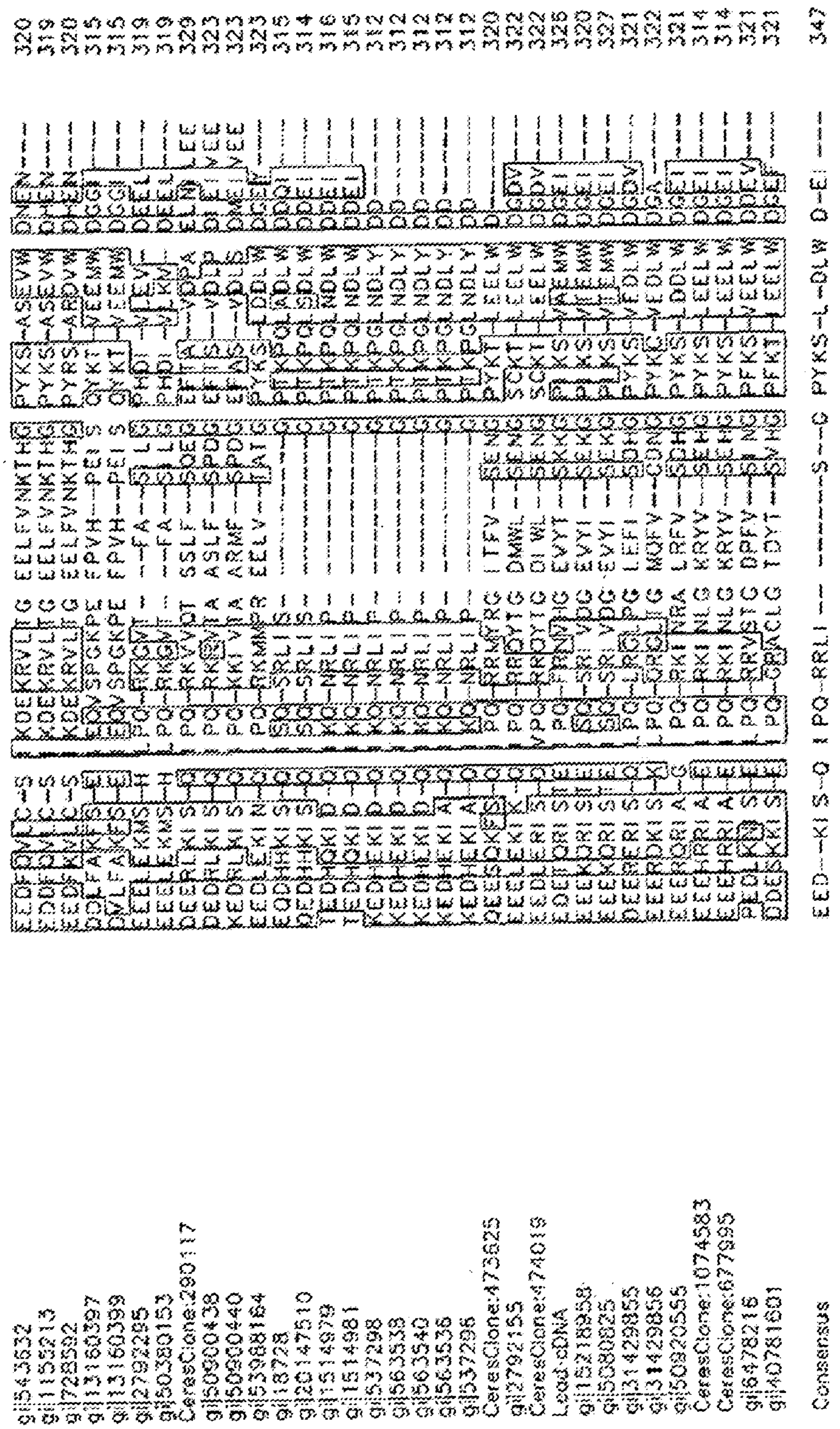
FIG. 5, continued

FIG. 6, continued

```
CeresClone:584111     MFRSMTTRR-  --GYERLGKE  SATTALLHEG  FKRSTSLPSW  GSNSSRKMAL    47
CeresClone:1068483    MFRAMSTRKV  HGGYEKLVED  EPK-------  LKRVTSVPAS  VYGNSRNPV-    42
Lead-clone10044       MFRAMSTRKV  HGGYEKLGDE  EAR-------  LKRVSSVPAS  VYGHSRNPV-    42
gi|4835241            MFRAMSTRKI  HGGYEKLGDE  EAR-------  LKRVSSVPAS  VYGHSRNPV-    42

Consensus             MFRAMSTRKV  HGGYEKLGDE  EAR-------  LKRV-SVPAS  VYGHSRNPV-    50

CeresClone:584111     GSTYGELNLK  RNPTKKGNNN  SDKKSHPLLS  FLAL---RRK  KKT-------    87
CeresClone:1068483    ------QEVK  KTPTVKPTGG  S---VHPLLS  FFDVRFQKKK  KKT--KKSLA    82
Lead-clone10044       ------QEVK  KTPTAKPTGG  S---VHPLFS  FFDVHFQRKK  KKTTKKKSLA    83
gi|4835241            ------QEVK  KTPTAKPTGG  S---VHPLFS  FFDVHFQRKK  KNTAKKKSLA    83

Consensus             ------QEVK  KTPTAKPTGG  S---VHPL-S  FFDVHFQRKK  KKT-KKKSLA   100

CeresClone:584111     TARPEFARYL  EYLKEGGMWD  FNSNKPVMYY  E      118
CeresClone:1068483    TAKPEFARYM  AYVKEGGVWD  PNSNAPVIHY  R      113
Lead-clone10044       TAKPEFARYM  EYVREGGVWD  PSSNAPVIHY  R      114
gi|4835241            TAKPEFARYM  EYVREGGVWD  PSSNAPVIHY  R      114

Consensus             TAKPEFARYM  EYV-EGGVWD  P-SNAPVIHY  R      131
```

FIG. 7

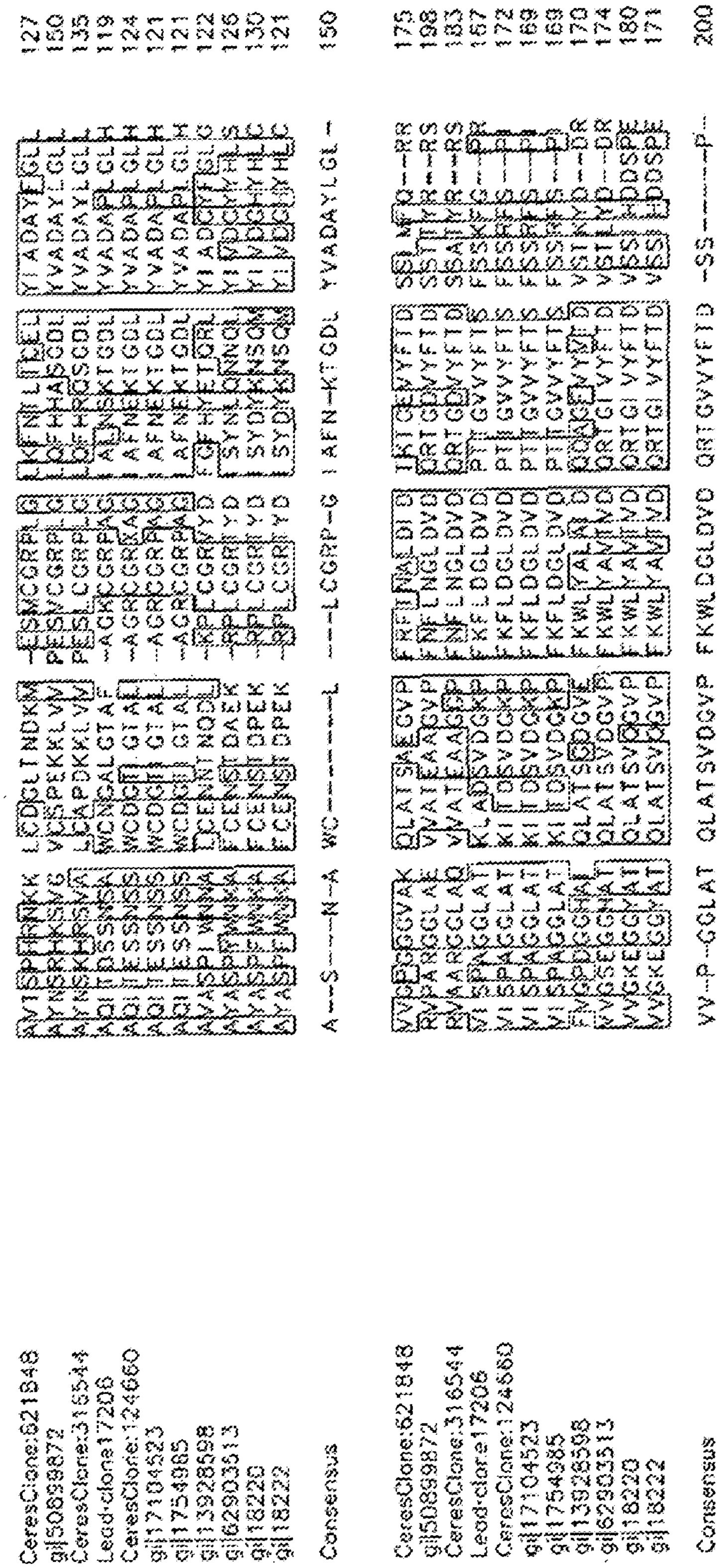
FIG. 8, continued

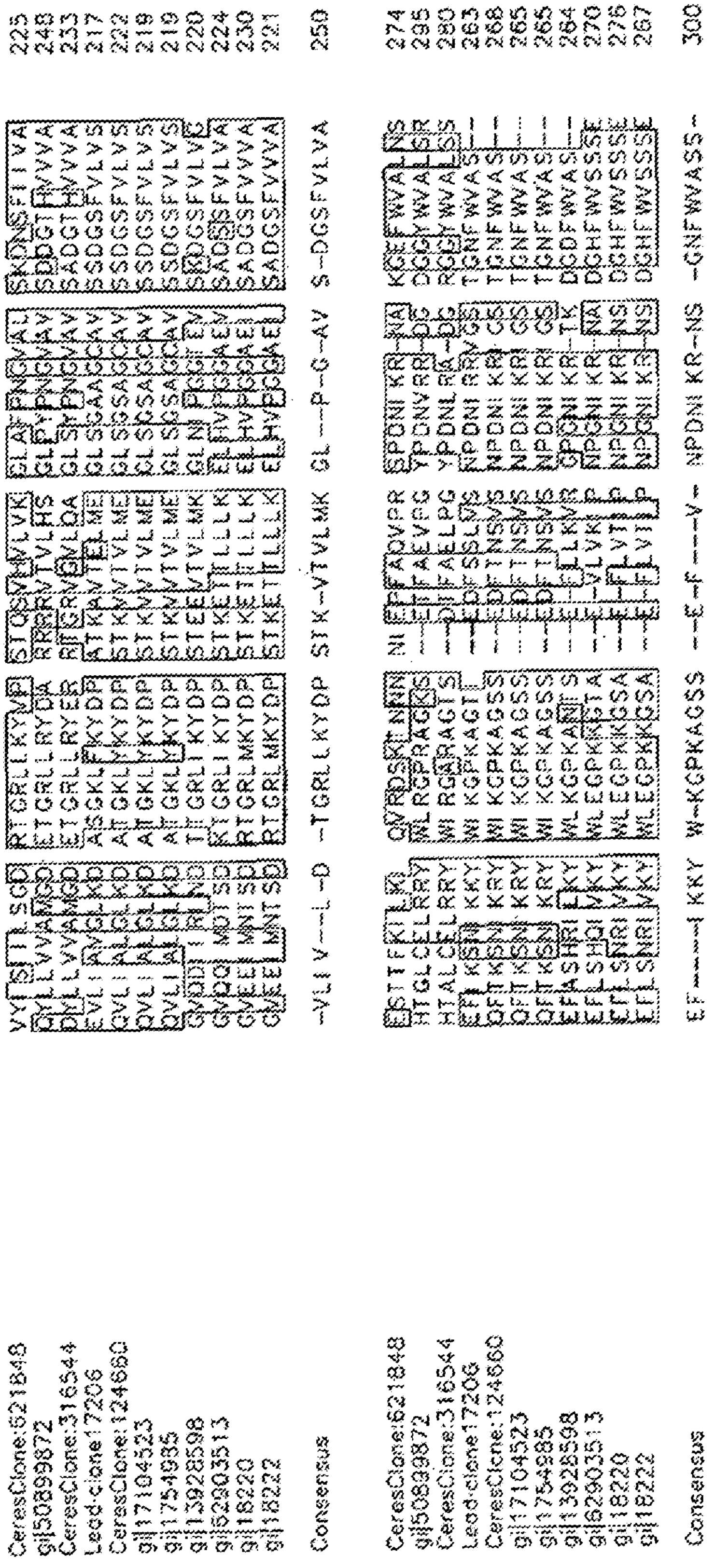
FIG. 8, continued

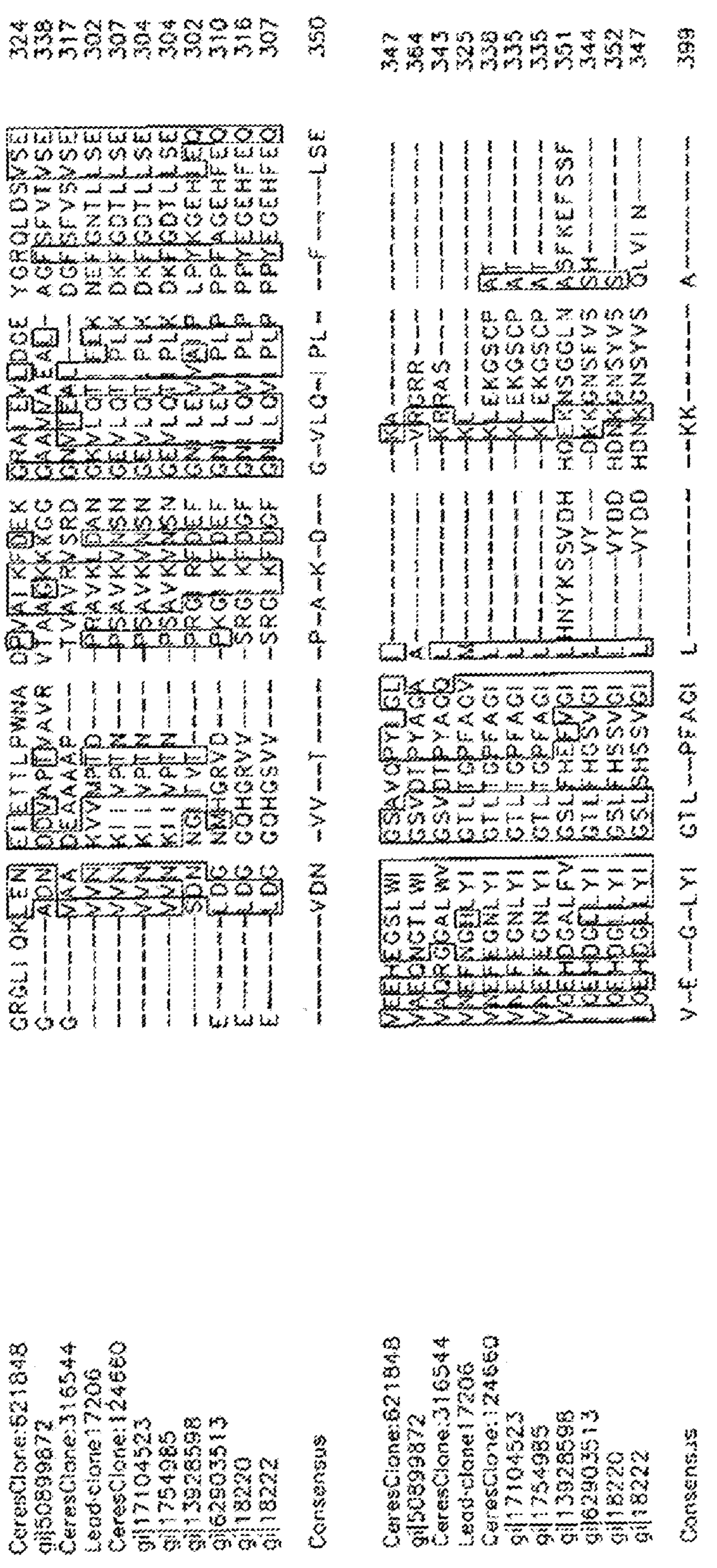
FIG. 8, continued

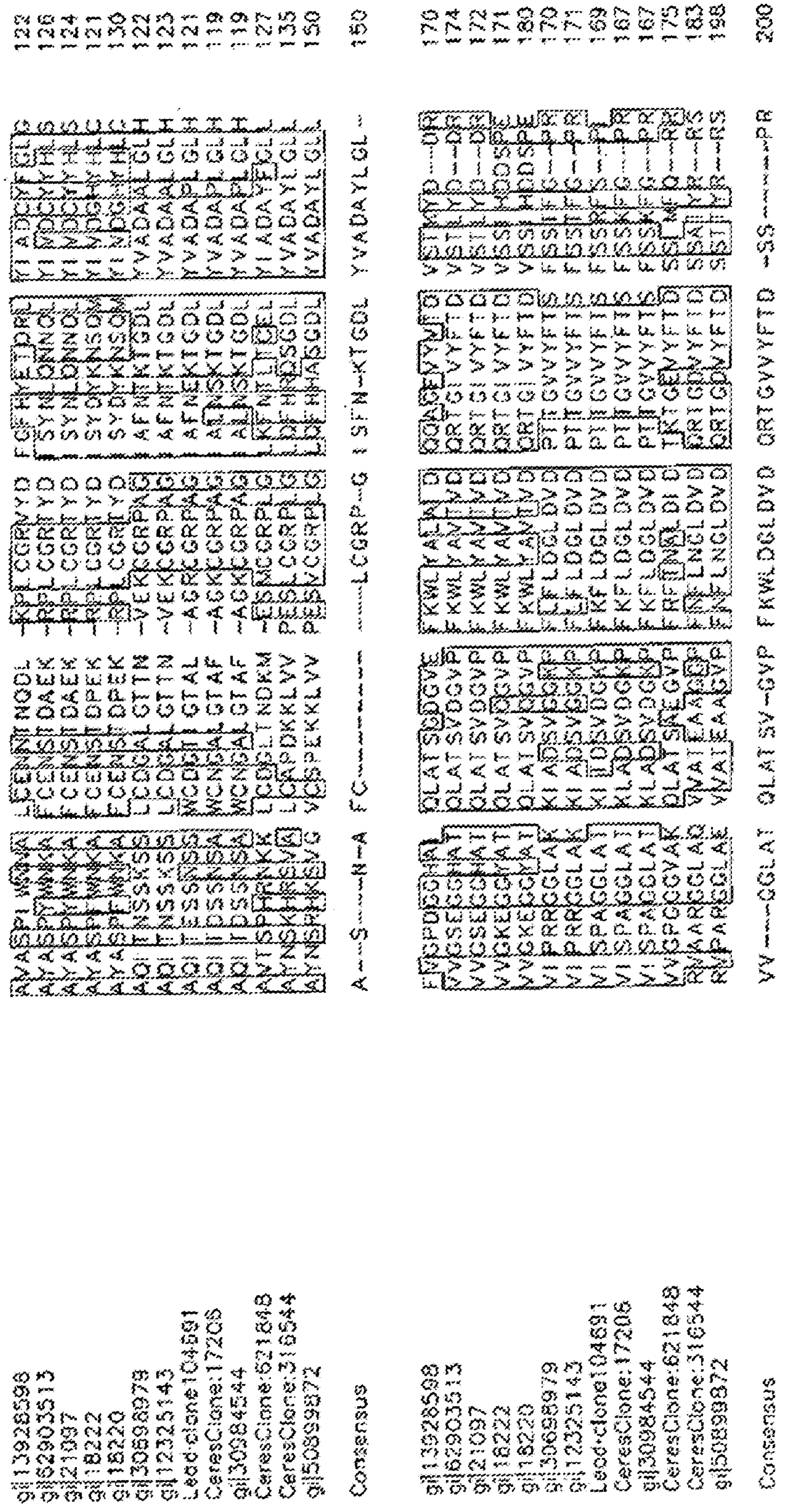
FIG. 9, continued

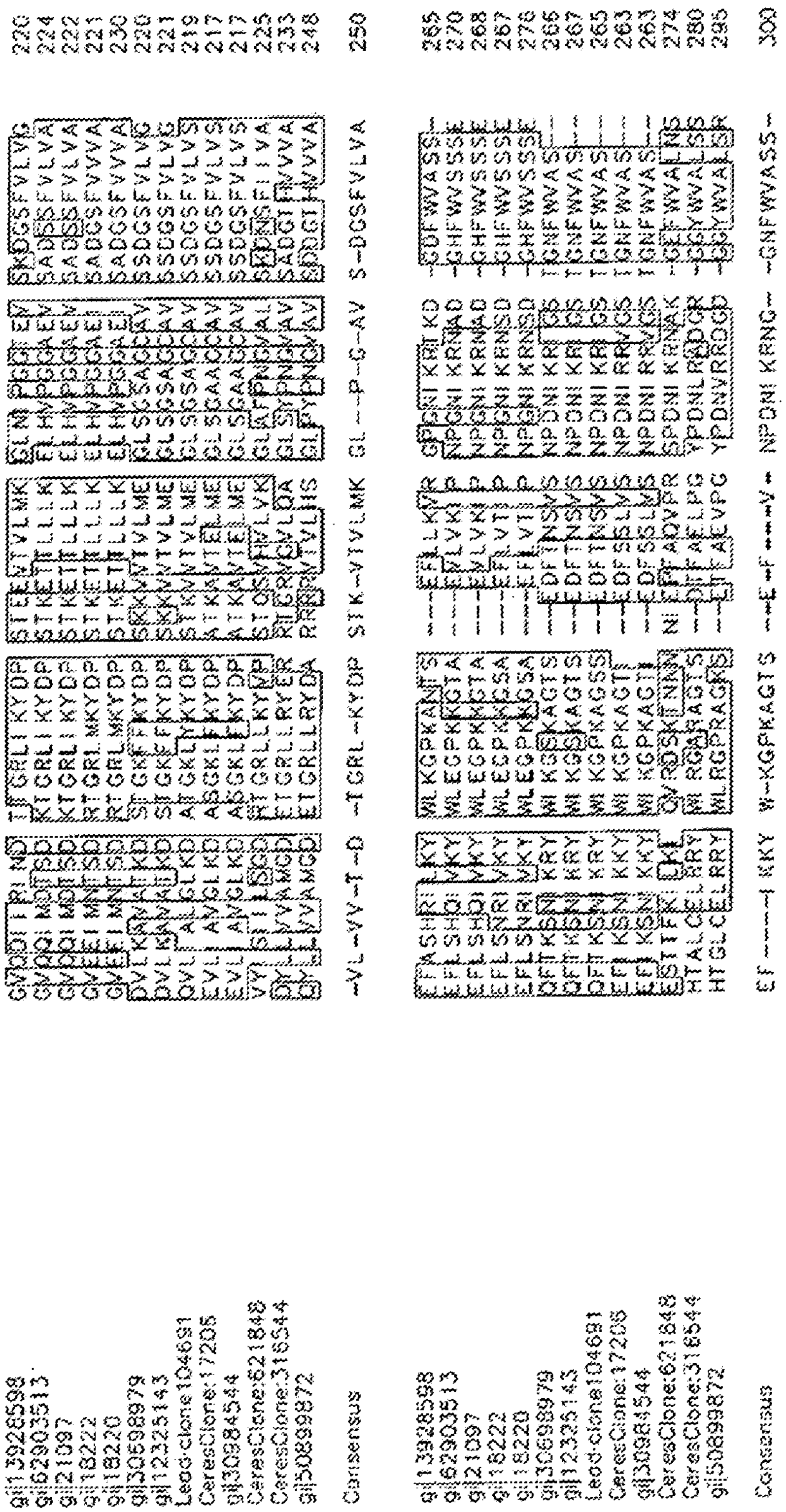
FIG. 9, continued

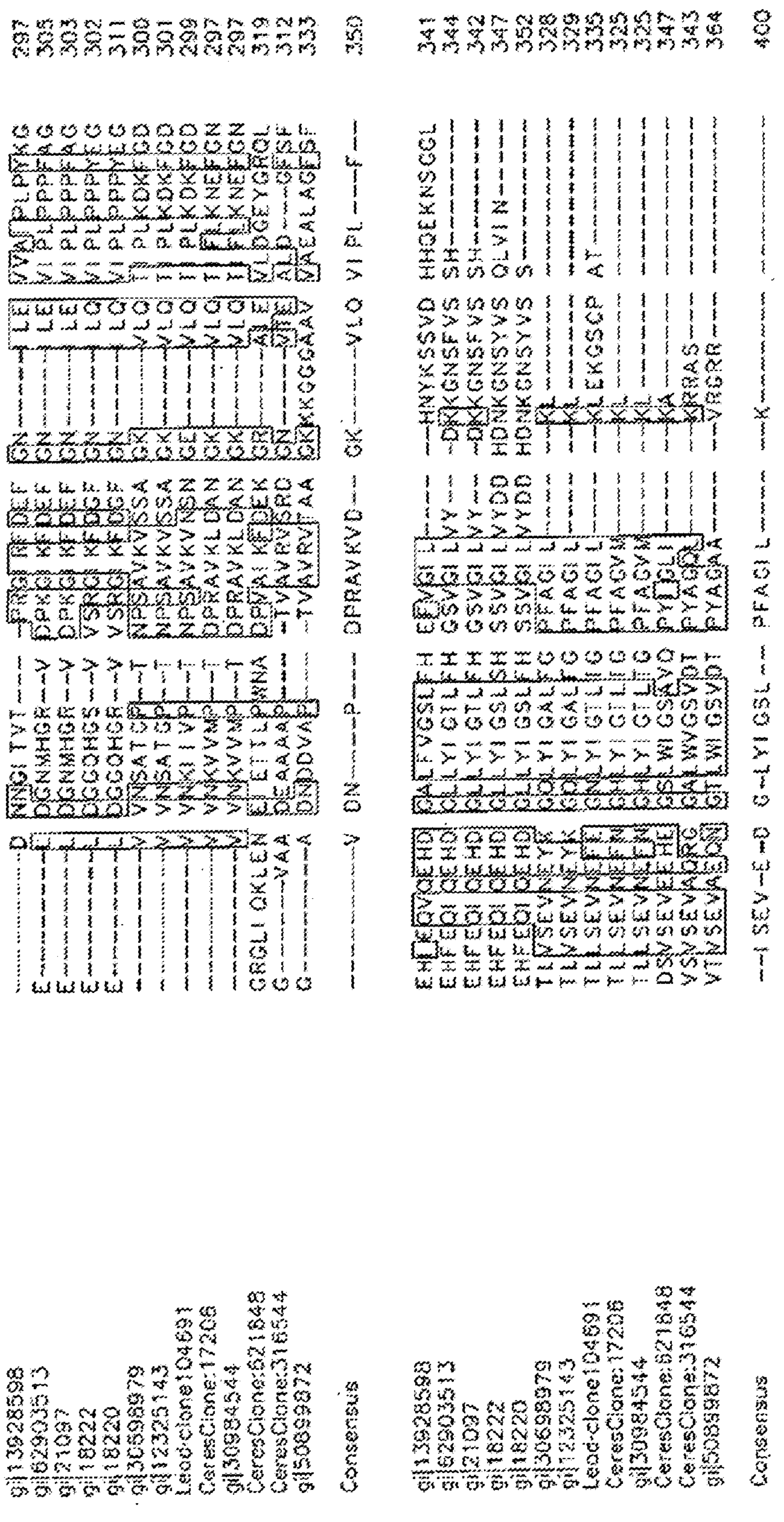
FIG. 9, continued

| | | |
|---|---|---|
| gi\|13928598 | NASFKEFSSF | 351 |
| gi\|62903513 | ---------- | 344 |
| gi\|21097 | ---------- | 342 |
| gi\|18222 | ---------- | 347 |
| gi\|18220 | ---------- | 352 |
| gi\|30698979 | ---------- | 328 |
| gi\|12325143 | ---------- | 329 |
| Lead-clone104691 | ---------- | 335 |
| CeresClone:17206 | ---------- | 325 |
| gi\|30984544 | ---------- | 325 |
| CeresClone:621848 | ---------- | 347 |
| CeresClone:316544 | ---------- | 343 |
| gi\|50899872 | ---------- | 364 |
| Consensus | ---------- | 410 |

FIG 9, continued

SEQUENCE LISTING

```
<160> NUMBER OF SEQ ID NOS: 262

<210> SEQ ID NO 1
<211> LENGTH: 577
<212> TYPE: DNA
<213> ORGANISM: Arabidopsis thaliana
```

```
<220> FEATURE:
<221> NAME/KEY: misc_feature
<223> OTHER INFORMATION: clone11830_inplanta_experimental_L18

<400> SEQUENCE: 1

aaacttccta actagataga tcagatctgg atctctctgc accactcatt gccttctcta      60

gaaacatgtc aactttcttg ataaggatac ttcttccttt gcttatcata gcaatgactc     120

ttcctcgacg ttcagaggca gagtcggaac aatggtgcat agcggatgaa caaacgccag     180

acgatgagtt gcaagcagcc ttagactggg cttgcggaaa aggtggagca gactgcagca     240

aaatgcagca ggaaaaccag ccttgcttct tgcctaacac aatcagagat catgcctcct     300

ttgctttcaa cagttactac caaacttata aaaacaaagg tggttcttgt tacttcaaag     360

gagctgccat gatcactgag cttgacccca gccatggttc ttgccagtat gagtataacc     420

cctgattcaa acgacacagc aaagacaaga tacagcaaga tgaaaagcta tgattttgca     480

tttatacgtt ttctctatgt aatgttttca ttccaaagca gtatccatgt actgttctcc     540

cattacactc cagtctgaga taaaaatttc ttcaacg                               577


<210> SEQ ID NO 2
<211> LENGTH: 119
<212> TYPE: PRT
<213> ORGANISM: Arabidopsis thaliana
<220> FEATURE:
<221> NAME/KEY: MISC_FEATURE
<223> OTHER INFORMATION: peptide_clone11830_inplanta_experimental_L18

<400> SEQUENCE: 2

Met Ser Thr Phe Leu Ile Arg Ile Leu Leu Pro Leu Leu Ile Ile Ala
1               5                   10                  15

Met Thr Leu Pro Arg Arg Ser Glu Ala Glu Ser Glu Gln Trp Cys Ile
            20                  25                  30

Ala Asp Glu Gln Thr Pro Asp Asp Glu Leu Gln Ala Ala Leu Asp Trp
        35                  40                  45

Ala Cys Gly Lys Gly Gly Ala Asp Cys Ser Lys Met Gln Gln Glu Asn
    50                  55                  60

Gln Pro Cys Phe Leu Pro Asn Thr Ile Arg Asp His Ala Ser Phe Ala
65                  70                  75                  80

Phe Asn Ser Tyr Tyr Gln Thr Tyr Lys Asn Lys Gly Gly Ser Cys Tyr
                85                  90                  95

Phe Lys Gly Ala Ala Met Ile Thr Glu Leu Asp Pro Ser His Gly Ser
            100                 105                 110

Cys Gln Tyr Glu Tyr Asn Pro
        115


<210> SEQ ID NO 3
<211> LENGTH: 118
<212> TYPE: PRT
<213> ORGANISM: Glycine max
<220> FEATURE:
<221> NAME/KEY: MISC_FEATURE
<223> OTHER INFORMATION: CeresClone:1058242

<400> SEQUENCE: 3

Met Ala Thr Phe Met Leu Lys Leu Val Leu Pro Leu Leu Phe Leu Phe
1               5                   10                  15

Met Ile Pro Pro Lys Thr Ala Tyr Ala Glu Phe Glu Gln Trp Cys Val
            20                  25                  30

Ala Asp Glu Gln Thr Thr Glu Ser Glu Leu Gln Ala Ala Leu Asp Trp
```

```
        35                  40                  45

Ala Cys Gly Lys Gly Gly Ala Asp Cys Ser Lys Ile Gln Val Asn Gln
    50                  55                  60

Pro Cys Tyr Leu Pro Asn Thr Leu Lys Asp His Ala Ser Tyr Ala Phe
65                  70                  75                  80

Asn Ser Tyr Tyr Gln Lys Phe Lys His Ser Gly Gly Ser Cys Tyr Phe
                85                  90                  95

Arg Gly Ala Ala Ile Thr Thr Glu Val Asp Pro Ser His Gly Ser Cys
            100                 105                 110

His Tyr Asp Phe Ile Pro
        115


<210> SEQ ID NO 4
<211> LENGTH: 123
<212> TYPE: PRT
<213> ORGANISM: Olea europaea
<220> FEATURE:
<221> NAME/KEY: MISC_FEATURE
<223> OTHER INFORMATION: gi|29465664

<400> SEQUENCE: 4

Met Arg Gly Thr Ala Gly Val Pro Asp Gln Pro Val Pro Thr Pro Thr
1               5                   10                  15

Pro Ser Val Pro Thr Ser Ser Ser Pro Val Pro Lys Pro Pro Thr Gln
            20                  25                  30

Gly Asn Lys Lys Trp Cys Val Pro Lys Ala Glu Ala Thr Asp Ala Gln
        35                  40                  45

Leu Gln Ser Asn Ile Asp Tyr Val Cys Ser Gln Ser Gly Met Asp Cys
    50                  55                  60

Gly Pro Ile Gln Ala Asn Gly Ala Cys Phe Asn Pro Asn Thr Val Arg
65                  70                  75                  80

Ala His Ala Ser Tyr Ala Met Asn Ser Trp Tyr Gln Ser Lys Gly Arg
                85                  90                  95

Asn Asp Phe Asp Cys Asp Phe Ser Gly Thr Gly Ala Ile Thr Ser Ser
            100                 105                 110

Asp Pro Ser Asn Gly Ser Cys Ser Phe Leu Ser
        115                 120


<210> SEQ ID NO 5
<211> LENGTH: 123
<212> TYPE: PRT
<213> ORGANISM: Parthenium argentatum
<220> FEATURE:
<221> NAME/KEY: MISC_FEATURE
<223> OTHER INFORMATION: CeresClone:1602924

<400> SEQUENCE: 5

Met Thr Thr Val Thr Thr Pro His Phe Ile Thr Val Leu Phe Phe Phe
1               5                   10                  15

Leu Leu Ile Ser Gly Gly Ile Phe Gly His Ala Lys Ala Gln Ala Pro
            20                  25                  30

Gly Gln Gly Thr Trp Cys Val Ala Lys Pro Ala Thr Ser Asp Glu Asp
        35                  40                  45

Leu Gln Asn Asn Ile Asn Tyr Ala Cys Thr Tyr Val Asp Cys Arg Ile
    50                  55                  60

Ile Arg Pro Gly Ser Val Cys Phe Glu Pro Gln Lys Leu Val Asn Arg
65                  70                  75                  80

Ala Ser Val Ala Met Asn Leu Tyr Tyr Gln Thr Asn Gly Arg Asn Tyr
```

```
                85                  90                  95

Trp Asn Cys Asp Phe Lys Gly Ser Gly Ile Ile Ala Val Thr Asp Pro
            100                 105                 110

Ser Tyr Gly Asp Cys Lys Tyr Ser Tyr Lys Gln
        115                 120


<210> SEQ ID NO 6
<211> LENGTH: 703
<212> TYPE: DNA
<213> ORGANISM: Arabidopsis thaliana
<220> FEATURE:
<221> NAME/KEY: MISC_FEATURE
<223> OTHER INFORMATION: clone35743_inplanta_experimental_L19

<400> SEQUENCE: 6

caataaccac aaacaacaat acacttctct tgacgcctat ctctttctca ccaccaccat     60

taccttcgtc acttctctct tccaagcaat ttaaaccttc aactaatcca gaaatgcaaa    120

tgctaagaaa cttaagcacg aggacgagga gtcgtcgcgg cggatatgag cgtgtaagcg    180

atgattccac cttcagccta cttggagcaa agctaaggag gtcaacgagc gttccatact    240

atgctccatc gataaggctt ggtggagatt ttcctgtgat tttggaaaag cttccacgcc    300

aaaaaccaac taaaacagtg gtgacaagca aattaagcca tccaatcttc agtttatttg    360

atggttatcg ccgccgtagc aagaagaaag cgacggccaa accggagttc tctagatacc    420

atgaatacct taaagaaagt ggaatgtggg atttgagatc taatagtccg gtcatctact    480

ttaagtagat atatatataa cactatatat gttatgattt gtgttcattt attatattat    540

ttgtgacaat tcttagtgat atgattgatc gatctataag agctatcttc agtttttatt    600

tttctccccc ttgtaaatat ttttttaatt gatctataaa tttaaacaca acgttttttg    660

gtcaacagtc ttgtgttatt ctattgtaaa cacaacgttt acc                      703


<210> SEQ ID NO 7
<211> LENGTH: 124
<212> TYPE: PRT
<213> ORGANISM: Arabidopsis thaliana
<220> FEATURE:
<221> NAME/KEY: MISC_FEATURE
<223> OTHER INFORMATION: peptide_clone35743_inplanta_experimental_L19

<400> SEQUENCE: 7

Met Gln Met Leu Arg Asn Leu Ser Thr Arg Thr Arg Ser Arg Arg Gly
1               5                   10                  15

Gly Tyr Glu Arg Val Ser Asp Asp Ser Thr Phe Ser Leu Leu Gly Ala
            20                  25                  30

Lys Leu Arg Arg Ser Thr Ser Val Pro Tyr Tyr Ala Pro Ser Ile Arg
        35                  40                  45

Leu Gly Gly Asp Phe Pro Val Ile Leu Glu Lys Leu Pro Arg Gln Lys
    50                  55                  60

Pro Thr Lys Thr Val Val Thr Ser Lys Leu Ser His Pro Ile Phe Ser
65                  70                  75                  80

Leu Phe Asp Gly Tyr Arg Arg Arg Ser Lys Lys Lys Ala Thr Ala Lys
                85                  90                  95

Pro Glu Phe Ser Arg Tyr His Glu Tyr Leu Lys Glu Ser Gly Met Trp
            100                 105                 110

Asp Leu Arg Ser Asn Ser Pro Val Ile Tyr Phe Lys
        115                 120
```

<210> SEQ ID NO 8
<211> LENGTH: 124
<212> TYPE: PRT
<213> ORGANISM: Arabidopsis thaliana
<220> FEATURE:
<221> NAME/KEY: MISC_FEATURE
<223> OTHER INFORMATION: gi|38603980

<400> SEQUENCE: 8

```
Met Gln Met Leu Arg Asn Leu Ser Thr Arg Thr Arg Ser Arg Arg Gly
1               5                   10                  15

Gly Tyr Glu Arg Val Ser Asp Asp Ser Thr Phe Ser Leu Leu Gly Ala
            20                  25                  30

Lys Leu Arg Arg Ser Thr Ser Val Pro Tyr Tyr Ala Pro Ser Ile Arg
        35                  40                  45

Leu Gly Gly Asp Phe Pro Val Ile Leu Glu Lys Leu Pro Arg Gln Lys
    50                  55                  60

Pro Thr Lys Thr Val Val Thr Ser Lys Leu Ser His Pro Ile Phe Ser
65                  70                  75                  80

Leu Phe Asp Gly Tyr Arg Arg His Asn Lys Lys Lys Ala Thr Ala Lys
                85                  90                  95

Pro Glu Phe Ser Arg Tyr His Glu Tyr Leu Lys Glu Ser Gly Met Trp
            100                 105                 110

Asp Leu Arg Ser Asn Ser Pro Val Ile Tyr Phe Lys
        115                 120
```

<210> SEQ ID NO 9
<211> LENGTH: 118
<212> TYPE: PRT
<213> ORGANISM: Brassica napus
<220> FEATURE:
<221> NAME/KEY: MISC_FEATURE
<223> OTHER INFORMATION: CeresClone:963524

<400> SEQUENCE: 9

```
Met Gln Met Leu Arg Ser Phe Ser Thr Arg Thr Arg Ser Arg Arg Gly
1               5                   10                  15

Gly Tyr Glu Arg Val Ile Asp Asp Ser Thr Phe Ser Leu Leu Gly Ala
            20                  25                  30

Lys Leu Arg Arg Ser Thr Ser Val Pro Tyr Tyr Ala Pro Ser Ile Lys
        35                  40                  45

Leu Gly Ala Gly Gly Val Pro Thr Ile Leu Glu Glu Leu Pro Arg Gln
    50                  55                  60

Lys Ser Lys Lys Val Lys Pro Thr Ser Lys Phe Ser His Pro Ile Phe
65                  70                  75                  80

Ser Phe Leu Tyr Gly Lys Lys Lys Lys Ser Thr Thr Arg Lys Pro Glu
                85                  90                  95

Phe Ser Arg Tyr Leu Glu Tyr Leu Lys Glu Gly Gly Met Trp Asp Ala
            100                 105                 110

Arg Thr Asn Thr Pro Val
        115
```

<210> SEQ ID NO 10
<211> LENGTH: 870
<212> TYPE: DNA
<213> ORGANISM: Arabidopsis thaliana
<220> FEATURE:
<221> NAME/KEY: MISC_FEATURE
<223> OTHER INFORMATION: clone26006_inplanta_experimental_L20

<400> SEQUENCE: 10

-continued

```
aaaaagtacg aaaggaaaat atgagtgagg agaagaggaa gcaacacttc gtgctagtac     60

atggtgcgtg ccacggcgca tggtgctggt acaaggttaa gcctcttctc gaggctttgg    120

gccatcgtgt aaccgcctta gacctagctg cttccggtat agacacaacc aggtcaatca    180

ctgacatttc tacatgtgaa caatattctg agccattgat gcagctaatg acttcattgc    240

cgaatgatga gaaggttgta ctcgttggtc atagctttgg aggtttgagt ttagccttag    300

ccatggataa gtttcccgat aaaatctctg tctctgtctt cgtgactgca ttcatgcccg    360

acaccaaaca ctcaccatcg ttcgtcgagg aaaagtttgc aagcagcatg acaccagaag    420

gatggatggg ctctgagctc gagacatatg gttcagataa ttccggcttg tctgtgttct    480

tcagcaccga cttcatgaag caccgtctct accaactttc tcctgtggag gatcttgagc    540

ttggattgct tctaaagagg cctagttcat tgtttattaa tgaattatcg aagatggaga    600

acttttctga gaaagggtat ggatctgttc ctcgagctta cattgtgtgc aaagaggaca    660

acattatctc ggaagaccat caacgatgga tgatccataa ttatccggcg aatttagtga    720

ttgagatgga agagacggat catatgccaa tgttttgcaa acctcaagta ctaagtgacc    780

atctattggc aatcgctgac aatttctctt aaataatatt ttgatgaaaa tgtatttgga    840

gtggatacaa taaaaatgtg ttctaaatgg                                     870


<210> SEQ ID NO 11
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: peptide_clone26006_inplanta_experimental_L20

<400> SEQUENCE: 11

Met Ser Glu Glu Lys Arg Lys Gln His Phe Val Leu Val His Gly Ala
1               5                   10                  15

Cys His Gly Ala Trp Cys Trp Tyr Lys Val Lys Pro Leu Leu Glu Ala
            20                  25                  30

Leu Gly His Arg Val Thr Ala Leu Asp Leu Ala Ala Ser Gly Ile Asp
        35                  40                  45

Thr Thr Arg Ser Ile Thr Asp Ile Ser Thr Cys Glu Gln Tyr Ser Glu
    50                  55                  60

Pro Leu Met Gln Leu Met Thr Ser Leu Pro Asn Asp Glu Lys Val Val
65                  70                  75                  80

Leu Val Gly His Ser Phe Gly Gly Leu Ser Leu Ala Leu Ala Met Asp
                85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Glu Glu Lys Phe Ala Ser
        115                 120                 125

Ser Met Thr Pro Glu Gly Trp Met Gly Ser Glu Leu Glu Thr Tyr Gly
    130                 135                 140

Ser Asp Asn Ser Gly Leu Ser Val Phe Phe Ser Thr Asp Phe Met Lys
145                 150                 155                 160

His Arg Leu Tyr Gln Leu Ser Pro Val Glu Asp Leu Glu Leu Gly Leu
                165                 170                 175

Leu Leu Lys Arg Pro Ser Ser Leu Phe Ile Asn Glu Leu Ser Lys Met
            180                 185                 190

Glu Asn Phe Ser Glu Lys Gly Tyr Gly Ser Val Pro Arg Ala Tyr Ile
```

```
        195                 200                 205

Val Cys Lys Glu Asp Asn Ile Ile Ser Glu Asp His Gln Arg Trp Met
    210                 215                 220

Ile His Asn Tyr Pro Ala Asn Leu Val Ile Glu Met Glu Glu Thr Asp
225                 230                 235                 240

His Met Pro Met Phe Cys Lys Pro Gln Val Leu Ser Asp His Leu Leu
                245                 250                 255

Ala Ile Ala Asp Asn Phe Ser
            260


<210> SEQ ID NO 12
<211> LENGTH: 267
<212> TYPE: PRT
<213> ORGANISM: Citrus sinensis
<220> FEATURE:
<221> NAME/KEY: MISC_FEATURE
<223> OTHER INFORMATION: gi|14279437

<400> SEQUENCE: 12

Met Glu Glu Val Val Gly Met Glu Glu Lys His Phe Val Leu Val His
1               5                   10                  15

Gly Val Asn His Gly Ala Trp Cys Trp Tyr Lys Leu Lys Ala Arg Leu
            20                  25                  30

Val Ala Gly Gly His Arg Val Thr Ala Val Asp Leu Ala Ala Ser Gly
        35                  40                  45

Ile Asn Met Lys Arg Ile Glu Asp Val His Thr Phe His Ala Tyr Ser
    50                  55                  60

Glu Pro Leu Met Glu Val Leu Ala Ser Leu Pro Ala Glu Glu Lys Val
65                  70                  75                  80

Ile Leu Val Gly His Ser Leu Gly Gly Val Thr Leu Ala Leu Ala Gly
                85                  90                  95

Asp Lys Phe Pro His Lys Ile Ser Val Ala Val Phe Val Thr Ala Phe
            100                 105                 110

Met Pro Asp Thr Thr His Arg Pro Ser Phe Val Leu Glu Gln Tyr Ser
        115                 120                 125

Glu Lys Met Gly Lys Glu Asp Asp Ser Trp Leu Asp Thr Gln Phe Ser
    130                 135                 140

Gln Cys Asp Ala Ser Asn Pro Ser His Ile Ser Met Leu Phe Gly Arg
145                 150                 155                 160

Glu Phe Leu Thr Ile Lys Ile Tyr Gln Leu Cys Pro Pro Glu Asp Leu
                165                 170                 175

Glu Leu Ala Lys Met Leu Val Arg Pro Gly Ser Met Phe Ile Asp Asn
            180                 185                 190

Leu Ser Lys Glu Ser Lys Phe Ser Asp Glu Gly Tyr Gly Ser Val Lys
        195                 200                 205

Arg Val Tyr Leu Val Cys Glu Glu Asp Ile Gly Leu Pro Lys Gln Phe
    210                 215                 220

Gln His Trp Met Ile Gln Asn Tyr Pro Val Asn Glu Val Met Glu Ile
225                 230                 235                 240

Lys Gly Gly Asp His Met Ala Met Leu Ser Asp Pro Gln Lys Leu Cys
                245                 250                 255

Asp Cys Leu Ser Gln Ile Ser Leu Lys Tyr Ala
            260                 265


<210> SEQ ID NO 13
<211> LENGTH: 263
```

<212> TYPE: PRT
<213> ORGANISM: Arabidopsis thaliana
<220> FEATURE:
<221> NAME/KEY: MISC_FEATURE
<223> OTHER INFORMATION: CeresClone:1010900

<400> SEQUENCE: 13

```
Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
    130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260
```

<210> SEQ ID NO 14
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: gi|20196998

<400> SEQUENCE: 14

```
Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45
```

-continued

```
Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
    130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260


<210> SEQ ID NO 15
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: gi|27754457

<400> SEQUENCE: 15

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Lys Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
    130                 135                 140
```

-continued

Ser Asp Asn Ser Gly Leu Ser Met Phe Phe Ser Pro Asp Phe Met Lys
145 150 155 160

Leu Gly Leu Tyr Gln Leu Ser Pro Val Glu Asp Leu Glu Leu Gly Leu
165 170 175

Leu Leu Met Arg Pro Gly Ser Leu Phe Ile Asn Asp Leu Ser Lys Met
180 185 190

Lys Asn Phe Ser Asp Glu Gly Tyr Gly Ser Val Pro Arg Val Phe Ile
195 200 205

Val Cys Lys Glu Asp Lys Ala Ile Pro Glu Glu Arg Gln Arg Trp Met
210 215 220

Ile Asp Asn Phe Pro Val Asn Leu Val Met Glu Met Glu Glu Thr Asp
225 230 235 240

His Met Pro Met Phe Cys Lys Pro Gln Gln Leu Ser Asp Tyr Phe Leu
245 250 255

Lys Ile Ala Asp Lys Phe Val
260

<210> SEQ ID NO 16
<211> LENGTH: 257
<212> TYPE: PRT
<213> ORGANISM: Hevea brasiliensis
<220> FEATURE:
<221> NAME/KEY: MISC_FEATURE
<223> OTHER INFORMATION: gi|50513520

<400> SEQUENCE: 16

Met Ala Phe Ala His Phe Val Leu Ile His Thr Ile Cys His Gly Ala
1 5 10 15

Trp Ile Trp His Lys Leu Lys Pro Leu Leu Glu Ala Leu Gly His Lys
20 25 30

Val Thr Ala Leu Asp Leu Ala Ala Ser Gly Val Asp Pro Arg Gln Ile
35 40 45

Glu Glu Ile Gly Ser Phe Asp Glu Tyr Ser Glu Pro Leu Leu Thr Phe
50 55 60

Leu Glu Ala Leu Pro Pro Gly Glu Lys Val Ile Leu Val Gly Glu Ser
65 70 75 80

Cys Gly Gly Leu Asn Ile Ala Ile Ala Ala Asp Lys Tyr Cys Glu Lys
85 90 95

Ile Ala Ala Ala Val Phe His Asn Ser Val Leu Pro Asp Thr Glu His
100 105 110

Cys Pro Ser Tyr Val Val Asp Lys Leu Met Glu Val Phe Pro Asp Trp
115 120 125

Lys Asp Thr Thr Tyr Phe Thr Tyr Thr Lys Asp Gly Lys Glu Ile Thr
130 135 140

Gly Leu Lys Leu Gly Phe Thr Leu Leu Arg Glu Asn Leu Tyr Thr Leu
145 150 155 160

Cys Gly Pro Glu Glu Tyr Glu Leu Ala Lys Met Leu Thr Arg Lys Gly
165 170 175

Ser Leu Phe Gln Asn Ile Leu Ala Lys Arg Pro Phe Phe Thr Lys Glu
180 185 190

Gly Tyr Gly Ser Ile Lys Lys Ile Tyr Val Trp Thr Asp Gln Asp Glu
195 200 205

Ile Phe Leu Pro Glu Phe Gln Leu Trp Gln Ile Glu Asn Tyr Lys Pro
210 215 220

Asp Lys Val Tyr Lys Val Glu Gly Gly Asp His Leu Leu Gln Leu Thr

-continued

```
225                 230                 235                 240

Lys Thr Lys Glu Ile Ala Glu Ile Leu Gln Glu Val Ala Asp Thr Tyr
                245                 250                 255

Asn


<210> SEQ ID NO 17
<211> LENGTH: 257
<212> TYPE: PRT
<213> ORGANISM: Hevea brasiliensis
<220> FEATURE:
<221> NAME/KEY: MISC_FEATURE
<223> OTHER INFORMATION: gi|6435646

<400> SEQUENCE: 17

Met Ala Phe Ala His Phe Val Leu Ile His Thr Ile Cys His Gly Ala
1               5                   10                  15

Trp Ile Trp His Lys Leu Lys Pro Leu Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
            100                 105                 110

Cys Pro Ser Tyr Val Val Asp Lys Leu Met Glu Val Phe Pro Asp Trp
        115                 120                 125

Lys Asp Thr Thr Tyr Phe Thr Tyr Thr Lys Asp Gly Lys Glu Ile Thr
    130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
        195                 200                 205

Ile Phe Leu Pro Glu Phe Gln Leu Trp Gln Ile Glu Asn Tyr Lys Pro
    210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn


<210> SEQ ID NO 18
<211> LENGTH: 258
<212> TYPE: PRT
<213> ORGANISM: Manihot esculenta
<220> FEATURE:
<221> NAME/KEY: MISC_FEATURE
<223> OTHER INFORMATION: gi|2780225

<400> SEQUENCE: 18
```

```
Met Ala Val Val Asp Phe Val Leu Ile His Thr Ile Cys His Gly Ala
1               5                   10                  15

Trp Ile Trp Tyr Lys Leu Lys Pro Val Leu Glu Ala Ala Gly His Lys
            20                  25                  30

Val Thr Ala Leu Asp Leu Ala Ala Ser Gly Val Asp Pro Arg Gln Ile
        35                  40                  45

Glu Gln Ile Asn Ser Phe Asp Glu Tyr Ser Glu Pro Leu Leu Thr Phe
    50                  55                  60

Met Glu Ser Leu Pro Gln Gly Glu Lys Val Ile Leu Val Gly Glu Ser
65                  70                  75                  80

Cys Gly Gly Leu Asn Ile Ala Ile Ala Ala Asp Lys Tyr Pro Glu Lys
                85                  90                  95

Ile Ala Ala Ala Val Phe Gln Asn Ser Leu Leu Pro Asp Thr Lys His
            100                 105                 110

Lys Pro Ser Tyr Val Val Asp Lys Leu Met Glu Val Phe Pro Asp Trp
        115                 120                 125

Lys Asp Thr Glu Tyr Phe Glu Phe Ser Asn Ser Asn Gly Glu Thr Ile
    130                 135                 140

Thr Gly Met Val Leu Gly Leu Lys Leu Met Arg Glu Asn Leu Tyr Thr
145                 150                 155                 160

Ile Cys Pro Pro Glu Asp Tyr Glu Leu Ala Lys Met Leu Thr Arg Arg
                165                 170                 175

Gly Ser Leu Phe Gln Ser Ile Leu Ala Gln Arg Glu Lys Phe Thr Glu
            180                 185                 190

Lys Gly Tyr Gly Ser Ile Lys Lys Ile Tyr Val Trp Thr Gly Asp Asp
        195                 200                 205

Lys Ile Phe Leu Pro Glu Phe Gln Leu Trp Gln Ile Glu Asn Tyr Lys
    210                 215                 220

Pro Asp Leu Val Phe Arg Val Met Gly Gly Asp His Lys Leu Gln Leu
225                 230                 235                 240

Thr Lys Thr Asn Glu Ile Ala Gly Ile Leu Gln Lys Val Ala Asp Ile
                245                 250                 255

Tyr Ala


<210> SEQ ID NO 19
<211> LENGTH: 258
<212> TYPE: PRT
<213> ORGANISM: Catharanthus roseus
<220> FEATURE:
<221> NAME/KEY: MISC_FEATURE
<223> OTHER INFORMATION: gi|53830670

<400> SEQUENCE: 19

Met Glu Val Met Lys His Phe Val Thr Val His Gly Val Gly His Gly
1               5                   10                  15

Ala Trp Val Tyr Tyr Lys Leu Lys Pro Arg Ile Glu Ala Ala Gly His
            20                  25                  30

Arg Cys Thr Ala Val Asn Leu Ala Ala Ser Gly Ile Asn Glu Lys Lys
        35                  40                  45

Leu Glu Glu Val Arg Ser Ser Ile Asp Tyr Ala Ala Pro Leu Leu Glu
    50                  55                  60

Val Leu Asp Ser Val Pro Glu Asn Glu Lys Val Ile Leu Val Gly His
65                  70                  75                  80

Ser Gly Gly Gly Met Thr Ala Ala Val Gly Met Glu Lys Phe Pro Asn
                85                  90                  95
```

-continued

Lys Ile Ser Leu Ala Val Phe Leu Asn Ala Ile Met Pro Asp Thr Glu
100 105 110

Asn Arg Pro Ser Tyr Val Leu Glu Glu Tyr Thr Ala Lys Thr Pro Pro
115 120 125

Glu Ala Trp Lys Asp Cys Gln Phe Ser Ala Tyr Gly Asp Pro Pro Ile
130 135 140

Thr Ser Leu Val Cys Gly Pro Glu Phe Ile Ser Ser Thr Leu Tyr His
145 150 155 160

Leu Ser Pro Ile Glu Asp His Ala Leu Gly Lys Ile Leu Val Arg Pro
165 170 175

Gly Ser Leu Phe Ile Glu Asp Leu Leu Lys Ala Glu Lys Phe Thr Glu
180 185 190

Glu Gly Phe Gly Ser Val Pro Arg Val Tyr Val Ile Ala Ala Glu Asp
195 200 205

Lys Thr Ile Pro Pro Glu Phe Gln Arg Trp Met Ile Glu Asn Asn Pro
210 215 220

Val Lys Glu Val Lys Glu Ile Lys Gly Ala Asp His Met Pro Met Phe
225 230 235 240

Ser Lys Pro Asp Glu Leu Ser Gln Cys Leu Leu Asp Ile Ala Lys Lys
245 250 255

His Ala

<210> SEQ ID NO 20
<211> LENGTH: 264
<212> TYPE: PRT
<213> ORGANISM: Rauvolfia serpentina
<220> FEATURE:
<221> NAME/KEY: MISC_FEATURE
<223> OTHER INFORMATION: gi|6651393

<400> SEQUENCE: 20

Met His Ser Ala Ala Asn Ala Lys Gln Gln Lys His Phe Val Leu Val
1 5 10 15

His Gly Gly Cys Leu Gly Ala Trp Ile Trp Tyr Lys Leu Lys Pro Leu
20 25 30

Leu Glu Ser Ala Gly His Lys Val Thr Ala Val Asp Leu Ser Ala Ala
35 40 45

Gly Ile Asn Pro Arg Arg Leu Asp Glu Ile His Thr Phe Arg Asp Tyr
50 55 60

Ser Glu Pro Leu Met Glu Val Met Ala Ser Ile Pro Pro Asp Glu Lys
65 70 75 80

Val Val Leu Leu Gly His Ser Phe Gly Gly Met Ser Leu Gly Leu Ala
85 90 95

Met Glu Thr Tyr Pro Glu Lys Ile Ser Val Ala Val Phe Met Ser Ala
100 105 110

Met Met Pro Asp Pro Asn His Ser Leu Thr Tyr Pro Phe Glu Lys Tyr
115 120 125

Asn Glu Lys Cys Pro Ala Asp Met Met Leu Asp Ser Gln Phe Ser Thr
130 135 140

Tyr Gly Asn Pro Glu Asn Pro Gly Met Ser Met Ile Leu Gly Pro Gln
145 150 155 160

Phe Met Ala Leu Lys Met Phe Gln Asn Cys Ser Val Glu Asp Leu Glu
165 170 175

Leu Ala Lys Met Leu Thr Arg Pro Gly Ser Leu Phe Phe Gln Asp Leu
180 185 190

```
Ala Lys Ala Lys Lys Phe Ser Thr Glu Arg Tyr Gly Ser Val Lys Arg
        195                 200                 205

Ala Tyr Ile Phe Cys Asn Glu Asp Lys Ser Phe Pro Val Glu Phe Gln
    210                 215                 220

Lys Trp Phe Val Glu Ser Val Gly Ala Asp Lys Val Lys Glu Ile Lys
225                 230                 235                 240

Glu Ala Asp His Met Gly Met Leu Ser Gln Pro Arg Glu Val Cys Lys
                245                 250                 255

Cys Leu Leu Asp Ile Ser Asp Ser
            260


<210> SEQ ID NO 21
<211> LENGTH: 262
<212> TYPE: PRT
<213> ORGANISM: Lycopersicon esculentum
<220> FEATURE:
<221> NAME/KEY: MISC_FEATURE
<223> OTHER INFORMATION: gi|41814856

<400> SEQUENCE: 21

Met Glu Lys Gly Asp Lys Asn His Phe Val Leu Val His Gly Ala Cys
1               5                   10                  15

His Gly Ala Trp Cys Trp Tyr Lys Val Val Thr Ile Leu Arg Ser Glu
            20                  25                  30

Gly His Lys Val Ser Val Leu Asp Met Ala Ala Ser Gly Ile Asn Pro
        35                  40                  45

Lys His Val Asp Asp Leu Asn Ser Met Ala Asp Tyr Asn Glu Pro Leu
    50                  55                  60

Met Glu Phe Met Asn Ser Leu Pro Gln Leu Glu Arg Val Val Leu Val
65                  70                  75                  80

Gly His Ser Met Gly Gly Ile Asn Ile Ser Leu Ala Met Glu Lys Phe
                85                  90                  95

Pro Gln Lys Ile Val Val Ala Val Phe Val Thr Ala Phe Met Pro Gly
            100                 105                 110

Pro Asp Leu Asn Leu Val Ala Leu Gly Gln Gln Tyr Asn Gln Gln Val
        115                 120                 125

Glu Ser His Met Asp Thr Glu Phe Val Tyr Asn Asn Gly Gln Asp Lys
    130                 135                 140

Ala Pro Thr Ser Leu Val Leu Gly Pro Glu Val Leu Ala Thr Asn Phe
145                 150                 155                 160

Tyr Gln Leu Ser Pro Pro Glu Asp Leu Thr Leu Ala Thr Tyr Leu Val
                165                 170                 175

Arg Pro Val Pro Leu Phe Asp Glu Ser Ile Leu Leu Ala Asn Thr Thr
            180                 185                 190

Leu Ser Lys Glu Lys Tyr Gly Ser Val His Arg Val Tyr Val Val Cys
        195                 200                 205

Asp Lys Asp Asn Val Leu Lys Glu Gln Gln Phe Gln Lys Trp Leu Ile
    210                 215                 220

Asn Asn Asn Pro Pro Asp Glu Val Gln Ile Ile His Asn Ala Asp His
225                 230                 235                 240

Met Val Met Phe Ser Lys Pro Arg Asp Leu Ser Ser Cys Leu Val Met
                245                 250                 255

Ile Ser Gln Lys Tyr Tyr
            260


<210> SEQ ID NO 22
```

```
<211> LENGTH: 260
<212> TYPE: PRT
<213> ORGANISM: Nicotiana tabacum
<220> FEATURE:
<221> NAME/KEY: MISC_FEATURE
<223> OTHER INFORMATION: gi|40549303

<400> SEQUENCE: 22

Met Lys Glu Gly Lys His Phe Val Leu Val His Gly Ala Cys His Gly
1               5                   10                  15

Gly Trp Ser Trp Tyr Lys Leu Lys Pro Leu Leu Glu Ala Ala Gly His
            20                  25                  30

Lys Val Thr Ala Leu Asp Leu Ala Ala Ser Gly Thr Asp Leu Arg Lys
        35                  40                  45

Ile Glu Glu Leu Arg Thr Leu Tyr Asp Tyr Thr Leu Pro Leu Met Glu
    50                  55                  60

Leu Met Glu Ser Leu Ser Ala Asp Glu Lys Val Ile Leu Val Gly His
65                  70                  75                  80

Ser Leu Gly Gly Met Asn Leu Gly Leu Ala Met Glu Lys Tyr Pro Gln
                85                  90                  95

Lys Ile Tyr Ala Ala Val Phe Leu Ala Ala Phe Met Pro Asp Ser Val
            100                 105                 110

His Asn Ser Ser Phe Val Leu Glu Gln Tyr Asn Glu Arg Thr Pro Ala
        115                 120                 125

Glu Asn Trp Leu Asp Thr Gln Phe Leu Pro Tyr Gly Ser Pro Glu Glu
    130                 135                 140

Pro Leu Thr Ser Met Phe Phe Gly Pro Lys Phe Leu Ala His Lys Leu
145                 150                 155                 160

Tyr Gln Leu Cys Ser Pro Glu Asp Leu Ala Leu Ala Ser Ser Leu Val
                165                 170                 175

Arg Pro Ser Ser Leu Phe Met Glu Asp Leu Ser Lys Ala Lys Tyr Phe
            180                 185                 190

Thr Asp Glu Arg Phe Gly Ser Val Lys Arg Val Tyr Ile Val Cys Thr
        195                 200                 205

Glu Asp Lys Gly Ile Pro Glu Glu Phe Gln Arg Trp Gln Ile Asp Asn
    210                 215                 220

Ile Gly Val Thr Glu Ala Ile Glu Ile Lys Gly Ala Asp His Met Ala
225                 230                 235                 240

Met Leu Cys Glu Pro Gln Lys Leu Cys Ala Ser Leu Leu Glu Ile Ala
                245                 250                 255

His Lys Tyr Asn
            260


<210> SEQ ID NO 23
<211> LENGTH: 262
<212> TYPE: PRT
<213> ORGANISM: Solanum tuberosum
<220> FEATURE:
<221> NAME/KEY: MISC_FEATURE
<223> OTHER INFORMATION: gi|56392765

<400> SEQUENCE: 23

Met Glu Lys Gly Asn Lys Asn His Phe Val Leu Val His Gly Ala Cys
1               5                   10                  15

His Gly Ala Trp Cys Trp Tyr Lys Val Val Thr Ile Leu Arg Ser Glu
            20                  25                  30

Gly His Lys Val Ser Val Leu Asp Met Ala Ala Ser Gly Ile Asn Pro
        35                  40                  45
```

```
Lys His Val Glu Asp Leu Asn Ser Met Ala Asp Tyr Asn Glu Pro Leu
    50                  55                  60

Met Glu Phe Met Asn Ser Leu Pro Gln Gln Glu Arg Val Val Leu Val
65                  70                  75                  80

Gly His Ser Met Gly Gly Ile Asn Ile Ser Leu Ala Met Glu Lys Phe
                85                  90                  95

Pro His Lys Ile Ala Val Ala Val Phe Val Ser Ala Ser Met Pro Gly
            100                 105                 110

Pro Asp Leu Asn Leu Val Ala Val Thr Gln Gln Tyr Ser Gln Gln Val
        115                 120                 125

Glu Thr Pro Met Asp Thr Glu Phe Val Tyr Asn Asn Gly Leu Asp Lys
    130                 135                 140

Gly Pro Thr Ser Val Val Leu Gly Pro Lys Val Leu Ala Thr Ile Tyr
145                 150                 155                 160

Tyr Gln Phe Ser Pro Pro Glu Asp Leu Thr Leu Ala Thr Tyr Leu Val
                165                 170                 175

Arg Pro Val Pro Leu Phe Asp Glu Ser Val Leu Leu Thr Asn Thr Thr
            180                 185                 190

Leu Ser Lys Glu Lys Tyr Gly Ser Val His Arg Val Tyr Val Val Cys
        195                 200                 205

Asp Lys Asp Lys Val Leu Lys Glu Glu Gln Phe Gln Arg Trp Leu Ile
    210                 215                 220

Lys Asn Asn Pro Pro Asn Glu Val Gln Met Ile His Asp Ala Gly His
225                 230                 235                 240

Met Val Met Phe Ser Lys Pro Arg Glu Leu Cys Ser Cys Leu Val Met
                245                 250                 255

Ile Ser Gln Lys Tyr His
            260
```

<210> SEQ ID NO 24
<211> LENGTH: 266
<212> TYPE: PRT
<213> ORGANISM: Triticum aestivum
<220> FEATURE:
<221> NAME/KEY: MISC_FEATURE
<223> OTHER INFORMATION: CeresClone:644331

<400> SEQUENCE: 24

```
Met Glu Ala Cys Ala Gly Gln Ala Ser Ser Ala His Ile Val Leu Val
1               5                   10                  15

His Gly Ala Cys Leu Gly Gly Trp Ser Trp Phe Lys Val Ala Thr Arg
            20                  25                  30

Leu Arg Ser Ala Gly His Arg Val Ser Thr Pro Asp Leu Ala Ala Ser
        35                  40                  45

Gly Val Asp Pro Arg Pro Leu Arg Glu Val Pro Thr Phe Arg Asp Tyr
    50                  55                  60

Thr Lys Pro Leu Leu Asp Leu Leu Glu Ser Leu Pro Ser Gly Glu Lys
65                  70                  75                  80

Val Val Leu Val Gly His Ser Leu Gly Gly Val Asn Val Ala Leu Ala
                85                  90                  95

Cys Glu Leu Phe Pro Glu Lys Ile Ala Ala Ala Val Phe Val Ala Ala
            100                 105                 110

Phe Met Pro Asp His Arg Ser Pro Pro Ser Tyr Val Leu Glu Lys Phe
        115                 120                 125

Val Glu Gly Arg Thr Leu Asp Trp Met Asp Thr Glu Phe Lys Pro Gln
```

```
    130                 135                 140

Asp Pro Glu Gly Lys Leu Pro Thr Ser Met Leu Phe Gly Pro Leu Val
145                 150                 155                 160

Thr Arg Ala Lys Phe Phe Gln Leu Cys Ser Pro Glu Asp Leu Thr Leu
                165                 170                 175

Gly Arg Ser Leu Met Arg Val Asn Ser Met Phe Val Asp Asp Leu Arg
            180                 185                 190

Leu Gln Pro Pro His Thr Glu Ala Arg Tyr Gly Ser Val Arg Lys Ala
        195                 200                 205

Tyr Val Val Phe Lys Asp Asp His Ala Ile Val Glu Gln Phe Gln Arg
    210                 215                 220

Trp Met Val His Asn Tyr Pro Val Asp Glu Val Met Glu Ile Asp Gly
225                 230                 235                 240

Ala Asp His Met Ala Leu Leu Ser Thr Pro Thr Glu Leu Ala Arg Cys
                245                 250                 255

Leu Ala Asp Ile Ala Val Lys Tyr Ala Ala
            260                 265


<210> SEQ ID NO 25
<211> LENGTH: 265
<212> TYPE: PRT
<213> ORGANISM: Triticum aestivum
<220> FEATURE:
<221> NAME/KEY: MISC_FEATURE
<223> OTHER INFORMATION: CeresClone:936068

<400> SEQUENCE: 25

Met Glu Gly Ser Ser Ser Gly Lys His Phe Ile Leu Ile His Gly Leu
1               5                   10                  15

Cys His Gly Ala Trp Cys Trp Tyr Lys Leu Val Pro Met Leu Arg Ala
            20                  25                  30

Ala Gly His Arg Val Thr Ala Leu Asp Met Ala Ala Ser Gly Ala His
        35                  40                  45

Pro Ala Arg Met Asp Glu Val Pro Ser Phe Glu Asp Tyr Ser Trp Pro
    50                  55                  60

Leu Leu Asp Ala Val Ala Ala Ala Pro Ala Gly Glu Arg Leu Val Leu
65                  70                  75                  80

Val Gly His Ser Leu Gly Gly Leu Asn Ile Ala Leu Ala Met Glu Arg
                85                  90                  95

Phe Pro Arg Lys Val Ala Ala Ala Val Phe Leu Ala Ala Cys Met Pro
            100                 105                 110

Cys Val Gly Arg His Met Gly Ala Thr Thr Glu Glu Ile Met Arg Arg
        115                 120                 125

Ile Lys Pro Asp Phe Phe Met Asp Met Lys Arg Met Val Leu Asn Thr
    130                 135                 140

Ser Gln Gly Pro Arg Pro Ala Leu Val Phe Gly Pro Lys Ile Leu Ala
145                 150                 155                 160

Ala Lys Leu Tyr Asp Arg Ser Ser Gly Glu Asp Gln Thr Leu Ala Thr
                165                 170                 175

Met Leu Val Arg Pro Gly Cys Gln Phe Leu Asp Asp Pro Thr Met Lys
            180                 185                 190

Asp Glu Ala Leu Leu Thr Glu Ala Lys Tyr Gly Ser Val Lys Lys Val
        195                 200                 205

Tyr Val Val Ala Met Ala Asp Ala Ser Asn Ser Glu Glu Met Gln Arg
    210                 215                 220
```

-continued

```
Trp Met Val Asp Met Ser Pro Gly Thr Glu Ala Glu Glu Ile Ala Gly
225                 230                 235                 240

Ala Asp His Met Ala Met Cys Ser Lys Pro Arg Glu Leu Cys Asp Val
                245                 250                 255

Leu Leu Arg Ile Ala Asp Lys Tyr Glu
            260                 265


<210> SEQ ID NO 26
<211> LENGTH: 268
<212> TYPE: PRT
<213> ORGANISM: Oryza sativa subsp. japonica
<220> FEATURE:
<221> NAME/KEY: MISC_FEATURE
<223> OTHER INFORMATION: gi|34907176

<400> SEQUENCE: 26

Met Glu Ile Ser Ser Ser Ser Lys Lys His Phe Ile Leu Val His Gly
1               5                   10                  15

Leu Cys His Gly Ala Trp Cys Trp Tyr Arg Val Val Ala Ala Leu Arg
            20                  25                  30

Ala Ala Gly His Arg Ala Thr Ala Leu Asp Met Ala Ala Ser Gly Ala
        35                  40                  45

His Pro Ala Arg Val Asp Glu Val Gly Thr Phe Glu Glu Tyr Ser Arg
    50                  55                  60

Pro Leu Leu Asp Ala Val Ala Ala Ala Ala Ala Pro Gly Glu Arg Leu
65                  70                  75                  80

Val Leu Val Gly His Ser His Gly Gly Leu Ser Val Ala Leu Ala Met
                85                  90                  95

Glu Arg Phe Pro Asp Lys Val Ala Ala Ala Val Phe Val Ala Ala Ala
            100                 105                 110

Met Pro Cys Val Gly Lys His Met Gly Val Pro Thr Glu Glu Phe Met
        115                 120                 125

Arg Arg Thr Ala Pro Glu Gly Leu Leu Met Asp Cys Glu Met Val Ala
    130                 135                 140

Ile Asn Asn Ser Gln Gly Ser Gly Val Ala Ile Asn Leu Gly Pro Thr
145                 150                 155                 160

Phe Leu Ala Gln Lys Tyr Tyr Gln Gln Ser Pro Ala Glu Asp Leu Ala
                165                 170                 175

Leu Ala Lys Met Leu Val Arg Pro Gly Asn Gln Phe Met Asp Asp Pro
            180                 185                 190

Val Met Lys Asp Glu Ser Leu Leu Thr Asn Gly Asn Tyr Gly Ser Val
        195                 200                 205

Lys Lys Val Tyr Val Ile Ala Lys Ala Asp Ser Ser Ser Thr Glu Glu
    210                 215                 220

Met Gln Arg Trp Met Val Ala Met Ser Pro Gly Thr Asp Val Glu Glu
225                 230                 235                 240

Ile Ala Gly Ala Asp His Ala Val Met Asn Ser Lys Pro Arg Glu Leu
                245                 250                 255

Cys Asp Ile Leu Ile Lys Ile Ala Asn Lys Tyr Glu
            260                 265


<210> SEQ ID NO 27
<211> LENGTH: 262
<212> TYPE: PRT
<213> ORGANISM: Oryza sativa (japonica cultivar-group)
<220> FEATURE:
<221> NAME/KEY: MISC_FEATURE
<223> OTHER INFORMATION: gi|57899620
```

<400> SEQUENCE: 27

Met Glu Gly Ser Ser Ser Ser Ser Lys His Phe Ile Leu Val His Gly
1 5 10 15

Leu Cys His Gly Ala Trp Cys Trp Tyr Lys Val Val Thr Met Leu Arg
20 25 30

Ser Glu Gly His Arg Val Thr Ala Leu Asp Leu Ala Ala Ser Gly Val
35 40 45

His Pro Ala Arg Val Asp Glu Val His Ser Phe Glu Glu Tyr Ser Gln
50 55 60

Pro Leu Leu Asp Ala Val Ala Glu Ala Pro Ala Gly Glu Arg Leu Ile
65 70 75 80

Leu Val Gly His Ser Phe Gly Gly Leu Ser Ile Ala Leu Ala Met Glu
85 90 95

Arg Phe Pro Glu Lys Ile Ala Val Ala Val Phe Val Ala Ala Ala Val
100 105 110

Pro Cys Val Gly Lys Arg Ile Ile Pro Glu Leu Ile Arg Glu Lys Ala
115 120 125

Pro Lys Asp Met Leu Leu Asp Ser Lys Met Ile Pro Ile Asn Asn Lys
130 135 140

Gln Gly Pro Gly Thr Ala Ile Leu Leu Gly Pro Asn Phe Leu Ala Glu
145 150 155 160

Lys Gly Tyr Pro Leu Ser Pro Ala Glu Asp Leu Thr Leu Ala Lys Leu
165 170 175

Leu Val Arg Pro Thr Ser Gln Phe Val Asp Asp Pro Thr Met Lys Asp
180 185 190

Asp Arg Leu Leu Thr Ser Ala Asn Tyr Gly Ser Val Lys Arg Val Cys
195 200 205

Leu Met Ala Met Glu Asp Asp Leu Lys Glu Val His Arg Tyr Met Ile
210 215 220

Thr Leu Ser Pro Gly Val Glu Val Glu Glu Ile Ala Gly Ala Asp His
225 230 235 240

Ala Val Met Cys Ser Arg Pro Arg Glu Leu Ser Asp Leu Leu Ala Lys
245 250 255

Ile Gly Ser Lys Tyr Asp
260

<210> SEQ ID NO 28
<211> LENGTH: 265
<212> TYPE: PRT
<213> ORGANISM: Capsella rubella
<220> FEATURE:
<221> NAME/KEY: MISC_FEATURE
<223> OTHER INFORMATION: gi|15866583

<400> SEQUENCE: 28

Met Gly Gly Asp Gly Gly Ala Glu Gln Pro Val Ile His Phe Val Phe
1 5 10 15

Val His Gly Ala Ser His Gly Ala Trp Cys Trp Tyr Lys Leu Thr Ser
20 25 30

Leu Leu Glu Thr Ala Gly Phe Lys Thr Thr Ser Val Asp Leu Thr Gly
35 40 45

Ala Gly Ile Ser Val Thr Asp Ser Asn Thr Val Leu Glu Ser Asp Gln
50 55 60

Tyr Asn Arg Pro Leu Phe Ser Leu Leu Ser Asp Leu Pro Pro Ser His
65 70 75 80

```
Lys Val Ile Leu Val Gly His Ser Ile Gly Gly Gly Ser Val Thr Asp
                85                  90                  95

Ala Leu Cys Arg Phe Thr Asp Lys Ile Ser Met Ala Ile Tyr Leu Ala
            100                 105                 110

Ala Ser Met Val Lys Pro Gly Ser Val Pro Ser Pro His Val Ser Asp
        115                 120                 125

Met His Ala Asp Ala Arg Glu Glu Asn Ile Trp Glu Tyr Thr Tyr Gly
    130                 135                 140

Glu Gly Thr Asp Lys Pro Pro Thr Gly Val Ile Met Lys Gln Glu Phe
145                 150                 155                 160

Leu Arg Gln Tyr Tyr Tyr Ser Gln Ser Pro Leu Glu Asp Val Ser Leu
                165                 170                 175

Ala Thr Lys Leu Leu Arg Pro Ala Pro Met Arg Ala Phe Gln Asp Leu
            180                 185                 190

Asp Lys Ser Pro Pro Asn Pro Glu Val Glu Lys Val Pro Arg Val Tyr
        195                 200                 205

Ile Lys Thr Gly Lys Asp Asn Leu Phe Ser Ser Val Arg Gln Asp Leu
    210                 215                 220

Leu Val Lys Asn Trp Pro Pro Ser Gln Phe Tyr Val Leu Glu Glu Ser
225                 230                 235                 240

Asp His Ser Ala Phe Phe Ser Val Pro Thr Thr Leu Phe Val Tyr Leu
                245                 250                 255

Leu Arg Ala Val Ser Phe Leu His Lys
            260                 265


<210> SEQ ID NO 29
<211> LENGTH: 265
<212> TYPE: PRT
<213> ORGANISM: Lycopersicon hirsutum f. glabratum
<220> FEATURE:
<221> NAME/KEY: MISC_FEATURE
<223> OTHER INFORMATION: gi|56393011
<220> FEATURE:
<221> NAME/KEY: misc_feature
<222> LOCATION: (46)..(46)
<223> OTHER INFORMATION: Xaa can be any naturally occurring amino acid

<400> SEQUENCE: 29

Met Glu Lys Ser Met Ser Pro Phe Val Lys Lys His Phe Val Leu Val
1               5                   10                  15

His Thr Ala Phe His Gly Ala Trp Cys Trp Tyr Lys Ile Val Ala Leu
            20                  25                  30

Met Arg Ser Ser Gly His Asn Val Thr Ala Leu Asp Leu Xaa Ala Ser
        35                  40                  45

Gly Ile Asn Pro Lys Gln Ala Leu Gln Ile Pro Asn Phe Ser Asp Tyr
    50                  55                  60

Leu Ser Pro Leu Met Glu Phe Met Ala Ser Leu Pro Ala Asn Glu Lys
65                  70                  75                  80

Ile Ile Leu Val Gly His Ala Leu Gly Gly Leu Ala Ile Ser Lys Ala
                85                  90                  95

Met Glu Thr Phe Pro Glu Lys Ile Ser Val Ala Val Phe Leu Ser Gly
            100                 105                 110

Leu Met Pro Gly Pro Asn Ile Asp Ala Thr Thr Val Cys Thr Lys Ala
        115                 120                 125

Gly Ser Ala Val Leu Gly Gln Leu Asp Asn Cys Val Thr Tyr Glu Asn
    130                 135                 140
```

-continued

```
Gly Pro Thr Asn Pro Pro Thr Thr Leu Ile Ala Gly Pro Lys Phe Leu
145                 150                 155                 160

Ala Thr Asn Val Tyr His Leu Ser Pro Ile Glu Asp Leu Ala Leu Ala
                165                 170                 175

Thr Ala Leu Val Arg Pro Leu Tyr Leu Tyr Leu Ala Glu Asp Ile Ser
            180                 185                 190

Lys Glu Val Val Leu Ser Ser Lys Arg Tyr Gly Ser Val Lys Arg Val
        195                 200                 205

Phe Ile Val Ala Thr Glu Asn Asp Ala Leu Lys Lys Glu Phe Leu Lys
    210                 215                 220

Leu Met Ile Glu Lys Asn Pro Pro Asp Glu Val Lys Glu Ile Glu Gly
225                 230                 235                 240

Ser Asp His Val Thr Met Met Ser Lys Pro Gln Gln Leu Phe Thr Thr
                245                 250                 255

Leu Leu Ser Ile Ala Asn Lys Tyr Lys
            260                 265
```

<210> SEQ ID NO 30
<211> LENGTH: 412
<212> TYPE: DNA
<213> ORGANISM: Arabidopsis thaliana
<220> FEATURE:
<221> NAME/KEY: MISC_FEATURE
<223> OTHER INFORMATION: clone34419_inplanta_experimental_L21

<400> SEQUENCE: 30

```
aacaacgcca caatcatggc tttgttctta tctcctaaaa ccatcactct tctcttcttc      60

tccctctccc tcgcactcta ctgcagcatc gatcctttcc acactgcgcc atttccgatt     120

tccccaattt cgtctctcac gaagttatct ctccacgtcc cgacgaagtt ccatgggaga     180

gagattcaca aaattcactt cagaaatcaa agattctgtt ttttaaccaa atccaaggtc     240

cagagagcgt cgcctttgat tctctcggac gtggtccgta cacggcgttg ctgatggtag     300

ggttttgttt tgggatggag agaaatggat tgatttcgct tatacttcga gtaatcgatc     360

ggagatttgt gatccgaagt ataagcgaaa tcaatccatt tctctccatc cc             412
```

<210> SEQ ID NO 31
<211> LENGTH: 92
<212> TYPE: PRT
<213> ORGANISM: Arabidopsis thaliana
<220> FEATURE:
<221> NAME/KEY: MISC_FEATURE
<223> OTHER INFORMATION: peptide_clone34419_inplanta_experimental_L21

<400> SEQUENCE: 31

```
Met Ala Leu Phe Leu Ser Pro Lys Thr Ile Thr Leu Leu Phe Phe Ser
1               5                   10                  15

Leu Ser Leu Ala Leu Tyr Cys Ser Ile Asp Pro Phe His Thr Ala Pro
            20                  25                  30

Phe Pro Ile Ser Pro Ile Ser Ser Leu Thr Lys Leu Ser Leu His Val
        35                  40                  45

Pro Thr Lys Phe His Gly Arg Glu Ile His Lys Ile His Phe Arg Asn
    50                  55                  60

Gln Arg Phe Cys Phe Leu Thr Lys Ser Lys Val Gln Arg Ala Ser Pro
65                  70                  75                  80

Leu Ile Leu Ser Asp Val Val Arg Thr Arg Arg Cys
                85                  90
```

<210> SEQ ID NO 32
<211> LENGTH: 1776
<212> TYPE: DNA
<213> ORGANISM: Arabidopsis thaliana
<220> FEATURE:
<221> NAME/KEY: MISC_FEATURE
<223> OTHER INFORMATION: cDNA12659859_inplanta_experimental_L22

<400> SEQUENCE: 32

```
gagcagaaga acttacttat agaaaaaaat gggaatttca aaaccactcc ttctattttc     60
gattttagtc ctctattttt cactctacac cattacacca acttcttcat tagcctccct    120
ccaagatcaa ttcatcaact gtgtccaaag aaacacacat gtttacttcc cacttgagaa    180
aacgttcttt gctcctacaa aaaatgtctc tatgttcagc caagttcttg aatcgacggc    240
tcaaaatctc cggttcttga aaaaatccat gcctaaaccg ggattcatat tcagccctat    300
tcacgagtct cacgtacaag cttccatcat ttgttccaag aaactccgaa tgcatctccg    360
tgtcagaagc ggcggtcacg actacgaagg cttgtcttat gtctctcaga tcgataaacc    420
gtttatattg atggatctgt caaagatgag acaggtcaac attaatattc aagacaacag    480
tgcttgggtt caatctggtg ccactgttgg tgaactttat tacaggattg cggagaagag    540
caaagtccat gggttcccgg cgggtttgtg ctcgagctta ggcataggag gacacataac    600
aggcggtgcg tacggttcca tgatgcggaa atatggtcta ggtgcagaca atgttctaga    660
cgcaaagatt gttgatgcca acggtaaatt actcgataga gccgcgatgg gtgaggatac    720
attttgggct attagaggag gcgctggagg gagttttggg ataattctag catggaagat    780
caagcttgtt cctgttccta agaccgtgac cgtctttacc gtcaccaaaa cgttacaaca    840
agacgtgggt aacaagatta tctcaaagtg gcaaagagtt gcggacaagc ttgttgaaga    900
gctattcatc agagtgctct tcaacgtagc tggaaccggt gggaacaaga ctgtgacgac    960
gtcgtacaat gctctgtttc ttggcgggaa aggaacgctg atgaacgtta tgaagaagag   1020
tttccccgag ctagggctaa catttaaaga ttgtatcgaa atgagctggc ttgaatccat   1080
tgcttacatt tctggattcc cgacccacac gcctactaat gttttgcttc aagggaagtc   1140
tccgttccca aaggtcagct tcaaagccaa atcggatttc gtgaaaaccc cgattcccga   1200
atccgggctt caagggatct tcaagaagct acttaaagaa gatattccat tgatgatatg   1260
gaatccttac ggaggaatga tggcgaaaat ccccgaatcc caaatccctt ttccgcatcg   1320
aaaaggagtc ctcttcaagg ttcagtacgt aacaagttgg ctagacagtg acaagagacc   1380
gagcagacac atcaactgga tcagagatct ctatagttac atgacgcctt atgtctcaag   1440
taacccacga gaagcttacg tgaactaccg tgatttagac ctgggaagga acacgaaaga   1500
cgtgaaaaca tgcatcaaac aagctcaagt ctggggagct aactacttca aaaacaattt   1560
caacagattg atgatgatta aagcaaaggt tgatccagag aacttcttta gacacgagca   1620
gagcattcca cctatgatgt aacgaggtca atcaaataag aataaattag aagaaaatca   1680
gataatggtt cttctgtatt tcggaaaaat gttattctag ctatgcttgt agtagtacta   1740
tgtttcacct aaaattcgat atgttgcttc ttagta                             1776
```

<210> SEQ ID NO 33
<211> LENGTH: 537
<212> TYPE: PRT
<213> ORGANISM: Arabidopsis thaliana
<220> FEATURE:
<221> NAME/KEY: MISC_FEATURE
<223> OTHER INFORMATION: peptide_cDNA12659859_inplanta_experimental_L22

<400> SEQUENCE: 33

```
Met Gly Ile Ser Lys Pro Leu Leu Leu Phe Ser Ile Leu Val Leu Tyr
1               5                   10                  15

Phe Ser Leu Tyr Thr Ile Thr Pro Thr Ser Ser Leu Ala Ser Leu Gln
            20                  25                  30

Asp Gln Phe Ile Asn Cys Val Gln Arg Asn Thr His Val Tyr Phe Pro
        35                  40                  45

Leu Glu Lys Thr Phe Phe Ala Pro Thr Lys Asn Val Ser Met Phe Ser
    50                  55                  60

Gln Val Leu Glu Ser Thr Ala Gln Asn Leu Arg Phe Leu Lys Lys Ser
65                  70                  75                  80

Met Pro Lys Pro Gly Phe Ile Phe Ser Pro Ile His Glu Ser His Val
                85                  90                  95

Gln Ala Ser Ile Ile Cys Ser Lys Lys Leu Arg Met His Leu Arg Val
            100                 105                 110

Arg Ser Gly Gly His Asp Tyr Glu Gly Leu Ser Tyr Val Ser Gln Ile
        115                 120                 125

Asp Lys Pro Phe Ile Leu Met Asp Leu Ser Lys Met Arg Gln Val Asn
    130                 135                 140

Ile Asn Ile Gln Asp Asn Ser Ala Trp Val Gln Ser Gly Ala Thr Val
145                 150                 155                 160

Gly Glu Leu Tyr Tyr Arg Ile Ala Glu Lys Ser Lys Val His Gly Phe
                165                 170                 175

Pro Ala Gly Leu Cys Ser Ser Leu Gly Ile Gly Gly His Ile Thr Gly
            180                 185                 190

Gly Ala Tyr Gly Ser Met Met Arg Lys Tyr Gly Leu Gly Ala Asp Asn
        195                 200                 205

Val Leu Asp Ala Lys Ile Val Asp Ala Asn Gly Lys Leu Leu Asp Arg
    210                 215                 220

Ala Ala Met Gly Glu Asp Thr Phe Trp Ala Ile Arg Gly Gly Ala Gly
225                 230                 235                 240

Gly Ser Phe Gly Ile Ile Leu Ala Trp Lys Ile Lys Leu Val Pro Val
                245                 250                 255

Pro Lys Thr Val Thr Val Phe Thr Val Thr Lys Thr Leu Gln Gln Asp
            260                 265                 270

Val Gly Asn Lys Ile Ile Ser Lys Trp Gln Arg Val Ala Asp Lys Leu
        275                 280                 285

Val Glu Glu Leu Phe Ile Arg Val Leu Phe Asn Val Ala Gly Thr Gly
    290                 295                 300

Gly Asn Lys Thr Val Thr Thr Ser Tyr Asn Ala Leu Phe Leu Gly Gly
305                 310                 315                 320

Lys Gly Thr Leu Met Asn Val Met Lys Lys Ser Phe Pro Glu Leu Gly
                325                 330                 335

Leu Thr Phe Lys Asp Cys Ile Glu Met Ser Trp Leu Glu Ser Ile Ala
            340                 345                 350

Tyr Ile Ser Gly Phe Pro Thr His Thr Pro Thr Asn Val Leu Leu Gln
        355                 360                 365

Gly Lys Ser Pro Phe Pro Lys Val Ser Phe Lys Ala Lys Ser Asp Phe
    370                 375                 380

Val Lys Thr Pro Ile Pro Glu Ser Gly Leu Gln Gly Ile Phe Lys Lys
385                 390                 395                 400

Leu Leu Lys Glu Asp Ile Pro Leu Met Ile Trp Asn Pro Tyr Gly Gly
                405                 410                 415
```

```
Met Met Ala Lys Ile Pro Glu Ser Gln Ile Pro Phe Pro His Arg Lys
            420                 425                 430

Gly Val Leu Phe Lys Val Gln Tyr Val Thr Ser Trp Leu Asp Ser Asp
        435                 440                 445

Lys Arg Pro Ser Arg His Ile Asn Trp Ile Arg Asp Leu Tyr Ser Tyr
    450                 455                 460

Met Thr Pro Tyr Val Ser Ser Asn Pro Arg Glu Ala Tyr Val Asn Tyr
465                 470                 475                 480

Arg Asp Leu Asp Leu Gly Arg Asn Thr Lys Asp Val Lys Thr Cys Ile
                485                 490                 495

Lys Gln Ala Gln Val Trp Gly Ala Asn Tyr Phe Lys Asn Asn Phe Asn
            500                 505                 510

Arg Leu Met Met Ile Lys Ala Lys Val Asp Pro Glu Asn Phe Phe Arg
        515                 520                 525

His Glu Gln Ser Ile Pro Pro Met Met
    530                 535


<210> SEQ ID NO 34
<211> LENGTH: 543
<212> TYPE: PRT
<213> ORGANISM: Glycine max
<220> FEATURE:
<221> NAME/KEY: MISC_FEATURE
<223> OTHER INFORMATION: CeresClone:522974

<400> SEQUENCE: 34

Asn Thr Arg Glu Ser Arg Asn Gln Arg Thr Met Lys Ser Leu Arg Ser
1               5                   10                  15

Ile Leu Ala Thr Phe Val Val Leu Leu Ser Ile Ser Leu Thr Ile Ser
            20                  25                  30

Leu Pro Ile Glu Glu Ala Phe Asn His Cys Leu Thr Gln His Ser Gln
        35                  40                  45

Thr Pro Asn Gln Phe Pro Ser Ser Ile Tyr Thr Tyr Thr Asn Gly Ser
    50                  55                  60

Phe Thr Ser Ile Leu Glu Ser Thr Ala Gln Asn Leu Arg Tyr Leu Leu
65                  70                  75                  80

Pro Ser Val Pro Lys Pro Asp Phe Ile Phe Thr Pro Leu Asp Asp Ser
                85                  90                  95

Gln Val Gln Ala Ala Val Val Cys Ala Lys Lys Leu Gly Ile His Met
            100                 105                 110

Arg Val Arg Ser Gly Gly His Asp Tyr Glu Gly Leu Ser Tyr Val Ser
        115                 120                 125

Leu Ile Glu Lys Pro Phe Met Ile Leu Asp Leu Ala Lys Leu Arg Ala
    130                 135                 140

Val Asn Val Asp Ile Ala Arg Asn Thr Ala Trp Ile Gln Ala Gly Ala
145                 150                 155                 160

Thr Ile Gly Glu Val Tyr Tyr Arg Ile Ser Glu Lys Ser Ala Val His
                165                 170                 175

Gly Phe Pro Ala Gly Leu Cys Thr Thr Leu Gly Ile Gly Gly His Ile
            180                 185                 190

Thr Gly Gly Ala Tyr Gly Ser Met Met Arg Lys Tyr Gly Leu Gly Ala
        195                 200                 205

Asp Asn Val Leu Asp Ala Arg Ile Val Asp Ala Asn Gly Lys Val Leu
    210                 215                 220

Asp Arg Lys Ala Met Gly Glu Asp Leu Phe Trp Ala Ile Arg Gly Gly
```

-continued

```
225                 230                 235                 240

Gly Gly Gly Ser Phe Gly Val Ile Leu Trp Trp Lys Ile Lys Leu Val
                245                 250                 255

Pro Val Pro Gln Thr Val Thr Val Phe Thr Val Thr Lys Thr Leu Glu
            260                 265                 270

Gln Gly Gly Ser Lys Leu Leu His Arg Trp Gln Gln Val Ala Pro His
        275                 280                 285

Ile Asp Glu Asn Leu Phe Ile Arg Val Ile Ile Gln Pro Gly Asn Gly
    290                 295                 300

Thr Val Pro Gly Lys Arg Thr Val Thr Thr Ser Tyr Asn Ala Leu Phe
305                 310                 315                 320

Leu Gly Gly Ala Asn Arg Leu Leu Gln Val Met Lys His Gly Phe Pro
                325                 330                 335

Glu Leu Gly Leu Thr Arg Lys Asp Cys Val Glu Thr Ser Trp Ile Glu
            340                 345                 350

Ser Val Leu Tyr Ile Ala Gly Tyr Pro Asp Gly Thr Ala Pro Glu Val
        355                 360                 365

Leu Leu Gln Gly Lys Ser Thr Thr Lys Ala Tyr Phe Lys Ala Lys Ser
    370                 375                 380

Asp Phe Val Arg Glu Val Ile Thr Glu Lys Ser Leu Asn Ala Leu Trp
385                 390                 395                 400

Lys Ile Phe Leu Gln Asp Asp Gly Pro Leu Met Ile Trp Asn Pro Tyr
                405                 410                 415

Gly Gly Lys Met Ser Arg Ile Ala Glu Ser Ala Thr Pro Phe Pro His
            420                 425                 430

Arg Lys Gly Val Leu Tyr Lys Ile Gln His Val Thr Gly Trp Leu Asp
        435                 440                 445

Gly Glu Lys Ser Met Ala Lys His Met Asn Trp Met Arg Lys Phe Tyr
    450                 455                 460

Phe Tyr Met Ala Pro Tyr Val Ser Lys Tyr Pro Arg Glu Thr Tyr Val
465                 470                 475                 480

Asn Tyr Arg Asp Leu Asp Ile Gly Met Asn Gln Lys Asn Asn Thr Ser
                485                 490                 495

Leu Leu Lys Ala Ser Ser Trp Gly Tyr Arg Tyr Phe Lys Gly Asn Phe
            500                 505                 510

Asn Arg Leu Val Lys Val Lys Thr Lys Val Asp Pro Ser Asn Phe Phe
        515                 520                 525

Arg His Glu Gln Ser Ile Pro Leu Leu Pro Thr Gly Lys Lys Glu
    530                 535                 540


<210> SEQ ID NO 35
<211> LENGTH: 538
<212> TYPE: PRT
<213> ORGANISM: Glycine max
<220> FEATURE:
<221> NAME/KEY: MISC_FEATURE
<223> OTHER INFORMATION: CeresClone:561310

<400> SEQUENCE: 35

Thr Glu Thr Arg Glu Ile Ile Val Asn Met Glu Leu Ser Tyr Cys Ala
1               5                   10                  15

Val Phe Leu Ile Leu Leu Ile Pro Ile Ser Arg Ala Asp Ala Thr Ser
            20                  25                  30

Val Glu Lys Gln Phe Lys Glu Cys Leu Leu Thr Gln Leu Asp Gly Asn
        35                  40                  45
```

-continued

```
Ser Glu His Ile Glu Lys Ile Thr Phe Thr Ser Ser Ser Thr Leu Tyr
    50                  55                  60

Pro Gln Val Trp Asp Ser Leu Ala Gln Asn Pro Arg Trp Val Asn Ile
65                  70                  75                  80

Ser Ser Arg Lys Pro Leu Met Ile Leu Thr Pro Phe His Glu Ser Glu
                85                  90                  95

Ile Gln Ala Ala Ile Leu Cys Ser Lys Glu Leu Lys Leu Gln Leu Arg
            100                 105                 110

Val Arg Ser Gly Gly His Asp Tyr Glu Gly Leu Ser Tyr Leu Ser Asp
        115                 120                 125

Val Pro Phe Val Met Val Asp Leu Ile Asn Ile Arg Ser Ile Glu Ile
    130                 135                 140

Asn Leu Ala Asp Glu Thr Ala Trp Val Gln Ala Gly Ala Ser Ile Gly
145                 150                 155                 160

Glu Leu Tyr Tyr Lys Ile Ser Lys Ala Ser Lys Val His Gly Phe Pro
                165                 170                 175

Ala Gly Thr Cys Pro Ser Val Gly Ile Gly Gly His Ile Ser Gly Gly
            180                 185                 190

Gly Gln Gly Leu Met Leu Arg Lys His Gly Leu Ala Ala Asp Asn Val
        195                 200                 205

Val Asp Ala Tyr Leu Ile Asp Ala Asn Gly Lys Ile His Asp Arg Lys
    210                 215                 220

Ser Met Gly Glu Asp Val Phe Trp Ala Ile Arg Gly Gly Asp Ala Ser
225                 230                 235                 240

Ser Phe Gly Val Ile Leu Ala Trp Lys Ile Lys Leu Val Arg Val Pro
                245                 250                 255

Pro Ile Val Thr Gly Phe Asn Val Pro Arg Thr Pro Glu Glu Gly Val
            260                 265                 270

Thr Asp Leu Ile His Arg Trp Gln Tyr Ile Ala His Asp Leu His Glu
        275                 280                 285

Asp Leu Val Ile Arg Val Ile Ala Gln Ile Ser Gly His Asp Lys Ser
    290                 295                 300

Lys Lys Phe Arg Ala Thr Phe Asn Ser Ile Phe Leu Gly Gly Val Asp
305                 310                 315                 320

Arg Leu Ile Pro Leu Met Asn Glu Ser Phe Pro Glu Leu Gly Leu Gln
                325                 330                 335

Ala Lys Asp Cys Thr Glu Met Ser Trp Ile Gln Ser Val Met Phe Ile
            340                 345                 350

Ala Gly Tyr Asn Ile Glu Asp Pro Leu Glu Leu Leu Leu Asn Arg Thr
        355                 360                 365

Thr Met Phe Lys Arg Ser Phe Lys Ala Lys Ser Asp Phe Phe Lys Glu
    370                 375                 380

Pro Val Pro Lys Ser Gly Leu Glu Gly Ala Trp Lys Leu Leu Leu Glu
385                 390                 395                 400

Glu Glu Ile Ala Phe Leu Ile Met Glu Pro Tyr Gly Gly Arg Met Asn
                405                 410                 415

Glu Ile Ser Glu Ser Glu Ile Pro Phe Pro His Arg Lys Gly Asn Leu
            420                 425                 430

Tyr Asn Leu Gln Tyr Leu Val Asn Trp Glu Val Asn Ser Asp Glu Ala
        435                 440                 445

Ser Arg Arg His Leu Gln Trp Ala Lys Met Val Tyr Lys Tyr Met Thr
    450                 455                 460

Pro Tyr Val Ser Lys Ser Pro Arg Ala Ala Tyr Phe Asn Tyr Lys Asp
```

```
465                 470                 475                 480

Leu Asp Leu Gly Lys Asn Lys Leu Asp Ser Thr Ser Tyr Ser Glu Ala
                485                 490                 495

Ser Val Trp Gly Lys Lys Tyr Phe Lys Gly Asn Phe Arg Arg Leu Ala
            500                 505                 510

Gln Ile Lys Thr Lys Phe Asp Pro Leu Asn Phe Phe Arg Asn Glu Gln
        515                 520                 525

Ser Ile Pro Leu Leu Asn Ser His His Ser
    530                 535


<210> SEQ ID NO 36
<211> LENGTH: 535
<212> TYPE: PRT
<213> ORGANISM: Vigna unguiculata
<220> FEATURE:
<221> NAME/KEY: MISC_FEATURE
<223> OTHER INFORMATION: gi|13161397

<400> SEQUENCE: 36

Met Lys Thr Leu Ser Cys Tyr Tyr Thr Phe Ala Thr Val Ile Ala Leu
1               5                   10                  15

Leu Phe Ser Phe Thr Pro Ser Ser Ala Asp Thr His Glu Asn Phe Leu
            20                  25                  30

Gln Cys Leu Tyr Ser Tyr Pro His Asn Thr Asn Ser Ile Ser Ser Val
        35                  40                  45

Leu Tyr Thr Gln Thr Asn Ser Ser Tyr Phe Ser Val Leu Asp Ala Thr
    50                  55                  60

Met Gln Asn Leu Arg Phe Ser Asp Ser Arg Lys Pro Leu Val Ile Val
65                  70                  75                  80

Thr Pro Gln Val Val Ser His Ile Gln Ala Thr Ile Lys Cys Ser Gln
                85                  90                  95

Arg His Gly Leu Gln Ile Arg Thr Arg Ser Gly Gly His Asp Tyr Glu
            100                 105                 110

Gly Leu Ser Tyr Val Ala Arg Val Pro Phe Val Ile Leu Asp Leu Leu
        115                 120                 125

Asn Phe Arg Glu Ile Lys Val Asp Val Glu Asn Arg Thr Ala Trp Val
    130                 135                 140

Gln Val Gly Ala Thr Leu Gly Glu Leu Tyr Tyr Thr Ile Ser Gln Ala
145                 150                 155                 160

Ser Lys Thr Leu Gly Phe Pro Ala Gly Val Cys Tyr Ser Val Gly Ala
                165                 170                 175

Gly Gly His Ile Ser Gly Gly Gly Tyr Gly Phe Leu Met Arg Lys Tyr
            180                 185                 190

Gly Leu Ala Ala Asp Asn Val Ile Asp Ala His Ile Ile Asp Val Asn
        195                 200                 205

Gly Asn Leu Leu Asp Arg Lys Ala Met Gly Glu Asp Leu Phe Trp Ala
    210                 215                 220

Ile Arg Gly Gly Gly Gly Ala Ser Phe Gly Val Ile Val Ser Trp Lys
225                 230                 235                 240

Ile Lys Leu Val Pro Val Pro Ser Thr Val Thr Val Phe Asn Val Glu
                245                 250                 255

Arg Ile Leu Glu Glu Asn Ala Thr Glu Ile Ile Glu Lys Trp Gln Leu
            260                 265                 270

Val Ala Asn Lys Leu Asp Glu Arg Ile Phe Leu Arg Met Asp Leu Ala
        275                 280                 285
```

```
Arg Ala Asn Ser Ser Gln His Gly Lys Leu Ala Leu Gln Ala Asn Phe
    290                 295                 300

Val Ala Met Phe Gln Gly Gly Val Glu Glu Leu Ile Pro Leu Met Gln
305                 310                 315                 320

Lys Asn Phe Pro Glu Leu Gly Leu Lys Arg Lys Asp Cys Thr Glu Thr
                325                 330                 335

Ser Trp Ile Gly Ser Ala Val Phe Thr Asn Gly Ala Leu Ile Gly Ser
            340                 345                 350

Ser Gly His Glu Ala Pro Glu Val Leu Leu Asn Arg Thr Gln Ile Arg
        355                 360                 365

Ser Gly Lys Tyr Lys Gly Lys Ser Asp Tyr Val Arg Lys Pro Ile Pro
    370                 375                 380

Val Asp Gly Leu Arg Gly Leu Trp Arg Trp Leu Asn Asp Asp Lys Val
385                 390                 395                 400

Gln Tyr Ser Gln Leu Gln Phe Ala Pro Tyr Gly Gly Lys Met Asp Asn
                405                 410                 415

Ile Ser Glu Ser Glu Ile Pro Phe Ala His Arg Ser Gly Tyr Ile Phe
            420                 425                 430

His Ile His Tyr Val Val Val Trp Gln Glu Glu Gly Asp Glu Ala Thr
        435                 440                 445

Gln Arg His Val Asn Trp Ile Arg Arg Leu Tyr Lys Tyr Met Glu Pro
    450                 455                 460

Tyr Val Ser Asn Ser Pro Arg Ala Ala Tyr Val Asn Tyr Arg Asp Leu
465                 470                 475                 480

Asp Ile Gly Val Asn Asn Asn Gly Tyr Thr Ser Tyr His Gln Ala Ser
                485                 490                 495

Ile Trp Gly Leu Lys Tyr Phe Ser Asn Asn Phe Lys Arg Leu Ala Thr
            500                 505                 510

Val Lys Thr Lys Val Asp Pro His Asn Phe Phe Arg Asn Glu Gln Ser
        515                 520                 525

Ile Pro Thr Leu Ser Lys Glu
    530                 535


<210> SEQ ID NO 37
<211> LENGTH: 538
<212> TYPE: PRT
<213> ORGANISM: Helianthus annuus
<220> FEATURE:
<221> NAME/KEY: MISC_FEATURE
<223> OTHER INFORMATION: gi|18652400

<400> SEQUENCE: 37

Met Ala Asn Ile Thr Ser Ser Phe Asn Met Gln Thr Ser Ile Leu Thr
1               5                   10                  15

Leu Leu Leu Leu Leu Leu Ser Thr Gln Ser Ser Ala Thr Ser Arg Ser
            20                  25                  30

Ile Thr Asp Arg Phe Ile Gln Cys Leu His Asp Arg Ala Asp Pro Ser
        35                  40                  45

Phe Pro Ile Thr Gly Glu Val Tyr Thr Pro Gly Asn Ser Ser Phe Pro
    50                  55                  60

Thr Val Leu Gln Asn Tyr Ile Arg Asn Leu Arg Phe Asn Glu Thr Thr
65                  70                  75                  80

Thr Pro Lys Pro Phe Leu Ile Ile Thr Ala Glu His Val Ser His Ile
                85                  90                  95

Gln Ala Ala Val Val Cys Gly Lys Gln Asn Arg Leu Leu Leu Lys Thr
            100                 105                 110
```

-continued

```
Arg Ser Gly Gly His Asp Tyr Glu Gly Leu Ser Tyr Leu Thr Asn Thr
        115                 120                 125

Asn Gln Pro Phe Phe Ile Val Asp Met Phe Asn Leu Arg Ser Ile Asn
    130                 135                 140

Val Asp Ile Glu Gln Glu Thr Ala Trp Val Gln Ala Gly Ala Thr Leu
145                 150                 155                 160

Gly Glu Val Tyr Tyr Arg Ile Ala Glu Lys Ser Asn Lys His Gly Phe
                165                 170                 175

Pro Ala Gly Val Cys Pro Thr Val Gly Val Gly Gly His Phe Ser Gly
            180                 185                 190

Gly Gly Tyr Gly Asn Leu Met Arg Lys Tyr Gly Leu Ser Val Asp Asn
        195                 200                 205

Ile Val Asp Ala Gln Ile Ile Asp Val Asn Gly Lys Leu Leu Asp Arg
    210                 215                 220

Lys Ser Met Gly Glu Asp Leu Phe Trp Ala Ile Thr Gly Gly Gly Gly
225                 230                 235                 240

Val Ser Phe Gly Val Val Leu Ala Tyr Lys Ile Lys Leu Val Arg Val
                245                 250                 255

Pro Glu Val Val Thr Val Phe Thr Ile Glu Arg Arg Glu Glu Gln Asn
            260                 265                 270

Leu Ser Thr Ile Ala Glu Arg Trp Val Gln Val Ala Asp Lys Leu Asp
        275                 280                 285

Arg Asp Leu Phe Leu Arg Met Thr Phe Ser Val Ile Asn Asp Thr Asn
    290                 295                 300

Gly Gly Lys Thr Val Arg Ala Ile Phe Pro Thr Leu Tyr Leu Gly Asn
305                 310                 315                 320

Ser Arg Asn Leu Val Thr Leu Leu Asn Lys Asp Phe Pro Glu Leu Gly
                325                 330                 335

Leu Gln Glu Ser Asp Cys Thr Glu Met Ser Trp Val Glu Ser Val Leu
            340                 345                 350

Tyr Tyr Thr Gly Phe Pro Ser Gly Thr Pro Thr Thr Ala Leu Leu Ser
        355                 360                 365

Arg Thr Pro Gln Arg Leu Asn Pro Phe Lys Ile Lys Ser Asp Tyr Val
    370                 375                 380

Gln Asn Pro Ile Ser Lys Arg Gln Phe Glu Phe Ile Phe Glu Arg Met
385                 390                 395                 400

Lys Glu Leu Glu Asn Gln Met Leu Ala Phe Asn Pro Tyr Gly Gly Arg
                405                 410                 415

Met Ser Glu Ile Ser Glu Phe Ala Lys Pro Phe Pro His Arg Ser Gly
            420                 425                 430

Asn Ile Ala Lys Ile Gln Tyr Glu Val Asn Trp Glu Asp Leu Ser Asp
        435                 440                 445

Glu Ala Glu Asn Arg Tyr Leu Asn Phe Thr Arg Leu Met Tyr Asp Tyr
    450                 455                 460

Met Thr Pro Phe Val Ser Lys Asn Pro Arg Glu Ala Phe Leu Asn Tyr
465                 470                 475                 480

Arg Asp Leu Asp Ile Gly Ile Asn Ser His Gly Arg Asn Ala Tyr Thr
                485                 490                 495

Glu Gly Met Val Tyr Gly His Lys Tyr Phe Lys Glu Thr Asn Tyr Lys
            500                 505                 510

Arg Leu Val Ser Val Lys Thr Lys Val Asp Pro Asp Asn Phe Phe Arg
        515                 520                 525
```

```
Asn Glu Gln Ser Ile Pro Thr Leu Ser Ser
    530                 535
```

<210> SEQ ID NO 38
<211> LENGTH: 522
<212> TYPE: PRT
<213> ORGANISM: Cynodon dactylon
<220> FEATURE:
<221> NAME/KEY: MISC_FEATURE
<223> OTHER INFORMATION: gi|41393750

<400> SEQUENCE: 38

```
Met Ala Arg Ser Arg Ala Phe Ala Phe Ala Leu Leu Ile Cys Ala Val
1               5                   10                  15

Ala Ala Ser Cys His Val Ala Leu Ser Ala Pro Pro Pro Tyr Ala Lys
            20                  25                  30

Gln Val Glu Arg Asp Phe Leu Thr Cys Leu Thr Lys Asp Ile Pro Pro
        35                  40                  45

Arg Gln Leu Tyr Ala Lys Ser Ser Pro Ala Tyr Ala Ser Val Trp Ser
    50                  55                  60

Ser Thr Val Arg Asn Ile Lys Phe Leu Ser Asp Lys Thr Val Lys Pro
65                  70                  75                  80

Leu Tyr Ile Ile Thr Pro Thr Asn Ala Ser His Ile Gln Ala Ala Val
                85                  90                  95

Val Cys Gly Arg Arg His Gly Met Arg Ile Arg Val Arg Ser Gly Gly
            100                 105                 110

His Asp Tyr Glu Gly Leu Ser Tyr Arg Ser Glu Lys Pro Glu Pro Phe
        115                 120                 125

Ala Val Val Asp Met Asn Lys Met Arg Ala Val Ser Ile Asp Gly Lys
    130                 135                 140

Ala Ala Thr Ala Trp Val Asp Ser Gly Ala Gln Leu Gly Asp Leu Tyr
145                 150                 155                 160

Tyr Gly Ile Ala Lys Ala Ser Pro Lys Leu Gly Phe Pro Ala Gly Val
                165                 170                 175

Cys Thr Thr Ile Gly Val Gly Gly His Phe Ser Gly Gly Gly Phe Gly
            180                 185                 190

Met Leu Leu Arg Lys Tyr Gly Thr Ala Ala Asp Asn Val Ile Asp Ala
        195                 200                 205

Lys Val Val Asp Ala Gln Gly Arg Leu Leu Asp Arg Lys Ala Met Gly
    210                 215                 220

Glu Asp His Phe Trp Ala Ile Arg Gly Gly Gly Gly Glu Ser Phe Gly
225                 230                 235                 240

Ile Val Ala Ser Trp Gln Val Lys Leu Leu Pro Val Pro Pro Lys Val
                245                 250                 255

Thr Val Phe Gln Val His Lys Gly Ile Lys Glu Gly Ala Ile Asp Leu
            260                 265                 270

Val Thr Lys Trp Gln Thr Val Ala Pro Ala Leu Pro Asp Asp Leu Met
        275                 280                 285

Ile Arg Ile Met Ala Met Gly Gln Gly Ala Met Phe Glu Ala Leu Tyr
    290                 295                 300

Leu Gly Thr Cys Lys Asp Leu Val Leu Leu Met Thr Ala Arg Phe Pro
305                 310                 315                 320

Glu Leu Gly Met Asn Ala Thr His Cys Lys Glu Met Thr Trp Ile Glu
                325                 330                 335

Ser Val Pro Tyr Ile Pro Met Gly Pro Lys Gly Thr Val Arg Asp Leu
            340                 345                 350
```

Leu Asn Arg Thr Ser Asn Ile Lys Ala Phe Gly Lys Tyr Lys Ser Asp
355 360 365

Tyr Val Leu Glu Pro Ile Pro Lys Ser Asp Trp Glu Lys Ile Phe Thr
370 375 380

Trp Leu Val Lys Pro Gly Ala Gly Val Met Ile Met Asp Pro Tyr Gly
385 390 395 400

Gly Gly Ile Ala Ser Val Pro Glu Ser Ala Thr Pro Phe Pro Arg Arg
405 410 415

Ser Gly Val Leu Phe Asn Ile Gln Tyr Val Val Tyr Trp Phe Gly Glu
420 425 430

Gly Ala Ala Ala Leu Pro Thr Gln Trp Thr Arg Asp Ile Tyr Asp Phe
435 440 445

Met Thr Pro Tyr Val Ser Lys Asn Pro Arg Gln Ala Tyr Val Asn Tyr
450 455 460

Arg Asp Leu Asp Leu Gly Val Asn Gln Val Val Gly Asn Val Ser Thr
465 470 475 480

Tyr Ala Ser Gly Lys Val Trp Gly Glu Lys Tyr Phe Lys Gly Asn Phe
485 490 495

Glu Arg Leu Ala Arg Thr Lys Gly Lys Ile Asp Pro Glu Asp Tyr Phe
500 505 510

Arg Asn Glu Gln Ser Ile Pro Pro Leu Leu
515 520

<210> SEQ ID NO 39
<211> LENGTH: 540
<212> TYPE: PRT
<213> ORGANISM: Lactuca sativa
<220> FEATURE:
<221> NAME/KEY: MISC_FEATURE
<223> OTHER INFORMATION: gi|18652398

<400> SEQUENCE: 39

Met Ala Ile Thr Tyr Ser Phe Asn Phe Lys Ser Tyr Ile Phe Pro Leu
1 5 10 15

Leu Leu Val Leu Leu Ser Thr His Ser Ser Ala Thr Ser Thr Ser Ile
20 25 30

Ile Asp Arg Phe Thr Gln Cys Leu Asn Asn Arg Ala Asp Pro Ser Phe
35 40 45

Pro Leu Ser Gly Gln Leu Tyr Thr Pro Asp Asn Ser Ser Phe Pro Ser
50 55 60

Val Leu Gln Ala Tyr Ile Arg Asn Leu Arg Phe Asn Glu Ser Thr Thr
65 70 75 80

Pro Lys Pro Ile Leu Ile Ile Thr Ala Leu His Pro Ser His Ile Gln
85 90 95

Ala Ala Val Val Cys Ala Lys Thr His Arg Leu Leu Met Lys Thr Arg
100 105 110

Ser Gly Gly His Asp Tyr Glu Gly Leu Ser Tyr Val Thr Asn Ser Asn
115 120 125

Gln Pro Phe Phe Val Val Asp Met Phe Asn Leu Arg Ser Ile Asn Val
130 135 140

Ser Ile Glu Asp Glu Thr Ala Trp Val Gln Ala Gly Ala Thr Leu Gly
145 150 155 160

Glu Val Tyr Tyr Arg Ile Ala Glu Lys Ser Asn Ser His Ala Phe Pro
165 170 175

Ala Gly Val Cys Pro Thr Val Gly Val Gly Gly His Phe Ser Gly Gly

```
            180                 185                 190

Gly Tyr Gly Asn Leu Met Gly Lys Tyr Gly Leu Ser Val Asp Asn Ile
        195                 200                 205

Val Asp Ala Gln Leu Ile Asp Val Asn Gly Lys Leu Leu Asn Arg Lys
    210                 215                 220

Ser Met Gly Glu Asp Leu Phe Trp Ala Ile Thr Gly Gly Gly Gly Val
225                 230                 235                 240

Ser Phe Gly Val Val Val Ala Tyr Lys Ile Lys Leu Val Arg Val Pro
                245                 250                 255

Thr Thr Val Thr Val Phe Asn Val Gln Arg Thr Ser Glu Gln Asn Leu
            260                 265                 270

Ser Thr Ile Ala His Arg Trp Ile Gln Val Ala Asp Lys Leu Asp Asn
        275                 280                 285

Asp Leu Phe Leu Arg Met Thr Phe Asn Val Ile Asn Asn Thr Asn Gly
    290                 295                 300

Glu Lys Thr Ile Arg Gly Leu Phe Pro Thr Leu Tyr Leu Gly Asn Ser
305                 310                 315                 320

Thr Ala Leu Val Ala Leu Leu Asn Lys Asp Phe Pro Glu Leu Gly Val
                325                 330                 335

Glu Ile Ser Asp Cys Ile Glu Met Ser Trp Ile Glu Ser Val Leu Phe
            340                 345                 350

Tyr Thr Asn Phe Pro Ile Gly Thr Pro Thr Thr Ala Leu Leu Ser Arg
        355                 360                 365

Thr Pro Gln Arg Leu Asn Pro Phe Lys Ile Lys Ser Asp Tyr Val Lys
    370                 375                 380

Asn Thr Ile Ser Lys Gln Gly Phe Glu Ser Ile Phe Glu Arg Met Lys
385                 390                 395                 400

Glu Leu Glu Asn Gln Met Leu Ala Phe Asn Pro Tyr Gly Gly Arg Met
                405                 410                 415

Ser Glu Ile Ser Glu Phe Ala Lys Pro Phe Pro His Arg Ser Gly Asn
            420                 425                 430

Ile Ala Lys Ile Gln Tyr Glu Val Asn Trp Asp Glu Leu Gly Val Glu
        435                 440                 445

Ala Ala Asn Arg Tyr Leu Asn Phe Thr Arg Val Met Tyr Asp Tyr Met
    450                 455                 460

Thr Pro Phe Val Ser Lys Asn Pro Arg Glu Ala Phe Leu Asn Tyr Arg
465                 470                 475                 480

Asp Leu Asp Ile Gly Val Asn Ser His Gly Lys Asn Ala Tyr Gly Glu
                485                 490                 495

Gly Met Val Tyr Gly His Lys Tyr Phe Lys Glu Thr Asn Tyr Lys Arg
            500                 505                 510

Leu Thr Met Val Lys Thr Arg Val Asp Pro Ser Asn Phe Phe Arg Asn
        515                 520                 525

Glu Gln Ser Ile Pro Thr Leu Ser Ser Ser Trp Lys
    530                 535                 540


<210> SEQ ID NO 40
<211> LENGTH: 545
<212> TYPE: PRT
<213> ORGANISM: Cannabis sativa
<220> FEATURE:
<221> NAME/KEY: MISC_FEATURE
<223> OTHER INFORMATION: gi|26005814

<400> SEQUENCE: 40
```

-continued

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415

Tyr Pro Tyr Gly Gly Ile Met Glu Glu Ile Ser Glu Ser Ala Ile Pro
```

```
            420                 425                 430

Phe Pro His Arg Ala Gly Ile Met Tyr Glu Leu Trp Tyr Thr Ala Ser
        435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Val Asp Pro Asn
        515                 520                 525

Asn Phe Phe Arg Asn Glu Gln Ser Ile Pro Pro Leu Pro Pro His His
    530                 535                 540

His
545


<210> SEQ ID NO 41
<211> LENGTH: 535
<212> TYPE: PRT
<213> ORGANISM: Oryza sativa subsp. japonica
<220> FEATURE:
<221> NAME/KEY: MISC_FEATURE
<223> OTHER INFORMATION: gi|53792953

<400> SEQUENCE: 41

Met Ser Thr Thr Pro Thr Ala Ala Ser Arg Arg Leu Val Leu Ile Leu
1               5                   10                  15

Cys Thr Leu Ala Ile Ser Cys Ser Ser Gly Ile Ala Gly Phe Ala Ala
            20                  25                  30

Gly Asp Asp Asp Ala Phe Ile Arg Cys Leu Ala Ala Ala Ala Val Pro
        35                  40                  45

Pro Arg Leu Val His Thr Pro Gly Ser Ala Ser Tyr Ala Pro Thr Leu
    50                  55                  60

Val Ser Ser Ile Arg Asn Leu Arg Phe Val Thr Pro Gly Thr Pro Arg
65                  70                  75                  80

Pro Leu Ala Ile Val Ala Ala Ala Glu Ala Gly His Ala Gln Ala Ala
                85                  90                  95

Val Arg Cys Gly Arg Arg His Gly Val Arg Val Arg Ala Arg Ser Gly
            100                 105                 110

Gly His Asp Tyr Glu Gly Leu Ser Tyr Leu Ser Leu Asp Arg Arg Glu
        115                 120                 125

Arg Phe Ala Val Leu Asp Leu Ala Ala Leu Arg Asp Val Arg Val Asp
    130                 135                 140

Ala Asp Arg Ala Glu Ala Trp Val Gly Ser Gly Ala Thr Leu Gly Glu
145                 150                 155                 160

Leu Tyr Tyr Ala Val Gly Ala Ala Ser Arg Thr Leu Ala Phe Pro Ala
                165                 170                 175

Gly Val Cys Pro Thr Val Gly Val Gly Gly His Ile Ser Gly Gly Gly
            180                 185                 190

Phe Gly Thr Leu Met Arg Arg Tyr Gly Leu Ala Ala Asp Asn Val Leu
        195                 200                 205

Asp Ala Val Leu Val Asp Ala Asp Gly Arg Leu Leu Asn Arg Thr Thr
    210                 215                 220
```

```
Met Gly Glu Gly Leu Phe Trp Ala Ile Arg Gly Gly Gly Gly Glu Ser
225                 230                 235                 240

Phe Gly Val Val Leu Ser Trp Lys Leu Arg Leu Val Arg Val Pro Glu
                245                 250                 255

Thr Val Thr Val Phe Thr Ile Arg Arg Pro Arg Asn Gln Ser Ala Thr
            260                 265                 270

Asp Leu Ile Thr Lys Trp Gln Glu Ile Ser Pro Ser Leu Pro Arg Asp
        275                 280                 285

Val Ile Leu Arg Val Val Val Gln Ser Gln His Ala Gln Phe Glu Ser
    290                 295                 300

Leu Phe Leu Gly Arg Cys Arg Arg Leu Ala Arg Leu Met Arg Ala Arg
305                 310                 315                 320

Phe Pro Glu Leu Gly Met Thr Gln Ser Asp Cys Glu Glu Ile Thr Trp
                325                 330                 335

Ile Gln Ser Thr Val Tyr Phe Ala Phe Tyr Ser Ser Ser Lys Pro Leu
            340                 345                 350

Glu Leu Leu Leu Asp Arg Gly Thr Glu Pro Asp Arg Tyr Phe Lys Ala
        355                 360                 365

Lys Ser Asp Tyr Val Gln Glu Pro Ile Pro Arg His Ala Trp Glu Ser
    370                 375                 380

Thr Trp Pro Trp Leu Glu Glu His Asp Ala Gly Leu Leu Ile Leu Asp
385                 390                 395                 400

Pro Tyr Gly Gly Glu Met Ala Arg Val Ser Pro Ala Ala Thr Pro Phe
                405                 410                 415

Pro His Arg Lys Gly Asn Leu Tyr Asn Leu Gln Tyr Tyr Ser Phe Trp
            420                 425                 430

Phe Glu His Gly Ala Glu Thr Leu Glu Arg His Leu Ser Trp Val Arg
        435                 440                 445

Gly Leu Tyr Gly Glu Met Glu Pro Tyr Val Ser Lys Asn Pro Arg Thr
    450                 455                 460

Gly Tyr Val Asn Tyr Arg Asp Met Asp Leu Gly Arg Asn Glu Ile Glu
465                 470                 475                 480

Gly Asn Val Thr Ser Tyr Thr Lys Gly Lys Val Trp Gly Glu Lys Tyr
                485                 490                 495

Phe Arg Gly Asn Phe Glu Arg Leu Ala Ala Val Lys Ala Met Val Asp
            500                 505                 510

Pro Asp Asp Phe Phe Arg Asn Glu Gln Ser Ile Pro Pro Leu Pro Ala
        515                 520                 525

Ala Lys Gly Trp Ser Ser Ile
    530                 535
```

<210> SEQ ID NO 42
<211> LENGTH: 542
<212> TYPE: PRT
<213> ORGANISM: Helianthus annuus
<220> FEATURE:
<221> NAME/KEY: MISC_FEATURE
<223> OTHER INFORMATION: gi|20563190

<400> SEQUENCE: 42

```
Met Asn Asn Ser Arg Ser Val Phe Leu Leu Val Leu Ala Leu Ser Phe
1               5                   10                  15

Cys Val Ser Phe Gly Ala Leu Ser Ser Ile Phe Asp Val Thr Ser Thr
            20                  25                  30

Ser Glu Asp Phe Ile Thr Cys Leu Gln Ser Asn Ser Asn Asn Val Thr
        35                  40                  45
```

-continued

```
Thr Ile Ser Gln Leu Val Phe Thr Pro Ala Asn Thr Ser Tyr Ile Pro
    50                  55                  60

Ile Trp Gln Ala Ala Ala Asp Pro Ile Arg Phe Asn Lys Ser Tyr Ile
65                  70                  75                  80

Pro Lys Pro Ser Val Ile Val Thr Pro Thr Asp Glu Thr Gln Ile Gln
                85                  90                  95

Thr Ala Leu Leu Cys Ala Lys Lys His Gly Tyr Glu Phe Arg Ile Arg
            100                 105                 110

Asp Gly Gly His Asp Phe Glu Gly Asn Ser Tyr Thr Ala Asn Ala Pro
        115                 120                 125

Phe Val Met Leu Asp Leu Val Asn Met Arg Ala Ile Glu Ile Asn Val
    130                 135                 140

Glu Asn Arg Thr Ala Leu Val Gln Gly Gly Ala Leu Leu Gly Glu Leu
145                 150                 155                 160

Tyr Tyr Thr Ile Ser Gln Lys Thr Asp Thr Leu Tyr Phe Pro Ala Gly
                165                 170                 175

Ile Trp Ala Gly Val Gly Val Ser Gly Phe Leu Ser Gly Gly Gly Tyr
            180                 185                 190

Gly Asn Leu Leu Arg Lys Tyr Gly Leu Gly Ala Asp Asn Val Leu Asp
        195                 200                 205

Ile Arg Phe Met Asp Val Asn Gly Asn Ile Leu Asp Arg Lys Ser Met
    210                 215                 220

Gly Glu Asp Leu Phe Trp Ala Leu Arg Gly Gly Gly Ala Ser Ser Phe
225                 230                 235                 240

Gly Ile Val Leu Gln Trp Lys Leu Asn Leu Val Pro Val Pro Glu Arg
                245                 250                 255

Val Thr Leu Phe Ser Val Ser Tyr Thr Leu Glu Gln Gly Ala Thr Asp
            260                 265                 270

Ile Phe His Lys Tyr Gln Tyr Val Leu Pro Lys Phe Asp Arg Asp Leu
        275                 280                 285

Leu Ile Arg Val Gln Leu Asn Thr Glu Tyr Ile Gly Asn Thr Thr Gln
    290                 295                 300

Lys Thr Val Arg Ile Leu Phe His Gly Ile Tyr Gln Gly Asn Ile Asp
305                 310                 315                 320

Thr Leu Leu Pro Leu Leu Asn Gln Ser Phe Pro Glu Leu Asn Val Thr
                325                 330                 335

Arg Glu Val Cys Gln Glu Val Arg Met Val Gln Thr Thr Leu Glu Phe
            340                 345                 350

Gly Gly Phe Asn Ile Ser Thr Pro Thr Ser Val Leu Ala Asn Arg Ser
        355                 360                 365

Ala Ile Pro Lys Leu Ser Phe Lys Gly Lys Ser Asp Tyr Val Arg Thr
    370                 375                 380

Pro Ile Pro Arg Ser Gly Leu Arg Lys Leu Trp Arg Lys Met Phe Glu
385                 390                 395                 400

Asn Asp Asn Ser Gln Thr Leu Phe Met Tyr Thr Phe Gly Gly Lys Met
                405                 410                 415

Glu Glu Tyr Ser Asp Thr Ala Ile Pro Tyr Pro His Arg Ala Gly Val
            420                 425                 430

Leu Tyr Gln Val Phe Lys Arg Val Asp Phe Val Asp Gln Pro Ser Asp
        435                 440                 445

Lys Thr Leu Ile Ser Leu Arg Arg Leu Ala Trp Leu Arg Ser Phe Asp
    450                 455                 460
```

-continued

```
Lys Thr Leu Glu Pro Tyr Val Thr Ser Asn Pro Arg Glu Ala Tyr Met
465                 470                 475                 480

Asn Tyr Asn Asp Leu Asp Leu Gly Phe Asp Ser Ala Ala Tyr Glu Glu
                485                 490                 495

Ala Ser Glu Trp Gly Glu Arg Tyr Trp Lys Arg Glu Asn Phe Lys Lys
            500                 505                 510

Leu Ile Arg Ile Lys Ala Lys Val Asp Pro Glu Asn Phe Phe Arg His
        515                 520                 525

Pro Gln Ser Ile Pro Val Phe Ser Arg Pro Leu Ser Asp Met
    530                 535                 540


<210> SEQ ID NO 43
<211> LENGTH: 1174
<212> TYPE: DNA
<213> ORGANISM: Arabidopsis thaliana
<220> FEATURE:
<221> NAME/KEY: MISC_FEATURE
<223> OTHER INFORMATION: cDNA12723147_L23

<400> SEQUENCE: 43

agtggctact gagtaaagct ttgggccacc gagagaaacc attttctgag agcacacttt     60

cgttgacttc tctttaacca atgtctttaa ccacagtccc tacgctcgcc atcagatccg    120

gaccatccgg tcatcactcg atgccggttc ttggttttgg aaccgccgct tctccgctac    180

cggaaccaac gatgctgaaa gagacggtga ttgaggctat taagcttggt tatcgccatt    240

tcgacacctc tccaaggtac caaacggagg agccgatcgg cgaagcttta gcggaggcgg    300

tttcactcgg cttagttcga tctcgatctg aattctttgt cactaccaaa ctttggtgtg    360

ctgatgctca tggtggtctc gtcgtaccgg cgatcaaacg gagtttgaaa aaccttaaac    420

tggactatct tgatctttat ataattcatt ggccggttag ctcgaaacct ggtaaataca    480

agtttcctat tgatgaagat gattttatgc caatggattt cgaagtagtg tggtctgaaa    540

tggaggagtg tcagagactt gggctcgcaa aatgcatagg agtaagcaat ttttcatgta    600

agaagcttca acacatactc tctatcgcga caatcccgcc tagcgtcaat caagttgaga    660

tgagtccaat atggcaacaa agaaagctaa gggagctttg tagatcgaac gacattgttg    720

tcacagcgta ctcggtgttg ggatctagag gagctttttg gggaactccc aaaattatgg    780

aatctgatgt tctcaaagaa atagcagaag caaaggaaaa aacagtggcc caggtgagta    840

tgagatgggc ttatgaacaa ggagtgagca tggtagtgaa gagctttacc aaagagagat    900

tagaagagaa tctaaagata tttgattggt ctttgacaga ggatgagaca cagagaattt    960

caactgagat tcctcagttc agaaacgtcc acggagaggt ttatacctct aagaaaggtc   1020

ccatcaaatc tgtcgccgag atgtgggacg gggagatctg atcactttgt gtgaaaatag   1080

cctattgaaa acggcacaat tatcattcgt cacaatgatt ttcttgtcat tctctctaat   1140

aatgaaataa tgaataatga ataaggacta tctc                               1174


<210> SEQ ID NO 44
<211> LENGTH: 326
<212> TYPE: PRT
<213> ORGANISM: Arabidopsis thaliana
<220> FEATURE:
<221> NAME/KEY: MISC_FEATURE
<223> OTHER INFORMATION: peptide_cDNA12723147_L23

<400> SEQUENCE: 44

Met Ser Leu Thr Thr Val Pro Thr Leu Ala Ile Arg Ser Gly Pro Ser
1               5                   10                  15
```

```
Gly His His Ser Met Pro Val Leu Gly Phe Gly Thr Ala Ala Ser Pro
            20                  25                  30

Leu Pro Glu Pro Thr Met Leu Lys Glu Thr Val Ile Glu Ala Ile Lys
        35                  40                  45

Leu Gly Tyr Arg His Phe Asp Thr Ser Pro Arg Tyr Gln Thr Glu Glu
    50                  55                  60

Pro Ile Gly Glu Ala Leu Ala Glu Ala Val Ser Leu Gly Leu Val Arg
65                  70                  75                  80

Ser Arg Ser Glu Phe Phe Val Thr Thr Lys Leu Trp Cys Ala Asp Ala
                85                  90                  95

His Gly Gly Leu Val Val Pro Ala Ile Lys Arg Ser Leu Lys Asn Leu
            100                 105                 110

Lys Leu Asp Tyr Leu Asp Leu Tyr Ile Ile His Trp Pro Val Ser Ser
        115                 120                 125

Lys Pro Gly Lys Tyr Lys Phe Pro Ile Asp Glu Asp Asp Phe Met Pro
    130                 135                 140

Met Asp Phe Glu Val Val Trp Ser Glu Met Glu Glu Cys Gln Arg Leu
145                 150                 155                 160

Gly Leu Ala Lys Cys Ile Gly Val Ser Asn Phe Ser Cys Lys Lys Leu
                165                 170                 175

Gln His Ile Leu Ser Ile Ala Thr Ile Pro Pro Ser Val Asn Gln Val
            180                 185                 190

Glu Met Ser Pro Ile Trp Gln Gln Arg Lys Leu Arg Glu Leu Cys Arg
        195                 200                 205

Ser Asn Asp Ile Val Val Thr Ala Tyr Ser Val Leu Gly Ser Arg Gly
    210                 215                 220

Ala Phe Trp Gly Thr Pro Lys Ile Met Glu Ser Asp Val Leu Lys Glu
225                 230                 235                 240

Ile Ala Glu Ala Lys Glu Lys Thr Val Ala Gln Val Ser Met Arg Trp
                245                 250                 255

Ala Tyr Glu Gln Gly Val Ser Met Val Val Lys Ser Phe Thr Lys Glu
            260                 265                 270

Arg Leu Glu Glu Asn Leu Lys Ile Phe Asp Trp Ser Leu Thr Glu Asp
        275                 280                 285

Glu Thr Gln Arg Ile Ser Thr Glu Ile Pro Gln Phe Arg Asn Val His
    290                 295                 300

Gly Glu Val Tyr Thr Ser Lys Lys Gly Pro Ile Lys Ser Val Ala Glu
305                 310                 315                 320

Met Trp Asp Gly Glu Ile
                325


<210> SEQ ID NO 45
<211> LENGTH: 321
<212> TYPE: PRT
<213> ORGANISM: Papaver somniferum
<220> FEATURE:
<221> NAME/KEY: MISC_FEATURE
<223> OTHER INFORMATION: gi|6478216

<400> SEQUENCE: 45

Met Glu Ile Gly Gly Val Pro Val Val Thr Leu Ser Ser Gly Arg Gly
1               5                   10                  15

Met Pro Ile Leu Gly Met Gly Thr Ala Glu Asn Asn Leu Gln Gly Ser
            20                  25                  30

Glu Arg Val Lys Leu Ala Ile Leu Lys Ala Ile Glu Val Gly Tyr Arg
```

```
        35                  40                  45

His Phe Asp Thr Ala Phe Val Tyr Gln Thr Glu Gly Ser Leu Gly Glu
    50                  55                  60

Ala Val Ala Glu Ala Leu Gln Asn Gly Leu Ile Lys Ser Arg Asp Glu
65                  70                  75                  80

Leu Phe Ile Thr Ser Lys Leu Trp Cys Ala Asp Ala Tyr Pro Asp His
                85                  90                  95

Val Leu Pro Ala Leu Gln Asn Ser Leu Arg Asn Leu Lys Leu Glu Tyr
            100                 105                 110

Leu Asp Leu Tyr Leu Ile His Trp Pro Val Ser Leu Lys Pro Gly Lys
        115                 120                 125

Phe Val His Pro Ile Pro Lys Asp Glu Ile Phe Pro Ile Asp Tyr Lys
    130                 135                 140

Ser Val Trp Ala Ala Met Glu Lys Cys Gln Met Leu Gly Leu Thr Lys
145                 150                 155                 160

Ser Ile Gly Val Ser Asn Phe Ser Cys Lys Lys Leu His Tyr Leu Met
                165                 170                 175

Ala Thr Ala Asn Ile Pro Pro Ala Val Asn Gln Val Glu Met Asn Pro
            180                 185                 190

Ile Trp Gln Gln Gln Lys Leu Arg Asp Tyr Cys Lys Thr Asn Asn Ile
        195                 200                 205

Met Val Thr Ala Tyr Ser Pro Leu Gly Ala Lys Gly Thr Met Trp Gly
    210                 215                 220

Ser Ser Gly Val Met Asp Ser Glu Val Leu Asn Gln Ile Ser Gln Val
225                 230                 235                 240

Arg Gly Lys Ser Val Ala Gln Val Ser Leu Arg Trp Val Tyr Glu Gln
                245                 250                 255

Gly Ala Ser Leu Leu Val Lys Ser Phe Asn Glu Glu Arg Met Lys Glu
            260                 265                 270

Asn Leu Lys Ile Phe Asp Trp Glu Leu Ser Pro Glu Asp Leu Lys Asn
        275                 280                 285

Ile Ser Glu Leu Pro Gln Arg Arg Val Ser Thr Gly Asp Pro Phe Val
    290                 295                 300

Ser Ile Asn Gly Pro Phe Lys Ser Val Glu Glu Leu Trp Asp Asp Glu
305                 310                 315                 320

Val


<210> SEQ ID NO 46
<211> LENGTH: 327
<212> TYPE: PRT
<213> ORGANISM: Arabidopsis thaliana
<220> FEATURE:
<221> NAME/KEY: MISC_FEATURE
<223> OTHER INFORMATION: gi|5080825

<400> SEQUENCE: 46

Met Val Ala Ser Gly His Glu Val Val Thr Leu Thr Phe Pro Ile Gly
1               5                   10                  15

Ser Val His His Leu Met Pro Val Leu Ala Leu Gly Thr Ala Ala Ser
            20                  25                  30

Pro Pro Pro Glu Pro Ile Val Leu Lys Arg Thr Val Leu Glu Ala Ile
        35                  40                  45

Lys Leu Gly Tyr Arg His Phe Asp Thr Ser Pro Arg Tyr Gln Thr Glu
    50                  55                  60

Glu Pro Leu Gly Glu Ala Leu Ala Glu Ala Val Ser Leu Gly Leu Ile
```

```
65                  70                  75                  80

Gln Ser Arg Ser Glu Leu Phe Val Thr Ser Lys Leu Trp Cys Ala Asp
                85                  90                  95

Ala His Gly Gly Leu Val Val Pro Ala Ile Gln Arg Ser Leu Glu Thr
            100                 105                 110

Leu Lys Leu Asp Tyr Leu Asp Leu Tyr Leu Ile His Trp Pro Val Ser
        115                 120                 125

Ser Lys Pro Gly Lys Tyr Lys Phe Pro Ile Glu Glu Asp Asp Phe Leu
    130                 135                 140

Pro Met Asp Tyr Glu Thr Val Trp Ser Glu Met Glu Glu Cys Gln Arg
145                 150                 155                 160

Leu Gly Val Ala Lys Cys Ile Gly Val Ser Asn Phe Ser Cys Lys Lys
                165                 170                 175

Leu Gln His Ile Leu Ser Ile Ala Lys Ile Pro Pro Ser Val Asn Gln
            180                 185                 190

Val Glu Met Ser Pro Val Trp Gln Gln Arg Lys Leu Arg Glu Leu Cys
        195                 200                 205

Lys Ser Lys Gly Ile Val Val Thr Ala Tyr Ser Val Leu Gly Ser Arg
    210                 215                 220

Gly Ala Phe Trp Gly Thr His Lys Ile Met Glu Ser Asp Val Leu Lys
225                 230                 235                 240

Glu Ile Ala Glu Ala Lys Gly Lys Thr Val Ala Gln Val Ser Met Arg
                245                 250                 255

Trp Ala Tyr Glu Glu Gly Val Ser Met Val Val Lys Ser Phe Arg Lys
            260                 265                 270

Asp Arg Leu Glu Glu Asn Leu Lys Ile Phe Asp Trp Ser Leu Thr Glu
        275                 280                 285

Glu Glu Lys Gln Arg Ile Ser Thr Glu Ile Ser Gln Ser Arg Ile Val
    290                 295                 300

Asp Gly Glu Val Tyr Ile Ser Glu Lys Gly Pro Ile Lys Ser Val Thr
305                 310                 315                 320

Glu Met Trp Asp Gly Glu Ile
                325


<210> SEQ ID NO 47
<211> LENGTH: 320
<212> TYPE: PRT
<213> ORGANISM: Arabidopsis thaliana
<220> FEATURE:
<221> NAME/KEY: MISC_FEATURE
<223> OTHER INFORMATION: gi|15218958

<400> SEQUENCE: 47

Met Ser Ala Leu Thr Phe Pro Ile Gly Ser Val His His Leu Met Pro
1               5                   10                  15

Val Leu Ala Leu Gly Thr Ala Ala Ser Pro Pro Pro Glu Pro Ile Val
            20                  25                  30

Leu Lys Arg Thr Val Leu Glu Ala Ile Lys Leu Gly Tyr Arg His Phe
        35                  40                  45

Asp Thr Ser Pro Arg Tyr Gln Thr Glu Glu Pro Leu Gly Glu Ala Leu
    50                  55                  60

Ala Glu Ala Val Ser Leu Gly Leu Ile Gln Ser Arg Ser Glu Leu Phe
65                  70                  75                  80

Val Thr Ser Lys Leu Trp Cys Ala Asp Ala His Gly Gly Leu Val Val
                85                  90                  95
```

-continued

Pro Ala Ile Gln Arg Ser Leu Glu Thr Leu Lys Leu Asp Tyr Leu Asp
100 105 110

Leu Tyr Leu Ile His Trp Pro Val Ser Ser Lys Pro Gly Lys Tyr Lys
115 120 125

Phe Pro Ile Glu Glu Asp Asp Phe Leu Pro Met Asp Tyr Glu Thr Val
130 135 140

Trp Ser Glu Met Glu Glu Cys Gln Arg Leu Gly Val Ala Lys Cys Ile
145 150 155 160

Gly Val Ser Asn Phe Ser Cys Lys Lys Leu Gln His Ile Leu Ser Ile
165 170 175

Ala Lys Ile Pro Pro Ser Val Asn Gln Val Glu Met Ser Pro Val Trp
180 185 190

Gln Gln Arg Lys Leu Arg Glu Leu Cys Lys Ser Lys Gly Ile Val Val
195 200 205

Thr Ala Tyr Ser Val Leu Gly Ser Arg Gly Ala Phe Trp Gly Thr His
210 215 220

Lys Ile Met Glu Ser Asp Val Leu Lys Glu Ile Ala Glu Ala Lys Gly
225 230 235 240

Lys Thr Val Ala Gln Val Ser Met Arg Trp Ala Tyr Glu Glu Gly Val
245 250 255

Ser Met Val Val Lys Ser Phe Arg Lys Asp Arg Leu Glu Glu Asn Leu
260 265 270

Lys Ile Phe Asp Trp Ser Leu Thr Glu Glu Glu Lys Gln Arg Ile Ser
275 280 285

Thr Glu Ile Ser Gln Ser Arg Ile Val Asp Gly Glu Val Tyr Ile Ser
290 295 300

Glu Lys Gly Pro Ile Lys Ser Val Thr Glu Met Trp Asp Gly Glu Ile
305 310 315 320

<210> SEQ ID NO 48
<211> LENGTH: 323
<212> TYPE: PRT
<213> ORGANISM: Fragaria x ananassa
<220> FEATURE:
<221> NAME/KEY: MISC_FEATURE
<223> OTHER INFORMATION: gi|53988164

<400> SEQUENCE: 48

Met Thr Ala Thr Gln Ile Pro Glu Val Val Leu Glu Ser Ser Asn Gly
1 5 10 15

Arg Arg Thr Met Pro Val Leu Gly Phe Gly Thr Ala Ser Asn Asn Leu
20 25 30

Gln Pro Glu Val Leu Ile Glu Ala Val Leu Glu Ala Ile Lys Leu Gly
35 40 45

Tyr Arg His Phe Asp Thr Ala Ser Ile Tyr Gly Ser Glu Gln Thr Leu
50 55 60

Gly Val Ala Ile Ala Gln Ala Leu Lys Leu Gly Leu Val Ala Ser Arg
65 70 75 80

Asp Glu Leu Phe Ile Thr Ser Lys Leu Trp Pro Asn Asp Gly His Pro
85 90 95

Asn Leu Val Ile Pro Ala Leu Lys Lys Ser Leu Gln Asn Leu Glu Leu
100 105 110

Glu Tyr Leu Asp Leu Tyr Leu Ile His Trp Pro Ile Ser Ala Lys Pro
115 120 125

Gly Lys Leu Ser His Ala Leu Glu Glu Lys Asp Gln Met Pro Met Asp
130 135 140

-continued

Phe Lys Gly Val Trp Ala Asp Met Glu Glu Ala Gln Arg Leu Gly Leu
145 150 155 160

Thr Lys Ser Ile Gly Ile Ser Asn Phe Ser Thr Lys Lys Thr Gln Asn
165 170 175

Leu Leu Ser Phe Ala Thr Ile Pro Pro Ser Val Asn Gln Val Glu Met
180 185 190

Ser Pro Phe Trp Gln Gln Lys Lys Leu Arg Asp Phe Cys Lys Ala Ser
195 200 205

Gly Ile Val Val Thr Ala Phe Ser Pro Leu Gly Ala Ile Gly Thr Ser
210 215 220

Trp Gly Thr Asn His Val Leu Glu Ser Lys Val Leu Asn Glu Ile Ala
225 230 235 240

Glu Ala His Gly Lys Thr Val Ala Gln Val Cys Ile Arg Trp Val Tyr
245 250 255

Gln Val Gly Ala Thr Leu Ala Val Lys Ser Tyr Asn Lys Glu Arg Leu
260 265 270

Lys Gln Asn Val Gln Val Phe Asp Trp Glu Leu Thr Glu Glu Asp Leu
275 280 285

Glu Lys Ile Asn Gln Ile Pro Gln Arg Lys Met Met Pro Arg Glu Glu
290 295 300

Leu Val Thr Ala Thr Gly Pro Tyr Lys Ser Leu Asp Asp Leu Trp Asp
305 310 315 320

Gly Glu Tyr

<210> SEQ ID NO 49
<211> LENGTH: 319
<212> TYPE: PRT
<213> ORGANISM: Fragaria x ananassa
<220> FEATURE:
<221> NAME/KEY: MISC_FEATURE
<223> OTHER INFORMATION: gi|2792295

<400> SEQUENCE: 49

Met Ala Lys Val Pro Ser Val Thr Leu Ser Ser Cys Gly Asp Asp Ile
1 5 10 15

Gln Thr Met Pro Val Ile Gly Met Gly Thr Ser Ser Tyr Pro Arg Ala
20 25 30

Asp Pro Glu Thr Ala Lys Ala Ala Ile Leu Glu Ala Ile Arg Ala Gly
35 40 45

Tyr Arg His Phe Asp Thr Ala Ala Ala Tyr Gly Ser Glu Lys Asp Leu
50 55 60

Gly Glu Ala Ile Ala Glu Ala Leu Arg Leu Gln Leu Ile Lys Ser Arg
65 70 75 80

Asp Glu Leu Phe Ile Thr Thr Lys Leu Trp Ala Ser Phe Ala Glu Lys
85 90 95

Asp Leu Val Leu Pro Ser Ile Lys Ala Ser Leu Ser Asn Leu Gln Val
100 105 110

Glu Tyr Ile Asp Met Tyr Ile Ile His Trp Pro Phe Lys Leu Gly Lys
115 120 125

Glu Val Arg Thr Met Pro Val Glu Arg Asp Leu Val Gln Pro Leu Asp
130 135 140

Ile Lys Ser Val Trp Glu Ala Met Glu Glu Cys Lys Lys Leu Gly Leu
145 150 155 160

Ala Arg Gly Ile Gly Val Ser Asn Phe Thr Ser Ser Met Leu Glu Glu
165 170 175

```
Leu Leu Ser Phe Ala Glu Ile Pro Pro Ala Val Asn Gln Leu Glu Met
            180                 185                 190

Asn Pro Ala Trp Gln Leu Lys Lys Leu Arg Asp Phe Cys Lys Ala Lys
        195                 200                 205

Gly Ile His Val Thr Ala Tyr Ser Pro Leu Gly Ala Ala Arg Thr Lys
    210                 215                 220

Trp Gly Asp Asp Arg Val Leu Gly Ser Asp Ile Ile Glu Glu Ile Ala
225                 230                 235                 240

Gln Ala Lys Gly Lys Ser Thr Ala Gln Ile Ser Leu Arg Trp Val Tyr
                245                 250                 255

Glu Gln Gly Val Ser Ile Val Thr Lys Ser Tyr Asn Lys Glu Arg Met
            260                 265                 270

Arg Gln Asn Leu Asp Ile Phe Asp Phe Cys Leu Thr Glu Glu Glu Leu
        275                 280                 285

Glu Lys Met Ser His Leu Pro Gln Arg Lys Gly Val Thr Phe Ala Ser
    290                 295                 300

Ile Leu Gly Pro His Asp Ile Val Leu Glu Val Asp Glu Glu Leu
305                 310                 315


<210> SEQ ID NO 50
<211> LENGTH: 319
<212> TYPE: PRT
<213> ORGANISM: Fragaria x ananassa
<220> FEATURE:
<221> NAME/KEY: MISC_FEATURE
<223> OTHER INFORMATION: gi|50380153

<400> SEQUENCE: 50

Met Ala Lys Val Pro Ser Val Thr Leu Ser Ser Cys Gly Asp Asp Ile
1               5                   10                  15

Gln Thr Met Pro Val Ile Gly Met Gly Thr Ser Ser Tyr Pro Arg Ala
            20                  25                  30

Asp Pro Glu Thr Ala Lys Ala Ala Ile Leu Glu Ala Ile Arg Ala Gly
        35                  40                  45

Tyr Arg His Phe Asp Thr Ala Ala Ala Tyr Gly Ser Glu Lys Asp Leu
    50                  55                  60

Gly Glu Ala Ile Ala Glu Ala Leu Arg Leu Gln Leu Ile Lys Ser Arg
65                  70                  75                  80

Asp Glu Leu Phe Ile Thr Thr Lys Leu Trp Ala Ser Phe Ala Glu Lys
                85                  90                  95

Asp Leu Val Leu Pro Ser Ile Lys Ala Ser Leu Ser Asn Leu Gln Val
            100                 105                 110

Glu Tyr Ile Asp Met Tyr Ile Ile His Trp Pro Phe Lys Leu Gly Lys
        115                 120                 125

Glu Val Arg Thr Met Pro Val Glu Arg Asp Leu Val Gln Pro Leu Asp
    130                 135                 140

Ile Lys Ser Val Trp Glu Ala Met Glu Glu Cys Lys Lys Leu Gly Leu
145                 150                 155                 160

Ala Arg Gly Ile Gly Val Ser Asn Phe Thr Ser Ser Met Leu Glu Glu
                165                 170                 175

Leu Leu Ser Phe Ala Glu Ile Pro Pro Ala Val Asn Gln Leu Glu Met
            180                 185                 190

Asn Pro Ala Trp Gln Leu Lys Lys Leu Arg Asp Phe Cys Lys Ala Lys
        195                 200                 205

Gly Ile His Val Thr Ala Tyr Ser Pro Leu Gly Ala Ala Arg Thr Lys
```

-continued

```
    210                 215                 220

Trp Gly Asp Asp Arg Val Leu Gly Ser Asp Ile Ile Glu Glu Ile Ala
225                 230                 235                 240

Gln Ala Lys Gly Lys Ser Thr Ala Gln Ile Ser Leu Arg Trp Val Tyr
                245                 250                 255

Glu Gln Gly Val Ser Ile Val Thr Lys Ser Tyr Asn Lys Glu Arg Met
            260                 265                 270

Arg Gln Asn Leu Asp Ile Phe Asp Phe Cys Leu Thr Glu Glu Glu Leu
        275                 280                 285

Glu Lys Met Ser His Leu Pro Gln Arg Lys Gly Val Thr Phe Ala Ser
    290                 295                 300

Ile Leu Gly Pro His Asp Ile Val Leu Lys Val Asp Glu Glu Leu
305                 310                 315


<210> SEQ ID NO 51
<211> LENGTH: 314
<212> TYPE: PRT
<213> ORGANISM: Glycine max
<220> FEATURE:
<221> NAME/KEY: MISC_FEATURE
<223> OTHER INFORMATION: CeresClone:1074583

<400> SEQUENCE: 51

Met Gly Ala Gly Asp Lys Thr Ala Ala Gly Met Pro Arg Ile Gly Met
1               5                   10                  15

Gly Thr Ala Val Gln Gly Pro Lys Pro Asp Pro Ile Arg Arg Ala Val
            20                  25                  30

Leu Arg Ala Ile Glu Val Gly Tyr Arg His Phe Asp Thr Ala Ala His
        35                  40                  45

Tyr Glu Thr Glu Ala Pro Ile Gly Glu Ala Ala Ala Glu Ala Val Arg
    50                  55                  60

Ser Gly Ala Val Ala Ser Arg Asp Asp Leu Phe Ile Thr Ser Lys Leu
65                  70                  75                  80

Trp Cys Ser Asp Ala His Arg Asp Arg Val Val Pro Ala Leu Arg Gln
                85                  90                  95

Thr Leu Arg Asn Leu Gln Met Glu Tyr Val Asp Leu Tyr Leu Val His
            100                 105                 110

Trp Pro Val Ser Met Lys Pro Gly Arg Phe Lys Ala Pro Phe Thr Ala
        115                 120                 125

Glu Asp Phe Val Pro Phe Asp Met Arg Ala Val Trp Glu Ala Met Glu
    130                 135                 140

Glu Cys His Arg Leu Gly Leu Ala Lys Ala Ile Gly Val Ala Asn Phe
145                 150                 155                 160

Ser Cys Lys Lys Leu Glu Thr Leu Leu Ser Phe Ala Thr Ile Pro Pro
                165                 170                 175

Thr Val Asn Gln Val Glu Val Asn Pro Val Trp Gln Gln Arg Lys Leu
            180                 185                 190

Arg Glu Phe Cys Arg Gly Lys Gly Ile Gln Leu Cys Ala Tyr Ser Pro
        195                 200                 205

Leu Gly Ala Lys Gly Thr His Trp Gly Ser Asp Ala Val Met Asp Ala
    210                 215                 220

Gly Val Leu Gln Glu Ile Ala Ala Ser Arg Gly Lys Ser Val Ala Gln
225                 230                 235                 240

Val Cys Leu Arg Trp Val Tyr Glu Gln Gly Asp Cys Leu Ile Val Lys
                245                 250                 255
```

-continued

```
Ser Phe Asp Glu Ala Arg Met Arg Glu Asn Leu Asp Val Asp Gly Trp
            260                 265                 270

Glu Leu Thr Glu Glu Glu His Arg Arg Ile Ala Glu Ile Pro Gln Arg
        275                 280                 285

Lys Ile Asn Leu Gly Lys Arg Tyr Val Ser Glu His Gly Pro Tyr Lys
    290                 295                 300

Ser Leu Glu Glu Leu Trp Asp Gly Glu Ile
305                 310


<210> SEQ ID NO 52
<211> LENGTH: 315
<212> TYPE: PRT
<213> ORGANISM: Glycine max
<220> FEATURE:
<221> NAME/KEY: MISC_FEATURE
<223> OTHER INFORMATION: gi|18728

<400> SEQUENCE: 52

Met Ala Ala Ala Ile Glu Ile Pro Thr Ile Val Phe Pro Asn Ser Ser
1               5                   10                  15

Ala Gln Gln Arg Met Pro Val Val Gly Met Gly Ser Ala Pro Asp Phe
            20                  25                  30

Thr Cys Lys Lys Asp Thr Lys Glu Ala Ile Ile Glu Ala Val Lys Gln
        35                  40                  45

Gly Tyr Arg His Phe Asp Thr Ala Ala Ala Tyr Gly Ser Glu Gln Ala
    50                  55                  60

Leu Gly Glu Ala Leu Lys Glu Ala Ile His Leu Gly Leu Val Ser Arg
65                  70                  75                  80

Gln Asp Leu Phe Val Thr Ser Lys Leu Trp Val Thr Glu Asn His Pro
                85                  90                  95

His Leu Val Leu Pro Ala Leu Arg Lys Ser Leu Lys Thr Leu Gln Leu
            100                 105                 110

Glu Tyr Leu Asp Leu Tyr Leu Ile His Trp Pro Leu Ser Ser Gln Pro
        115                 120                 125

Gly Lys Phe Ser Phe Pro Ile Glu Val Glu Asp Leu Leu Pro Phe Asp
    130                 135                 140

Val Lys Gly Val Trp Glu Ser Met Glu Glu Cys Gln Lys Leu Gly Leu
145                 150                 155                 160

Thr Lys Ala Ile Gly Val Ser Asn Phe Ser Val Lys Lys Leu Gln Asn
                165                 170                 175

Leu Leu Ser Val Ala Thr Ile Arg Pro Val Val Asp Gln Val Glu Met
            180                 185                 190

Asn Leu Ala Trp Gln Gln Lys Lys Leu Arg Glu Phe Cys Lys Glu Asn
        195                 200                 205

Gly Ile Ile Val Thr Ala Phe Ser Pro Leu Arg Lys Gly Ala Ser Arg
    210                 215                 220

Gly Pro Asn Glu Val Met Glu Asn Asp Val Leu Lys Glu Ile Ala Glu
225                 230                 235                 240

Ala His Gly Lys Ser Ile Ala Gln Val Ser Leu Arg Trp Leu Tyr Glu
                245                 250                 255

Gln Gly Val Thr Phe Val Pro Lys Ser Tyr Asp Lys Glu Arg Met Asn
            260                 265                 270

Gln Asn Leu His Ile Phe Asp Trp Ala Leu Thr Glu Gln Asp His His
        275                 280                 285

Lys Ile Ser Gln Ile Ser Gln Ser Arg Leu Ile Ser Gly Pro Thr Lys
    290                 295                 300
```

Pro Gln Leu Ala Asp Leu Trp Asp Asp Gln Ile
305 310 315

<210> SEQ ID NO 53
<211> LENGTH: 320
<212> TYPE: PRT
<213> ORGANISM: Glycine max
<220> FEATURE:
<221> NAME/KEY: MISC_FEATURE
<223> OTHER INFORMATION: CeresClone:473625

<400> SEQUENCE: 53

Met Glu Ala Lys Lys Ile Pro Glu Val Ile Leu Asn Ser Gly Lys Lys
1 5 10 15

Met Pro Val Ile Gly Leu Gly Thr Ala Ser Ile Pro Leu Pro Ser His
20 25 30

Glu Ala Leu Thr Ser Ile Leu Ile Asp Ala Phe Glu Val Gly Tyr Arg
35 40 45

His Phe Asp Thr Ala Ser Leu Tyr Glu Ser Glu Glu Ser Leu Gly Lys
50 55 60

Ala Val Ala Lys Ala Leu Glu Leu Gly Leu Ile Asn Ser Arg Glu Glu
65 70 75 80

Leu Phe Ile Thr Ser Lys Leu Trp Ser Thr Asp Ala His Pro Asp Leu
85 90 95

Val Val Pro Ala Leu Lys Thr Ser Leu Gln Lys Leu Gly Leu Glu Tyr
100 105 110

Val Asp Leu Tyr Leu Ile His Trp Pro Val Arg Leu Lys Pro Glu Ala
115 120 125

Lys Gly Tyr His Asn Ile Leu Lys Glu Asn Val Leu Pro Ser Phe Asp
130 135 140

Met Lys Gly Ile Trp Glu Ala Met Glu Glu Cys Tyr Arg Leu Gly Leu
145 150 155 160

Ala Lys Ser Ile Gly Val Ser Asn Phe Gly Ile Lys Lys Leu Ser Gln
165 170 175

Leu Leu Glu Asn Ala Thr Ile Pro Pro Ala Val Asn Gln Val Glu Met
180 185 190

Ser Pro Thr Trp Gln Gln Gly Lys Leu Lys Glu Phe Cys Lys Gln Lys
195 200 205

Gly Ile His Val Ser Ala Trp Ser Pro Leu Gly Ala Tyr Lys Ser Ala
210 215 220

Gln Gly Thr Asn Ala Val Met Glu Ser Pro Ile Leu Lys Glu Ile Ala
225 230 235 240

Cys Glu Arg Gln Lys Ser Met Ala Gln Ile Ala Leu Arg Trp Ile Tyr
245 250 255

Glu Gln Gly Ala Ile Ala Ile Val Lys Ser Phe Asn Lys Glu Arg Met
260 265 270

Lys Gln Asn Leu Asp Ile Phe Asp Trp Glu Leu Ser Gln Glu Glu Ser
275 280 285

Gln Lys Phe Ser Gln Ile Pro Gln Arg Arg Met Tyr Arg Gly Ile Thr
290 295 300

Phe Val Ser Glu Asn Gly Pro Tyr Lys Thr Leu Glu Glu Leu Trp Asp
305 310 315 320

<210> SEQ ID NO 54
<211> LENGTH: 322
<212> TYPE: PRT

<213> ORGANISM: Glycine max
<220> FEATURE:
<221> NAME/KEY: MISC_FEATURE
<223> OTHER INFORMATION: CeresClone:474019
<220> FEATURE:
<221> NAME/KEY: misc_feature
<222> LOCATION: (274)..(274)
<223> OTHER INFORMATION: Xaa can be any naturally occurring amino acid

<400> SEQUENCE: 54

Met Ala Gly Lys Lys Ile Pro Asp Val Leu Leu Asn Ser Gly His Lys
1 5 10 15

Met Pro Val Ile Gly Met Gly Thr Ser Val Glu Asn Arg Pro Ser Asn
20 25 30

Glu Thr Leu Ala Ser Ile Tyr Val Glu Ala Ile Glu Val Gly Tyr Arg
35 40 45

His Phe Asp Thr Ala Ala Val Tyr Gly Thr Glu Glu Ala Ile Gly Leu
50 55 60

Ala Val Ala Lys Ala Ile Asp Lys Gly Leu Ile Lys Ser Arg Asp Glu
65 70 75 80

Val Phe Ile Thr Ser Lys Pro Trp Asn Thr Asp Ala His Arg Asp Leu
85 90 95

Ile Val Pro Ala Leu Lys Thr Thr Leu Lys Lys Leu Gly Thr Glu Tyr
100 105 110

Val Asp Leu Tyr Leu Ile His Trp Pro Val Arg Leu Arg His Asp Leu
115 120 125

Glu Asn Pro Thr Val Phe Thr Lys Glu Asp Val Leu Pro Phe Asp Ile
130 135 140

Glu Gly Thr Trp Lys Ala Met Glu Glu Cys Tyr Lys Leu Gly Ile Ala
145 150 155 160

Lys Ser Ile Gly Ile Cys Asn Tyr Gly Ile Lys Lys Leu Thr Lys Leu
165 170 175

Leu Glu Ile Ala Thr Ile Pro Pro Ala Val Asn Gln Val Glu Met Asn
180 185 190

Pro Ser Trp Gln Gln Gly Lys Leu Arg Glu Phe Cys Lys Gln Lys Gly
195 200 205

Ile His Val Ser Ala Trp Ser Ala Leu Gly Ala Tyr Lys Ile Phe Trp
210 215 220

Gly Ser Gly Ala Val Met Glu Asn Pro Ile Leu Gln Asp Ile Ala Lys
225 230 235 240

Ala Lys Gly Lys Thr Ile Ala Gln Val Ala Leu Arg Trp Val Tyr Gln
245 250 255

Gln Gly Ser Ser Ala Met Ala Lys Ser Thr Asn Ser Glu Arg Met Lys
260 265 270

Gln Xaa Leu Asp Ile Phe Asp Phe Val Leu Ser Glu Glu Asp Leu Glu
275 280 285

Arg Ile Ser Gln Val Pro Gln Arg Arg Gln Tyr Thr Gly Asp Ile Trp
290 295 300

Leu Ser Glu Asn Gly Ser Cys Lys Thr Leu Glu Glu Leu Trp Asp Gly
305 310 315 320

Asp Val

<210> SEQ ID NO 55
<211> LENGTH: 312
<212> TYPE: PRT
<213> ORGANISM: Medicago sativa
<220> FEATURE:

```
<221> NAME/KEY: MISC_FEATURE
<223> OTHER INFORMATION: gi|563536

<400> SEQUENCE: 55

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Asp
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala His Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Arg Ile Phe Asp Trp Ser Leu Thr Lys Glu Asp His Glu Lys
        275                 280                 285

Ile Ala Gln Ile Lys Gln Asn Arg Leu Ile Pro Gly Pro Thr Lys Pro
    290                 295                 300

Gly Leu Asn Asp Leu Tyr Asp Asp
305                 310


<210> SEQ ID NO 56
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi|537298

<400> SEQUENCE: 56

Met Gly Ser Val Glu Ile Pro Thr Lys Val Leu Thr Asn Thr Ser Ser
1               5                   10                  15
```

```
Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Glu
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala Asn Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Cys Ile Phe Asp Trp Ser Leu Thr Lys Glu Asp His Glu Lys
        275                 280                 285

Ile Asp Gln Ile Lys Gln Asn Arg Leu Ile Pro Gly Pro Thr Lys Pro
    290                 295                 300

Gly Leu Asn Asp Leu Tyr Asp Asp
305                 310


<210> SEQ ID NO 57
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi|563538

<400> SEQUENCE: 57

Met Asp Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60
```

```
Gly Glu Ala Leu Lys Glu Ala Ile Glu Leu Gly Leu Val Thr Arg Glu
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala Asn Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Cys Ile Phe Asp Trp Ser Leu Thr Lys Glu Asp His Glu Lys
        275                 280                 285

Ile Asp Gln Ile Lys Gln Asn Arg Leu Ile Pro Gly Pro Thr Lys Pro
    290                 295                 300

Gly Leu Asn Asp Leu Tyr Asp Asp
305                 310


<210> SEQ ID NO 58
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi|563540

<400> SEQUENCE: 58

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Asp
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
```

```
            100                 105                 110

Tyr Leu Asp Leu Tyr Leu Ile His Trp Pro Leu Ser Ser Gln Pro Gly
        115                 120                 125

Lys Phe Thr Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala His Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Arg Ile Phe Asp Trp Ser Leu Thr Lys Glu Asp His Glu Lys
        275                 280                 285

Ile Asp Gln Ile Lys Gln Asn Arg Leu Ile Pro Gly Pro Thr Lys Pro
    290                 295                 300

Gly Leu Asn Asp Leu Tyr Asp Asp
305                 310


<210> SEQ ID NO 59
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi|537296

<400> SEQUENCE: 59

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Asp
65                  70                  75                  80

Asp Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
    130                 135                 140
```

```
Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala His Gly
        195                 200                 205

Ile Val Leu Thr Ala Phe Ser Pro Val Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Arg Ile Phe Asp Trp Ser Leu Thr Lys Glu Asp His Glu Lys
        275                 280                 285

Ile Ala Gln Ile Lys Gln Asn Arg Leu Ile Pro Gly Pro Thr Lys Pro
    290                 295                 300

Gly Leu Asn Asp Leu Tyr Asp Asp
305                 310


<210> SEQ ID NO 60
<211> LENGTH: 314
<212> TYPE: PRT
<213> ORGANISM: Pueraria lobata
<220> FEATURE:
<221> NAME/KEY: MISC_FEATURE
<223> OTHER INFORMATION: gi|20147510

<400> SEQUENCE: 60

Met Ala Ala Ile Glu Ile Pro Thr Ile Val Phe Pro Asn Ser Phe Ala
1               5                   10                  15

Gln His Arg Val Pro Val Val Glu Met Gly Ser Ala Pro Asp Phe Thr
            20                  25                  30

Cys Lys Lys Asp Thr Lys Glu Ala Ile Ile Glu Ala Val Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Val Asp Leu Gly Leu Val Ser Arg Gln
65                  70                  75                  80

Asp Leu Phe Val Thr Ser Lys Leu Trp Val Thr Asp Asn His Pro His
                85                  90                  95

Leu Val Val Ser Ala Leu Arg Lys Ser Leu Lys Thr Leu Gln Leu Glu
            100                 105                 110

Tyr Leu Asp Leu Tyr Leu Ile His Trp Pro Leu Ser Ser Gln Pro Gly
        115                 120                 125

Lys Phe Ser Phe Pro Ile Glu Val Glu Asp Leu Leu Pro Phe Asp Val
    130                 135                 140

Lys Gly Val Trp Glu Ala Met Gln Glu Cys Gln Lys Leu Gly Leu Thr
145                 150                 155                 160

Lys Ala Ile Gly Val Ser Asn Phe Ser Val Lys Lys Leu Gln Asn Leu
                165                 170                 175

Leu Ser Val Ala Thr Ile Arg Pro Val Val Asn Gln Val Glu Met Asn
            180                 185                 190
```

```
Leu Ala Trp Gln Gln Lys Lys Leu Arg Glu Phe Cys Lys Glu Asn Gly
        195                 200                 205

Ile Val Ile Thr Ala Phe Ser Pro Leu Arg Lys Gly Ala Ser Arg Gly
    210                 215                 220

Pro Asn Glu Val Met Glu Asn Asp Val Leu Lys Glu Ile Ala Asp Ala
225                 230                 235                 240

His Gly Lys Ser Ile Ala Gln Val Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Gln Ile Phe Asp Trp Ala Leu Thr Gln Glu Asp His His Lys
        275                 280                 285

Ile Ser Gln Ile Ser Gln Ser Arg Leu Ile Ser Gly Pro Thr Lys Pro
    290                 295                 300

Gln Leu Ser Asp Leu Trp Asp Asp Glu Ile
305                 310
```

<210> SEQ ID NO 61
<211> LENGTH: 322
<212> TYPE: PRT
<213> ORGANISM: Sesbania rostrata
<220> FEATURE:
<221> NAME/KEY: MISC_FEATURE
<223> OTHER INFORMATION: gi|2792155

<400> SEQUENCE: 61

```
Met Ala Glu Lys Lys Ile Pro Glu Val Leu Leu Asn Ser Gly His Lys
1               5                   10                  15

Met Pro Val Ile Gly Met Gly Thr Ser Val Glu Ser Arg Pro Ser Asn
            20                  25                  30

Asp Val Leu Ala Ser Ile Phe Val Asp Ala Ile Gln Val Gly Tyr Arg
        35                  40                  45

His Phe Asp Ser Ala Ser Val Tyr Gly Thr Glu Glu Ala Ile Gly Met
    50                  55                  60

Ala Val Ser Lys Ala Ile Glu Gln Gly Leu Ile Lys Ser Arg Asp Glu
65                  70                  75                  80

Val Phe Ile Thr Ser Lys Pro Trp Asn Thr Asp Ala His His Asp Leu
                85                  90                  95

Ile Val Pro Ala Leu Lys Thr Thr Leu Lys Lys Leu Gly Met Glu Tyr
            100                 105                 110

Val Asp Leu Tyr Leu Ile His Trp Pro Val Arg Leu Arg His Asp Leu
        115                 120                 125

Glu Asn Pro Val Ile Phe Ser Lys Glu Asp Leu Leu Pro Phe Asp Ile
    130                 135                 140

Glu Gly Thr Trp Lys Ala Met Glu Glu Cys Tyr Arg Leu Gly Leu Ala
145                 150                 155                 160

Lys Ser Ile Gly Ile Cys Asn Tyr Gly Thr Lys Lys Leu Thr Lys Leu
                165                 170                 175

Leu Glu Ile Ala Thr Ile Pro Pro Ala Val Asn Gln Val Glu Met Asn
            180                 185                 190

Pro Ser Trp Gln Gln Gly Asn Leu Arg Glu Phe Cys Lys Gln Lys Gly
        195                 200                 205

Ile His Val Ser Ala Trp Ser Pro Leu Gly Ala Tyr Lys Ile Phe Trp
    210                 215                 220

Gly Ser Gly Ala Val Met Glu Asn Gln Ile Leu Gln Asp Ile Ala Thr
```

225 230 235 240

Ala Lys Gly Lys Thr Ile Ala Gln Val Ala Leu Arg Trp Val Tyr Gln
245 250 255

Gln Gly Ser Ser Ala Met Ala Lys Ser Phe Asn Lys Glu Arg Met Lys
260 265 270

Gln Asn Leu Glu Ile Phe Asp Phe Glu Leu Ser Glu Glu Glu Leu Glu
275 280 285

Lys Ile Lys Gln Ile Pro Gln Arg Arg Gln Tyr Thr Gly Asp Met Trp
290 295 300

Leu Ser Glu Asn Gly Ser Cys Lys Thr Leu Glu Glu Leu Trp Asp Gly
305 310 315 320

Asp Val

<210> SEQ ID NO 62
<211> LENGTH: 315
<212> TYPE: PRT
<213> ORGANISM: Digitalis purpurea
<220> FEATURE:
<221> NAME/KEY: MISC_FEATURE
<223> OTHER INFORMATION: gi|13160397

<400> SEQUENCE: 62

Met Ala Glu Glu Ile Arg Phe Phe Lys Leu Asn Thr Gly Ala Lys Ile
1 5 10 15

Pro Ser Val Gly Leu Gly Thr Trp Gln Ser Ser Pro Gly Asp Ala Ala
20 25 30

Gln Ala Val Glu Val Ala Ile Lys Cys Gly Tyr Arg His Ile Asp Gly
35 40 45

Ala Arg Leu Tyr Glu Asn Glu Lys Glu Ile Gly Val Val Leu Lys Lys
50 55 60

Leu Phe Asp Asp Gly Val Val Lys Arg Glu Asp Leu Phe Ile Thr Ser
65 70 75 80

Lys Leu Trp Ser Thr Asp His Ala Pro Glu Asp Val Pro Val Ala Leu
85 90 95

Asp Lys Thr Leu Glu Asp Leu Gln Leu Asp Tyr Ile Asp Leu Tyr Leu
100 105 110

Ile His Trp Pro Val Arg Leu Lys Lys Gly Ser Val Gly Leu Asp Pro
115 120 125

Glu Asn Phe Ile Pro Thr Asp Ile Pro Gly Thr Trp Lys Ala Met Glu
130 135 140

Ala Leu Tyr Asp Ser Gly Lys Ala Arg Ala Ile Gly Val Ser Asn Phe
145 150 155 160

Thr Leu Lys Lys Leu Ser Asp Leu Leu Asp Val Ala Arg Ile Pro Pro
165 170 175

Ala Val Asn Gln Val Gly Cys His Pro Ser Cys Ala Gln Thr Lys Leu
180 185 190

Arg Ala Phe Cys Lys Ser Lys Gly Val His Leu Ser Gly Tyr Ser Pro
195 200 205

Leu Gly Ser Pro Gly Thr Pro Trp Val Lys His Asp Val Leu Glu Asn
210 215 220

Pro Ile Leu Val Asp Val Ala Glu Lys Leu Gly Lys Thr Pro Ala Gln
225 230 235 240

Val Ala Ile Arg Trp Gly Leu Gln Met Gly His Ser Val Leu Pro Lys
245 250 255

Ser Val His Glu Ser Arg Ile Lys Glu Asn Ile Asp Val Phe Ser Trp

```
            260                 265                 270

Cys Ile Pro Asp Asp Leu Phe Ala Lys Phe Ser Glu Ile Glu Gln Val
        275                 280                 285

Ser Pro Gly Lys Pro Glu Phe Pro Val His Pro Glu Ile Ser Gln Tyr
    290                 295                 300

Lys Thr Val Glu Glu Met Trp Asp Gly Gly Ile
305                 310                 315


<210> SEQ ID NO 63
<211> LENGTH: 315
<212> TYPE: PRT
<213> ORGANISM: Digitalis purpurea
<220> FEATURE:
<221> NAME/KEY: MISC_FEATURE
<223> OTHER INFORMATION: gi|13160399

<400> SEQUENCE: 63

Met Ala Glu Glu Ile Arg Phe Phe Glu Leu Asn Thr Gly Ala Lys Ile
1               5                   10                  15

Pro Ser Val Gly Leu Gly Thr Trp Gln Ser Ser Pro Gly Asp Ala Ala
            20                  25                  30

Gln Ala Val Glu Val Ala Ile Lys Cys Gly Tyr Arg His Ile Asp Gly
        35                  40                  45

Ala Arg Leu Tyr Glu Asn Glu Lys Glu Ile Gly Val Val Leu Lys Lys
    50                  55                  60

Leu Phe Asp Asp Gly Val Val Lys Arg Glu Asp Leu Phe Ile Thr Ser
65                  70                  75                  80

Lys Leu Trp Ser Thr Asp His Ala Pro Glu Asp Val Pro Val Ala Leu
                85                  90                  95

Asp Lys Thr Leu Glu Asp Leu Gln Leu Asp Tyr Ile Asp Leu Tyr Leu
            100                 105                 110

Ile His Trp Pro Val Arg Leu Lys Lys Gly Ser Val Gly Leu Asp Pro
        115                 120                 125

Glu Asn Phe Val Pro Thr Asp Ile Pro Gly Thr Trp Lys Ala Met Glu
    130                 135                 140

Ala Leu Tyr Asp Ser Gly Lys Ala Arg Ala Ile Gly Val Ser Asn Phe
145                 150                 155                 160

Thr Leu Lys Lys Leu Ser Asp Leu Leu Asp Val Ala Arg Ile Pro Pro
                165                 170                 175

Ala Val Asn Gln Val Gly Cys His Pro Ser Cys Ala Gln Thr Lys Leu
            180                 185                 190

Arg Ala Phe Cys Lys Ser Lys Gly Ile His Leu Ser Gly Tyr Ser Pro
        195                 200                 205

Leu Gly Ser Pro Gly Thr Pro Trp Val Lys His Asp Val Leu Glu Asn
    210                 215                 220

Pro Ile Leu Val Asp Val Ala Glu Lys Leu Gly Lys Thr Pro Ala Gln
225                 230                 235                 240

Val Ala Leu Arg Trp Gly Leu Gln Met Gly His Ser Val Leu Pro Lys
                245                 250                 255

Ser Val His Glu Ser Arg Ile Lys Glu Asn Ile Asp Val Phe Ser Trp
            260                 265                 270

Cys Ile Pro Asp Val Leu Phe Ala Lys Phe Ser Glu Ile Glu Gln Val
        275                 280                 285

Ser Pro Gly Lys Pro Glu Phe Pro Val His Pro Glu Ile Ser Gln Tyr
    290                 295                 300
```

Lys Thr Val Glu Glu Met Trp Asp Gly Gly Ile
305 310 315

<210> SEQ ID NO 64
<211> LENGTH: 319
<212> TYPE: PRT
<213> ORGANISM: Avena fatua
<220> FEATURE:
<221> NAME/KEY: MISC_FEATURE
<223> OTHER INFORMATION: gi|1155213

<400> SEQUENCE: 64

Met Ala Ser Ala Lys Ala Met Gly Gln Gly Glu Gln Asp Arg Phe Val
1 5 10 15

Leu Lys Ser Gly His Ala Ile Pro Ala Val Gly Leu Gly Thr Trp Arg
20 25 30

Ala Gly Ser Asp Thr Ala His Ser Val Gln Thr Ala Ile Thr Glu Ala
35 40 45

Gly Tyr Arg His Val Asp Thr Ala Ala Gln Tyr Gly Ile Glu Lys Glu
50 55 60

Val Asp Lys Gly Leu Lys Ala Ala Met Glu Ala Gly Ile Asp Arg Lys
65 70 75 80

Asp Leu Phe Val Thr Ser Lys Ile Trp Arg Thr Asn Leu Ala Pro Glu
85 90 95

Arg Ala Arg Pro Ala Leu Glu Asn Thr Leu Lys Asp Leu Gln Leu Asp
100 105 110

Tyr Ile Asp Leu Tyr Leu Ile His Trp Pro Phe Arg Leu Lys Asp Gly
115 120 125

Ala His Gln Pro Pro Glu Ala Gly Glu Val Leu Glu Phe Asp Met Glu
130 135 140

Gly Val Trp Lys Glu Met Glu Lys Leu Val Lys Asp Gly Leu Val Lys
145 150 155 160

Asp Ile Asp Val Cys Asn Phe Thr Val Thr Lys Leu Asn Arg Leu Leu
165 170 175

Arg Ser Ala Asn Ile Pro Pro Ala Val Cys Gln Met Glu Met His Pro
180 185 190

Gly Trp Lys Asn Asp Lys Ile Phe Glu Ala Cys Lys Lys His Gly Ile
195 200 205

His Val Thr Ala Tyr Ser Pro Leu Gly Ser Ser Glu Lys Asn Leu Val
210 215 220

His Asp Pro Val Val Glu Lys Val Ala Asn Lys Leu Asn Lys Thr Pro
225 230 235 240

Gly Gln Val Leu Ile Lys Trp Ala Leu Gln Arg Gly Thr Ser Val Ile
245 250 255

Pro Lys Ser Ser Lys Asp Glu Arg Ile Lys Glu Asn Ile Gln Ala Phe
260 265 270

Gly Trp Glu Ile Pro Glu Asp Asp Phe Gln Val Leu Cys Ser Ile Lys
275 280 285

Asp Glu Lys Arg Val Leu Thr Gly Glu Glu Leu Phe Val Asn Lys Thr
290 295 300

His Gly Pro Tyr Lys Ser Ala Ser Glu Val Trp Asp His Glu Asn
305 310 315

<210> SEQ ID NO 65
<211> LENGTH: 320
<212> TYPE: PRT
<213> ORGANISM: Hordeum vulgare
<220> FEATURE:
<221> NAME/KEY: MISC_FEATURE
<223> OTHER INFORMATION: gi|728592

<400> SEQUENCE: 65

```
Met Ala Ser Ala Lys Ala Thr Met Gly Gln Gly Glu Gln Asp His Phe
1               5                   10                  15

Val Leu Lys Ser Gly His Ala Met Pro Ala Val Gly Leu Gly Thr Trp
            20                  25                  30

Arg Ala Gly Ser Asp Thr Ala His Ser Val Arg Thr Ala Ile Thr Glu
        35                  40                  45

Ala Gly Tyr Arg His Val Asp Thr Ala Ala Glu Tyr Gly Val Glu Lys
    50                  55                  60

Glu Val Gly Lys Gly Leu Lys Ala Ala Met Glu Ala Gly Ile Asp Arg
65                  70                  75                  80

Lys Asp Leu Phe Val Thr Ser Lys Ile Trp Cys Thr Asn Leu Ala Pro
                85                  90                  95

Glu Arg Val Arg Pro Ala Leu Glu Asn Thr Leu Lys Asp Leu Gln Leu
            100                 105                 110

Asp Tyr Ile Asp Leu Tyr His Ile His Trp Pro Phe Arg Leu Lys Asp
        115                 120                 125

Gly Ala His Met Pro Pro Glu Ala Gly Glu Val Leu Glu Phe Asp Met
    130                 135                 140

Glu Gly Val Trp Lys Glu Met Glu Asn Leu Val Lys Asp Gly Leu Val
145                 150                 155                 160

Lys Asp Ile Gly Val Cys Asn Tyr Thr Val Thr Lys Leu Asn Arg Leu
                165                 170                 175

Leu Arg Ser Ala Lys Ile Pro Pro Ala Val Cys Gln Met Glu Met His
            180                 185                 190

Pro Gly Trp Lys Asn Asp Lys Ile Phe Glu Ala Cys Lys Lys His Gly
        195                 200                 205

Ile His Ile Thr Ala Tyr Ser Pro Leu Gly Ser Ser Glu Lys Asn Leu
    210                 215                 220

Ala His Asp Pro Val Val Glu Lys Val Ala Asn Lys Leu Asn Lys Thr
225                 230                 235                 240

Pro Gly Gln Val Leu Ile Lys Trp Ala Leu Gln Arg Gly Thr Ser Val
                245                 250                 255

Ile Pro Lys Ser Ser Lys Asp Glu Arg Ile Lys Glu Asn Ile Gln Val
            260                 265                 270

Phe Gly Trp Glu Ile Pro Glu Glu Asp Phe Lys Val Leu Cys Ser Ile
        275                 280                 285

Lys Asp Glu Lys Arg Val Leu Thr Gly Glu Glu Leu Phe Val Asn Lys
    290                 295                 300

Thr His Gly Pro Tyr Arg Ser Ala Arg Asp Val Trp Asp His Glu Asn
305                 310                 315                 320
```

<210> SEQ ID NO 66
<211> LENGTH: 321
<212> TYPE: PRT
<213> ORGANISM: Oryza sativa subsp. japonica
<220> FEATURE:
<221> NAME/KEY: MISC_FEATURE
<223> OTHER INFORMATION: gi|31429855

<400> SEQUENCE: 66

```
Met Ala Thr Ile Pro Glu Val Pro Ala Ser Glu Leu Ile Gln Thr Met
1               5                   10                  15
```

-continued

```
Pro Arg Val Gly Met Gly Thr Ala Ala Phe Pro Phe Thr Ser Ser Glu
            20                  25                  30

Asp Thr Thr Ala Ala Met Leu Arg Ala Ile Glu Leu Gly Tyr Arg His
        35                  40                  45

Phe Asp Thr Ala Arg Ile Tyr Ala Thr Glu Gly Cys Val Gly Glu Ala
    50                  55                  60

Val Ala Glu Ala Val Arg Arg Gly Leu Ile Ala Ser Arg Ala Asp Val
65                  70                  75                  80

Phe Val Thr Ser Lys Ile Trp Cys Ser Asp Leu His Ala Gly Arg Val
                85                  90                  95

Val Pro Ala Ala Arg Glu Thr Leu Arg Asn Leu Gly Met Asp Tyr Val
            100                 105                 110

Asp Leu Leu Leu Val His Trp Pro Val Ser Leu Thr Pro Gly Asn Tyr
        115                 120                 125

Asp Phe Pro Phe Pro Lys Glu Val Ile Leu Pro Ser Phe Asp Met Glu
    130                 135                 140

Gly Val Trp Arg Gly Met Glu Glu Cys His Arg Leu Gly Leu Ala Arg
145                 150                 155                 160

Ala Ile Gly Val Ser Asn Phe Ser Ala Lys Lys Leu Glu Gln Leu Leu
                165                 170                 175

Ser Leu Ala Ala Val Arg Pro Ala Val Asn Gln Val Glu Val Asn Pro
            180                 185                 190

Met Trp Gln Gln Arg Thr Leu Arg Glu Val Cys Arg Arg Glu Gly Val
        195                 200                 205

Gln Leu Cys Gly Tyr Ser Pro Leu Gly Ala Lys Gly Thr Pro Trp Gly
    210                 215                 220

Ser Ala Ala Val Met Asp Ser Gly Val Leu Gln Glu Ile Ala Gly Ala
225                 230                 235                 240

Lys Gly Lys Thr Leu Ala Gln Ile Cys Leu Arg Trp Leu Tyr Glu Gln
                245                 250                 255

Gly Asp Val Leu Leu Val Lys Thr Tyr Asn Glu Lys Arg Met Lys Glu
            260                 265                 270

Asn Leu Asp Ile Phe Asn Trp Glu Leu Thr Asp Glu Glu Arg Glu Arg
        275                 280                 285

Ile Ser Gln Leu Pro Gln Leu Arg Gly Leu Pro Gly Leu Glu Phe Ile
    290                 295                 300

Ser Asp His Gly Pro Tyr Lys Ser Val Glu Asp Leu Trp Asp Gly Asp
305                 310                 315                 320

Val


<210> SEQ ID NO 67
<211> LENGTH: 322
<212> TYPE: PRT
<213> ORGANISM: Oryza sativa subsp. japonica
<220> FEATURE:
<221> NAME/KEY: MISC_FEATURE
<223> OTHER INFORMATION: gi|31429856

<400> SEQUENCE: 67

Met Ala Met Ala Thr Ile Pro Glu Val Pro Ala Ser Ala Leu Leu Pro
1               5                   10                  15

Thr Met Pro Arg Ile Gly Met Gly Thr Ala Ala Phe Pro Phe Thr Ser
            20                  25                  30

Ser Glu Glu Thr Thr Ala Ala Leu Leu Arg Ala Ile Glu Leu Gly Tyr
        35                  40                  45
```

```
Arg His Phe Asp Thr Ala Arg Leu Tyr Ala Thr Glu Gly Cys Val Ser
    50                  55                  60

Glu Ala Val Ala Glu Ala Val Arg Arg Gly Leu Val Ala Ser Arg Ala
65                  70                  75                  80

Asp Val Phe Val Thr Ser Lys Leu Trp Cys Ser Asp Leu His Ala Gly
                85                  90                  95

Arg Val Val Pro Ala Ala Arg Glu Thr Leu Arg Asn Leu Gly Met Asp
            100                 105                 110

Tyr Val Asp Leu Leu Leu Val His Trp Pro Ala Thr Val Ala Pro Gly
        115                 120                 125

Ser Tyr Asp Phe Pro Phe Pro Lys Glu Glu Met Ala Pro Ala Phe Asp
    130                 135                 140

Met Glu Gly Val Trp Arg Gly Met Glu Glu Cys His Arg Leu Gly Leu
145                 150                 155                 160

Ala Arg Ala Ile Gly Val Ser Asn Phe Ser Ala Lys Lys Leu Glu Gln
                165                 170                 175

Leu Leu Ser Phe Ala Val Val Arg Pro Ala Ala Asn Gln Val Glu Met
            180                 185                 190

Asn Pro Met Trp Gln Gln Arg Thr Leu Arg Glu Val Cys Arg Arg Glu
        195                 200                 205

Gly Val Gln Leu Cys Gly Tyr Ser Pro Leu Gly Ala Lys Gly Thr Pro
    210                 215                 220

Trp Gly Ser Ala Ala Val Met Asp Ser Gly Val Leu His Asp Ile Ala
225                 230                 235                 240

Gln Thr Lys Gly Lys Thr Leu Ala Gln Ile Cys Leu Arg Trp Met Tyr
                245                 250                 255

Glu Gln Gly Asp Val Leu Leu Val Lys Thr Tyr Asn Glu Asn Arg Met
            260                 265                 270

Lys Glu Asn Leu Asp Ile Phe Asp Trp Glu Leu Thr Glu Glu Glu Arg
        275                 280                 285

Asp Lys Ile Ser Lys Leu Pro Gln Gln Arg Gly Leu Thr Gly Met Gln
    290                 295                 300

Phe Val Cys Asp Asn Gly Pro Tyr Lys Cys Val Glu Asp Leu Trp Asp
305                 310                 315                 320

Gly Ala
```

<210> SEQ ID NO 68
<211> LENGTH: 314
<212> TYPE: PRT
<213> ORGANISM: Triticum aestivum
<220> FEATURE:
<221> NAME/KEY: MISC_FEATURE
<223> OTHER INFORMATION: CeresClone:677995

<400> SEQUENCE: 68

```
Met Gly Ala Gly Asp Lys Thr Ala Ala Gly Met Pro Arg Ile Gly Met
1               5                   10                  15

Gly Thr Ala Val Gln Gly Pro Lys Pro Asp Pro Ile Arg Arg Ala Val
            20                  25                  30

Leu Arg Ala Ile Glu Val Gly Tyr Arg His Phe Asp Thr Ala Ala His
        35                  40                  45

Tyr Glu Thr Glu Ala Pro Ile Gly Glu Ala Ala Ala Glu Ala Val Arg
    50                  55                  60

Ser Gly Ala Val Ala Ser Arg Asp Asp Leu Phe Ile Thr Ser Lys Leu
65                  70                  75                  80
```

```
Trp Cys Ser Asp Ala His Arg Asp Arg Val Val Pro Ala Leu Arg Gln
                85                  90                  95

Thr Leu Arg Asn Leu Gln Met Glu Tyr Val Asp Leu Tyr Leu Val His
            100                 105                 110

Trp Pro Val Ser Met Lys Pro Gly Arg Phe Lys Ala Pro Phe Thr Ala
        115                 120                 125

Glu Asp Phe Val Pro Phe Asp Met Arg Ala Val Trp Glu Ala Met Glu
    130                 135                 140

Glu Cys His Arg Leu Gly Leu Ala Lys Ala Ile Gly Val Ala Asn Phe
145                 150                 155                 160

Ser Cys Lys Lys Leu Glu Thr Leu Leu Ser Phe Ala Thr Ile Pro Pro
                165                 170                 175

Thr Val Asn Gln Val Glu Val Asn Pro Val Trp Gln Gln Arg Lys Leu
            180                 185                 190

Arg Glu Phe Cys Arg Gly Lys Gly Ile Gln Leu Cys Thr Tyr Ser Pro
        195                 200                 205

Leu Gly Ala Lys Gly Thr His Trp Gly Ser Asp Ala Val Met Asp Ala
    210                 215                 220

Gly Val Leu Gln Glu Ile Ala Ala Ser Arg Gly Lys Ser Val Ala Gln
225                 230                 235                 240

Val Cys Leu Arg Trp Val Tyr Glu Gln Gly Asp Cys Leu Ile Val Lys
                245                 250                 255

Ser Phe Asp Glu Ala Arg Met Arg Glu Asn Leu Asp Val Asp Gly Trp
            260                 265                 270

Glu Leu Thr Glu Glu Glu His Arg Arg Ile Ala Glu Ile Pro Gln Arg
        275                 280                 285

Lys Ile Asn Leu Gly Lys Arg Tyr Val Ser Glu His Gly Pro Tyr Lys
    290                 295                 300

Ser Leu Glu Glu Leu Trp Asp Gly Glu Ile
305                 310


<210> SEQ ID NO 69
<211> LENGTH: 329
<212> TYPE: PRT
<213> ORGANISM: Zea mays
<220> FEATURE:
<221> NAME/KEY: MISC_FEATURE
<223> OTHER INFORMATION: CeresClone:290117

<400> SEQUENCE: 69

Met Ala Ser Ala Gly Thr Thr Ala Val Val Pro Glu Val Ala Leu Arg
1               5                   10                  15

Ser Gly Asn Ala Arg Thr Ala Met Pro Met Val Gly Met Gly Thr Ala
            20                  25                  30

Ser Phe Pro Leu Val His Glu Ala Val Lys Asp Ala Val Leu Ser Ala
        35                  40                  45

Ile Glu Val Gly Phe Arg His Phe Asp Thr Ala Ser Met Tyr Gly Thr
    50                  55                  60

Glu Lys Pro Leu Gly Asp Ala Val Ala Glu Ala Leu Arg Arg Gly Thr
65                  70                  75                  80

Leu Arg Ser Arg Glu Asp Leu Phe Val Thr Ser Lys Leu Trp Cys Ser
                85                  90                  95

Gln Asn His Pro Asp Leu Val Leu Pro Ser Leu Arg Glu Thr Leu Lys
            100                 105                 110

Asn Leu Gln Met Glu Tyr Val Asp Leu Tyr Leu Ile His Trp Pro Val
```

```
        115                 120                 125

Cys Leu Lys Pro Gly Pro Pro Glu Leu Pro Thr Arg Lys Glu Asn Ala
    130                 135                 140

Val Pro Leu Asp Leu Ala Gly Val Trp Arg Ala Met Glu Glu Cys Gln
145                 150                 155                 160

Arg Leu Gly Leu Ala Lys Ala Ile Gly Val Ser Asn Phe Thr Thr Arg
                165                 170                 175

His Leu Asp Gly Val Leu Ala Val Ala Thr Val Pro Pro Ala Val Asn
            180                 185                 190

Gln Val Glu Leu Asn Pro Ala Trp Gln Gln Arg Thr Leu Arg Ala Tyr
        195                 200                 205

Cys Ala Asp Arg Gly Ile His Val Ala Ala Tyr Ser Pro Leu Gly Gly
    210                 215                 220

Gln Asn Trp Asp Gly Gln Gly Ser Ala Val Leu Asp Ser Glu Val Leu
225                 230                 235                 240

Ala Ala Ile Ala Lys Ala Arg Gly Lys Thr Val Ala Gln Val Ala Leu
                245                 250                 255

Arg Trp Ile His Glu Gln Gly Val Thr Cys Ile Val Lys Ser Tyr Ser
            260                 265                 270

Lys Glu Arg Leu Arg Gln Asn Leu Gly Ile Phe Asp Trp Glu Leu Thr
        275                 280                 285

Asp Glu Glu Arg Leu Lys Ile Ser Gln Ile Pro Gln Arg Lys Val Val
    290                 295                 300

Gln Thr Ser Ser Leu Phe Ser Gln Glu Gly Glu Phe Thr Ala Val Asp
305                 310                 315                 320

Pro Ala Glu Leu Asn Ile Leu Glu Glu
                325


<210> SEQ ID NO 70
<211> LENGTH: 320
<212> TYPE: PRT
<213> ORGANISM: Bromus inermis
<220> FEATURE:
<221> NAME/KEY: MISC_FEATURE
<223> OTHER INFORMATION: gi|543632

<400> SEQUENCE: 70

Met Ala Ser Ala Lys Ala Met Met Gly Gln Glu Arg Gln Asp His Phe
1               5                   10                  15

Val Leu Lys Ser Gly His Ala Ile Pro Ala Val Gly Leu Gly Thr Trp
            20                  25                  30

Arg Ala Gly Ser Asp Thr Ala His Ser Val Gln Thr Ala Ile Thr Glu
        35                  40                  45

Ala Gly Tyr Arg His Val Asp Thr Ala Ala Glu Tyr Gly Val Glu Lys
    50                  55                  60

Glu Val Gly Lys Gly Leu Lys Ala Ala Met Glu Ala Gly Ile Asp Arg
65                  70                  75                  80

Lys Asp Leu Phe Val Thr Ser Lys Leu Trp Cys Thr Asp Leu Val Pro
                85                  90                  95

Asp Arg Val Arg Pro Ala Leu Glu Lys Thr Leu Lys Asp Leu Gln Leu
            100                 105                 110

Asp Tyr Leu Asp Leu Tyr Leu Ile His Trp Pro Phe Arg Leu Lys Asp
        115                 120                 125

Gly Ala His Lys Pro Pro Glu Ala Gly Glu Val Leu Glu Phe Asp Met
    130                 135                 140
```

```
Glu Gly Val Trp Lys Glu Met Glu Asn Leu Val Lys Asp Gly Leu Val
145                 150                 155                 160

Lys Asp Ile Gly Val Cys Asn Tyr Thr Val Thr Lys Leu Asn Arg Leu
                165                 170                 175

Leu Gln Ser Ala Lys Ile Ala Pro Ala Val Cys Gln Met Glu Met His
            180                 185                 190

Pro Gly Trp Lys Asn Asp Lys Ile Leu Glu Ala Cys Lys Lys His Gly
        195                 200                 205

Ile His Ala Thr Ala Tyr Ser Pro Leu Cys Ser Ser Glu Lys Asn Leu
    210                 215                 220

Ala His Asp Pro Val Val Glu Lys Val Ala Asn Lys Leu Asn Lys Thr
225                 230                 235                 240

Pro Gly Gln Val Leu Ile Lys Trp Ala Leu Gln Arg Gly Thr Ile Val
                245                 250                 255

Ile Pro Lys Ser Ser Lys Asp Glu Arg Ile Lys Glu Asn Ile Gln Val
            260                 265                 270

Phe Gly Trp Glu Ile Pro Glu Glu Asp Phe Gln Val Leu Cys Ser Ile
        275                 280                 285

Lys Asp Glu Lys Arg Val Leu Thr Gly Glu Glu Leu Phe Val Asn Lys
    290                 295                 300

Thr His Gly Pro Tyr Lys Ser Ala Ser Glu Val Trp Asp Asn Glu Asn
305                 310                 315                 320


<210> SEQ ID NO 71
<211> LENGTH: 321
<212> TYPE: PRT
<213> ORGANISM: Hydrangea macrophylla
<220> FEATURE:
<221> NAME/KEY: MISC_FEATURE
<223> OTHER INFORMATION: gi|40781601

<400> SEQUENCE: 71

Met Ala Phe Thr Ile Pro Glu Val Pro Leu Ser Ser Gly Gly Arg Lys
1               5                   10                  15

Met Pro Val Leu Gly Leu Gly Thr Ala Ala Asp Pro Pro Val Asp Pro
            20                  25                  30

Glu Thr Val Arg Lys Ala Val Thr Glu Ala Leu Lys Leu Gly Tyr Arg
        35                  40                  45

His Phe Asp Thr Ala Ala Leu Tyr Asn Ser Glu Gln Pro Leu Gly Asp
    50                  55                  60

Ala Ile Ala Glu Ala Leu Gly Glu Gly Leu Ile Lys Ser Arg Asp Glu
65                  70                  75                  80

Leu Phe Ile Thr Ser Lys Leu Trp Cys Ser Asp Ala His Arg Glu Asn
                85                  90                  95

Val Glu Pro Ala Leu Gln Lys Thr Leu Lys Asn Leu Lys Leu Glu Tyr
            100                 105                 110

Ile Asp Met Tyr Leu Ile His Trp Pro Val Ser Ser Lys Pro Gly Asn
        115                 120                 125

Tyr Glu Tyr Pro Ile Lys Lys Glu Asp Phe Leu Gln Met Asp Tyr Lys
    130                 135                 140

Ser Val Trp Glu Ala Met Glu Glu Cys Gln Lys Leu Gly Leu Thr Lys
145                 150                 155                 160

Ala Ile Gly Val Ser Asn Phe Ser Cys Lys Lys Leu Ser Asp Val Leu
                165                 170                 175

Ala Asn Ala Lys Val Pro Pro Ala Val Asn Gln Val Glu Val Asn Pro
            180                 185                 190
```

```
Cys Trp Gln Gln Lys Gln Leu Thr Glu Phe Cys Lys Ser Asn Gly Ile
        195                 200                 205

Leu Val Val Ala Tyr Ala Ala Leu Gly Ala Val Gly Thr Phe Tyr Gly
    210                 215                 220

Thr Asn Arg Val Met Gly Ser Glu Val Leu Asn Glu Ile Ala Arg Ile
225                 230                 235                 240

Arg Gly Asn Thr Val Ala Gln Val Cys Leu Arg Trp Ala Tyr Glu Gln
                245                 250                 255

Gly Ile Gly Val Leu Val Lys Ser Phe Asn Lys Glu Arg Met Glu Gln
            260                 265                 270

Asn Leu Gln Ile Phe Asn Trp Thr Leu Ser Asp Asp Glu Ser Lys Lys
        275                 280                 285

Ile Ser Glu Ile Pro Gln Gly Arg Ala Cys Leu Gly Thr Asp Tyr Thr
    290                 295                 300

Ser Val His Gly Pro Phe Lys Thr Ile Glu Glu Leu Trp Asp Gly Glu
305                 310                 315                 320

Phe


<210> SEQ ID NO 72
<211> LENGTH: 321
<212> TYPE: PRT
<213> ORGANISM: Oryza sativa subsp. japonica
<220> FEATURE:
<221> NAME/KEY: MISC_FEATURE
<223> OTHER INFORMATION: gi|50920555

<400> SEQUENCE: 72

Met Ser Asp Gly Gly Ala Gly Ala Lys Gly Ala Gly Phe Gly Met Pro
1               5                   10                  15

Arg Val Gly Met Gly Thr Ala Val Gln Gly Pro Arg Pro Glu Pro Ile
            20                  25                  30

Arg Arg Ala Val Leu Lys Ala Ile Glu Ala Gly Tyr Arg His Phe Asp
        35                  40                  45

Thr Ala Ala His Tyr Glu Thr Glu Ala Pro Ile Gly Glu Ala Ala Ala
    50                  55                  60

Glu Ala Val Arg Ser Gly Ala Ile Ala Ser Arg Ala Asp Leu Phe Ile
65                  70                  75                  80

Thr Ser Lys Leu Trp Cys Ser Asp Ala His Arg Asp Arg Val Leu Pro
                85                  90                  95

Ala Leu Arg Gln Thr Leu Trp Asn Leu Gln Met Glu Tyr Val Asp Leu
            100                 105                 110

Tyr Leu Val His Trp Pro Val Ser Met Lys Pro Gly Arg Tyr Lys Ala
        115                 120                 125

Pro Phe Thr Ala Asp Asp Phe Val Pro Phe Asp Met Arg Ala Val Trp
    130                 135                 140

Glu Ala Met Glu Glu Cys His Arg Leu Gly Leu Ala Lys Ala Ile Gly
145                 150                 155                 160

Val Cys Asn Phe Ser Cys Lys Lys Leu Asp Thr Leu Leu Ser Phe Ala
                165                 170                 175

Thr Ile Pro Pro Ala Val Asn Gln Val Glu Val Asn Pro Val Trp Gln
            180                 185                 190

Gln Arg Lys Leu Arg Glu Leu Cys Arg Glu Lys Gly Val Gln Ile Cys
        195                 200                 205

Ala Tyr Ser Pro Leu Gly Ala Ser Gly Thr His Trp Gly Ser Asp Ser
    210                 215                 220
```

```
Val Met Ala Ser Ala Val Leu Arg Asp Ile Ala Gln Ser Lys Gly Lys
225                 230                 235                 240

Thr Val Ala Gln Ala Arg His Val Cys Leu Arg Trp Val Tyr Glu Gln
                245                 250                 255

Gly Asp Cys Leu Ile Val Lys Ser Phe Asp Glu Ala Arg Met Arg Glu
            260                 265                 270

Asn Leu Asp Ile Val Gly Trp Glu Leu Thr Glu Glu Glu Arg Gln Arg
        275                 280                 285

Ile Ala Gly Ile Pro Gln Arg Lys Ile Asn Arg Ala Leu Arg Phe Val
    290                 295                 300

Ser Asp His Gly Pro Tyr Lys Ser Leu Asp Asp Leu Trp Asp Gly Glu
305                 310                 315                 320

Ile


<210> SEQ ID NO 73
<211> LENGTH: 323
<212> TYPE: PRT
<213> ORGANISM: Oryza sativa subsp. japonica
<220> FEATURE:
<221> NAME/KEY: MISC_FEATURE
<223> OTHER INFORMATION: gi|50900440

<400> SEQUENCE: 73

Met Ala Ala Val Pro Glu Val Ala Leu Arg His Gly Ala Gly Arg Pro
1               5                   10                  15

Met Pro Ala Val Gly Val Gly Thr Ala Asp Ser Ala Ala Thr Ser Pro
            20                  25                  30

Glu Thr Lys Arg Gly Ala Ala Leu Ala Ala Leu Glu Val Gly Phe Arg
        35                  40                  45

His Phe Asp Thr Ala Ala Leu Tyr Gly Thr Glu Ala Pro Leu Gly Glu
    50                  55                  60

Ala Ile Ala Glu Ala Thr Arg Arg Gly Leu Val Ala Ser Arg Glu Glu
65                  70                  75                  80

Val Phe Val Thr Thr Lys Leu Trp Cys Thr Gln Cys His Pro Gly Leu
                85                  90                  95

Val Leu Pro Ser Leu Arg Glu Ser Leu Arg Asn Leu Gln Met Glu Tyr
            100                 105                 110

Val Asp Leu Tyr Leu Val His Trp Pro Ile Ser Val Lys Pro Gly Pro
        115                 120                 125

Pro Met Leu Pro Val Lys Arg Glu Asp Ala Val Pro Phe Asp Phe Glu
    130                 135                 140

Gly Val Trp Arg Ala Met Glu Glu Cys His Arg Leu Gly Leu Ala Lys
145                 150                 155                 160

Ala Ile Gly Val Ser Asn Phe Thr Thr Lys His Leu Asp Lys Leu Leu
                165                 170                 175

Ala Val Ala Thr Ile Pro Pro Ala Val Asn Gln Val Glu Met Asn Pro
            180                 185                 190

Val Trp Gln Gln Arg Thr Val Arg Glu Tyr Cys Ala Ala Lys Gly Ile
        195                 200                 205

Arg Val Ala Ala Tyr Ser Pro Leu Gly Gly Gln Asn Trp Ile Gly Glu
    210                 215                 220

Gly Asn Asp Val Met Glu Ser Pro Val Leu Ala Asp Ile Ala Arg Ala
225                 230                 235                 240

Arg Gly Lys Ser Ile Ala Gln Val Ser Leu Arg Trp Ile His Glu Gln
                245                 250                 255
```

```
Gly Val Thr Pro Ile Pro Lys Ser Tyr Asn Lys Glu Arg Leu Lys Gln
            260                 265                 270

Asn Leu Glu Ile Phe Asp Trp Glu Leu Thr Lys Glu Asp Arg Leu Lys
        275                 280                 285

Ile Ser Gln Ile Pro Gln Lys Lys Ile Val Thr Ala Ala Arg Met Phe
    290                 295                 300

Ser Pro Asp Gly Glu Phe Ala Ser Val Asp Leu Ser Asp Met Glu Ile
305                 310                 315                 320

Val Glu Glu


<210> SEQ ID NO 74
<211> LENGTH: 323
<212> TYPE: PRT
<213> ORGANISM: Oryza sativa subsp. japonica
<220> FEATURE:
<221> NAME/KEY: MISC_FEATURE
<223> OTHER INFORMATION: gi|50900438

<400> SEQUENCE: 74

Met Ala Val Val Val Pro Glu Ala Val Leu Arg His Gly Asp Ala Arg
1               5                   10                  15

Pro Met Pro Ala Val Gly Met Gly Val Ala Glu Tyr Pro Ser Thr Pro
            20                  25                  30

Glu Arg Thr Arg Asp Ala Val Leu Ala Ala Leu Glu Ala Gly Phe Arg
        35                  40                  45

His Phe Asp Thr Ala Ser Leu Tyr Arg Thr Glu Ala Pro Leu Gly Glu
    50                  55                  60

Ala Ile Ala Glu Ala Thr Arg Arg Gly Leu Leu Ala Ser Arg Glu Glu
65                  70                  75                  80

Ala Phe Val Thr Thr Lys Leu Trp Cys Thr Gln Cys His Pro Asp Leu
                85                  90                  95

Val Leu Pro Ser Leu Arg Glu Ser Leu Arg Asn Leu Gln Met Glu Tyr
            100                 105                 110

Val Asp Leu Tyr Leu Ile His Leu Pro Ile Ser Val Lys Pro Gly Pro
        115                 120                 125

Met Val Phe Pro Val Lys Lys Glu Asp Val Val Pro Phe Asp Phe Gly
    130                 135                 140

Gly Val Trp Arg Ala Met Glu Glu Cys His Arg Leu Gly Leu Ala Lys
145                 150                 155                 160

Ala Ile Gly Val Ser Asn Phe Thr Thr Lys His Ile Asp Lys Leu Leu
                165                 170                 175

Ala Val Ala Thr Ile Leu Pro Ala Val Asn Gln Val Glu Met Asn Pro
            180                 185                 190

Thr Trp Gln Gln Arg Thr Val Arg Glu Tyr Cys Asp Ala Lys Gly Ile
        195                 200                 205

Arg Val Thr Ala Tyr Ser Pro Leu Gly Gly Gln Asn Trp Gly Gly Ser
    210                 215                 220

Ala Asn Tyr Val Met Glu Ser Ser Val Leu Thr Glu Ile Ala Arg Ala
225                 230                 235                 240

Arg Gly Lys Ser Ile Ala Gln Val Ser Leu Arg Trp Ile Tyr Glu Gln
                245                 250                 255

Gly Val Thr Pro Ile Ala Lys Ser Tyr Arg Lys Glu Arg Leu Lys Glu
            260                 265                 270

Asn Leu Glu Ile Phe Asp Trp Glu Leu Thr Asp Glu Asp Arg Leu Lys
        275                 280                 285
```

```
Ile Ser Gln Ile Pro Gln Arg Lys Arg Val Thr Ala Ala Ser Leu Phe
    290                 295                 300

Ser Pro Asp Gly Glu Phe Thr Ser Val Asp Leu Pro Asp Ile Glu Ile
305                 310                 315                 320

Val Glu Glu


<210> SEQ ID NO 75
<211> LENGTH: 316
<212> TYPE: PRT
<213> ORGANISM: Glycyrrhiza glabra
<220> FEATURE:
<221> NAME/KEY: MISC_FEATURE
<223> OTHER INFORMATION: gi|1514979

<400> SEQUENCE: 75

Met Ala Ala Ala Ala Ile Glu Ile Pro Thr Lys Val Leu Pro Asn Ser
1               5                   10                  15

Thr Cys Glu Leu Arg Val Pro Val Ile Gly Met Gly Ser Ala Pro Asp
            20                  25                  30

Phe Thr Cys Lys Lys Asp Thr Lys Glu Ala Ile Ile Glu Ala Ile Lys
        35                  40                  45

Gln Gly Tyr Arg His Phe Asp Thr Ala Ala Ala Tyr Gly Ser Glu Thr
    50                  55                  60

Ala Leu Gly Glu Ala Leu Lys Glu Ala Arg Asp Leu Gly Leu Val Thr
65                  70                  75                  80

Arg Glu Asp Leu Phe Val Thr Ser Lys Leu Trp Val Thr Glu Asn His
                85                  90                  95

Pro His Leu Val Val Pro Ala Leu Arg Lys Ser Leu Glu Thr Leu Gln
            100                 105                 110

Leu Glu Tyr Leu Asp Leu Tyr Leu Ile His Trp Pro Leu Ser Ser Gln
        115                 120                 125

Pro Gly Lys Phe Ser Phe Pro Ile Gln Ala Glu Asp Leu Leu Pro Phe
    130                 135                 140

Asp Val Lys Gly Val Trp Glu Ser Met Glu Glu Ser Leu Lys Leu Gly
145                 150                 155                 160

Leu Thr Lys Ala Ile Gly Val Ser Asn Phe Ser Val Lys Lys Leu Gln
                165                 170                 175

Asn Leu Leu Ser Val Ala Thr Ile Arg Pro Ala Val Asn Gln Val Glu
            180                 185                 190

Met Asn Leu Ala Trp Gln Gln Lys Lys Leu Arg Glu Phe Cys Asn Ala
        195                 200                 205

Asn Gly Ile Val Leu Thr Ala Phe Ser Pro Leu Arg Lys Gly Ala Ser
    210                 215                 220

Arg Gly Pro Asn Glu Val Met Glu Asn Asp Met Leu Lys Gly Ile Ala
225                 230                 235                 240

Glu Ala His Gly Lys Ser Ile Ala Gln Val Ser Leu Arg Trp Leu Tyr
                245                 250                 255

Glu Gln Gly Val Thr Phe Val Ala Lys Ser Tyr Asp Lys Glu Arg Met
            260                 265                 270

Asn Gln Asn Leu Gln Ile Phe Asp Trp Glu Leu Thr Thr Glu Asp His
        275                 280                 285

Gln Lys Ile Asp Gln Ile Lys Gln Asn Arg Leu Ile Pro Gly Pro Thr
    290                 295                 300

Lys Pro Gln Leu Asn Asp Leu Trp Asp Asp Glu Ile
305                 310                 315
```

<210> SEQ ID NO 76
<211> LENGTH: 315
<212> TYPE: PRT
<213> ORGANISM: Glycyrrhiza glabra
<220> FEATURE:
<221> NAME/KEY: MISC_FEATURE
<223> OTHER INFORMATION: gi|1514981

<400> SEQUENCE: 76

Met Ala Ala Ala Ile Glu Ile Pro Thr Lys Val Leu Pro Asn Ser Thr
1               5                   10                  15

Cys Glu Leu Arg Val Pro Val Ile Gly Met Gly Ser Ala Pro Asp Phe
            20                  25                  30

Thr Cys Lys Lys Asp Thr Lys Glu Ala Ile Ile Glu Ala Ile Lys Gln
        35                  40                  45

Gly Tyr Arg His Phe Asp Thr Ala Ala Ala Tyr Gly Ser Glu Thr Ala
    50                  55                  60

Leu Gly Glu Ala Leu Lys Glu Ala Arg Asp Leu Gly Leu Val Thr Arg
65                  70                  75                  80

Glu Asp Leu Phe Val Thr Ser Lys Leu Trp Val Thr Glu Asn His Pro
                85                  90                  95

His Leu Val Val Pro Ala Leu Arg Lys Ser Leu Glu Thr Leu Gln Leu
            100                 105                 110

Glu Tyr Leu Asp Leu Tyr Leu Ile His Trp Pro Leu Ser Ser Gln Pro
        115                 120                 125

Gly Lys Phe Ser Phe Pro Ile Gln Ala Glu Asp Leu Leu Pro Phe Asp
    130                 135                 140

Val Lys Gly Val Trp Glu Ser Met Glu Glu Ser Leu Lys Leu Gly Leu
145                 150                 155                 160

Thr Lys Ala Ile Gly Val Ser Asn Phe Ser Val Lys Lys Leu Gln Asn
                165                 170                 175

Leu Leu Ser Val Ala Thr Ile Arg Pro Ala Val Asn Gln Val Glu Met
            180                 185                 190

Asn Leu Ala Trp Gln Gln Lys Lys Leu Arg Glu Phe Cys Asn Ala Asn
        195                 200                 205

Gly Ile Val Leu Thr Ala Phe Ser Pro Leu Arg Lys Gly Ala Ser Arg
    210                 215                 220

Gly Pro Asn Glu Val Met Glu Asn Asp Met Leu Lys Gly Ile Ala Glu
225                 230                 235                 240

Ala His Gly Lys Ser Ile Ala Gln Val Ser Leu Arg Trp Leu Tyr Glu
                245                 250                 255

Gln Gly Val Thr Phe Val Ala Lys Ser Tyr Asp Lys Glu Arg Met Asn
            260                 265                 270

Gln Asn Leu Gln Ile Phe Asp Trp Glu Leu Thr Thr Glu Asp His Gln
        275                 280                 285

Lys Ile Asp Gln Ile Lys Gln Asn Arg Leu Ile Pro Gly Pro Thr Lys
    290                 295                 300

Pro Gln Leu Asn Asp Leu Trp Asp Asp Glu Ile
305                 310                 315

<210> SEQ ID NO 77
<211> LENGTH: 1133
<212> TYPE: DNA
<213> ORGANISM: Arabidopsis thaliana
<220> FEATURE:
<221> NAME/KEY: MISC_FEATURE
<223> OTHER INFORMATION: clone125039_inplanta_experimental_L24

<400> SEQUENCE: 77

```
aagtttttga tttcagagtc caccgttgag cctgttcaat taaatcgttg aatctcgcgg     60
tgcgttttac tttgattctt tcgaattttt tttatatgga tgttgccgcg atggcgagat    120
gtgtgggaag gtgctacgtt tcgccggcgt tcggtgagtc tgaatcgcac cggttatcgg    180
agcggcggtt tctgaaattg tctagctcca cgaattcgga tcccgccggt agtaaaagtt    240
tgaagcttcg cgggaaaatt catcggagaa tgagctactt ccgtccgatc atggcaaaag    300
atgaatccat ttcatcgcgg tccggtgaaa cgaagcaaat caatggaaag caaaagaaca    360
ttgtctggca tgattgtccc gttactaaat ccgacaggca agaattaatt aagcataagg    420
gatgtgtgat ttggattact ggcttaagtg gttcaggtaa aagtagtctg gcatgtgctc    480
ttagtcgagc tttgcacaat cgtggaaagc tttcgtatat acttgatggt gacaatgttc    540
gacatggttt aaacagcgat cttagtttcg aagcagatga tcgagctgaa aacattcgaa    600
gagttggtga agtggctaaa ctgtttgcag attctggtat tatctgtatt gcaagtttaa    660
tatctcctta ccggatagaa cgagctgcct gccgtgcatt attaccacaa ggagatttca    720
ttgaggtatt tatggatgtg ccactccatg tttgtgaagc tagagatcca aagggcttat    780
acaaacgtgc acgcgctggt aaaatcaaag gttttacagg agtagatgat ccatatgaag    840
cgcctttgga ttgcgagatt gtaatacaaa acagtagaga caaggggctt tcttcttcat    900
cttcatcttc atcttcacct tcatcttcgt cttcttctct gtgtgaaatg gcagatattg    960
ttgtgtcgta cttggaccaa aatggatacc tgaagaaaca ctccacaaaa tcacgtgatt   1020
gtatgtaaat gtaatattaa tatcattgtt gtaacgtttc ttaaacctat tttacctatg   1080
gacgattaaa ttgtgaaaac ataaatgtaa ttcacaatct gcaaagagtt ggc          1133
```

<210> SEQ ID NO 78
<211> LENGTH: 310
<212> TYPE: PRT
<213> ORGANISM: Arabidopsis thaliana
<220> FEATURE:
<221> NAME/KEY: MISC_FEATURE
<223> OTHER INFORMATION: peptide_clone125039_inplanta_experimental_L24

<400> SEQUENCE: 78

```
Met Asp Val Ala Ala Met Ala Arg Cys Val Gly Arg Cys Tyr Val Ser
1               5                   10                  15

Pro Ala Phe Gly Glu Ser Glu Ser His Arg Leu Ser Glu Arg Arg Phe
            20                  25                  30

Leu Lys Leu Ser Ser Ser Thr Asn Ser Asp Pro Ala Gly Ser Lys Ser
        35                  40                  45

Leu Lys Leu Arg Gly Lys Ile His Arg Arg Met Ser Tyr Phe Arg Pro
    50                  55                  60

Ile Met Ala Lys Asp Glu Ser Ile Ser Ser Arg Ser Gly Glu Thr Lys
65                  70                  75                  80

Gln Ile Asn Gly Lys Gln Lys Asn Ile Val Trp His Asp Cys Pro Val
                85                  90                  95

Thr Lys Ser Asp Arg Gln Glu Leu Ile Lys His Lys Gly Cys Val Ile
            100                 105                 110

Trp Ile Thr Gly Leu Ser Gly Ser Gly Lys Ser Ser Leu Ala Cys Ala
        115                 120                 125

Leu Ser Arg Ala Leu His Asn Arg Gly Lys Leu Ser Tyr Ile Leu Asp
    130                 135                 140
```

```
Gly Asp Asn Val Arg His Gly Leu Asn Ser Asp Leu Ser Phe Glu Ala
145                 150                 155                 160

Asp Asp Arg Ala Glu Asn Ile Arg Arg Val Gly Glu Val Ala Lys Leu
                165                 170                 175

Phe Ala Asp Ser Gly Ile Ile Cys Ile Ala Ser Leu Ile Ser Pro Tyr
            180                 185                 190

Arg Ile Glu Arg Ala Ala Cys Arg Ala Leu Leu Pro Gln Gly Asp Phe
        195                 200                 205

Ile Glu Val Phe Met Asp Val Pro Leu His Val Cys Glu Ala Arg Asp
    210                 215                 220

Pro Lys Gly Leu Tyr Lys Arg Ala Arg Ala Gly Lys Ile Lys Gly Phe
225                 230                 235                 240

Thr Gly Val Asp Asp Pro Tyr Glu Ala Pro Leu Asp Cys Glu Ile Val
                245                 250                 255

Ile Gln Asn Ser Arg Asp Lys Gly Leu Ser Ser Ser Ser Ser Ser Ser
            260                 265                 270

Ser Ser Pro Ser Ser Ser Ser Ser Ser Leu Cys Glu Met Ala Asp Ile
        275                 280                 285

Val Val Ser Tyr Leu Asp Gln Asn Gly Tyr Leu Lys Lys His Ser Thr
    290                 295                 300

Lys Ser Arg Asp Cys Met
305                 310


<210> SEQ ID NO 79
<211> LENGTH: 271
<212> TYPE: PRT
<213> ORGANISM: Enteromorpha intestinalis
<220> FEATURE:
<221> NAME/KEY: MISC_FEATURE
<223> OTHER INFORMATION: gi|3329471

<400> SEQUENCE: 79

Met Leu Arg Ala Ile Ala Gln Arg Ala Arg Gly Ser Ala Leu Gln Cys
1               5                   10                  15

Ala Ala Pro Gly Thr Glu Trp Ala Ser Cys Val Arg Gly Ser Ser Gly
            20                  25                  30

Phe Thr Ala Tyr Asp Val Gly Glu Ser Thr Asn Ile Lys Trp His Glu
        35                  40                  45

Thr Met Val Ser Arg Gly Asp Lys Glu Arg Leu Leu Asn Gln Arg Gly
    50                  55                  60

Cys Val Leu Trp Phe Thr Gly Leu Ser Gly Ser Gly Lys Ser Thr Val
65                  70                  75                  80

Ala Cys Thr Leu Glu His Ala Leu Asn Ala Arg Gly Lys Met Thr Ala
                85                  90                  95

Leu Leu Asp Gly Asp Asn Val Arg His Gly Leu Asn Ser Asn Leu Thr
            100                 105                 110

Phe Thr Ala Glu Asp Arg Thr Glu His Pro Pro His Arg Arg Ser Glu
        115                 120                 125

Gln Ala Leu Cys Arg Arg Trp Arg Pro Pro Leu Arg Glu Leu His Leu
    130                 135                 140

Arg Pro Ile Ala Pro Thr Arg Pro Val Arg Glu Arg Cys Ala Gly Asp
145                 150                 155                 160

Phe Val Glu Cys Tyr Met Lys Ile Pro Ile Glu Leu Cys Glu Gln Arg
                165                 170                 175

Asp Pro Lys Gly Leu Tyr Lys Lys Ala Arg Ala Gly Leu Met Lys Gly
```

```
            180                 185                 190

Phe Thr Gly Ile Asp Asp Pro Tyr Glu Glu Pro Leu Glu Pro Glu Leu
        195                 200                 205

Thr Ile Thr Val Arg Glu Glu Gly Ser Asp Met Asn Ser Pro Glu Ala
    210                 215                 220

Met Ala Lys Gln Ile Phe Asp Tyr Leu Glu Ala Lys Gly Phe Leu Lys
225                 230                 235                 240

Gly Pro Ala Val Ala Ser Ser Gly Gly Ser Cys Ala Arg Val Ala Arg
                245                 250                 255

Trp Gly Gly His Gly Arg Arg Arg Gly Arg Gln Arg Leu Ala Trp
            260                 265                 270


<210> SEQ ID NO 80
<211> LENGTH: 290
<212> TYPE: PRT
<213> ORGANISM: Arabidopsis thaliana
<220> FEATURE:
<221> NAME/KEY: MISC_FEATURE
<223> OTHER INFORMATION: gi|9757873

<400> SEQUENCE: 80

Met Ala Arg Cys Val Gly Arg Cys Tyr Val Ser Pro Ala Phe Gly Glu
1               5                   10                  15

Ser Glu Ser His Arg Leu Ser Glu Arg Arg Phe Leu Lys Leu Ser Ser
            20                  25                  30

Ser Thr Asn Ser Asp Pro Ala Gly Ser Lys Ser Leu Lys Leu Arg Gly
        35                  40                  45

Lys Ile His Arg Arg Met Ser Tyr Phe Arg Pro Ile Met Ala Lys Asp
    50                  55                  60

Glu Ser Ile Ser Ser Arg Ser Gly Glu Thr Lys Gln Ile Asn Gly Lys
65                  70                  75                  80

Gln Lys Asn Ile Val Trp His Asp Cys Pro Val Thr Lys Ser Asp Arg
                85                  90                  95

Gln Glu Leu Ile Lys Gln Lys Gly Cys Val Ile Trp Ile Thr Gly Leu
            100                 105                 110

Ser Gly Ser Gly Lys Ser Ser Leu Ala Cys Ala Leu Ser Arg Ala Leu
        115                 120                 125

His Asn Arg Gly Lys Leu Ser Tyr Ile Leu Asp Gly Asp Asn Val Arg
    130                 135                 140

His Gly Leu Asn Ser Asp Leu Ser Phe Glu Ala Asp Asp Arg Ala Glu
145                 150                 155                 160

Asn Ile Arg Arg Val Gly Glu Val Ala Lys Leu Phe Ala Asp Ser Gly
                165                 170                 175

Ile Ile Cys Ile Ala Ser Leu Ile Ser Pro Tyr Arg Ile Glu Arg Ala
            180                 185                 190

Ala Cys Arg Ala Leu Leu Pro Gln Gly Asp Phe Ile Glu Val Phe Met
        195                 200                 205

Asp Val Pro Leu His Val Cys Glu Ala Arg Asp Pro Lys Gly Leu Tyr
    210                 215                 220

Lys Arg Ala Arg Ala Gly Lys Ile Lys Gly Phe Thr Gly Val Asp Asp
225                 230                 235                 240

Pro Tyr Glu Ala Pro Leu Asp Cys Glu Val His Ile Ile Ser Asn Phe
                245                 250                 255

Ser Ser Ser Ser Ser Leu Cys Glu Met Ala Asp Ile Val Val Ser Tyr
            260                 265                 270
```

```
Leu Asp Gln Asn Gly Tyr Leu Lys Lys His Ser Thr Lys Ser Arg Asn
        275                 280                 285

Cys Met
    290


<210> SEQ ID NO 81
<211> LENGTH: 312
<212> TYPE: PRT
<213> ORGANISM: Catharanthus roseus
<220> FEATURE:
<221> NAME/KEY: MISC_FEATURE
<223> OTHER INFORMATION: gi|2832300

<400> SEQUENCE: 81

Met Ile Gly Ser Val Lys Arg Pro Val Val Ser Cys Val Leu Pro Glu
1               5                   10                  15

Phe Asp Phe Thr Glu Ser Thr Gly Leu Gly Lys Lys Ser Ser Ser Val
            20                  25                  30

Lys Leu Pro Val Asn Phe Gly Ala Phe Gly Ser Gly Gly Gly Glu Val
        35                  40                  45

Lys Leu Gly Phe Leu Ala Pro Ile Lys Ala Thr Glu Gly Ser Lys Thr
    50                  55                  60

Ser Ser Phe Gln Val Asn Gly Lys Val Asp Asn Phe Arg His Leu Gln
65                  70                  75                  80

Pro Ser Asp Cys Asn Ser Asn Ser Asp Ser Ser Leu Asn Asn Cys Asn
                85                  90                  95

Gly Phe Pro Gly Lys Lys Ile Leu Gln Thr Thr Thr Val Gly Asn Ser
            100                 105                 110

Thr Asn Ile Leu Trp His Lys Cys Ala Val Glu Lys Ser Glu Arg Gln
        115                 120                 125

Glu Pro Leu Gln Gln Arg Gly Cys Val Ile Trp Ile Thr Gly Leu Ser
    130                 135                 140

Gly Ser Gly Lys Ser Thr Leu Ala Cys Ala Leu Ser Arg Gly Leu His
145                 150                 155                 160

Ala Lys Gly Lys Leu Thr Tyr Ile Leu Asp Gly Asp Asn Val Arg His
                165                 170                 175

Gly Leu Asn Ser Asp Leu Ser Phe Lys Ala Glu Asp Arg Ala Glu Asn
            180                 185                 190

Ile Arg Arg Ile Gly Glu Val Ala Lys Leu Phe Ala Asp Ala Gly Val
        195                 200                 205

Ile Cys Ile Ala Ser Leu Ile Ser Pro Tyr Arg Lys Pro Pro Asp Ala
    210                 215                 220

Cys Arg Ser Leu Leu Pro Glu Gly Asp Phe Ile Glu Val Phe Met Asp
225                 230                 235                 240

Val Pro Leu Lys Val Cys Glu Ala Arg Asp Pro Lys Gly Leu Tyr Lys
                245                 250                 255

Leu Ala Arg Ala Gly Lys Ile Lys Gly Phe Thr Gly Ile Asp Asp Pro
            260                 265                 270

Tyr Glu Pro Pro Leu Lys Ser Glu Ile Val Leu His Gln Lys Leu Gly
        275                 280                 285

Met Cys Asp Ser Pro Cys Asp Leu Ala Asp Ile Val Ile Ser Tyr Leu
    290                 295                 300

Glu Glu Asn Gly Tyr Leu Lys Ala
305                 310


<210> SEQ ID NO 82
```

<211> LENGTH: 275
<212> TYPE: PRT
<213> ORGANISM: Zea mays
<220> FEATURE:
<221> NAME/KEY: MISC_FEATURE
<223> OTHER INFORMATION: CeresClone:300011

<400> SEQUENCE: 82

```
Met Leu Ala Arg Ala Pro Pro Pro Arg Pro Cys Ser Ser Gly Val Cys
1               5                   10                  15

Ile Ala Arg Ala His Pro Arg Ala Ala Ala Val Ala Ala Arg Pro Gly
            20                  25                  30

Thr Thr Arg Thr Thr Thr Thr Val Ala Ala Ala Ala Ala Glu Ala Ala
        35                  40                  45

Ser Asn Gly Ser Ala Ala Ala Ala Val Ala Gly Ile Ser Ser Ser Ser
    50                  55                  60

Ser Ala Leu Val Thr Ser Thr Val Gly Lys Ser Thr Asn Ile Leu Trp
65                  70                  75                  80

His Glu Cys Ala Ile Gly Gln Lys Glu Arg Gln Gly Leu Leu Asn Gln
                85                  90                  95

Lys Gly Cys Val Val Trp Ile Thr Gly Leu Ser Gly Ser Gly Lys Ser
            100                 105                 110

Thr Leu Ala Cys Ala Leu Ser Arg Glu Leu His Gly Arg Gly His Leu
        115                 120                 125

Thr Tyr Val Leu Asp Gly Asp Asn Leu Arg His Gly Leu Asn Arg Asp
    130                 135                 140

Leu Ser Phe Gly Ala Glu Asp Arg Ala Glu Asn Ile Arg Arg Val Gly
145                 150                 155                 160

Glu Val Ala Lys Leu Phe Ala Asp Ala Gly Leu Val Cys Ile Ala Ser
                165                 170                 175

Leu Ile Ser Pro Tyr Arg Ser Asp Arg Ser Ala Cys Arg Asp Leu Leu
            180                 185                 190

Pro Lys His Ser Phe Ile Glu Val Phe Leu Asp Val Pro Leu Gln Val
        195                 200                 205

Cys Glu Ala Arg Asp Pro Lys Gly Leu Tyr Lys Leu Ala Arg Ala Gly
    210                 215                 220

Lys Ile Lys Gly Phe Thr Gly Ile Asp Asp Pro Tyr Glu Pro Pro Ser
225                 230                 235                 240

Asp Cys Glu Ile Val Ile Gln Cys Lys Val Gly Asp Cys Pro Ser Pro
                245                 250                 255

Glu Ser Met Ala Gly His Val Val Ser Tyr Leu Glu Thr Asn Gly Phe
            260                 265                 270

Leu Gln Asp
        275
```

<210> SEQ ID NO 83
<211> LENGTH: 345
<212> TYPE: PRT
<213> ORGANISM: Oryza sativa subsp. japonica
<220> FEATURE:
<221> NAME/KEY: MISC_FEATURE
<223> OTHER INFORMATION: gi|50938537

<400> SEQUENCE: 83

```
Met Glu Ala Ser Leu Pro Phe His His His His Pro Ala Ala Ser Ser
1               5                   10                  15

Thr Ala Ala His His Ala Ala Arg Leu Thr Pro Pro Pro Pro Pro Arg
            20                  25                  30
```

```
Asp Pro Arg Ala Thr Ala Arg Trp Val Pro Pro Ala Ala Ala Pro Val
        35                  40                  45

Arg Ser Arg Ser Pro Ala Asn Leu Gly Leu Pro Pro His Pro Pro Arg
    50                  55                  60

Arg Leu Arg Leu Arg Leu Ala Pro Pro Arg Ile Thr Ala Ala Val Thr
65                  70                  75                  80

Gly Gly Pro Arg Arg Pro Arg Arg Arg Ala Pro Pro Pro Leu Glu Cys
                85                  90                  95

Ala Gly Gly Ser Ser Ser Ser Leu Arg Arg Pro Arg Glu Glu Glu Glu
            100                 105                 110

Glu Glu Glu Glu Glu Glu Arg Ser Ser Thr Ala His Ala Gly Val Ser
        115                 120                 125

Leu Val Gly Glu Asn Lys Val Leu Gln Met Ser Ser Ile Val Pro Lys
    130                 135                 140

Ala Ser Asn Ile Phe Trp His Asp Cys Ala Val Gly Gln Ala Asp Arg
145                 150                 155                 160

Gln Lys Leu Leu Lys Gln Lys Gly Cys Val Val Trp Ile Thr Gly Leu
                165                 170                 175

Ser Gly Ser Gly Lys Ser Thr Leu Ala Cys Thr Leu Asp Arg Glu Leu
            180                 185                 190

His Thr Arg Gly Lys Leu Ser Tyr Val Leu Asp Gly Asp Asn Leu Arg
        195                 200                 205

His Gly Leu Asn Lys Asp Leu Gly Phe Lys Ala Glu Asp Arg Ala Glu
    210                 215                 220

Asn Ile Arg Arg Val Gly Glu Val Ala Lys Leu Phe Ala Asp Ala Gly
225                 230                 235                 240

Leu Val Cys Ile Ala Ser Phe Ile Ser Pro Tyr Arg Arg Asp Arg Glu
                245                 250                 255

Ser Cys Arg Ala Leu Leu Ser Asp Gly Ser Phe Ile Glu Val Phe Leu
            260                 265                 270

Asn Met Pro Leu Glu Leu Cys Glu Ser Arg Asp Pro Lys Gly Leu Tyr
        275                 280                 285

Lys Leu Ala Arg Ala Gly Lys Ile Lys Gly Phe Thr Gly Ile Asp Asp
    290                 295                 300

Pro Tyr Glu Ser Pro Leu Asn Ser Glu Ile Glu Ile Lys Glu Val Asp
305                 310                 315                 320

Gly Val Cys Pro Ser Pro Ser Asp Met Ala Gly Gln Val Val Thr Tyr
                325                 330                 335

Leu Glu Glu Lys Gly Phe Leu His Asp
            340                 345
```

<210> SEQ ID NO 84
<211> LENGTH: 497
<212> TYPE: DNA
<213> ORGANISM: Arabidopsis thaliana
<220> FEATURE:
<221> NAME/KEY: MISC_FEATURE
<223> OTHER INFORMATION: 10044_13489782_L33

<400> SEQUENCE: 84

```
aagaactcac ctaacacaca aacaaaggaa cttcactttt ttttcccaca ccacatcaca      60

ccatgtttag agccatgagc acaaggaaag tccatggtgg ctacgaaaag ctcggcgatg     120

aagaagcgag actgaagagg gtctctagcg ttccggctag tgtttatggt cattcaagaa     180

acccggttca agaagtgaag aagacaccga cagcgaaacc aaccggtggt tctgttcatc     240
```

```
ctttgtttag tttctttgac gttcattttc aaagaaagaa gaagaagacg acgaagaaga    300

agagtttagc aacggcgaaa ccagagtttg ctaggtatat ggagtatgtg agagaaggag    360

gtgtatggga tccgagttct aacgcaccag tgattcatta cagatagatt cgtcaaggaa    420

aatgaataaa agatttgtat atcgtctttt ttttcaaata tataatctat gagaaagcca    480

aacaatcctt gattcgg                                                   497


<210> SEQ ID NO 85
<211> LENGTH: 114
<212> TYPE: PRT
<213> ORGANISM: Arabidopsis thaliana
<220> FEATURE:
<221> NAME/KEY: MISC_FEATURE
<223> OTHER INFORMATION: peptide_10044_13489782_L33

<400> SEQUENCE: 85

Met Phe Arg Ala Met Ser Thr Arg Lys Val His Gly Gly Tyr Glu Lys
1               5                   10                  15

Leu Gly Asp Glu Glu Ala Arg Leu Lys Arg Val Ser Ser Val Pro Ala
            20                  25                  30

Ser Val Tyr Gly His Ser Arg Asn Pro Val Gln Glu Val Lys Lys Thr
        35                  40                  45

Pro Thr Ala Lys Pro Thr Gly Gly Ser Val His Pro Leu Phe Ser Phe
    50                  55                  60

Phe Asp Val His Phe Gln Arg Lys Lys Lys Lys Thr Thr Lys Lys Lys
65                  70                  75                  80

Ser Leu Ala Thr Ala Lys Pro Glu Phe Ala Arg Tyr Met Glu Tyr Val
                85                  90                  95

Arg Glu Gly Gly Val Trp Asp Pro Ser Ser Asn Ala Pro Val Ile His
            100                 105                 110

Tyr Arg


<210> SEQ ID NO 86
<211> LENGTH: 114
<212> TYPE: PRT
<213> ORGANISM: Arabidopsis thaliana
<220> FEATURE:
<221> NAME/KEY: MISC_FEATURE
<223> OTHER INFORMATION: gi|4835241

<400> SEQUENCE: 86

Met Phe Arg Ala Met Ser Thr Arg Lys Ile His Gly Gly Tyr Glu Lys
1               5                   10                  15

Leu Gly Asp Glu Glu Ala Arg Leu Lys Arg Val Ser Ser Val Pro Ala
            20                  25                  30

Ser Val Tyr Gly His Ser Arg Asn Pro Val Gln Glu Val Lys Lys Thr
        35                  40                  45

Pro Thr Ala Lys Pro Thr Gly Gly Ser Val His Pro Leu Phe Ser Phe
    50                  55                  60

Phe Asp Val His Phe Gln Arg Lys Lys Lys Asn Thr Ala Lys Lys Lys
65                  70                  75                  80

Ser Leu Ala Thr Ala Lys Pro Glu Phe Ala Arg Tyr Met Glu Tyr Val
                85                  90                  95

Arg Glu Gly Gly Val Trp Asp Pro Ser Ser Asn Ala Pro Val Ile His
            100                 105                 110

Tyr Arg
```

<210> SEQ ID NO 87
<211> LENGTH: 113
<212> TYPE: PRT
<213> ORGANISM: Brassica napus
<220> FEATURE:
<221> NAME/KEY: MISC_FEATURE
<223> OTHER INFORMATION: CeresClone:1068483

<400> SEQUENCE: 87

```
Met Phe Arg Ala Met Ser Thr Arg Lys Val His Gly Gly Tyr Glu Lys
1               5                   10                  15

Leu Val Glu Asp Glu Pro Lys Leu Lys Arg Val Thr Ser Val Pro Ala
            20                  25                  30

Ser Val Tyr Gly Asn Ser Arg Asn Pro Val Gln Glu Glu Val Lys Lys
        35                  40                  45

Thr Pro Thr Val Lys Pro Thr Gly Gly Ser Val His Pro Leu Leu Ser
    50                  55                  60

Phe Phe Asp Val Arg Phe Gln Lys Lys Lys Lys Lys Thr Lys Lys Ser
65                  70                  75                  80

Leu Ala Thr Ala Lys Pro Glu Phe Ala Arg Tyr Met Ala Tyr Val Lys
                85                  90                  95

Glu Gly Gly Val Trp Asp Pro Asn Ser Asn Ala Pro Val Ile His Tyr
            100                 105                 110

Arg
```

<210> SEQ ID NO 88
<211> LENGTH: 118
<212> TYPE: PRT
<213> ORGANISM: Glycine max
<220> FEATURE:
<221> NAME/KEY: MISC_FEATURE
<223> OTHER INFORMATION: CeresClone:584111

<400> SEQUENCE: 88

```
Met Phe Arg Ser Met Thr Thr Arg Arg Gly Tyr Glu Arg Leu Gly Lys
1               5                   10                  15

Glu Ser Ala Thr Thr Ala Leu Leu His Glu Gly Phe Lys Arg Ser Thr
            20                  25                  30

Ser Leu Pro Ser Trp Gly Ser Asn Ser Ser Arg Lys Met Ala Leu Gly
        35                  40                  45

Ser Thr Tyr Gly Glu Ile Asn Leu Lys Arg Asn Pro Thr Lys Lys Gly
    50                  55                  60

Asn Asn Asn Ser Asp Lys Lys Ser His Pro Leu Leu Ser Phe Leu Ala
65                  70                  75                  80

Leu Arg Arg Lys Lys Lys Thr Thr Ala Arg Pro Glu Phe Ala Arg Tyr
                85                  90                  95

Leu Glu Tyr Leu Lys Glu Gly Gly Met Trp Asp Phe Asn Ser Asn Lys
            100                 105                 110

Pro Val Met Tyr Tyr Glu
        115
```

<210> SEQ ID NO 89
<211> LENGTH: 913
<212> TYPE: DNA
<213> ORGANISM: Arabidopsis thaliana
<220> FEATURE:
<221> NAME/KEY: MISC_FEATURE
<223> OTHER INFORMATION: 10987_3769_L34

<400> SEQUENCE: 89

```
aaaaatctgg aacggataaa ataatttgct cggcttcctc agctccaatg gcggcgacga     60
tgatcggaat taacctctcc tgcttcaaat caacatcgtt cttctcaccg gacctcaatt    120
ctctccaatc aaagctctct ctcctatctc tcaaaccctc tccaacacag ccacggaaat    180
caacagtcat ccgtatgggc ggtggtccga gaactttccc cggcggtgta tcaaaatggc    240
aatggaaaag gatgcaagcg aagaaacaga aacagcttct caaagcaagg ttatgcagag    300
aacgtcagat ctacgagatg cgaaaacgcg ccgagctaaa agcggcggtg gctgagctag    360
aacgaccatg ggaaccgatt cataaaccac cgaatctatt ctcagtttgt gctgatgagc    420
aagttaaagt actcgcggat cggtttcaga aacctggtgg atttgattta tggactgata    480
gagatggtcc tcaattgttt gagagtgttg atgatttgcc ttctgctagg tttttcccta    540
aaggtgttgt tcatagtgtt aaaccttatg gtagattatc atctagctct gttgttgatg    600
atggtgatga gagtgaggtt aaagatgaag aaattgggaa gaagttacgt ggtcgtaggg    660
tgaggaagag aggtgatgat ggaggtaaga ggaggactga aaatcgtggt aatggtggga    720
gattgagaaa tggagggtct tcttcttctc aggtgtatga tatgactttg cagaatgatg    780
ggagatatga aattggatct taggtatgag ttcttctttg ttgtgtttgg atcattgatg    840
tctctgaaca taatttgtat gtaatctgga atagtttgat tgtgattatg caagttttca    900
gttttaggga agc                                                       913
```

```
<210> SEQ ID NO 90
<211> LENGTH: 251
<212> TYPE: PRT
<213> ORGANISM: Arabidopsis thaliana
<220> FEATURE:
<221> NAME/KEY: MISC_FEATURE
<223> OTHER INFORMATION: peptide_10987_3769_L34

<400> SEQUENCE: 90

Met Ala Ala Thr Met Ile Gly Ile Asn Leu Ser Cys Phe Lys Ser Thr
1               5                   10                  15

Ser Phe Phe Ser Pro Asp Leu Asn Ser Leu Gln Ser Lys Leu Ser Leu
            20                  25                  30

Leu Ser Leu Lys Pro Ser Pro Thr Gln Pro Arg Lys Ser Thr Val Ile
        35                  40                  45

Arg Met Gly Gly Gly Pro Arg Thr Phe Pro Gly Gly Val Ser Lys Trp
    50                  55                  60

Gln Trp Lys Arg Met Gln Ala Lys Lys Gln Lys Gln Leu Leu Lys Ala
65                  70                  75                  80

Arg Leu Cys Arg Glu Arg Gln Ile Tyr Glu Met Arg Lys Arg Ala Glu
                85                  90                  95

Leu Lys Ala Ala Val Ala Glu Leu Glu Arg Pro Trp Glu Pro Ile His
            100                 105                 110

Lys Pro Pro Asn Leu Phe Ser Val Cys Ala Asp Glu Gln Val Lys Val
        115                 120                 125

Leu Ala Asp Arg Phe Gln Lys Pro Gly Gly Phe Asp Leu Trp Thr Asp
    130                 135                 140

Arg Asp Gly Pro Gln Leu Phe Glu Ser Val Asp Asp Leu Pro Ser Ala
145                 150                 155                 160

Arg Phe Phe Pro Lys Gly Val Val His Ser Val Lys Pro Tyr Gly Arg
                165                 170                 175

Leu Ser Ser Ser Ser Val Val Asp Asp Gly Asp Glu Ser Glu Val Lys
            180                 185                 190
```

Asp Glu Glu Ile Gly Lys Lys Leu Arg Gly Arg Arg Val Arg Lys Arg
195 200 205

Gly Asp Asp Gly Gly Lys Arg Arg Thr Glu Asn Arg Gly Asn Gly Gly
210 215 220

Arg Leu Arg Asn Gly Gly Ser Ser Ser Ser Gln Val Tyr Asp Met Thr
225 230 235 240

Leu Gln Asn Asp Gly Arg Tyr Glu Ile Gly Ser
245 250

<210> SEQ ID NO 91
<211> LENGTH: 1252
<212> TYPE: DNA
<213> ORGANISM: Arabidopsis thaliana
<220> FEATURE:
<221> NAME/KEY: MISC_FEATURE
<223> OTHER INFORMATION: cdna13500101_clone17206_L35

<400> SEQUENCE: 91
atcattcgtg tactaatttt accttcatag acttaattaa gatacgatca tggcgtcgtt 60
tgtctttgtg atttctcttc ttcttctctc tttttcgtcg gctgttttct ccgatgatgc 120
ttcttttcag aaacttccgg tgcctgacaa gaggtcaggc cctgaatctt tcgcctttga 180
ctctaccggc ggattctaca ccggagtctc cggtggtaaa atcctcaagt acgttcctgg 240
gaagggttat gtcgattttg cccagatcac agattcctcg aactcggcat ggtgcaacgg 300
agcattagga accgctttcg ccggaaagtg tggtcgacca gcgggaatag ccttaaacag 360
caaaacaggt gatctctatg tcgccgatgc tccgttgggt cttcacgtta tctctcccgc 420
aggaggtttg gccacaaagc tggccgacag tgttgacgga aagcctttca agtttcttga 480
cggtcttgat gttgatccca ccaccggcgt cgtctacttc acttccttca gttccaagtt 540
tggaccccgg gaagtgttaa tcgcagtggg attaaaagac gcgagcggaa agctgttcaa 600
atacgaccca gcgaccaaag ccgtgactga gttaatggaa ggtctaagtg gtgctgctgg 660
ttgtgcagtg agctcagatg gttcattcgt gctagttagc gagttcataa agagtaacat 720
caagaaatat tggattaaag ggcccaaagc tggaactatt gaagacttct caagtcttgt 780
ctcgaacccc gacaacatca ggagggtagg ttctaccgga aatttctggg tcgcctctgt 840
cgtgaacaag gttgttatgc ctaccgaccc tagggcggtc aaactagacg ctaatggaaa 900
agtgctccag accattttcc tcaagaatga gtttgggaat actttgctta gtgaagtcaa 960
cgagttcaac ggccatcttt acatcggaac tcttactgga cctttcgccg gagtcatgaa 1020
actttaaatt ggtatcaact atatggttct ttggtgatta ccatttttga tatcattttg 1080
aaaggtctgt ttacagttat tttaaccata ataatatccc ctcaaatgtc ctgcttgtta 1140
cgtgggtgac acatttgttc ggtgattcct tgaataggct actactactt attgtttcat 1200
attttcgaag agattatctc tagttcttaa ggctttggtt ttctttgttt cc 1252

<210> SEQ ID NO 92
<211> LENGTH: 325
<212> TYPE: PRT
<213> ORGANISM: Arabidopsis thaliana
<220> FEATURE:
<221> NAME/KEY: MISC_FEATURE
<223> OTHER INFORMATION: peptide_cdna13500101_clone17206_L35

<400> SEQUENCE: 92

Met Ala Ser Phe Val Phe Val Ile Ser Leu Leu Leu Leu Ser Phe Ser
1 5 10 15

```
Ser Ala Val Phe Ser Asp Asp Ala Ser Phe Gln Lys Leu Pro Val Pro
            20                  25                  30

Asp Lys Arg Ser Gly Pro Glu Ser Phe Ala Phe Asp Ser Thr Gly Gly
        35                  40                  45

Phe Tyr Thr Gly Val Ser Gly Gly Lys Ile Leu Lys Tyr Val Pro Gly
    50                  55                  60

Lys Gly Tyr Val Asp Phe Ala Gln Ile Thr Asp Ser Ser Asn Ser Ala
65                  70                  75                  80

Trp Cys Asn Gly Ala Leu Gly Thr Ala Phe Ala Gly Lys Cys Gly Arg
                85                  90                  95

Pro Ala Gly Ile Ala Leu Asn Ser Lys Thr Gly Asp Leu Tyr Val Ala
            100                 105                 110

Asp Ala Pro Leu Gly Leu His Val Ile Ser Pro Ala Gly Gly Leu Ala
        115                 120                 125

Thr Lys Leu Ala Asp Ser Val Asp Gly Lys Pro Phe Lys Phe Leu Asp
    130                 135                 140

Gly Leu Asp Val Asp Pro Thr Thr Gly Val Val Tyr Phe Thr Ser Phe
145                 150                 155                 160

Ser Ser Lys Phe Gly Pro Arg Glu Val Leu Ile Ala Val Gly Leu Lys
                165                 170                 175

Asp Ala Ser Gly Lys Leu Phe Lys Tyr Asp Pro Ala Thr Lys Ala Val
            180                 185                 190

Thr Glu Leu Met Glu Gly Leu Ser Gly Ala Ala Gly Cys Ala Val Ser
        195                 200                 205

Ser Asp Gly Ser Phe Val Leu Val Ser Glu Phe Ile Lys Ser Asn Ile
    210                 215                 220

Lys Lys Tyr Trp Ile Lys Gly Pro Lys Ala Gly Thr Ile Glu Asp Phe
225                 230                 235                 240

Ser Ser Leu Val Ser Asn Pro Asp Asn Ile Arg Arg Val Gly Ser Thr
                245                 250                 255

Gly Asn Phe Trp Val Ala Ser Val Val Asn Lys Val Val Met Pro Thr
            260                 265                 270

Asp Pro Arg Ala Val Lys Leu Asp Ala Asn Gly Lys Val Leu Gln Thr
        275                 280                 285

Ile Phe Leu Lys Asn Glu Phe Gly Asn Thr Leu Leu Ser Glu Val Asn
    290                 295                 300

Glu Phe Asn Gly His Leu Tyr Ile Gly Thr Leu Thr Gly Pro Phe Ala
305                 310                 315                 320

Gly Val Met Lys Leu
                325


<210> SEQ ID NO 93
<211> LENGTH: 335
<212> TYPE: PRT
<213> ORGANISM: Arabidopsis thaliana
<220> FEATURE:
<221> NAME/KEY: MISC_FEATURE
<223> OTHER INFORMATION: gi|17104523

<400> SEQUENCE: 93

Met Thr Ser Phe Cys Ser Met Ile Ser Leu Leu Leu Leu Leu Ser Leu
1               5                   10                  15

Ser Ser Ala Val Phe Ser Asp Asp Ala Ser Phe Gln Lys Leu Pro Val
            20                  25                  30

Pro Glu Thr Arg Ser Gly Pro Glu Ala Phe Ala Phe Asp Ser Thr Gly
```

```
        35                  40                  45

Lys Gly Phe Tyr Thr Gly Val Ser Gly Gly Lys Ile Leu Lys Tyr Leu
    50                  55                  60

Pro Glu Thr Gly Tyr Val Asp Phe Ala Gln Ile Thr Glu Ser Ser Asn
65                  70                  75                  80

Ser Ser Trp Cys Asp Gly Thr Ile Gly Thr Ala Leu Ala Gly Arg Cys
                85                  90                  95

Gly Arg Pro Ala Gly Ile Ala Phe Asn Glu Lys Thr Gly Asp Leu Tyr
            100                 105                 110

Val Ala Asp Ala Pro Leu Gly Leu His Val Ile Ser Pro Ala Gly Gly
        115                 120                 125

Leu Ala Thr Lys Ile Thr Asp Ser Val Asp Gly Lys Pro Phe Lys Phe
    130                 135                 140

Leu Asp Gly Leu Asp Val Asp Pro Thr Thr Gly Val Val Tyr Phe Thr
145                 150                 155                 160

Ser Phe Ser Ser Arg Phe Ser Pro Ile Gln Val Leu Ile Ala Leu Gly
                165                 170                 175

Leu Lys Asp Ala Thr Gly Lys Leu Tyr Lys Tyr Asp Pro Ser Thr Lys
            180                 185                 190

Val Val Thr Val Leu Met Glu Gly Leu Ser Gly Ser Ala Gly Cys Ala
        195                 200                 205

Val Ser Ser Asp Gly Ser Phe Val Leu Val Ser Gln Phe Thr Lys Ser
    210                 215                 220

Asn Ile Lys Arg Tyr Trp Ile Lys Gly Pro Lys Ala Gly Ser Ser Glu
225                 230                 235                 240

Asp Phe Thr Asn Ser Val Ser Asn Pro Asp Asn Ile Lys Arg Ile Gly
                245                 250                 255

Ser Thr Gly Asn Phe Trp Val Ala Ser Val Val Asn Lys Ile Ile Val
            260                 265                 270

Pro Thr Asn Pro Ser Ala Val Lys Val Asn Ser Asn Gly Glu Val Leu
        275                 280                 285

Gln Thr Ile Pro Leu Lys Asp Lys Phe Gly Asp Thr Leu Leu Ser Glu
    290                 295                 300

Val Asn Glu Phe Glu Gly Asn Leu Tyr Ile Gly Thr Leu Thr Gly Pro
305                 310                 315                 320

Phe Ala Gly Ile Leu Lys Leu Glu Lys Gly Ser Cys Pro Ala Thr
                325                 330                 335


<210> SEQ ID NO 94
<211> LENGTH: 335
<212> TYPE: PRT
<213> ORGANISM: Arabidopsis thaliana
<220> FEATURE:
<221> NAME/KEY: MISC_FEATURE
<223> OTHER INFORMATION: gi|1754985

<400> SEQUENCE: 94

Met Thr Ser Phe Cys Ser Met Ile Ser Leu Leu Leu Leu Leu Ser Leu
1               5                   10                  15

Ser Ser Pro Val Phe Ser Asp Asp Ala Ser Phe Gln Lys Leu Pro Val
            20                  25                  30

Pro Glu Thr Arg Ser Gly Pro Glu Ala Phe Ala Phe Asp Ser Thr Gly
        35                  40                  45

Lys Gly Phe Tyr Thr Gly Val Ser Gly Gly Lys Ile Leu Lys Tyr Leu
    50                  55                  60
```

```
Pro Glu Thr Gly Tyr Val Asp Phe Ala Gln Ile Thr Glu Ser Ser Asn
65                  70                  75                  80

Ser Ser Trp Cys Asp Gly Thr Ile Gly Thr Ala Leu Ala Gly Arg Cys
                85                  90                  95

Gly Arg Pro Ala Gly Ile Ala Phe Asn Glu Lys Thr Gly Asp Leu Tyr
            100                 105                 110

Val Ala Asp Ala Pro Leu Gly Leu His Val Ile Ser Pro Ala Gly Gly
        115                 120                 125

Leu Ala Thr Lys Ile Thr Asp Ser Val Asp Gly Lys Pro Phe Lys Phe
    130                 135                 140

Leu Asp Gly Leu Asp Val Asp Pro Thr Thr Gly Val Val Tyr Phe Thr
145                 150                 155                 160

Ser Phe Ser Ser Arg Phe Ser Pro Ile Gln Val Leu Ile Ala Leu Gly
                165                 170                 175

Leu Lys Asp Ala Thr Gly Lys Leu Tyr Lys Tyr Asp Pro Ser Thr Lys
            180                 185                 190

Val Val Thr Val Leu Met Glu Gly Leu Ser Gly Ser Ala Gly Cys Ala
        195                 200                 205

Val Ser Ser Asp Gly Ser Phe Val Leu Val Ser Gln Phe Thr Lys Ser
    210                 215                 220

Asn Ile Lys Arg Tyr Trp Ile Lys Gly Pro Lys Ala Gly Ser Ser Glu
225                 230                 235                 240

Asp Phe Thr Asn Ser Val Ser Asn Pro Asp Asn Ile Lys Arg Ile Gly
                245                 250                 255

Ser Thr Gly Asn Phe Trp Val Ala Ser Val Val Asn Lys Ile Ile Val
            260                 265                 270

Pro Thr Asn Pro Ser Ala Val Lys Val Asn Ser Asn Gly Glu Val Leu
        275                 280                 285

Gln Thr Ile Pro Leu Lys Asp Lys Phe Gly Asp Thr Leu Leu Ser Glu
    290                 295                 300

Val Asn Glu Phe Glu Gly Asn Leu Tyr Ile Gly Thr Leu Thr Gly Pro
305                 310                 315                 320

Phe Ala Gly Ile Leu Lys Ile Glu Lys Gly Ser Cys Pro Ala Thr
                325                 330                 335


<210> SEQ ID NO 95
<211> LENGTH: 338
<212> TYPE: PRT
<213> ORGANISM: Arabidopsis thaliana
<220> FEATURE:
<221> NAME/KEY: MISC_FEATURE
<223> OTHER INFORMATION: CeresClone:124660
<220> FEATURE:
<221> NAME/KEY: misc_feature
<222> LOCATION: (102)..(102)
<223> OTHER INFORMATION: Xaa can be any naturally occurring amino acid

<400> SEQUENCE: 95

Met Thr Ser Phe Cys Ser Met Ile Ser Leu Leu Leu Leu Leu Leu Leu
1               5                   10                  15

Leu Ser Leu Ser Ser Ala Val Ile Ser Asp Asp Ala Ser Phe Gln Lys
            20                  25                  30

Leu Pro Val Pro Glu Thr Arg Ser Gly Pro Glu Ala Phe Ala Phe Asp
        35                  40                  45

Ser Thr Gly Lys Gly Phe Tyr Thr Gly Val Ser Gly Gly Lys Ile Leu
    50                  55                  60

Lys Tyr Leu Pro Glu Thr Gly Tyr Val Asp Phe Ala Gln Ile Thr Glu
```

```
65                  70                  75                  80

Ser Ser Asn Ser Ser Trp Cys Asp Gly Thr Ile Gly Thr Ala Leu Ala
                85                  90                  95

Gly Arg Cys Gly Arg Xaa Ala Gly Ile Ala Phe Asn Glu Lys Thr Gly
            100                 105                 110

Asp Leu Tyr Val Ala Asp Ala Pro Leu Gly Leu His Val Ile Ser Pro
        115                 120                 125

Ala Gly Gly Leu Ala Thr Lys Ile Thr Asp Ser Val Asp Gly Lys Pro
    130                 135                 140

Phe Lys Phe Leu Asp Gly Leu Asp Val Asp Pro Thr Thr Gly Val Val
145                 150                 155                 160

Tyr Phe Thr Ser Phe Ser Ser Arg Phe Ser Pro Ile Gln Val Leu Ile
                165                 170                 175

Ala Leu Gly Leu Lys Asp Ala Thr Gly Lys Leu Tyr Lys Tyr Asp Pro
            180                 185                 190

Ser Thr Lys Val Val Thr Val Leu Met Glu Gly Leu Ser Gly Ser Ala
        195                 200                 205

Gly Cys Ala Val Ser Ser Asp Gly Ser Phe Val Leu Val Ser Gln Phe
    210                 215                 220

Thr Lys Ser Asn Ile Lys Arg Tyr Trp Ile Lys Gly Pro Lys Ala Gly
225                 230                 235                 240

Ser Ser Glu Asp Phe Thr Asn Ser Val Ser Asn Pro Asp Asn Ile Lys
                245                 250                 255

Arg Ile Gly Ser Thr Gly Asn Phe Trp Val Ala Ser Val Val Asn Lys
            260                 265                 270

Ile Ile Val Pro Thr Asn Pro Ser Ala Val Lys Val Asn Ser Asn Gly
        275                 280                 285

Glu Val Leu Gln Thr Ile Pro Leu Lys Asp Lys Phe Gly Asp Thr Leu
    290                 295                 300

Leu Ser Glu Val Asn Glu Phe Glu Gly Asn Leu Tyr Ile Gly Thr Leu
305                 310                 315                 320

Thr Gly Pro Phe Ala Gly Ile Leu Lys Leu Glu Lys Gly Ser Cys Pro
                325                 330                 335

Ala Thr


<210> SEQ ID NO 96
<211> LENGTH: 344
<212> TYPE: PRT
<213> ORGANISM: Rauvolfia serpentina
<220> FEATURE:
<221> NAME/KEY: MISC_FEATURE
<223> OTHER INFORMATION: gi|62903513

<400> SEQUENCE: 96

Met Ala Lys Leu Ser Asp Ser Gln Thr Met Ala Leu Phe Thr Val Phe
1               5                   10                  15

Leu Leu Phe Leu Ser Ser Ser Leu Ala Leu Ser Ser Pro Ile Leu Lys
            20                  25                  30

Glu Ile Leu Ile Glu Ala Pro Ser Tyr Ala Pro Asn Ser Phe Thr Phe
        35                  40                  45

Asp Ser Thr Asn Lys Gly Phe Tyr Thr Ser Val Gln Asp Gly Arg Val
    50                  55                  60

Ile Lys Tyr Glu Gly Pro Asn Ser Gly Phe Val Asp Phe Ala Tyr Ala
65                  70                  75                  80

Ser Pro Tyr Trp Asn Lys Ala Phe Cys Glu Asn Ser Thr Asp Ala Glu
```

-continued

```
                85                  90                  95

Lys Arg Pro Leu Cys Gly Arg Thr Tyr Asp Ile Ser Tyr Asn Leu Gln
            100                 105                 110

Asn Asn Gln Leu Tyr Ile Val Asp Cys Tyr Tyr His Leu Ser Val Val
        115                 120                 125

Gly Ser Glu Gly Gly His Ala Thr Gln Leu Ala Thr Ser Val Asp Gly
    130                 135                 140

Val Pro Phe Lys Trp Leu Tyr Ala Val Thr Val Asp Gln Arg Thr Gly
145                 150                 155                 160

Ile Val Tyr Phe Thr Asp Val Ser Thr Leu Tyr Asp Asp Arg Gly Val
                165                 170                 175

Gln Gln Ile Met Asp Thr Ser Asp Lys Thr Gly Arg Leu Ile Lys Tyr
            180                 185                 190

Asp Pro Ser Thr Lys Glu Thr Thr Leu Leu Leu Lys Glu Leu His Val
        195                 200                 205

Pro Gly Gly Ala Glu Val Ser Ala Asp Ser Ser Phe Val Leu Val Ala
    210                 215                 220

Glu Phe Leu Ser His Gln Ile Val Lys Tyr Trp Leu Glu Gly Pro Lys
225                 230                 235                 240

Lys Gly Thr Ala Glu Val Leu Val Lys Ile Pro Asn Pro Gly Asn Ile
                245                 250                 255

Lys Arg Asn Ala Asp Gly His Phe Trp Val Ser Ser Ser Glu Glu Leu
            260                 265                 270

Asp Gly Asn Met His Gly Arg Val Asp Pro Lys Gly Ile Lys Phe Asp
        275                 280                 285

Glu Phe Gly Asn Ile Leu Glu Val Ile Pro Leu Pro Pro Pro Phe Ala
    290                 295                 300

Gly Glu His Phe Glu Gln Ile Gln Glu His Asp Gly Leu Leu Tyr Ile
305                 310                 315                 320

Gly Thr Leu Phe His Gly Ser Val Gly Ile Leu Val Tyr Asp Lys Lys
                325                 330                 335

Gly Asn Ser Phe Val Ser Ser His
            340


<210> SEQ ID NO 97
<211> LENGTH: 1150
<212> TYPE: DNA
<213> ORGANISM: Arabidopsis thaliana
<220> FEATURE:
<221> NAME/KEY: MISC_FEATURE
<223> OTHER INFORMATION: clone104691_L45

<400> SEQUENCE: 97

acgactacaa agtacaagaa agtctcattt gagaataatt gagcgataaa gaaacggtat      60

gacgtcgttt tgctccatga tttctcttct tcttcttctc tctctttcat cggcggtttt     120

ctccgatgac gcttctttcc agaaacttcc ggtgccggaa actaggtcag gtcccgaagc     180

tttcgctttt gattccaccg gtaaagggtt ctataccggt gtctccggtg gtaaaatcct     240

caagtacctc cccgagacgg gttatgttga ctttgcccag atcactgaat cctcgaactc     300

ttcatggtgc gatggtacta ttggaacggc tttagccgga cgctgtggtc gaccagcagg     360

aatagcattc aacgagaaaa caggtgatct ttacgtcgcc gatgctccgt tgggtcttca     420

cgttatttct cccgccggtg gtttggctac gaagatcacc gacagtgttg acggaaagcc     480

tttcaagttt cttgacggtc ttgacgttga tcccactact ggtgtcgtct acttcacttc     540
```

```
cttcagctca cgcttctccc caatccaagt gttgattgca ttggggttaa aggacgcgac    600

cggaaagctc tacaaatacg acccatcgac caaagtcgtg actgtactga tggaagggct    660

aagtggttca gccgggtgtg cagtgagctc agatggttcg tttgtgctgg ttagtcagtt    720

cacaaaaagt aacatcaaga ggtattggat caagggaccc aaagctggtt cttctgaaga    780

cttcaccaac tcagtctcaa accctgacaa tatcaaaaga attggctcta ctggaaactt    840

ttgggtcgct tcagtggtga acaagatcat cgtacctacg aacccatcag cagtcaaagt    900

taactctaat ggtgaagttc ttcaaacaat tcctctcaaa gataaatttg gagacactct    960

gctcagcgaa gtcaacgaat tcgagggcaa tttatatata ggaactctca ccggaccatt   1020

tgctggaatt cttaagctcg aaaagggttc ttgtcctgcc acttagatct cttatttgaa   1080

tgcatccgat gtgttacaat aatatatata tatgagcttt ttatttattt ctgaataaaa   1140

taaccactta                                                          1150
```

```
<210> SEQ ID NO 98
<211> LENGTH: 335
<212> TYPE: PRT
<213> ORGANISM: Arabidopsis thaliana
<220> FEATURE:
<221> NAME/KEY: MISC_FEATURE
<223> OTHER INFORMATION: peptide_clone104691_L45

<400> SEQUENCE: 98

Met Thr Ser Phe Cys Ser Met Ile Ser Leu Leu Leu Leu Leu Ser Leu
1               5                   10                  15

Ser Ser Ala Val Phe Ser Asp Asp Ala Ser Phe Gln Lys Leu Pro Val
            20                  25                  30

Pro Glu Thr Arg Ser Gly Pro Glu Ala Phe Ala Phe Asp Ser Thr Gly
        35                  40                  45

Lys Gly Phe Tyr Thr Gly Val Ser Gly Gly Lys Ile Leu Lys Tyr Leu
    50                  55                  60

Pro Glu Thr Gly Tyr Val Asp Phe Ala Gln Ile Thr Glu Ser Ser Asn
65                  70                  75                  80

Ser Ser Trp Cys Asp Gly Thr Ile Gly Thr Ala Leu Ala Gly Arg Cys
                85                  90                  95

Gly Arg Pro Ala Gly Ile Ala Phe Asn Glu Lys Thr Gly Asp Leu Tyr
            100                 105                 110

Val Ala Asp Ala Pro Leu Gly Leu His Val Ile Ser Pro Ala Gly Gly
        115                 120                 125

Leu Ala Thr Lys Ile Thr Asp Ser Val Asp Gly Lys Pro Phe Lys Phe
    130                 135                 140

Leu Asp Gly Leu Asp Val Asp Pro Thr Thr Gly Val Val Tyr Phe Thr
145                 150                 155                 160

Ser Phe Ser Ser Arg Phe Ser Pro Ile Gln Val Leu Ile Ala Leu Gly
                165                 170                 175

Leu Lys Asp Ala Thr Gly Lys Leu Tyr Lys Tyr Asp Pro Ser Thr Lys
            180                 185                 190

Val Val Thr Val Leu Met Glu Gly Leu Ser Gly Ser Ala Gly Cys Ala
        195                 200                 205

Val Ser Ser Asp Gly Ser Phe Val Leu Val Ser Gln Phe Thr Lys Ser
    210                 215                 220

Asn Ile Lys Arg Tyr Trp Ile Lys Gly Pro Lys Ala Gly Ser Ser Glu
225                 230                 235                 240

Asp Phe Thr Asn Ser Val Ser Asn Pro Asp Asn Ile Lys Arg Ile Gly
```

-continued

```
                245                 250                 255

Ser Thr Gly Asn Phe Trp Val Ala Ser Val Val Asn Lys Ile Ile Val
            260                 265                 270

Pro Thr Asn Pro Ser Ala Val Lys Val Asn Ser Asn Gly Glu Val Leu
        275                 280                 285

Gln Thr Ile Pro Leu Lys Asp Lys Phe Gly Asp Thr Leu Leu Ser Glu
    290                 295                 300

Val Asn Glu Phe Glu Gly Asn Leu Tyr Ile Gly Thr Leu Thr Gly Pro
305                 310                 315                 320

Phe Ala Gly Ile Leu Lys Leu Glu Lys Gly Ser Cys Pro Ala Thr
                325                 330                 335


<210> SEQ ID NO 99
<211> LENGTH: 325
<212> TYPE: PRT
<213> ORGANISM: Arabidopsis thaliana
<220> FEATURE:
<221> NAME/KEY: MISC_FEATURE
<223> OTHER INFORMATION: CeresClone:17206

<400> SEQUENCE: 99

Met Ala Ser Phe Val Phe Val Ile Ser Leu Leu Leu Leu Ser Phe Ser
1               5                   10                  15

Ser Ala Val Phe Ser Asp Asp Ala Ser Phe Gln Lys Leu Pro Val Pro
            20                  25                  30

Asp Lys Arg Ser Gly Pro Glu Ser Phe Ala Phe Asp Ser Thr Gly Gly
        35                  40                  45

Phe Tyr Thr Gly Val Ser Gly Gly Lys Ile Leu Lys Tyr Val Pro Gly
    50                  55                  60

Lys Gly Tyr Val Asp Phe Ala Gln Ile Thr Asp Ser Ser Asn Ser Ala
65                  70                  75                  80

Trp Cys Asn Gly Ala Leu Gly Thr Ala Phe Ala Gly Lys Cys Gly Arg
                85                  90                  95

Pro Ala Gly Ile Ala Leu Asn Ser Lys Thr Gly Asp Leu Tyr Val Ala
            100                 105                 110

Asp Ala Pro Leu Gly Leu His Val Ile Ser Pro Ala Gly Gly Leu Ala
        115                 120                 125

Thr Lys Leu Ala Asp Ser Val Asp Gly Lys Pro Phe Lys Phe Leu Asp
    130                 135                 140

Gly Leu Asp Val Asp Pro Thr Thr Gly Val Val Tyr Phe Thr Ser Phe
145                 150                 155                 160

Ser Ser Lys Phe Gly Pro Arg Glu Val Leu Ile Ala Val Gly Leu Lys
                165                 170                 175

Asp Ala Ser Gly Lys Leu Phe Lys Tyr Asp Pro Ala Thr Lys Ala Val
            180                 185                 190

Thr Glu Leu Met Glu Gly Leu Ser Gly Ala Ala Gly Cys Ala Val Ser
        195                 200                 205

Ser Asp Gly Ser Phe Val Leu Val Ser Glu Phe Ile Lys Ser Asn Ile
    210                 215                 220

Lys Lys Tyr Trp Ile Lys Gly Pro Lys Ala Gly Thr Ile Glu Asp Phe
225                 230                 235                 240

Ser Ser Leu Val Ser Asn Pro Asp Asn Ile Arg Arg Val Gly Ser Thr
                245                 250                 255

Gly Asn Phe Trp Val Ala Ser Val Val Asn Lys Val Val Met Pro Thr
            260                 265                 270
```

```
Asp Pro Arg Ala Val Lys Leu Asp Ala Asn Gly Lys Val Leu Gln Thr
        275                 280                 285

Ile Phe Leu Lys Asn Glu Phe Gly Asn Thr Leu Leu Ser Glu Val Asn
    290                 295                 300

Glu Phe Asn Gly His Leu Tyr Ile Gly Thr Leu Thr Gly Pro Phe Ala
305                 310                 315                 320

Gly Val Met Lys Leu
                325


<210> SEQ ID NO 100
<211> LENGTH: 325
<212> TYPE: PRT
<213> ORGANISM: Arabidopsis thaliana
<220> FEATURE:
<221> NAME/KEY: MISC_FEATURE
<223> OTHER INFORMATION: gi|30984544

<400> SEQUENCE: 100

Met Ala Ser Phe Val Phe Val Ile Ser Leu Leu Leu Leu Ser Phe Ser
1               5                   10                  15

Ser Ala Val Phe Ser Asp Asp Ala Ser Phe Gln Lys Leu Pro Val Pro
            20                  25                  30

Asp Lys Arg Ser Gly Pro Glu Ser Phe Ala Phe Asp Ser Thr Gly Gly
        35                  40                  45

Phe Tyr Thr Gly Val Ser Gly Gly Lys Ile Leu Lys Tyr Val Pro Gly
    50                  55                  60

Lys Gly Tyr Val Asp Phe Ala Gln Ile Thr Asp Ser Ser Asn Ser Ala
65                  70                  75                  80

Trp Cys Asn Gly Ala Leu Gly Thr Ala Phe Ala Gly Lys Cys Gly Arg
                85                  90                  95

Pro Ala Gly Ile Ala Leu Asn Ser Lys Thr Gly Asp Leu Tyr Val Ala
            100                 105                 110

Asp Ala Pro Leu Gly Leu His Val Ile Ser Pro Ala Gly Gly Leu Ala
        115                 120                 125

Thr Lys Leu Ala Asp Ser Val Asp Gly Lys Pro Phe Lys Phe Leu Asp
    130                 135                 140

Gly Leu Asp Val Asp Pro Thr Thr Gly Val Val Tyr Phe Thr Ser Phe
145                 150                 155                 160

Ser Ser Lys Phe Gly Pro Arg Glu Val Leu Ile Ala Val Gly Leu Lys
                165                 170                 175

Asp Ala Ser Gly Lys Leu Phe Lys Tyr Asp Pro Ala Thr Lys Ala Val
            180                 185                 190

Thr Glu Leu Met Glu Gly Leu Ser Gly Ala Ala Gly Cys Ala Val Ser
        195                 200                 205

Ser Asp Gly Ser Phe Val Leu Val Ser Glu Phe Ile Lys Ser Asn Ile
    210                 215                 220

Lys Lys Tyr Trp Ile Lys Gly Pro Lys Ala Gly Thr Ile Glu Asp Phe
225                 230                 235                 240

Ser Ser Leu Val Ser Asn Pro Asp Asn Ile Arg Arg Val Gly Ser Thr
                245                 250                 255

Gly Asn Phe Trp Val Ala Ser Val Val Asn Lys Val Val Met Pro Thr
            260                 265                 270

Asp Pro Arg Ala Val Lys Leu Asp Ala Asn Gly Lys Val Leu Gln Thr
        275                 280                 285

Ile Phe Leu Lys Asn Glu Phe Gly Asn Thr Leu Leu Ser Glu Val Asn
    290                 295                 300
```

```
Glu Phe Asn Gly His Leu Tyr Ile Gly Thr Leu Thr Gly Pro Phe Ala
305                 310                 315                 320

Gly Val Met Lys Leu
                325


<210> SEQ ID NO 101
<211> LENGTH: 328
<212> TYPE: PRT
<213> ORGANISM: Arabidopsis thaliana
<220> FEATURE:
<221> NAME/KEY: MISC_FEATURE
<223> OTHER INFORMATION: gi|30698979

<400> SEQUENCE: 101

Met Arg Ser Phe Val Ser Leu Ile Ser Leu Leu Leu Leu Leu Ser Phe
1               5                   10                  15

Ser Ser Ser Val Leu Ser Thr Lys Lys Ser Ser Phe Gln Lys Leu Pro
            20                  25                  30

Val Pro Gly Asn Arg Thr Gly Pro Glu Ala Phe Ala Phe Asp Ser Thr
        35                  40                  45

Gly Lys Gly Phe Tyr Thr Gly Val Thr Gly Gly Lys Ile Leu Lys Tyr
    50                  55                  60

Leu Pro Lys Lys Gly Tyr Val Asp Phe Ala Gln Ile Thr Asn Ser Ser
65                  70                  75                  80

Lys Ser Ser Leu Cys Asp Gly Ala Leu Gly Thr Thr Asn Val Glu Lys
                85                  90                  95

Cys Gly Arg Pro Ala Gly Ile Ala Phe Asn Thr Lys Thr Gly Asp Leu
            100                 105                 110

Tyr Val Ala Asp Ala Ala Leu Gly Leu His Val Ile Pro Arg Arg Gly
        115                 120                 125

Gly Leu Ala Lys Lys Ile Ala Asp Ser Val Gly Gly Lys Pro Phe Leu
    130                 135                 140

Phe Leu Asp Gly Leu Asp Val Asp Pro Thr Thr Gly Val Val Tyr Phe
145                 150                 155                 160

Thr Ser Phe Ser Ser Thr Phe Gly Pro Arg Asp Val Leu Lys Ala Val
                165                 170                 175

Ala Thr Lys Asp Ser Thr Gly Lys Phe Phe Lys Tyr Asp Pro Ser Lys
            180                 185                 190

Lys Val Val Thr Val Leu Met Glu Gly Leu Ser Gly Ser Ala Gly Cys
        195                 200                 205

Ala Val Ser Ser Asp Gly Ser Phe Val Leu Val Gly Gln Phe Thr Lys
    210                 215                 220

Ser Asn Ile Lys Arg Tyr Trp Ile Lys Gly Ser Lys Ala Gly Thr Ser
225                 230                 235                 240

Glu Asp Phe Thr Asn Ser Val Ser Asn Pro Asp Asn Ile Lys Arg Ile
                245                 250                 255

Gly Ser Thr Gly Asn Phe Trp Val Ala Ser Val Val Asn Ser Ala Thr
            260                 265                 270

Gly Pro Thr Asn Pro Ser Ala Val Lys Val Ser Ser Ala Gly Lys Val
        275                 280                 285

Leu Gln Thr Ile Pro Leu Lys Asp Lys Phe Gly Asp Thr Leu Val Ser
    290                 295                 300

Glu Val Asn Glu Tyr Lys Gly Gln Leu Tyr Ile Gly Ala Leu Phe Gly
305                 310                 315                 320

Pro Phe Ala Gly Ile Leu Lys Leu
```

325

<210> SEQ ID NO 102
<211> LENGTH: 329
<212> TYPE: PRT
<213> ORGANISM: Arabidopsis thaliana
<220> FEATURE:
<221> NAME/KEY: MISC_FEATURE
<223> OTHER INFORMATION: gi|12325143

<400> SEQUENCE: 102

```
Met Met Arg Ser Phe Val Ser Leu Ile Ser Leu Leu Leu Leu Leu Ser
1               5                   10                  15

Phe Ser Ser Ser Val Leu Ser Thr Lys Lys Ser Ser Phe Gln Lys Leu
            20                  25                  30

Pro Val Pro Gly Asn Arg Thr Gly Pro Glu Ala Phe Ala Phe Asp Ser
        35                  40                  45

Thr Gly Lys Gly Phe Tyr Thr Gly Val Thr Gly Gly Lys Ile Leu Lys
    50                  55                  60

Tyr Leu Pro Lys Lys Gly Tyr Val Asp Phe Ala Gln Ile Thr Asn Ser
65                  70                  75                  80

Ser Lys Ser Ser Leu Cys Asp Gly Ala Leu Gly Thr Thr Asn Val Glu
                85                  90                  95

Lys Cys Gly Arg Pro Ala Gly Ile Ala Phe Asn Thr Lys Thr Gly Asp
            100                 105                 110

Leu Tyr Val Ala Asp Ala Ala Leu Gly Leu His Val Ile Pro Arg Arg
        115                 120                 125

Gly Gly Leu Ala Lys Lys Ile Ala Asp Ser Val Gly Gly Lys Pro Phe
    130                 135                 140

Leu Phe Leu Asp Gly Leu Asp Val Asp Pro Thr Thr Gly Val Val Tyr
145                 150                 155                 160

Phe Thr Ser Phe Ser Ser Thr Phe Gly Pro Arg Asp Val Leu Lys Ala
                165                 170                 175

Val Ala Thr Lys Asp Ser Thr Gly Lys Phe Phe Lys Tyr Asp Pro Ser
            180                 185                 190

Lys Lys Val Val Thr Val Leu Met Glu Gly Leu Ser Gly Ser Ala Gly
        195                 200                 205

Cys Ala Val Ser Ser Asp Gly Ser Phe Val Leu Val Gly Gln Phe Thr
    210                 215                 220

Lys Ser Asn Ile Lys Arg Tyr Trp Ile Lys Gly Ser Lys Ala Gly Thr
225                 230                 235                 240

Ser Glu Asp Phe Thr Asn Ser Val Ser Asn Pro Asp Asn Ile Lys Arg
                245                 250                 255

Ile Gly Ser Thr Gly Asn Phe Trp Val Ala Ser Val Val Asn Ser Ala
            260                 265                 270

Thr Gly Pro Thr Asn Pro Ser Ala Val Lys Val Ser Ser Ala Gly Lys
        275                 280                 285

Val Leu Gln Thr Ile Pro Leu Lys Asp Lys Phe Gly Asp Thr Leu Val
    290                 295                 300

Ser Glu Val Asn Glu Tyr Lys Gly Gln Leu Tyr Ile Gly Ala Leu Phe
305                 310                 315                 320

Gly Pro Phe Ala Gly Ile Leu Lys Leu
                325
```

<210> SEQ ID NO 103
<211> LENGTH: 347

<212> TYPE: PRT
<213> ORGANISM: Glycine max
<220> FEATURE:
<221> NAME/KEY: MISC_FEATURE
<223> OTHER INFORMATION: CeresClone:621848

<400> SEQUENCE: 103

```
Met Lys Leu Ser Thr Leu Phe Leu Phe Leu Phe His Leu Ala His Ala
1               5                   10                  15

Ala Leu Ser Asp Glu Ala Thr Phe Ile Arg Asp Gly Leu Lys Ser Tyr
            20                  25                  30

Ser Gln Leu Asp Leu Pro His Ser Val Phe Gly Ser Glu Ser Val Ala
        35                  40                  45

Phe Asp Cys His Gly Lys Gly Pro Tyr Val Gly Val Ser Asp Gly Arg
    50                  55                  60

Ile Leu Lys Trp His Glu Thr Lys Arg Glu Trp Ile Asp Phe Ala Val
65                  70                  75                  80

Thr Ser Pro His Arg Asn Lys Lys Leu Cys Asp Gly Leu Thr Asn Asp
                85                  90                  95

Lys Met Glu Ser Met Cys Gly Arg Pro Leu Gly Leu Lys Phe Asn Thr
            100                 105                 110

Leu Thr Cys Glu Leu Tyr Ile Ala Asp Ala Tyr Phe Gly Leu Leu Val
        115                 120                 125

Val Gly Pro Gly Gly Gly Val Ala Lys Gln Leu Ala Thr Ser Ala Glu
    130                 135                 140

Gly Val Pro Phe Arg Phe Thr Asn Ala Leu Asp Ile Asp Thr Lys Thr
145                 150                 155                 160

Gly Glu Val Tyr Phe Thr Asp Ser Ser Ile Met Phe Gln Arg Arg Val
                165                 170                 175

Tyr Ile Ser Ile Ile Leu Ser Gly Asp Arg Thr Gly Arg Leu Leu Lys
            180                 185                 190

Tyr Val Pro Ser Thr Gln Ser Val His Val Leu Val Lys Gly Leu Ala
        195                 200                 205

Phe Pro Asn Gly Val Ala Leu Ser Lys Asp Asn Ser Phe Ile Ile Val
    210                 215                 220

Ala Glu Ser Thr Thr Phe Lys Ile Leu Lys Ile Gln Val Arg Asp Ser
225                 230                 235                 240

Lys Thr Asn Asn Asn Asn Ile Glu Pro Phe Ala Gln Val Pro Arg Ser
                245                 250                 255

Pro Asp Asn Ile Lys Arg Asn Ala Lys Gly Glu Phe Trp Val Ala Leu
            260                 265                 270

Asn Ser Gly Arg Gly Leu Ile Gln Lys Leu Glu Asn Glu Ile Glu Thr
        275                 280                 285

Thr Leu Pro Trp Asn Ala Asp Pro Val Ala Ile Lys Phe Asp Glu Lys
    290                 295                 300

Gly Arg Ala Ile Glu Val Leu Asp Gly Glu Tyr Gly Arg Gln Leu Asp
305                 310                 315                 320

Ser Val Ser Glu Val Glu Glu His Glu Gly Ser Leu Trp Ile Gly Ser
                325                 330                 335

Ala Val Gln Pro Tyr Ile Gly Leu Ile Lys Ala
            340                 345
```

<210> SEQ ID NO 104
<211> LENGTH: 347
<212> TYPE: PRT
<213> ORGANISM: Catharanthus roseus
<220> FEATURE:
<221> NAME/KEY: MISC_FEATURE
<223> OTHER INFORMATION: gi|18222

<400> SEQUENCE: 104

```
Met Met Ala Val Phe Phe Met Phe Phe Leu Leu Leu Leu Ser Ser Ser
1               5                   10                  15

Ser Ser Ser Ser Ser Ser Ser Pro Ile Leu Lys Lys Ile Phe Ile Glu
            20                  25                  30

Ser Pro Ser Tyr Ala Pro Asn Ala Phe Thr Phe Asp Ser Thr Asp Lys
        35                  40                  45

Gly Phe Tyr Thr Ser Val Gln Asp Gly Arg Val Ile Lys Tyr Glu Gly
    50                  55                  60

Pro Asn Ser Gly Phe Thr Asp Phe Ala Tyr Ala Ser Pro Phe Trp Asn
65                  70                  75                  80

Lys Ala Phe Cys Glu Asn Ser Thr Asp Pro Glu Lys Arg Pro Leu Cys
                85                  90                  95

Gly Arg Thr Tyr Asp Ile Ser Tyr Asp Tyr Lys Asn Ser Gln Met Tyr
            100                 105                 110

Ile Val Asp Gly His Tyr His Leu Cys Val Val Gly Lys Glu Gly Gly
        115                 120                 125

Tyr Ala Thr Gln Leu Ala Thr Ser Val Gln Gly Val Pro Phe Lys Trp
    130                 135                 140

Leu Tyr Ala Val Thr Val Asp Gln Arg Thr Gly Ile Val Tyr Phe Thr
145                 150                 155                 160

Asp Val Ser Ser Ile His Asp Asp Ser Pro Glu Gly Val Glu Glu Ile
                165                 170                 175

Met Asn Thr Ser Asp Arg Thr Gly Arg Leu Met Lys Tyr Asp Pro Ser
            180                 185                 190

Thr Lys Glu Thr Thr Leu Leu Leu Lys Glu Leu His Val Pro Gly Gly
        195                 200                 205

Ala Glu Ile Ser Ala Asp Gly Ser Phe Val Val Val Ala Glu Phe Leu
    210                 215                 220

Ser Asn Arg Ile Val Lys Tyr Trp Leu Glu Gly Pro Lys Lys Gly Ser
225                 230                 235                 240

Ala Glu Phe Leu Val Thr Ile Pro Asn Pro Gly Asn Ile Lys Arg Asn
                245                 250                 255

Ser Asp Gly His Phe Trp Val Ser Ser Ser Glu Glu Leu Asp Gly Gly
            260                 265                 270

Gln His Gly Ser Val Val Ser Arg Gly Ile Lys Phe Asp Gly Phe Gly
        275                 280                 285

Asn Ile Leu Gln Val Ile Pro Leu Pro Pro Pro Tyr Glu Gly Glu His
    290                 295                 300

Phe Glu Gln Ile Gln Glu His Asp Gly Leu Leu Tyr Ile Gly Ser Leu
305                 310                 315                 320

Ser His Ser Ser Val Gly Ile Leu Val Tyr Asp Asp His Asp Asn Lys
                325                 330                 335

Gly Asn Ser Tyr Val Ser Gln Leu Val Ile Asn
            340                 345
```

<210> SEQ ID NO 105
<211> LENGTH: 352
<212> TYPE: PRT
<213> ORGANISM: Catharanthus roseus
<220> FEATURE:
<221> NAME/KEY: MISC_FEATURE
<223> OTHER INFORMATION: gi|18220

<400> SEQUENCE: 105

Met Ala Asn Phe Ser Glu Ser Lys Ser Met Met Ala Val Phe Phe Met
1               5                   10                  15

Phe Phe Leu Leu Leu Leu Ser Ser Ser Ser Ser Ser Ser Ser Ser Ser
            20                  25                  30

Pro Ile Leu Lys Lys Ile Phe Ile Glu Ser Pro Ser Tyr Ala Pro Asn
        35                  40                  45

Ala Phe Thr Phe Asp Ser Thr Asp Lys Gly Phe Tyr Thr Ser Val Gln
    50                  55                  60

Asp Gly Arg Val Ile Lys Tyr Glu Gly Pro Asn Ser Gly Phe Thr Asp
65                  70                  75                  80

Phe Ala Tyr Ala Ser Pro Phe Trp Asn Lys Ala Phe Cys Glu Asn Ser
                85                  90                  95

Thr Asp Pro Glu Lys Arg Pro Leu Cys Gly Arg Thr Tyr Asp Ile Ser
            100                 105                 110

Tyr Asp Tyr Lys Asn Ser Gln Met Tyr Ile Val Asp Gly His Tyr His
        115                 120                 125

Leu Cys Val Val Gly Lys Glu Gly Gly Tyr Ala Thr Gln Leu Ala Thr
    130                 135                 140

Ser Val Gln Gly Val Pro Phe Lys Trp Leu Tyr Ala Val Thr Val Asp
145                 150                 155                 160

Gln Arg Thr Gly Ile Val Tyr Phe Thr Asp Val Ser Ser Ile His Asp
                165                 170                 175

Asp Ser Pro Glu Gly Val Glu Glu Ile Met Asn Thr Ser Asp Arg Thr
            180                 185                 190

Gly Arg Leu Met Lys Tyr Asp Pro Ser Thr Lys Glu Thr Thr Leu Leu
        195                 200                 205

Leu Lys Glu Leu His Val Pro Gly Gly Ala Glu Ile Ser Ala Asp Gly
    210                 215                 220

Ser Phe Val Val Val Ala Glu Phe Leu Ser Asn Arg Ile Val Lys Tyr
225                 230                 235                 240

Trp Leu Glu Gly Pro Lys Lys Gly Ser Ala Glu Phe Leu Val Thr Ile
                245                 250                 255

Pro Asn Pro Gly Asn Ile Lys Arg Asn Ser Asp Gly His Phe Trp Val
            260                 265                 270

Ser Ser Ser Glu Glu Leu Asp Gly Gly Gln His Gly Arg Val Val Ser
        275                 280                 285

Arg Gly Ile Lys Phe Asp Gly Phe Gly Asn Ile Leu Gln Val Ile Pro
    290                 295                 300

Leu Pro Pro Pro Tyr Glu Gly Glu His Phe Glu Gln Ile Gln Glu His
305                 310                 315                 320

Asp Gly Leu Leu Tyr Ile Gly Ser Leu Phe His Ser Ser Val Gly Ile
                325                 330                 335

Leu Val Tyr Asp Asp His Asp Asn Lys Gly Asn Ser Tyr Val Ser Ser
            340                 345                 350

<210> SEQ ID NO 106
<211> LENGTH: 343
<212> TYPE: PRT
<213> ORGANISM: Zea mays
<220> FEATURE:
<221> NAME/KEY: MISC_FEATURE
<223> OTHER INFORMATION: CeresClone:316544

<400> SEQUENCE: 106

Met Ala Ala Ala Ala Thr Arg Ser Leu His Ser Phe Leu Ala Leu Leu
1               5                   10                  15

Leu Leu Leu Ala Ala Ala Ala Ala Ala Ala Ala Leu Ser Tyr Glu Thr
            20                  25                  30

Lys Ser Ile Asp Pro Gly Leu Val Val Met Thr Leu Pro Glu Pro Val
        35                  40                  45

Ser Gly Pro Glu Ser Leu Ala Phe Asp Gly Arg Gly Gly Gly Pro Tyr
    50                  55                  60

Ser Gly Val Ser Asp Gly Arg Val Leu Arg Trp Gln Gly Pro Leu Arg
65                  70                  75                  80

Gly Trp Thr Glu Phe Ala Tyr Asn Ser Lys His Arg Ser Val Ala Leu
                85                  90                  95

Cys Ala Pro Asp Lys Lys Leu Val Val Pro Glu Ser Leu Cys Gly Arg
            100                 105                 110

Pro Leu Gly Leu Gln Phe His Arg Gln Ser Gly Asp Leu Tyr Val Ala
        115                 120                 125

Asp Ala Tyr Leu Gly Leu Leu Arg Val Ala Ala Arg Gly Gly Leu Ala
    130                 135                 140

Gln Val Val Ala Thr Glu Ala Ala Gly Gly Pro Phe Asn Phe Leu Asn
145                 150                 155                 160

Gly Leu Asp Val Asp Gln Arg Thr Gly Asp Val Tyr Phe Thr Asp Ser
                165                 170                 175

Ser Ala Thr Tyr Arg Arg Ser Asp Tyr Leu Leu Val Val Ala Met Gly
            180                 185                 190

Asp Glu Thr Gly Arg Leu Leu Arg Tyr Glu Arg Arg Thr Gly Arg Val
        195                 200                 205

Gly Val Leu Gln Ala Gly Leu Ser Tyr Pro Asn Gly Val Ala Val Ser
    210                 215                 220

Ala Asp Gly Thr His Val Val Val Ala His Thr Ala Leu Cys Glu Leu
225                 230                 235                 240

Arg Arg Tyr Trp Ile Arg Gly Ala Arg Ala Gly Thr Ser Asp Thr Phe
                245                 250                 255

Ala Glu Leu Pro Gly Tyr Pro Asp Asn Leu Arg Ala Asp Gly Arg Gly
            260                 265                 270

Gly Tyr Trp Val Ala Leu Ser Ser Gly Val Ala Ala Asp Glu Ala Ala
        275                 280                 285

Ala Ala Pro Thr Val Ala Val Arg Val Ser Arg Asp Gly Asn Val Thr
    290                 295                 300

Glu Ala Leu Asp Gly Phe Ser Phe Val Ser Val Ser Glu Val Ala Gln
305                 310                 315                 320

Arg Gly Gly Ala Leu Trp Val Gly Ser Val Asp Thr Pro Tyr Ala Gly
                325                 330                 335

Gln Leu Lys Arg Arg Ala Ser
            340

<210> SEQ ID NO 107
<211> LENGTH: 364
<212> TYPE: PRT
<213> ORGANISM: Oryza sativa subsp. japonica
<220> FEATURE:
<221> NAME/KEY: MISC_FEATURE
<223> OTHER INFORMATION: gi|50899872

<400> SEQUENCE: 107

-continued

```
Met Arg Lys Gly Ala Ala Gly Met Ala Cys Thr Cys Ser Ala Ala Ala
1               5                   10                  15

Ala Ala Ser Ala Leu Val Lys Leu Leu Val Leu Val Ala Ala Val Ala
            20                  25                  30

Ala Thr Thr Ser Ala Gly Gly Gly Asp Glu Pro Thr Tyr Glu Thr Lys
        35                  40                  45

Ser Ile Asp Pro Ser Leu Ala Val Met Thr Leu Pro Ala Pro Val Thr
    50                  55                  60

Gly Pro Glu Ser Leu Ala Phe Asp Gly Arg Gly Asp Gly Pro Tyr Thr
65                  70                  75                  80

Gly Gly Ser Asp Gly Arg Ile Leu Arg Trp Arg Gly Gly Arg Leu Gly
                85                  90                  95

Trp Thr Glu Phe Ala Tyr Asn Ser Arg His Lys Ser Val Gly Val Cys
            100                 105                 110

Ser Pro Glu Lys Lys Leu Val Val Pro Glu Ser Val Cys Gly Arg Pro
        115                 120                 125

Leu Gly Leu Gln Phe His His Ala Ser Gly Asp Leu Tyr Val Ala Asp
    130                 135                 140

Ala Tyr Leu Gly Leu Leu Arg Val Pro Ala Arg Gly Gly Leu Ala Glu
145                 150                 155                 160

Val Val Ala Thr Glu Ala Ala Gly Val Pro Phe Asn Phe Leu Asn Gly
                165                 170                 175

Leu Asp Val Asp Gln Arg Thr Gly Asp Val Tyr Phe Thr Asp Ser Ser
            180                 185                 190

Thr Thr Tyr Arg Arg Ser Gln Tyr Leu Leu Val Val Ala Met Gly Asp
        195                 200                 205

Glu Thr Gly Arg Leu Leu Arg Tyr Asp Ala Arg Arg Arg Arg Val Thr
    210                 215                 220

Val Leu His Ser Gly Leu Pro Tyr Pro Asn Gly Val Ala Val Ser Asp
225                 230                 235                 240

Asp Gly Thr His Val Val Val Ala His Thr Gly Leu Cys Glu Leu Arg
                245                 250                 255

Arg Tyr Trp Leu Arg Gly Pro Arg Ala Gly Lys Ser Glu Thr Phe Ala
            260                 265                 270

Glu Val Pro Gly Tyr Pro Asp Asn Val Arg Arg Asp Gly Asp Gly Gly
        275                 280                 285

Tyr Trp Val Ala Leu Ser Arg Gly Ala Asp Asn Asp Asp Val Ala Pro
    290                 295                 300

Thr Val Ala Val Arg Val Thr Ala Ala Gly Lys Lys Lys Gly Gly Gly
305                 310                 315                 320

Ala Ala Val Val Ala Glu Ala Leu Ala Gly Phe Ser Phe Val Thr Val
                325                 330                 335

Ser Glu Val Ala Glu Gln Asn Gly Thr Leu Trp Ile Gly Ser Val Asp
            340                 345                 350

Thr Pro Tyr Ala Gly Ala Ala Val Arg Gly Arg Arg
        355                 360
```

<210> SEQ ID NO 108
<211> LENGTH: 351
<212> TYPE: PRT
<213> ORGANISM: Ophiorrhiza pumila
<220> FEATURE:
<221> NAME/KEY: MISC_FEATURE
<223> OTHER INFORMATION: gi|13928598

<400> SEQUENCE: 108

Met His Ser Ser Glu Ala Met Val Val Ser Ile Leu Cys Ala Leu Phe
1 5 10 15

Leu Ser Ser Leu Ser Leu Val Ser Ser Ser Pro Glu Phe Phe Glu Phe
20 25 30

Ile Glu Ala Pro Ser Tyr Gly Pro Asn Ala Tyr Ala Phe Asp Ser Asp
35 40 45

Gly Glu Leu Tyr Ala Ser Val Glu Asp Gly Arg Ile Ile Lys Tyr Asp
50 55 60

Lys Pro Ser Asn Lys Phe Leu Thr His Ala Val Ala Ser Pro Ile Trp
65 70 75 80

Asn Asn Ala Leu Cys Glu Asn Asn Thr Asn Gln Asp Leu Lys Pro Leu
85 90 95

Cys Gly Arg Val Tyr Asp Phe Gly Phe His Tyr Glu Thr Gln Arg Leu
100 105 110

Tyr Ile Ala Asp Cys Tyr Phe Gly Leu Gly Phe Val Gly Pro Asp Gly
115 120 125

Gly His Ala Ile Gln Leu Ala Thr Ser Gly Asp Gly Val Glu Phe Lys
130 135 140

Trp Leu Tyr Ala Leu Ala Ile Asp Gln Gln Ala Gly Phe Val Tyr Val
145 150 155 160

Thr Asp Val Ser Thr Lys Tyr Asp Asp Arg Gly Val Gln Asp Ile Ile
165 170 175

Arg Ile Asn Asp Thr Thr Gly Arg Leu Ile Lys Tyr Asp Pro Ser Thr
180 185 190

Glu Glu Val Thr Val Leu Met Lys Gly Leu Asn Ile Pro Gly Gly Thr
195 200 205

Glu Val Ser Lys Asp Gly Ser Phe Val Leu Val Gly Glu Phe Ala Ser
210 215 220

His Arg Ile Leu Lys Tyr Trp Leu Lys Gly Pro Lys Ala Asn Thr Ser
225 230 235 240

Glu Phe Leu Leu Lys Val Arg Gly Pro Gly Asn Ile Lys Arg Thr Lys
245 250 255

Asp Gly Asp Phe Trp Val Ala Ser Ser Asp Asn Asn Gly Ile Thr Val
260 265 270

Thr Pro Arg Gly Ile Arg Phe Asp Glu Phe Gly Asn Ile Leu Glu Val
275 280 285

Val Ala Ile Pro Leu Pro Tyr Lys Gly Glu His Ile Glu Gln Val Gln
290 295 300

Glu His Asp Gly Ala Leu Phe Val Gly Ser Leu Phe His Glu Phe Val
305 310 315 320

Gly Ile Leu His Asn Tyr Lys Ser Ser Val Asp His His Gln Glu Lys
325 330 335

Asn Ser Gly Gly Leu Asn Ala Ser Phe Lys Glu Phe Ser Ser Phe
340 345 350

<210> SEQ ID NO 109
<211> LENGTH: 342
<212> TYPE: PRT
<213> ORGANISM: Rauvolfia mannii
<220> FEATURE:
<221> NAME/KEY: MISC_FEATURE
<223> OTHER INFORMATION: gi|21097

<400> SEQUENCE: 109

Lys Leu Ser Asp Ser Gln Thr Met Ala Leu Phe Thr Val Phe Leu Leu

-continued

```
1               5                   10                  15

Phe Leu Ser Ser Ser Leu Ala Leu Ser Ser Pro Ile Leu Lys Glu Ile
            20                  25                  30

Leu Ile Glu Ala Pro Ser Tyr Ala Pro Asn Ser Phe Thr Phe Asp Ser
        35                  40                  45

Thr Asn Lys Gly Phe Tyr Thr Ser Val Gln Asp Gly Arg Val Ile Lys
    50                  55                  60

Tyr Glu Gly Pro Asn Ser Gly Phe Val Asp Phe Ala Tyr Ala Ser Pro
65                  70                  75                  80

Tyr Trp Asn Lys Ala Phe Cys Glu Asn Ser Thr Asp Ala Glu Lys Arg
                85                  90                  95

Pro Leu Cys Gly Arg Thr Tyr Asp Ile Ser Tyr Asn Leu Gln Asn Asn
            100                 105                 110

Gln Leu Tyr Ile Val Asp Cys Tyr Tyr His Leu Ser Val Val Gly Ser
        115                 120                 125

Glu Gly Gly His Ala Thr Gln Leu Ala Thr Ser Val Asp Gly Val Pro
    130                 135                 140

Phe Lys Trp Leu Tyr Ala Val Thr Val Asp Gln Arg Thr Gly Ile Val
145                 150                 155                 160

Tyr Phe Thr Asp Val Ser Thr Leu Tyr Asp Asp Arg Gly Val Gln Gln
                165                 170                 175

Ile Met Asp Thr Ser Asp Lys Thr Gly Arg Leu Ile Lys Tyr Asp Pro
            180                 185                 190

Ser Thr Lys Glu Thr Thr Leu Leu Leu Lys Glu Leu His Val Pro Gly
        195                 200                 205

Gly Ala Glu Val Ser Ala Asp Ser Ser Phe Val Leu Val Ala Glu Phe
    210                 215                 220

Leu Ser His Gln Ile Val Lys Tyr Trp Leu Glu Gly Pro Lys Lys Gly
225                 230                 235                 240

Thr Ala Glu Val Leu Val Lys Ile Pro Asn Pro Gly Asn Ile Lys Arg
                245                 250                 255

Asn Ala Asp Gly His Phe Trp Val Ser Ser Ser Glu Glu Leu Asp Gly
            260                 265                 270

Asn Met His Gly Arg Val Asp Pro Lys Gly Ile Lys Phe Asp Glu Phe
        275                 280                 285

Gly Asn Ile Leu Glu Val Ile Pro Leu Pro Pro Pro Phe Ala Gly Glu
    290                 295                 300

His Phe Glu Gln Ile Gln Glu His Asp Gly Leu Leu Tyr Ile Gly Thr
305                 310                 315                 320

Leu Phe His Gly Ser Val Gly Ile Leu Val Tyr Asp Lys Lys Gly Asn
                325                 330                 335

Ser Phe Val Ser Ser His
            340
```

<210> SEQ ID NO 110
<211> LENGTH: 1954
<212> TYPE: DNA
<213> ORGANISM: Arabidopsis thaliana
<220> FEATURE:
<221> NAME/KEY: MISC_FEATURE
<223> OTHER INFORMATION: PROMOTER: 326 REPORT: 56

<400> SEQUENCE: 110

```
gtgggtaaaa gtatccttct ttgtgcattt ggtattttta agcatgtaat aagaaaaacc      60

aaaatagacg gctggtattt aataaaagga gactaatgta tgtatagtat atgatttgtg     120
```

```
tggaatataa taaagttgta aaatatagat gtgaagcgag tatctatctt ttgactttca    180

aaggtgatcg atcgtgttct ttgtgatagt tttggtcgtc ggtctacaag tcaacaacca    240

ccttgaagtt ttcgcgtctc ggtttcctct tcgcatctgg tatccaatag catacatata    300

ccagtgcgga aaatggcgaa gactagtggg cttgaaccat aaggtttggc cccaatacgg    360

attccaaaca acaagcctag cgcagtcttt tgggatgcat aagactaaac tgtcgcagtg    420

atagacgtaa gatatatcga cttgattgga atcgtctaag ctaataagtt taccttgacc    480

gtttatagtt gcgtcaacgt ccttatggag attgatgccc atcaaataaa cctgaaaatc    540

catcaccatg accaccataa actcccttgc tgccgctgct ttggcttgag caaggtgttt    600

ccttgtaaag ctccgatctt tggataaagt gttccacttt ttgcaagtag ctctgacccc    660

tctcagagat gtcaccggaa tcttagacag aacctcctct gccaaatcac ttggaagatc    720

ggacaatgtc atcatttttg caggtaattt ctccttcgtt gctgctttgg cttgagcacg    780

gtgcttcttt gtaaagctcc gatctttgga taagagcgga tcggaatcct ctaggaggtg    840

ccagtccctt gacctattaa tttatagaag gttttagtgt attttgttcc aatttcttct    900

ctaacttaac aaataacaac tgcctcatag tcatgggctt caaattttat cgcttggtgt    960

atttcgttat ttgcaaggcc ttggcccatt ttgagcccaa taactaaatc tagccttttc   1020

agaccggaca tgaacttcgc atattggcgt aactgtgcag ttttaccttt ttcggatcag   1080

acaagatcag atttagacca cccaacaata gtcagtcata tttgacaacc taagctagcc   1140

gacactacta aaaagcaaac aaaagaagaa ttctatgttg tcattttacc ggtggcaagt   1200

ggacccttct ataaaagagt aaagagacag cctgtgtgtg tataatctct aattatgttc   1260

accgacacaa tcacacaaac ccttctctaa tcacacaact tcttcatgat ttacgacatt   1320

aattatcatt aactctttaa attcacttta catgctcaaa aatatctaat ttgcagcatt   1380

aatttgagta ccgataacta ttattataat cgtcgtgatt cgcaatcttc ttcattagat   1440

gctgtcaagt tgtactcgca cgcggtggtc cagtgaagca aatccaacgg tttaaaacct   1500

tcttacattt ctagatctaa tctgaaccgt cagatatcta gatctcattg tctgaacaca   1560

gttagatgaa actgggaatg aatctggacg aaattacgat cttacaccaa ccccctcgac   1620

gagctcgtat atataaagct tatacgctcc tccttcacct tcgtactact actaccacca   1680

catttcttta gctcaacctt cattactaat ctccttttaa ggtatgttca cttttcttcg   1740

attcatactt tctcaagatt cctgcatttc tgtagaattt gaaccaagtg tcgatttttg   1800

tttgagagaa gtgttgattt atagatctgg ttattgaatc tagattccaa tttttaattg   1860

attcgagttt gttatgtgtg tttatactac ttctcattga tcttgtttga tttctctgct   1920

ctgtattagg tttctttcgt gaatcagatc ggaa                               1954
```

<210> SEQ ID NO 111
<211> LENGTH: 2016
<212> TYPE: DNA
<213> ORGANISM: Arabidopsis thaliana
<220> FEATURE:
<221> NAME/KEY: MISC_FEATURE
<223> OTHER INFORMATION: PROMOTER: 32449; REPORT: 92

<400> SEQUENCE: 111

```
gatcggcctt cttcaggtct tctctgtagc tctgttactt ctatcacagt tatcgggtat     60

ttgagaaaaa agagttagct aaaatgaatt tctccatata atcatggttt actacaggtt    120

tacttgattc gcgttagctt tatctgcatc caaagttttt tccatgatgt tatgtcatat    180
```

```
gtgataccgt tactatgttt ataactttat acagtctggt tcactggagt ttctgtgatt    240
atgttgagta catactcatt catcctttgg taactctcaa gtttaggttg tttgaattgc    300
ctctgttgtg atacttattg tctattgcat caatcttcta atgcaccacc ctagactatt    360
tgaacaaaga gctgtttcat tcttaaacct ctgtgtctcc ttgctaaatg gtcatgcttt    420
aatgtcttca cctgtctttc tcttctatag atatgtagtc ttgctagata gttagttcta    480
cagctctctt ttgtagtctt gttagagagt tagttgagat attacctctt aaaagtatcc    540
ttgaacgctt tccggttatg accaatttgt tgtagctcct tgtaagtaga acttactggg    600
accagcgaga cagtttatgt gaatgttcat gcttaagtgt cgaacgtatc tatctctact    660
atagctctgt agtcttgtta gacagttagt tttatatctc catttttttg tagtcttgct    720
agttgagata ttacctcttc tcttcaaagt atccttgaac gctcaccggt tatgaaatct    780
ctacactata gctctgtagt cttgctagat agttagttct ttagctctct ttttgtagcc    840
tagttcttta gctctccttt tgtagccttg ctacagagta agatgggata ttacctcctt    900
gaacgctctc cggttatgac caatttgttg tagctccttg taagtagaac ttaggataga    960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgtttta attttaccaa attctttatg   1260
aagtttaaat tatactcaca ttaaaaggat tattggataa tgtaaaaatt ctgaacaatt   1320
actgattttg gaaaattaac aaatattctt tgaaatagaa gaaaaagcct ttttcctttt   1380
gacaacaaca tataaaatca tactcccatt aaaaagattt taatgtaaaa ttctgaatat   1440
aagatatttt ttacaacaac aaccaaaaat atttattttt ttcctttttt acagcaacaa   1500
gaaggaaaaa cttttttttt tgtcaagaaa aggggagatt atgtaaacag ataaaacagg   1560
gaaaataact aaccgaactc tcttaattaa catcttcaaa taaggaaaat tatgatccgc   1620
atatttagga agatcaatgc attaaaacaa cttgcacgtg gaaagagaga ctatacgctc   1680
cacacaagtt gcactaatgg tacctctcac aaaccaatca aaatactgaa taatgccaac   1740
gtgtacaaat tagggtttta cctcacaacc atcgaacatt ctcgaaacat tttaaacagc   1800
ctggcgccat agatctaaac tctcatcgac caatttttga ccgtccgatg gaaactctag   1860
cctcaaccca aaactctata taaagaaatc ttttccttcg ttattgctta ccaaatacaa   1920
accctagccg ccttattcgt cttcttcgtt ctctagtttt ttcctcagtc tctgttctta   1980
gatcccttgt agtttccaaa tcttccgata aggcct                              2016
```

<210> SEQ ID NO 112
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 1-4

<400> SEQUENCE: 112

```
Gln Trp Cys Val Ala
1               5
```

```
<210> SEQ ID NO 113
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 1-4

<400> SEQUENCE: 113

Glu Gln Thr Thr Asp
1               5


<210> SEQ ID NO 114
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 1-4

<400> SEQUENCE: 114

Glu Leu Gln Ala
1


<210> SEQ ID NO 115
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 1-4

<400> SEQUENCE: 115

Asp Cys Ser Lys Ile
1               5


<210> SEQ ID NO 116
<211> LENGTH: 17
<212> TYPE: PRT
<213> ORGANISM: Artificial sequence
<220> FEATURE:
<221> NAME/KEY: misc_feature
<222> LOCATION: (1)..(17)
<223> OTHER INFORMATION: Fragment of consensus sequence of Table 1-4

<400> SEQUENCE: 116

Asn Gln Pro Cys Phe Leu Pro Asn Thr Ile Arg Asp His Ala Ser Tyr
1               5                   10                  15

Ala


<210> SEQ ID NO 117
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 1-4

<400> SEQUENCE: 117

Asn Ser Tyr Tyr Gln Thr
1               5


<210> SEQ ID NO 118
<211> LENGTH: 4
```

<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 1-4

<400> SEQUENCE: 118

Phe Lys Gly Ala
1

<210> SEQ ID NO 119
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 1-4

<400> SEQUENCE: 119

Ile Ile Thr Glu
1

<210> SEQ ID NO 120
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 1-4

<400> SEQUENCE: 120

Asp Pro Ser His Gly Ser Cys
1               5

<210> SEQ ID NO 121
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 2-8

<400> SEQUENCE: 121

Met Gln Met Leu Arg
1               5

<210> SEQ ID NO 122
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 2-8

<400> SEQUENCE: 122

Leu Ser Thr Arg Thr Arg Ser Arg Arg Gly Gly Tyr Glu Arg Val
1               5                   10                  15

<210> SEQ ID NO 123
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 2-8

<400> SEQUENCE: 123

Ser Asp Asp Ser Thr Phe Ser Leu Leu Gly Ala Lys Leu Arg Arg Ser
1 5 10 15

Thr Ser Val Pro Tyr Tyr Ala Pro Ser
20 25

<210> SEQ ID NO 124
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 2-8

<400> SEQUENCE: 124

Ile Arg Leu Gly
1

<210> SEQ ID NO 125
<211> LENGTH: 30
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 2-8

<400> SEQUENCE: 125

Gly Asp Phe Pro Val Ile Leu Glu Lys Leu Pro Arg Gln Lys Pro Thr
1 5 10 15

Lys Thr Val Val Thr Ser Lys Leu Ser His Pro Ile Phe Ser
20 25 30

<210> SEQ ID NO 126
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 2-8

<400> SEQUENCE: 126

Asp Gly Tyr Arg Arg Arg
1 5

<210> SEQ ID NO 127
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 2-8

<400> SEQUENCE: 127

Thr Ala Lys Pro Glu Phe Ser Arg Tyr
1 5

<210> SEQ ID NO 128
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 2-8

<400> SEQUENCE: 128

Glu Tyr Leu Lys Glu
1               5

<210> SEQ ID NO 129
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 2-8

<400> SEQUENCE: 129

Gly Met Trp Asp Leu Arg Ser Asn Ser Pro Val Ile Tyr Phe Lys
1               5                   10                  15

<210> SEQ ID NO 130
<211> LENGTH: 19
<212> TYPE: PRT
<213> ORGANISM: Artificial sequence
<220> FEATURE:
<221> NAME/KEY: misc_feature
<222> LOCATION: (1)..(19)
<223> OTHER INFORMATION: Fragment of consensus sequence of Table 3-9

<400> SEQUENCE: 130

Lys Lys His Phe Val Leu Val His Gly Ala Cys His Gly Ala Trp Cys
1               5                   10                  15

Trp Tyr Lys

<210> SEQ ID NO 131
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 131

Lys Pro Leu Leu Glu Ala
1               5

<210> SEQ ID NO 132
<211> LENGTH: 13
<212> TYPE: PRT
<213> ORGANISM: Artificial sequence
<220> FEATURE:
<221> NAME/KEY: misc_feature
<222> LOCATION: (1)..(13)
<223> OTHER INFORMATION: Fragment of consensus sequence of Table 3-9

<400> SEQUENCE: 132

Gly His Arg Val Thr Ala Leu Asp Leu Ala Ala Ser Gly
1               5                   10

<210> SEQ ID NO 133
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 133

Pro Arg Gln Ile
1

<210> SEQ ID NO 134
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 3-9

<400> SEQUENCE: 134

Tyr Ser Glu Pro Leu Met Glu Leu Met
1               5

<210> SEQ ID NO 135
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 3-9

<400> SEQUENCE: 135

Glu Lys Val Val Leu Val Gly His Ser
1               5

<210> SEQ ID NO 136
<211> LENGTH: 22
<212> TYPE: PRT
<213> ORGANISM: Artificial sequence
<220> FEATURE:
<221> NAME/KEY: misc_feature
<222> LOCATION: (1)..(22)
<223> OTHER INFORMATION: Fragment of consensus sequence of Table 3-9

<400> SEQUENCE: 136

Gly Gly Leu Asn Ile Ala Leu Ala Met Glu Lys Phe Pro Glu Lys Ile
1               5                   10                  15

Ser Val Ala Val Phe Leu
            20

<210> SEQ ID NO 137
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 137

Met Pro Asp Thr Glu His
1               5

<210> SEQ ID NO 138
<211> LENGTH: 4
<212> TYPE: PRT
<213> ORGANISM: Artificial sequence
<220> FEATURE:
<221> NAME/KEY: misc_feature
<222> LOCATION: (1)..(4)

<223> OTHER INFORMATION: Fragment of consensus sequence of Table 3-9

<400> SEQUENCE: 138

Val Leu Glu Lys
1

<210> SEQ ID NO 139
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 139

Trp Met Asp Thr Glu Phe
1 5

<210> SEQ ID NO 140
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 140

Thr Ser Met Ile
1

<210> SEQ ID NO 141
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 141

Leu Tyr Gln Leu Ser Pro
1 5

<210> SEQ ID NO 142
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 3-9

<400> SEQUENCE: 142

Met Leu Val Arg Pro Gly Ser Leu Phe Ile
1 5 10

<210> SEQ ID NO 143
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 3-9

<400> SEQUENCE: 143

```
Tyr Gly Ser Val Lys Arg Val Tyr Ile Tyr
1               5                   10


<210> SEQ ID NO 144
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 3-9

<400> SEQUENCE: 144

Phe Gln Arg Trp Met Ile Glu Asn Tyr Pro
1               5                   10


<210> SEQ ID NO 145
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 145

Glu Ile Glu Gly
1


<210> SEQ ID NO 146
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 3-9

<400> SEQUENCE: 146

Ser Lys Pro Gln Glu Leu Ser
1               5


<210> SEQ ID NO 147
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 147

Phe Ile Gln Cys Leu
1               5


<210> SEQ ID NO 148
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 148

Lys Leu Val Tyr Thr Pro
1               5
```

-continued

<210> SEQ ID NO 149
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 5-8

<400> SEQUENCE: 149

Ser Thr Tyr Gln Asn Leu Arg Phe Leu
1               5

<210> SEQ ID NO 150
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 5-8

<400> SEQUENCE: 150

Thr Pro Lys Pro Leu Val Ile Ile Thr Pro
1               5                   10

<210> SEQ ID NO 151
<211> LENGTH: 16
<212> TYPE: PRT
<213> ORGANISM: Artificial sequence
<220> FEATURE:
<221> NAME/KEY: misc_feature
<222> LOCATION: (1)..(16)
<223> OTHER INFORMATION: Fragment of consensus sequence of Table 5-8

<400> SEQUENCE: 151

Ser His Ile Gln Ala Ala Val Val Cys Ser Lys Lys His Gly Leu Gln
1               5                   10                  15

<210> SEQ ID NO 152
<211> LENGTH: 16
<212> TYPE: PRT
<213> ORGANISM: Artificial sequence
<220> FEATURE:
<221> NAME/KEY: misc_feature
<222> LOCATION: (1)..(16)
<223> OTHER INFORMATION: Fragment of consensus sequence of Table 5-8

<400> SEQUENCE: 152

Arg Val Arg Ser Gly Gly His Asp Tyr Glu Gly Leu Ser Tyr Val Ser
1               5                   10                  15

<210> SEQ ID NO 153
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 5-8

<400> SEQUENCE: 153

Pro Phe Val Val Val Asp Leu
1               5

<210> SEQ ID NO 154
<211> LENGTH: 17
<212> TYPE: PRT
<213> ORGANISM: Artificial sequence
<220> FEATURE:
<221> NAME/KEY: misc_feature
<222> LOCATION: (1)..(17)
<223> OTHER INFORMATION: Fragment of consensus sequence of Table 5-8

<400> SEQUENCE: 154

Thr Ala Trp Val Gln Ala Gly Ala Thr Leu Gly Glu Leu Tyr Tyr Arg
1 5 10 15

Ile

<210> SEQ ID NO 155
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 155

Glu Lys Ser Lys
1

<210> SEQ ID NO 156
<211> LENGTH: 22
<212> TYPE: PRT
<213> ORGANISM: Artificial sequence
<220> FEATURE:
<221> NAME/KEY: misc_feature
<222> LOCATION: (1)..(22)
<223> OTHER INFORMATION: Fragment of consensus sequence of Table 5-8

<400> SEQUENCE: 156

Gly Phe Pro Ala Gly Val Cys Pro Thr Val Gly Val Gly Gly His Ile
1 5 10 15

Ser Gly Gly Gly Tyr Gly
20

<210> SEQ ID NO 157
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 5-8

<400> SEQUENCE: 157

Leu Met Arg Lys Tyr Gly Leu Ala Ala Asp Asn Val Ile Asp Ala
1 5 10 15

<210> SEQ ID NO 158
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 5-8

<400> SEQUENCE: 158

Val Asp Asn Gly Lys Leu Leu Asp Arg Lys Ser Met Gly Glu Asp Leu
1 5 10 15

Phe Trp Ala Ile Arg Gly Gly Gly Gly
20 25

<210> SEQ ID NO 159
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 159

Ser Phe Gly Val
1

<210> SEQ ID NO 160
<211> LENGTH: 17
<212> TYPE: PRT
<213> ORGANISM: Artificial sequence
<220> FEATURE:
<221> NAME/KEY: misc_feature
<222> LOCATION: (1)..(17)
<223> OTHER INFORMATION: Fragment of consensus sequence of Table 5-8

<400> SEQUENCE: 160

Leu Ala Trp Lys Ile Lys Leu Val Pro Val Pro Glu Thr Val Thr Val
1               5                   10                  15

Phe

<210> SEQ ID NO 161
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 161

Arg Thr Leu Glu Gln Asn
1               5

<210> SEQ ID NO 162
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 162

Lys Trp Gln Gln Val Ala
1               5

<210> SEQ ID NO 163
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 163

Thr Val Arg Ala
1

<210> SEQ ID NO 164
<211> LENGTH: 5

<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 164

Leu Phe Leu Gly Gly
1               5

<210> SEQ ID NO 165
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 165

Leu Met Asn Lys
1

<210> SEQ ID NO 166
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 166

Phe Pro Glu Leu Gly Leu
1               5

<210> SEQ ID NO 167
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 5-8

<400> SEQUENCE: 167

Glu Met Ser Trp Ile Glu Ser Val Leu Tyr Tyr
1               5                   10

<210> SEQ ID NO 168
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 168

Glu Val Leu Leu Asn
1               5

<210> SEQ ID NO 169
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 5-8

<400> SEQUENCE: 169

Lys Ser Asp Tyr Val Lys Glu Pro Ile Pro Lys Ser Gly Leu Glu
1 5 10 15

<210> SEQ ID NO 170
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 170

Pro Tyr Gly Gly
1

<210> SEQ ID NO 171
<211> LENGTH: 26
<212> TYPE: PRT
<213> ORGANISM: Artificial sequence
<220> FEATURE:
<221> NAME/KEY: misc_feature
<222> LOCATION: (1)..(26)
<223> OTHER INFORMATION: Fragment of consensus sequence of Table 5-8

<400> SEQUENCE: 171

Glu Ile Ser Glu Ser Ala Ile Pro Phe Pro His Arg Ser Gly Val Leu
1 5 10 15

Tyr Lys Ile Gln Tyr Val Val Asn Trp Glu
20 25

<210> SEQ ID NO 172
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 172

Gly Asp Glu Ala
1

<210> SEQ ID NO 173
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 173

Arg His Leu Asn Trp
1 5

<210> SEQ ID NO 174
<211> LENGTH: 26
<212> TYPE: PRT
<213> ORGANISM: Artificial sequence
<220> FEATURE:
<221> NAME/KEY: misc_feature
<222> LOCATION: (1)..(26)

<223> OTHER INFORMATION: Fragment of consensus sequence of Table 5-8

<400> SEQUENCE: 174

Tyr Met Thr Pro Tyr Val Ser Lys Asn Pro Arg Glu Ala Tyr Val Asn
1               5                   10                  15

Tyr Arg Asp Leu Asp Leu Gly Val Asn Ser
            20                  25

<210> SEQ ID NO 175
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 5-8

<400> SEQUENCE: 175

Val Trp Gly Glu Lys Tyr Phe Lys
1               5

<210> SEQ ID NO 176
<211> LENGTH: 13
<212> TYPE: PRT
<213> ORGANISM: Artificial sequence
<220> FEATURE:
<221> NAME/KEY: misc_feature
<222> LOCATION: (1)..(13)
<223> OTHER INFORMATION: Fragment of consensus sequence of Table 5-8

<400> SEQUENCE: 176

Asn Phe Lys Arg Leu Val Val Lys Thr Lys Val Asp Pro
1               5                   10

<210> SEQ ID NO 177
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 5-8

<400> SEQUENCE: 177

Asn Phe Phe Arg Asn Glu Gln Ser Ile Pro
1               5                   10

<210> SEQ ID NO 178
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 178

Met Pro Val Val Gly Met Gly Thr Ala
1               5

<210> SEQ ID NO 179
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 6-8

<400> SEQUENCE: 179

Ala Ile Leu Glu Ala Ile Lys
1 5

<210> SEQ ID NO 180
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 180

Gly Tyr Arg His Phe Asp Thr Ala Ala
1 5

<210> SEQ ID NO 181
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 181

Leu Gly Glu Ala Leu Ala Glu Ala Ile
1 5

<210> SEQ ID NO 182
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 182

Asp Leu Phe Val Thr Ser Lys Leu Trp
1 5

<210> SEQ ID NO 183
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 6-8

<400> SEQUENCE: 183

Leu Val Val Pro Ala Leu
1 5

<210> SEQ ID NO 184
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 6-8

<400> SEQUENCE: 184

Lys Ser Leu Lys Asn Leu Gln Leu Asp Tyr Ile Asp Leu Tyr Leu Ile

```
1               5                   10                  15

His Trp Pro Ile Ser Leu Lys Pro Gly
            20                  25


<210> SEQ ID NO 185
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 6-8

<400> SEQUENCE: 185

Glu Asp Leu Leu Pro
1               5


<210> SEQ ID NO 186
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 186

Lys Gly Val Trp
1


<210> SEQ ID NO 187
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 6-8

<400> SEQUENCE: 187

Ala Met Glu Glu Cys
1               5


<210> SEQ ID NO 188
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 6-8

<400> SEQUENCE: 188

Lys Leu Gly Leu Ala Lys Ala Ile Gly Val Ser Asn Phe Ser
1               5                   10


<210> SEQ ID NO 189
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 189

Lys Lys Leu Glu
1
```

<210> SEQ ID NO 190
<211> LENGTH: 18
<212> TYPE: PRT
<213> ORGANISM: Artificial sequence
<220> FEATURE:
<221> NAME/KEY: misc_feature
<222> LOCATION: (1)..(18)
<223> OTHER INFORMATION: Fragment of consensus sequence of Table 6-8

<400> SEQUENCE: 190

Leu Leu Ser Val Ala Thr Ile Pro Pro Ala Val Asn Gln Val Glu Met
1 5 10 15

Asn Pro

<210> SEQ ID NO 191
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 6-8

<400> SEQUENCE: 191

Trp Gln Gln Lys Lys Leu Arg Glu Phe Cys Lys
1 5 10

<210> SEQ ID NO 192
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 6-8

<400> SEQUENCE: 192

Val Thr Ala Tyr Ser Pro Leu Gly Ala Lys Gly
1 5 10

<210> SEQ ID NO 193
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 6-8

<400> SEQUENCE: 193

Val Leu Lys Glu Ile Ala Glu Ala Lys Gly Lys Thr Val Ala Gln
1 5 10 15

<210> SEQ ID NO 194
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 6-8

<400> SEQUENCE: 194

Val Ser Leu Arg Trp Val Tyr Glu Gln Gly Val Thr Leu Ile
1 5 10

<210> SEQ ID NO 195
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 6-8

<400> SEQUENCE: 195

Lys Glu Arg Met Lys Gln Asn Leu
1               5

<210> SEQ ID NO 196
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 6-8

<400> SEQUENCE: 196

Ile Phe Asp Trp Glu Leu Thr Glu Glu Asp
1               5                   10

<210> SEQ ID NO 197
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 197

Gln Ile Pro Gln
1

<210> SEQ ID NO 198
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 198

Arg Arg Leu Ile
1

<210> SEQ ID NO 199
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 6-8

<400> SEQUENCE: 199

Gly Pro Tyr Lys Ser
1               5

<210> SEQ ID NO 200
<211> LENGTH: 4
<212> TYPE: PRT
<213> ORGANISM: Artificial sequence

```
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 200

Asp Leu Trp Asp
1


<210> SEQ ID NO 201
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 7-6

<400> SEQUENCE: 201

Val Ser Pro Ala Phe
1               5


<210> SEQ ID NO 202
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 7-6

<400> SEQUENCE: 202

Ala Gly Ser Ser
1


<210> SEQ ID NO 203
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 7-6

<400> SEQUENCE: 203

Ser Asp Ser Ser Ile
1               5


<210> SEQ ID NO 204
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 7-6

<400> SEQUENCE: 204

Val Gly Lys Ser Thr Asn Ile
1               5


<210> SEQ ID NO 205
<211> LENGTH: 44
<212> TYPE: PRT
<213> ORGANISM: Artificial sequence
<220> FEATURE:
<221> NAME/KEY: misc_feature
<222> LOCATION: (1)..(44)
<223> OTHER INFORMATION: Fragment of consensus sequence of Table 7-6
```

<400> SEQUENCE: 205

Trp His Asp Cys Ala Val Ser Lys Ser Asp Arg Gln Glu Leu Leu Lys
1 5 10 15

Gln Lys Gly Cys Val Ile Trp Ile Thr Gly Leu Ser Gly Ser Gly Lys
20 25 30

Ser Thr Leu Ala Cys Ala Leu Ser Arg Ala Leu His
35 40

<210> SEQ ID NO 206
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 7-6

<400> SEQUENCE: 206

Arg Gly Lys Leu
1

<210> SEQ ID NO 207
<211> LENGTH: 18
<212> TYPE: PRT
<213> ORGANISM: Artificial sequence
<220> FEATURE:
<221> NAME/KEY: misc_feature
<222> LOCATION: (1)..(18)
<223> OTHER INFORMATION: Fragment of consensus sequence of Table 7-6

<400> SEQUENCE: 207

Tyr Ile Leu Asp Gly Asp Asn Val Arg His Gly Leu Asn Ser Asp Leu
1 5 10 15

Ser Phe

<210> SEQ ID NO 208
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 7-6

<400> SEQUENCE: 208

Ala Glu Asp Arg Ala Glu
1 5

<210> SEQ ID NO 209
<211> LENGTH: 16
<212> TYPE: PRT
<213> ORGANISM: Artificial sequence
<220> FEATURE:
<221> NAME/KEY: misc_feature
<222> LOCATION: (1)..(16)
<223> OTHER INFORMATION: Fragment of consensus sequence of Table 7-6

<400> SEQUENCE: 209

Asn Ile Arg Arg Val Gly Glu Val Ala Lys Leu Phe Ala Asp Ala Gly
1 5 10 15

<210> SEQ ID NO 210
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 7-6

<400> SEQUENCE: 210

Val Cys Ile Ala Ser Leu Ile Ser Pro Tyr Arg
1 5 10

<210> SEQ ID NO 211
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 7-6

<400> SEQUENCE: 211

Ala Cys Arg Ala Leu Leu Pro
1 5

<210> SEQ ID NO 212
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 7-6

<400> SEQUENCE: 212

Gly Asp Phe Ile Glu Val Phe Met Asp Val Pro Leu Glu Val Cys Glu
1 5 10 15

Ala Arg Asp Pro Lys Gly Leu Tyr Lys
20 25

<210> SEQ ID NO 213
<211> LENGTH: 27
<212> TYPE: PRT
<213> ORGANISM: Artificial sequence
<220> FEATURE:
<221> NAME/KEY: misc_feature
<222> LOCATION: (1)..(27)
<223> OTHER INFORMATION: Fragment of consensus sequence of Table 7-6

<400> SEQUENCE: 213

Ala Arg Ala Gly Lys Ile Lys Gly Phe Thr Gly Ile Asp Asp Pro Tyr
1 5 10 15

Glu Ala Pro Leu Asp Cys Glu Ile Val Ile Gln
20 25

<210> SEQ ID NO 214
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 7-6

<400> SEQUENCE: 214

Met Ala Asp Ile Val Val Ser Tyr Leu Glu
1 5 10

<210> SEQ ID NO 215
<211> LENGTH: 23

<212> TYPE: PRT
<213> ORGANISM: Artificial sequence
<220> FEATURE:
<221> NAME/KEY: misc_feature
<222> LOCATION: (1)..(23)
<223> OTHER INFORMATION: Fragment of consensus sequence of Table 8-7

<400> SEQUENCE: 215

Met Phe Arg Ala Met Ser Thr Arg Lys Val His Gly Gly Tyr Glu Lys
1 5 10 15

Leu Gly Asp Glu Glu Ala Arg
20

<210> SEQ ID NO 216
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 8-7

<400> SEQUENCE: 216

Leu Lys Arg Val
1

<210> SEQ ID NO 217
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 8-7

<400> SEQUENCE: 217

Ser Val Pro Ala Ser Val Tyr Gly His Ser Arg Asn Pro Val
1 5 10

<210> SEQ ID NO 218
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 8-7

<400> SEQUENCE: 218

Gln Glu Val Lys Lys Thr Pro Thr Ala Lys Pro Thr Gly Gly Ser
1 5 10 15

<210> SEQ ID NO 219
<211> LENGTH: 18
<212> TYPE: PRT
<213> ORGANISM: Artificial sequence
<220> FEATURE:
<221> NAME/KEY: misc_feature
<222> LOCATION: (1)..(18)
<223> OTHER INFORMATION: Fragment of consensus sequence of Table 8-7

<400> SEQUENCE: 219

Val His Pro Leu Ser Phe Phe Asp Val His Phe Gln Arg Lys Lys Lys
1 5 10 15

Lys Thr

<210> SEQ ID NO 220

```
<211> LENGTH: 19
<212> TYPE: PRT
<213> ORGANISM: Artificial sequence
<220> FEATURE:
<221> NAME/KEY: misc_feature
<222> LOCATION: (1)..(19)
<223> OTHER INFORMATION: Fragment of consensus sequence of Table 8-7

<400> SEQUENCE: 220

Lys Lys Lys Ser Leu Ala Thr Ala Lys Pro Glu Phe Ala Arg Tyr Met
1               5                   10                  15

Glu Tyr Val


<210> SEQ ID NO 221
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 8-7

<400> SEQUENCE: 221

Glu Gly Gly Val Trp Asp Pro
1               5


<210> SEQ ID NO 222
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 8-7

<400> SEQUENCE: 222

Ser Asn Ala Pro Val Ile His Tyr Arg
1               5


<210> SEQ ID NO 223
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 10-6

<400> SEQUENCE: 223

Leu Leu Leu Leu Leu Ser Ala Ser Ser Ala Val
1               5                   10


<210> SEQ ID NO 224
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 10-6

<400> SEQUENCE: 224

Asp Pro Ser Phe Gln Lys
1               5


<210> SEQ ID NO 225
<211> LENGTH: 27
<212> TYPE: PRT
```

<213> ORGANISM: Artificial sequence
<220> FEATURE:
<221> NAME/KEY: misc_feature
<222> LOCATION: (1)..(27)
<223> OTHER INFORMATION: Fragment of consensus sequence of Table 10-6

<400> SEQUENCE: 225

Ser Gly Pro Glu Ala Phe Ala Phe Asp Ser Thr Gly Lys Gly Phe Tyr
1 5 10 15

Thr Gly Val Ser Asp Gly Arg Ile Leu Lys Tyr
20 25

<210> SEQ ID NO 226
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 10-6

<400> SEQUENCE: 226

Val Asp Phe Ala
1

<210> SEQ ID NO 227
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 10-6

<400> SEQUENCE: 227

Leu Cys Gly Arg Pro
1 5

<210> SEQ ID NO 228
<211> LENGTH: 19
<212> TYPE: PRT
<213> ORGANISM: Artificial sequence
<220> FEATURE:
<221> NAME/KEY: misc_feature
<222> LOCATION: (1)..(19)
<223> OTHER INFORMATION: Fragment of consensus sequence of Table 10-6

<400> SEQUENCE: 228

Gly Ile Ala Phe Asn Lys Thr Gly Asp Leu Tyr Val Ala Asp Ala Tyr
1 5 10 15

Leu Gly Leu

<210> SEQ ID NO 229
<211> LENGTH: 35
<212> TYPE: PRT
<213> ORGANISM: Artificial sequence
<220> FEATURE:
<221> NAME/KEY: misc_feature
<222> LOCATION: (1)..(35)
<223> OTHER INFORMATION: Fragment of consensus sequence of Table 10-6

<400> SEQUENCE: 229

Gly Gly Leu Ala Thr Gln Leu Ala Thr Ser Val Asp Gly Val Pro Phe
1 5 10 15

Lys Trp Leu Asp Gly Leu Asp Val Asp Gln Arg Thr Gly Val Val Tyr
20 25 30

Phe Thr Asp
        35

<210> SEQ ID NO 230
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 10-6

<400> SEQUENCE: 230

Val Leu Ile Val
1

<210> SEQ ID NO 231
<211> LENGTH: 12
<212> TYPE: PRT
<213> ORGANISM: Artificial sequence
<220> FEATURE:
<221> NAME/KEY: misc_feature
<222> LOCATION: (1)..(12)
<223> OTHER INFORMATION: Fragment of consensus sequence of Table 10-6

<400> SEQUENCE: 231

Thr Gly Arg Leu Leu Lys Tyr Asp Pro Ser Thr Lys
1               5                   10

<210> SEQ ID NO 232
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 10-6

<400> SEQUENCE: 232

Val Thr Val Leu Met Lys Gly Leu
1               5

<210> SEQ ID NO 233
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 10-6

<400> SEQUENCE: 233

Asp Gly Ser Phe Val Leu Val Ala Glu Phe
1               5                   10

<210> SEQ ID NO 234
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 10-6

<400> SEQUENCE: 234

Ile Lys Lys Tyr Trp
1               5

<210> SEQ ID NO 235
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 10-6

<400> SEQUENCE: 235

Lys Gly Pro Lys Ala Gly Ser Ser
1               5

<210> SEQ ID NO 236
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 10-6

<400> SEQUENCE: 236

Asn Pro Asp Asn Ile Lys Arg
1               5

<210> SEQ ID NO 237
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 10-6

<400> SEQUENCE: 237

Gly Asn Phe Trp Val Ala Ser Ser
1               5

<210> SEQ ID NO 238
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 10-6

<400> SEQUENCE: 238

Leu Ser Glu Val
1

<210> SEQ ID NO 239
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 10-6

<400> SEQUENCE: 239

Leu Tyr Ile Gly Thr Leu
1               5

<210> SEQ ID NO 240
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 10-6

<400> SEQUENCE: 240

Pro Phe Ala Gly Ile Leu
1               5

<210> SEQ ID NO 241
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 11-6

<400> SEQUENCE: 241

Ala Leu Val Ser Leu Leu Leu Leu Leu Ser
1               5                   10

<210> SEQ ID NO 242
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 11-6

<400> SEQUENCE: 242

Pro Ser Phe Gln Lys Leu
1               5

<210> SEQ ID NO 243
<211> LENGTH: 27
<212> TYPE: PRT
<213> ORGANISM: Artificial sequence
<220> FEATURE:
<221> NAME/KEY: misc_feature
<222> LOCATION: (1)..(27)
<223> OTHER INFORMATION: Fragment of consensus sequence of Table 11-6

<400> SEQUENCE: 243

Ser Gly Pro Glu Ser Phe Ala Phe Asp Ser Thr Gly Lys Gly Phe Tyr
1               5                   10                  15

Thr Gly Val Ser Asp Gly Arg Ile Leu Lys Tyr
            20                  25

<210> SEQ ID NO 244
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 11-6

<400> SEQUENCE: 244

Val Asp Phe Ala
1

<210> SEQ ID NO 245
<211> LENGTH: 5
<212> TYPE: PRT
<213> ORGANISM: Artificial sequence
<220> FEATURE:

<221> NAME/KEY: misc_feature
<222> LOCATION: (1)..(5)
<223> OTHER INFORMATION: Fragment of consensus sequence of Table 11-6

<400> SEQUENCE: 245

Leu Cys Gly Arg Pro
1 5

<210> SEQ ID NO 246
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 11-6

<400> SEQUENCE: 246

Gly Ile Ser Phe Asn
1 5

<210> SEQ ID NO 247
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 11-6

<400> SEQUENCE: 247

Lys Thr Gly Asp Leu Tyr Val Ala Asp Ala Tyr Leu Gly Leu
1 5 10

<210> SEQ ID NO 248
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 11-6

<400> SEQUENCE: 248

Gly Gly Leu Ala Thr Gln Leu Ala Thr Ser Val
1 5 10

<210> SEQ ID NO 249
<211> LENGTH: 23
<212> TYPE: PRT
<213> ORGANISM: Artificial sequence
<220> FEATURE:
<221> NAME/KEY: misc_feature
<222> LOCATION: (1)..(23)
<223> OTHER INFORMATION: Fragment of consensus sequence of Table 11-6

<400> SEQUENCE: 249

Gly Val Pro Phe Lys Trp Leu Asp Gly Leu Asp Val Asp Gln Arg Thr
1 5 10 15

Gly Val Val Tyr Phe Thr Asp
20

<210> SEQ ID NO 250
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 11-6

<400> SEQUENCE: 250

Thr Gly Arg Leu
1

<210> SEQ ID NO 251
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 11-6

<400> SEQUENCE: 251

Lys Tyr Asp Pro Ser Thr Lys
1               5

<210> SEQ ID NO 252
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 252

Val Thr Val Leu Met Lys Gly Leu
1               5

<210> SEQ ID NO 253
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 11-6

<400> SEQUENCE: 253

Asp Gly Ser Phe Val Leu Val Ala Glu Phe
1               5                   10

<210> SEQ ID NO 254
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 11-6

<400> SEQUENCE: 254

Ile Lys Lys Tyr Trp
1               5

<210> SEQ ID NO 255
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 255

Lys Gly Pro Lys Ala Gly Thr Ser
1 5

<210> SEQ ID NO 256
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 11-6

<400> SEQUENCE: 256

Asn Pro Asp Asn Ile Lys Arg Asn Gly
1 5

<210> SEQ ID NO 257
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 257

Gly Asn Phe Trp Val Ala Ser Ser
1 5

<210> SEQ ID NO 258
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 258

Asp Pro Arg Ala Val Lys Val Asp
1 5

<210> SEQ ID NO 259
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 11-6

<400> SEQUENCE: 259

Val Leu Gln Val Ile Pro Leu
1 5

<210> SEQ ID NO 260
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 11-6

<400> SEQUENCE: 260

Ile Ser Glu Val
1

-continued

```
<210> SEQ ID NO 261
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 11-6

<400> SEQUENCE: 261

Leu Tyr Ile Gly Ser Leu
1               5


<210> SEQ ID NO 262
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 11-6

<400> SEQUENCE: 262

Pro Phe Ala Gly Ile Leu
1               5
```

NUCLEOTIDE SEQUENCES AND POLYPEPTIDES ENCODED THEREBY USEFUL FOR MODIFYING PLANT CHARACTERISTICS

This application is a divisional of application Ser. No. 16/793,481 filed on Feb. 18, 2020 (now U.S. Pat. No. 11,142,773), which application is a divisional of application Ser. No. 15/953,264, filed on Apr. 13, 2018 (now U.S. Pat. No. 10,655,139), which application is a continuation of application Ser. No. 14/565,186, filed on Dec. 9, 2014 (now U.S. Pat. No. 9,957,521), which is a divisional of application Ser. No. 13/184,361 filed on Jul. 15, 2011 (now U.S. Pat. No. 8,962,921), which claims priority to application Ser. No. 11/140,450 filed on May 27, 2005 (now U.S. Pat. No. 8,022,273), which claims priority under 35 U.S.C. § 119(e) of U.S. Provisional Application No. 60/575,253 filed on May 27, 2004. The entirety of each of the above-mentioned patent applications is hereby incorporated by reference.

FIELD OF THE INVENTION

The present invention relates to isolated polynucleotides, polypeptides encoded thereby, and the use of those sequences for making transgenic plants with modulated water use efficiency.

BACKGROUND OF THE INVENTION

Plants are constantly exposed to a variety of biotic (e.g., pathogen infection and insect herbivory) and abiotic (e.g., high or low temperature, drought, flood, anaerobic conditions and salinity) stresses. To survive these challenges, plants have developed elaborate mechanisms to perceive external signals and to manifest adaptive responses with proper physiological and morphological changes (Bohnert et al., 1995). Plants exposed to heat and/or low water or drought conditions typically have low yields of plant material, seeds, fruit and other edible products. Some countries of the world consistently have very low rainfall and therefore have problems growing sufficient food crops for their population. Yet it has been observed that some plants survive and thrive in low water environments. It would, therefore, be of great interest and importance to be able to identify genes that confer improved water efficiency characteristics to thereby enable one to create transformed plants (such as crop plants) with modulated water efficiency characteristics to, thereby, better survive high and/or low heat, high and/or low water, and drought or flood conditions. Exogenous application to plants of high concentrations of PEG and mannitol are known to produce osmotic stress resulting in the retardation of growth and vigor and are used to assess drought responses. Exogenous application of ABA stimulates drought-responses in plants and can, therefore, be an important screen to identify genes that confer improved water efficiency.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. (Zhang et al. (2004) *Plant Physiol.* 135:615). There is a need for generally applicable processes that improve forest or agricultural plant growth potential. Therefore, the present invention relates to a process for increasing the abiotic stress tolerance and consequently the growth potential in plants, characterized by expression of recombinant DNA molecules stably integrated into the plant genome.

SUMMARY OF THE INVENTION

The present invention, therefore, relates to isolated polynucleotides, polypeptides encoded thereby, and the use of those sequences for making transgenic plants with modulated water use efficiency.

The present invention also relates to processes for increasing the growth potential in plants under abnormal water conditions, recombinant nucleic acid molecules and polypeptides used for these processes and their uses, as well as to plants themselves.

Unless otherwise defined, all technical and scientific terms used herein have the same meaning as commonly understood by one of ordinary skill in the art to which this invention belongs.

BRIEF DESCRIPTION OF THE DRAWINGS

FIG. 2 provides the results of a consensus sequence (SEQ ID NOs: 121-129) analysis based on Ceres cDNA 12334963.

DETAILED DESCRIPTION OF THE INVENTION

1. Definitions

Figure 1:
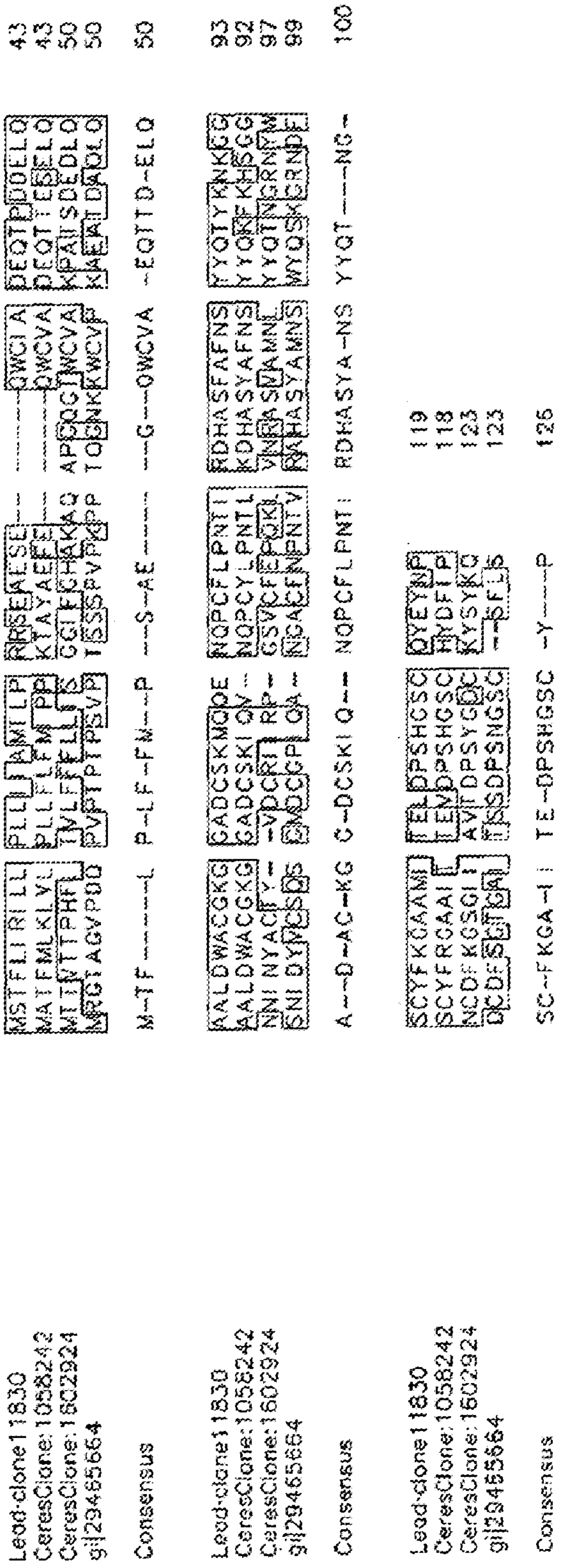
FIG. 1 provides the results of a consensus sequence (SEQ ID NOs: 112-120) analysis based on Ceres cDNA 12331850.

The following terms are utilized throughout this application:

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Drought: Plant species vary in their capacity to tolerate drought conditions. For each species, optimal growth can be achieved if a certain level of water is always available. Other factors such as temperature and soil conditions have a significant impact on the availability of water to the plant. “Drought” can be defined as the set of environmental conditions under which a plant will begin to suffer the effects of water deprivation, such as decreased photosynthesis, loss of turgor (wilting) and decreased stomatal conductance. This drought condition results in a significant reduction in yield. Water deprivation may be caused by lack of rainfall or limited irrigation. Alternatively, water deficit may also be caused by high temperatures, low humidity, saline soils, freezing temperatures or water-logged soils that damage roots and limit water uptake to the shoot. Since plant species vary in their capacity to tolerate water deficit, the precise environmental conditions that cause drought stress can not be generalized. However, drought tolerant plants produce higher biomass and yield than plants that are not drought tolerant. Differences in physical appearance, recovery and yield can be quantified and statistically analyzed using well known measurement and analysis methods.

Endogenous: The term “endogenous,” within the context of the current invention refers to any polynucleotide, polypeptide or protein sequence which is a natural part of a cell or organisms regenerated from said cell.

Exogenous: “Exogenous,” as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term “exogenous” as used herein is also intended to encompass inserting a naturally found element into a non-naturally found location.

Flood: Plant species vary in their capacity to tolerate flooding. Some plants, such as rice, are cultivated in water while plants such as corn do not tolerate flooding. “Flood,” as referred to within, is the state of water saturation at which soils become hypoxic or anoxic, thus limiting respiration in the root. Reduced respiration damages roots and can limit the permeability of roots to water, resulting in decreased leaf water potential and wilting. Since plant species vary in their capacity to tolerate flooding, the precise environmental conditions that cause flood stress can not be generalized. However, flood tolerant plants are characterized by their ability to retain their normal appearance or recover quickly from flood. Such flood tolerant plants produce higher biomass and yield than plants that are not flood tolerant. Differences in physical appearance, recovery and yield can be quantified and statistically analyzed using well known measurement and analysis methods.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical and within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily to the same degree. Typically, comparable proteins give the same characteristics where the quantitative measurement due to one of the comparables is at least 20% of the other; more typically, between 30 to 40%; even more typically, between 50-60%; even more typically, 70 to 80%; even more typically between 90 to 100%.

Heterologous sequences: “Heterologous sequences” are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

High Temperature: Plant species vary in their capacity to tolerate high temperatures. Very few plant species can survive temperatures higher than 45° C. The effects of high temperatures on plants, however, can begin at lower temperatures depending on the species and other environmental conditions such as humidity and soil moisture. "High temperature" can be defined as the temperature at which a given plant species will be adversely affected as evidenced by symptoms such as decreased photosynthesis. Since plant species vary in their capacity to tolerate high temperature, the precise environmental conditions that cause high temperature stress can not be generalized. However, high temperature tolerant plants are characterized by their ability to retain their normal appearance or recover quickly from high temperature conditions. Such high temperature tolerant plants produce higher biomass and yield than plants that are not high temperature tolerant. Differences in physical appearance, recovery and yield can be quantified and statistically analyzed using well know measurement and analysis methods.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light.

Low Temperature: Plant species vary in their capacity to tolerate low temperatures. Chilling-sensitive plant species, including may agronomically important species, can be injured by cold, above-freezing temperatures. At temperatures below the freezing-point of water most plant species will be damaged. Thus, "low temperature" can be defined as the temperature at which a given plant species will be adversely affected as evidenced by symptoms such as decreased photosynthesis and membrane damage (measured by electrolyte leakage). Since plant species vary in their capacity to tolerate low temperature, the precise environmental conditions that cause low temperature stress can not be generalized. However, low temperature tolerant plants are characterized by their ability to retain their normal appearance or recover quickly from low temperature conditions. Such low temperature tolerant plants produce higher biomass and yield than plants that are not low temperature tolerant. Differences in physical appearance, recovery and yield can be quantified and statistically analyzed using well known measurement and analysis methods.

Plant seeds vary considerably in their ability to germinate under low temperature conditions. Seeds of most plant species will not germinate at temperatures less than 10° C. Once seeds have imbibed water they become very susceptible to disease, water and chemical damage. Seeds that are tolerant to low temperature stress during germination can survive for relatively long periods under which the temperature is too low to germinate. Since plant species vary in their capacity to tolerate low temperature during germination, the precise environmental conditions that cause low temperature stress during germination can not be generalized. However, plants that tolerate low temperature during germination are characterized by their ability to remain viable or recover quickly from low temperature conditions. Such low temperature tolerant plants produce, germinate, become established, grow more quickly and ultimately produce more biomass and yield than plants that are not low temperature tolerant. Differences in germination rate, appearance, recovery and yield can be quantified and statistically analyzed using well known measurement and analysis methods.

Masterpool: The "master pools" discussed in these experiments are a pool of seeds from five different transgenic plants transformed with the same exogenous gene.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2414 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BES 1'1"1'1 are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases.

Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Specific Promoter: In the context of the current invention, "specific promoters" refers to promoters that have a high preference for being active in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30(2):321-9); RCc2 and RCc3, promoters that direct root-specific gene transcription in rice (Xu et al., *Plant Mol. Biol.* 27:237 (1995) and TobRB27, a root-specific promoter from tobacco (Yamamoto et al. (1991) *Plant Cell* 3:371).

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$−5° C. to $T_m$−10° C. Medium or moderate stringency conditions are those providing $T_m$−20° C. to $T_m$−29° C. Low stringency conditions are those providing a condition of $T_m$−40° C. to $T_m$−48° C. The relationship of hybridization conditions to $T_m$ (in ° C.) is expressed in the mathematical equation $$T_m=81.5-16.6(\log_{10}[Na^+])+0.41(\%\ G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6\log\{[Na^+]/(1+0.7[Na^+])\}+0.41(\%\ G+C)-500/L0.63(\%\ \text{formamide}) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools". Thus, the superpool contains an equal amount of seed from 500 different events, but only represents 100 transgenic plants with a distinct exogenous nucleotide sequence transformed into them, because the master pools are of 5 different events with the same exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

2. Important Characteristics of the Polynucleotides and Polypeptides of the Invention The polynucleotides and polypeptides of the present invention are of interest because when they are misexpressed (i.e. when expressed at a non-natural location or in an increased or decreased amount) they produce plants with modified water use efficiency. "Water use efficiency" is a term that includes various responses to environmental conditions that affect the amount of water available to the plant. For example, under high heat conditions water is rapidly evaporated from both the soil and from the plant itself, resulting in a decrease of available water for maintaining or initiating physiological processes. Likewise, water availability is limited during cold or drought conditions or when there is low water content in the soil. Interestingly, flood conditions also affect the amount of water available to the plant because it damages the roots and thus limits the plant's ability to transport water to the shoot. As used herein, modulating water use efficiency is intended to encompass all of these situations as well as other environmental situations that affect the plant's ability to use and/or maintain water effectively (e.g. osmotic stress, salinity, etc.).

The polynucleotides and polypeptides of the invention, as discussed below and as evidenced by the results of various experiments, are useful for modulating water use efficiency. These traits can be used to exploit or maximize plant products for agricultural, ornamental or forestry purposes in different environment conditions of water supply. Modulating the expression of the nucleotides and polypeptides of the present invention leads to transgenic plants that will require less water and result in better yield in high heat and/or drought conditions, or that have increased tolerance levels for an excess of water and result in better yield in wet conditions. Both categories of transgenic plants lead to reduced costs for the farmer and better yield in their respective environmental conditions.

3. The Polynucleotides and Polypeptides of the Invention

The polynucleotides of the invention, and the proteins expressed thereby, are set forth in the Sequence Listing. Some of these sequences are functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity and generally share at least one biochemical and/or phenotypic activity. For example, biochemical functionally comparable proteins are proteins that act on the same reactant to give the same product.

Another class of functionally comparable proteins is phenotypic functionally comparable proteins. The members of this class regulate the same physical characteristic, such as increased drought tolerance. Proteins can be considered phenotypic functionally comparable proteins even if the proteins give rise to the same physical characteristic, but to a different degree.

The polypeptides of the invention also include those comprising the consensus sequences described in Tables 1-4, 2-8, 3-9, 5-8, 6-8, 7-6, 8-7, 10-6 and 11-6. A consensus sequence defines the important conserved amino acids and/or domains within a polypeptide. Thus, all those sequences that conform to the consensus sequence are suitable for the same purpose. Polypeptides comprised of a sequence within and defined by one of the consensus sequences can be utilized for the purposes of the invention namely to make transgenic plants with improved water use efficiency, including improved tolerance to heat or high or low water conditions.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);

(b) YAC: Burke et al., Science 236:806-812 (1987);

(c) PAC: Sternberg N. et al., Proc Natl Acad Sci USA. January; 87(1):103-7 (1990);

(d) Bacteria-Yeast Shuttle Vectors: Bradshaw et al., Nucl Acids Res 23: 4850-4856 (1995);

(e) Lambda Phage Vectors: Replacement Vector, e.g., Frischauf et al., J. Mol Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors: Walden et al., Mol Cell Biol 1: 175-194 (1990); and (g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as p326 or CaMV35S. Alternatively, the plant promoter directs transcription of a sequence of the invention in a specific tissue manner (tissue-specific promoter) or is otherwise under more precise environmental control (inducible promoter). Various plant promoters, including constitutive, tissue-specific and inducible, are known to those skilled in the art and can be utilized in the present invention. Typically, preferred promoters to use in the present invention are those that are induced by heat or low water conditions Such as the RD29a promoter (Kasuga et al., *Plant Cell Physiol.* 45:346 (2004) and Yamaguchi-Shinozaki and Shinozaki, *Mol Gen Genet.* 236: 331 (1993)) or other DRE-containing (dehydration-responsive elements) promoters (Liu et al, Cell 10: 1391 (1998)). Another preferred embodiment of the present invention is the use of root specific promoters such as those present in the AtXTH17, AtXTH18, AtXTH19 and AtXTH20 genes of *Arabidopsis* (Vissenberg et al. (2005) *Plant Cell Physiol* 46:192) or guard cell specific promoters such as TGG1 or KST1 (Husebye et al. (2002) *Plant Physiol* 128:1180; Plesch et al. (2001) *Plant J* 28:455).

Alternatively, misexpression can be accomplished using a two component system, whereby the first component comprises a transgenic plant comprising a transcriptional activator operatively linked to a promoter and the second component comprises a transgenic plant comprising a sequence of the invention operatively linked to the target binding sequence/region of the transcriptional activator. The two transgenic plants are crossed and the sequence of the invention is expressed in their progeny. In another alternative, the misexpression can be accomplished by transforming the sequences of the two component system into one transgenic plant line.

Any promoter that functions in plants can be used in the first component, such as those discussed above. Suitable transcriptional activator polypeptides include, but are not limited to, those encoding HAP1 and GAL4. The binding sequence recognized and targeted by the selected transcriptional activator protein (e.g. a UAS element) is used in the second component.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al., *Ann. Rev. Genet.* 22:421 (1988); and Christou, Euphytica, v. 85, n. 1-3:13-27, (1995).

Processes for the transformation and regeneration of monocotyledonous and dicotyledonous plants are known to the person skilled in the art. For the introduction of DNA into a plant host cell a variety of techniques is available. These techniques include transformation of plant cells by injection (e.g. Newell, 2000), microinjection (e.g. Griesbach (1987) *Plant Sci.* 50 69-77), electroporation of DNA (e.g. Fromm et al. (1985) *Proc. Natl Acad. Sci. USA* 82:5824 and Wan and Lemaux, Plant Physiol. 104 (1994), 37-48), PEG (e.g. Paszkowski et al. (1984) *EMBO J.* 3:2717), use of biolistics (e.g. Klein et al. (1987) *Nature* 327:773), fusion of cells or protoplasts (Willmitzer, L., 1993 Transgenic plants. In: Biotechnology, A Multi-Volume Comprehensive Treatise (H. J. Rehm, G. Reed, A. Piihler, P. Stadler, eds., Vol. 2, 627-659, VCH Weinheim-New York-Basel-Cambridge), via T-DNA using *Agrobacterium tumefaciens* (e.g. Fraley et al. (Crit. Rev. Plant. Sci. 4, 1-46 and Fromm et al., Biotechnology 8 (1990), 833-844) or *Agrobacterium rhizogenes* (e.g. Cho et al. (2000) *Planta* 210:195-204) or other bacterial hosts (e.g. Brootghaerts et al. (2005) Nature 433:629-633), as well as further possibilities.

In addition, a number of non-stable transformation methods well known to those skilled in the art may be desirable for the present invention. Such methods include, but are not limited to, transient expression (e.g. Lincoln et al. (1998) *Plant Mol. Biol. Rep.* 16:1-4) and viral transfection (e.g. Lacomme et al. (2001) In "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to heat and/or low water conditions, without reduction in fertility, on essentially any plant.

The nucleotide sequences according to the invention encode appropriate proteins from any organism, in particular from plants, fungi, bacteria or animals.

The process according to the invention can be applied to any plant, preferably higher plants, pertaining to the classes of Angiospennae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The method of the invention is preferably used with plants that are interesting for agriculture, horticulture, biomass for bioconversion and/or forestry. Examples are tobacco, oilseed rape, sugar beet, potato, tomato, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

Homologs Encompassed by the Invention

Sequences of the invention include proteins comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid and amino acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

It is understood that certain amino acids may be substituted for other amino acids in a protein or peptide structure (and the nucleic acid sequence that codes for it) without appreciable change or loss of its biological utility or activity. The amino acid changes may be achieved by changing the codons of the nucleic acid sequence.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs (see below). Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

In a further aspect of the present invention, nucleic acid molecules of the present invention can comprise sequences that differ from those encoding a protein or fragment thereof selected from the group consisting of the sequences present in the Sequence Listing due to the fact that the different nucleic acid sequence encodes a protein having one or more conservative amino acid changes.

In another aspect, biologically functional equivalents of the proteins or fragments thereof of the present invention can have about 10 or fewer conservative amino acid changes, more preferably about 7 or fewer conservative amino acid changes, and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

5. Experiments Confirming the Usefulness of the Polynucleotides and Polypeptides of the Invention

5.1 Procedures

The nucleotide sequences of the invention were identified by use of a variety of screens for modified water conditions, including heat and/or low water conditions. These screens are recognized by those skilled in the art to be predictive of nucleotide sequences that provide plants with improved water use efficiency including improved tolerance to heat and/or low water conditions because they emulate the different environmental conditions that can result from increased heat and/or low water conditions. These screens generally fall into two categories (1) soil screens and (2) in vitro screens.

Soil screens have the advantage of assaying the response of the entire plant to particular conditions, such as drought or high heat. On the other hand, in vitro screens have the advantage of relying on defined media and so allow more defined manipulation of growth conditions. "Surrogate" in vitro screens use particular chemicals to alter the water available to the plant by manipulating the concentrations and/or components of the growth media. For example, the ability of the plant to maintain the water concentration within its cells, which can occur during times of low water in the soil, can be tested by growing plants on high sucrose media. Such a screen thus allows one to separate the effects of water loss from roots from, for example, the water loss from leaves during high heat conditions. Each of the screens used is described in more detail below.

In general, the screens used to identify the polynucleotides and polypeptides of the invention were conducted using superpools of *Arabidopsis* $T_2$ transformed plants. The $T_1$ plants were transformed with a Ti plasmid containing a particular SEQ ID NO in the sense orientation relative to a constitutive promoter and harboring the plant-selectable marker gene phosphinothricin acetyltransferase (PAT), which confers herbicide resistance to transformed plants. For surrogate screens, seed from multiple superpools (1,200 $T_2$ seeds from each superpool) were tested. $T_3$ seed were collected from the resistant plants and retested on all other surrogate screens. The results of the screens conducted for each SEQ ID NO can be found in the Examples below.

5.1.1. Mannitol

Screens for mannitol resistant seedlings are surrogate screens for drought (see Quesada et al., Genetic analysis of salt-tolerant mutants in *Arabidopsis thaliana*. Genetics. 2000 154:421-36).

Seeds are sterilized in 30% household bleach for 5 minutes and then washed with double distilled deionized water three times. Sterilized seed is stored in the dark at 4° C. for a minimum of 3 days before use.

Manitol media is prepared by mixing 375 ml sterile 1 mM mannitol with 375 ml sterile 1× MS. Approximately 1200 seeds are evenly spaced per PEG plate before incubating at 22° C. for 14 days.

Putative mannitol-resistant seedlings are transferred to MS with 3% sucrose for recovery. Approximately one week later, resistant seedlings are transferred to soil and sprayed with Finale. Finale resistant plants are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested on 375 mM mannitol media.

5.1.2. Polyethylene Glycol (PEG)

Screens for PEG resistant seedlings are surrogate screens for drought (see van der Weele et al., Growth of *Arabidopsis thaliana* seedlings under water deficit studied by control of water potential in nutrient-agar media. *J Exp Bot.* 2000 51(350):1555-62).

Seeds are sterilized in 30% household bleach for 5 minutes and then washed with double distilled deionized water three times. Sterilized seed is stored in the dark at 4° C. for a miniumum of 3 days before use.

18% PEG media is prepared by mixing 360 ml of hot sterile 50% PEG with 400 ml of hot sterile 0.5×MS media. Approximately 1200 seeds are evenly spaced per PEG plate before incubating at 22° C. for 14 days.

Putative PEG-resistant seedlings are transferred to MS with 0.01% Finale. One week later, resistant seedlings are transferred to soil. Three days later the seedlings are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested using 20% PEG media.

5.1.3. Soil Drought

Soil drought screens identify plants with enhanced tolerance to drought and enhanced recovery after drought.

Seeds are planted in holed flats containing Zonolite vermiculite that are placed in no-holed flats. Flats are watered with 3 L of Hoagland's solution and covered with a plastic dome before being placed at at 4° C. After 4 days, the flats are moved to the Greenhouse (22° C.) and grown 2 weeks, with 1.5 L Hoagland's solution being added every 4 days, or when top of vermiculite is dry. The final application of Hoagland's solution is 4 days prior to the end of the 2 weeks. After 2 weeks, 1 L Hoagland's solution is added to the no-holed flat. After 10 days plants are wilted but still green.

Green, turgid plants are transplanted to 4" square pots containing 60% sunshine mix #5 and 40% thermo-o-rock vermiculite, with Osmocote (1 tbsp/8 L) and Marathon (1 tbsp/8 L). The soil is moistened and the pots sub-irrigated with water. They are grown under a plastic dome for one day, then the plastic dome is removed for the remaining growth period.

To assess plants for enhanced recovery after drought the green wilted plants remaining in the flats are sub-irrigated with 2.5 L Hoagland's solution and cover with cleared with a plastic dome. The following day, the dome is removed and green survivors transplanted to 4" square pots containing 60% sunshine mix #5, 40% Therm-o-rock vermiculite, Osmocote (1 tbsp/8 L) and marathon (1 tbsp/8 L). The soil is moistened and the pots sub-irrigated with water. They are grown under a plastic dome for one day, then the plastic dome is removed for the remaining growth period.

DNA from a leaf from each plant is transferred to FTA paper via pressure and an aliquot of the DNA containing paper used in PCR reactions using the following cycling conditions 94° C. for 10 min, five cycles of 94° C. for 30 sec, 60° C. for 30 sec, 72° C. for 3 min, five cycles of 94° C. for 30 sec, 60° C. for 30 sec, 72° C. for 3 min, 30 cycles of 94° C. for 30 sec, 53° C. for 30 sec, 72° C. for 3 min, 72° C. for 7 min and 4° C. hold. Aliquots of the reaction product are analyzed on a 1% agarose gel stained with ethidium bromide.

$T_3$ Seed from those plants containing the expected PCR product are collected and retested using 50 seeds from each line.

5.1.4. Heat

High heat screens identify plants with enhanced tolerance to heat and enhanced recovery after heat.

Seeds are sterilized in 30% household bleach for 5 minutes and then washed with double distilled deionized water three times. Sterilized seed is stored in the dark at 4° C. for a minimum of 3 days before use.

MS media, pH 5.7 is prepared. Approximately 12 seeds are evenly spaced per MS plate before incubating in the vertical position at 22° C. for 14 days. Under these conditions, the plates are exposed to 12,030 LUX from above and 3,190 LUX from the bottom.

On day 15 the plates are transferred to a 22° C. oven, which increased temperature in 5° C. increments to 45° C. The duration of treatment at 45° C. was based on complete and homogenous wilting of 100 wild-type seedlings (~10 plates). After exposure to 45° C., seedlings were placed in the horizontal position at 23° C. for recovery, where they remained for 4-11 days. Heat recovery was assessed based on vigor and greenness and continued growth after treatment.

Leaves of control and non-resistant plants become wilted and yellowed after only 2 days, completely bleaching after an additional 4 days. All wild type (WS) and non-heat resistant plants die by day 6.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested.

To differentiate between natural acquired thermo tolerance of recovered $T_3$ events, seeds were sterilized and stratified in parallel to wildtype seed that was never heat treated and wild-type controls previously heat treated with the $T_2$ events. 15 day old seedlings were heat shocked in the dark at 45° C. for 5 hours, as described above. Duration of treatment at 45° C. was based on complete and homogenous wilting of pre-heat treated wild-type seed and un-pretreated wild-type controls. After exposure to 45° C., seedlings were returned to the permissive temperature of 23° C. for recovery where they remained for another 7 days. Thermo tolerance was assessed based on prolonged greenness and continued growth after treatment.

5.1.5 Heat (Soil)

Seeds are sown in pots containing soil of the following composition: 60% autoclaved Sunshine Mix #5, 40% vermiculite with 2.5 Tbsp Osmocote and 2.5 Tbsp 1% granular Marathon per 25 L of soil. After sowing, pots are covered with plastic propagation domes and seed is placed at 4° C. in the dark for at least 3 days. Pots are then returned to the greenhouse (long day light conditions of 16 hours), covered with 55% shade cloth and provided a normal watering regime.

After 7 days, seedlings were transferred to a 36° C. growth chamber under continuous light and allowed to grow until harvest. Plants were watered minimally so as to allow for some drying of the top soil similar to that in heat-induced drought conditions in the field.

Plants are sprayed with a mixture of 3 ml Finale in 48 oz of water. Spraying is repeated every 3-4 days until only transformants remain. The remaining transformants were weeded to a maximum of 5 evenly spaced transformants per pot.

T3 seed was recovered and tested for thermotolerance and recovery as described above.

5.1.6 High Sucrose

Screens for germination and growth on limited nutrients and 9% sucrose are surrogate screens for the altered carbon/nitrogen balance frequently associated with drought (see Laby et al., The *Arabidopsis* sugar-insensitive mutants sis4 and sis5 are defective in abscisic acid synthesis and response. *Plant Journal* 23: 587-596).

Seeds are sterilized in 30% household bleach for 5 minutes and then washed with double distilled deionized water three times. Sterilized seed is stored in the dark at 4° C. for a minimum of 3 days before use.

MS media containing 9% sucrose is prepared. Approximately 1200 seeds are evenly spaced per MS-sucrose plate before incubating at 22° C. for 9 days.

Putative sucrose-resistant green seedlings are transferred to MS plates. After one week of recovery, resistant the seedlings are genotyped as described below.

DNA from a leaf from each plant is transferred to FTA paper via pressure and an aliquot of the DNA containing paper used in PCR reactions using the following cycling conditions 94° C. for 10 min, five cycles of 94° C. for 30 sec, 60° C. for 30 sec, 72° C. for 3 min, five cycles of 94° C. for 30 sec, 60° C. for 30 sec, 72° C. for 3 min, 30 cycles of 94° C. for 30 sec, 53° C. for 30 sec, 72° C. for 3 min, 72° C. for 7 min and 4° C. hold. Aliquots of the reaction product are analyzed on a 1% agarose gel stained with ethidium bromide.

$T_3$ Seed from those plants containing the expected PCR product are collected and retested using 9% sucrose MS media.

5.1.7. ABA

Screens for ABA resistant seedlings are surrogate screens for drought.

Seeds are sterilized in 30% household bleach for 5 minutes and then washed with double distilled deionized water three times. Sterilized seed is stored in the dark at 4° C. for a minimum of 3 days before use.

MS media containing 1.5 μM ABA is prepared. Approximately 1200 seeds are evenly spaced per PEG plate before incubating at 22° C. for 14 days.

Putative ABA-resistant seedlings are transferred to MS with 0.01% Finale. One week later, resistant seedlings are transferred to soil. Three days later the seedlings are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested using 1.5 μM ABA MS media.

5.1.8. Procedure for Identifying Functional Homologs and Consensus Sequences

The isolated sequence of the invention was compared to the sequences present in the various gene banks. Pairwise comparisons were conducted and those sequences having the highest percent identity to the query sequence identified as functional homologs.

A multi-pairwise alignment was generated using the amino acid query sequence and the amino acid sequence of the functional homologs. This allowed identification of the conserved regions or domains of the polypeptide. Using the conserved regions as a guide, a consensus sequence was generated. This consensus sequence indicates the critical amino acid residues and those can be either substituted and/or deleted without impacting the biological function of the protein.

5.2 Results

The results of the above experiments are set forth below wherein each individual example relates to all of the experimental results for a particular polynucleotide/polypeptide of the invention.

Example 1— Ceres cDNA 12331850

Clone 11830, Ceres cDNA 12331850, encodes a full-length glycosyl hydrolase family 17 protein, which has similarity to elicitor inducible chitinase Nt-SubE76 GI:11071974 from (*Nicotiana tabacum* (C-terminal homology only) and β-1,3-glucanase. Ectopic expression of Ceres cDNA 12331850 under the control of the CaMV35S or 32449 promoter induces the following phenotypes:

- Germination on high concentrations of polyethylene glycol (PEG), mannitol, and abscissic acid (ABA).
- Continued growth on high concentration of PEG, mannitol, and ABA.

Generation and Phenotypic Evaluation of $T_1$ Lines Containing 35S::cDNA 12331850.

Wild-type *Arabidopsis* Wassilewskija (WS) plants were transformed with a Ti plasmid containing cDNA 12331850 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12331850 was identified in resistant plants from each of the three surrogate drought screens, the five individual $T_2$ events containing this cDNA (ME01297) were screened on high PEG, mannitol, and ABA to identify events with the resistance phenotype. Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the $18^{th}$ plant isolated from a mannitol screen of Superpool 1.

Results:

Qualitative Analysis of 13 Superpools on PEG, Mannitol, and ABA

Resistant candidates were selected based on increased size compared to the largest wild-type control. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta® to eliminate any false-positives, or any lines where the Basta® marker was suppressed. All of the Basta®-resistant candidates flowered and set seed. Resistant seedlings were recovered from Superpools 1, 7 and 11 on all screens (Table 1-1).

TABLE 1-1

Number of $Basta^R$ seedlings identified on several screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12331850 on PEG, Mannitol, and ABA Screens.

Seedlings that survived transfer to soil and which were Basta®-resistant were subjected to PCR and sequencing. At least one resistant plant in each of the three screens contained 35S::cDNA 12331850 (ME01297) making this a good candidate for further testing. $T_2$ seeds from the 5 independent transformants that contain this clone and that were used in the pooling process were tested for Basta® resistance and for stress tolerance in the 3 surrogate drought screens.

To identify two independent events of 35S::cDNA 12331850 showing PEG, mannitol and ABA resistance, 36 seedlings from each of five events, ME01297-01, 02, 03, 04, and 05 were screened as previously described. Simultaneously, Basta® segregation was assessed to identify events containing a single insert segregating in a 3:1 (R:S) ratio as calculated by a chi-square test (Table 1-2). All of the events segregated for a single functional insert.

TABLE 1-2

Basta segregation for ME01297 individual events

| Event | Resistant | Sensitive | Total | Probability of Chi-test* |
|---|---|---|---|---|
| ME01297-01 | 22 | 14 | 36 | 0.05429 |
| ME01297-02 | 26 | 10 | 36 | 0.70031 |
| ME01297-03 | 25 | 11 | 36 | 0.44142 |
| ME01297-04 | 22 | 14 | 36 | 0.05429 |
| ME01297-05 | 24 | 12 | 36 | 0.24821 |

*Chi-test to determine whether actual ratio of resistant to sensitive differs from the expected 3:1 ratio.

Events ME01297-02 and 03 were chosen as the two events because they had the strongest and most consistent resistance to PEG, mannitol and ABA. Resistance was observed for ME01297-01, 04, and 05 although not in expected ratios in all three screens (data not shown). The controls were sown the same day and on the same plate as the individual events. The transgenic control in each of these plates is a segregant, from this ME line or another ME line being tested, that failed to show resistance to the particular stress. The PEG, mannitol and ABA (Table 1-3) segregation ratios observed for ME01297-02 and 03 are consistent with the presence of a single insert, similar to what we observed for Basta resistance (Table 1-1).

On 18% PEG, the resistant seedlings from these two events show some root growth and they are green with new leaves emerging. The mannitol resistant seedlings also showed more root and shoot growth than the sensitive seedlings. The ABA resistant seedlings showed a slight increase in growth. The phenotype of the resistant seedlings is unique to each of the screens.

TABLE 1-3

Segregation of Resistance to PEG, mannitol and ABA in ME01297-02 and ME01297-03 Progeny.

| | PEG | | | mannitol | | | ABA | | |
|---|---|---|---|---|---|---|---|---|---|
| | R | S | Probability of Chi-test | R | S | Probability of Chi-test | R | S | Probability of Chi-test |
| ME01297-02 | 49 | 23 | 0.174 | 47 | 25 | 0.057 | 50 | 22 | 0.276 |
| ME01297-03 | 58 | 14 | 0.276 | 51 | 21 | 0.414 | 56 | 16 | 0.586 |
| Expected (3:1 segregation) | 54 | 18 | | 54 | 18 | | 54 | 18 | |

Qualitative and Quantitative Analysis of Progeny of $T_2$ Plants Isolated on High Concentrations of PEG, Mannitol, and ABA Screens.

Progeny from $T_2$ plants that were recovered from the three screens and which contained cDNA 12331850 (SP1-A1, SP1-P1, and SP1-M18) were analyzed and also found to be resistant to PEG, mannitol and ABA indicating that resistance is transmitted to the next generation. Taken together, 1) the isolation of resistant seedlings containing cDNA 12331850 from all three screens, 2) the inheritance of this resistance in a subsequent generation, and 3) the fact that the progeny from two or more events from the original transformation also segregated for resistance to the stresses, provide strong evidence that cDNA 12331850 when over-expressed can provide tolerance to osmotic stress.

This gene is annotated as a glycosyl hydrolase family 17, which has similarity to elicitor inducible chitinase Nt-SubE76 GI:11071974 from *Nicotiana tabacum* (C-terminal homology only). TIGR also notes that the protein contains similarity to beta-1,3-glucanase.

FIG. 1 provides the results of the consensus sequence (SEQ ID NOs: 112-120) analysis based on Ceres cDNA 12331850.

Example 2—Ceres cDNA 12334963

Clone 35743, Ceres cDNA 12334963, encodes a full-length putative hypothetical protein. Ectopic expression of Ceres cDNA 12334963 under the control of the 35S promoter induces the following phenotypes:

Germination on high concentrations of polyethylene glycol (PEG), mannitol, and abscissic acid (ABA).

Continued growth on high PEG, mannitol, and ABA.

Generation and Phenotypic Evaluation of $T_1$ Lines Containing 35S::cDNA 12334963.

Wild-type *Arabidopsis* Wassilewskija (WS) plants were transformed with a Ti plasmid containing cDNA 12334963 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol and ABA) as described above. $T_3$ seeds were collected from the resistant plants and analyzed for resistance on all three surrogate drought screens.

Once cDNA 12334963 was identified in resistant plants from each of the three surrogate drought screens, the five individual $T_2$ events containing this cDNA (ME01467) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the $18^{th}$ plant isolated from a mannitol screen of Superpool 1.

Results:

Qualitative Analysis of 13 Superpools on PEG, Mannitol, and ABA.

Resistant candidates were selected based on increased size when compared to the largest wild-type control seedlings. All three screens resulted in a decrease in germination for both wildtype and superpools compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta® to eliminate any false-positives, or any lines where the Basta® marker was suppressed. All of the Basta®-resistant candidates flowered and set seed. Resistant seedlings were recovered from Superpools 1, 7 and 11 on all screens (Table 2-1).

TABLE 2-1

Number of stress-tolerant and $Basta^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 353 | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12334963 on PEG, Mannitol, and ABA Seedlings that survived transfer to soil and which were Basta®-resistant were subjected to PCR and sequencing. At least one resistant plant in each of the three osmotic screens contained 35S::cDNA 12334963 (ME01467) making this a good candidate for further testing. $T_2$ seeds from the 5 independent transformants that contain this clone and that were used in the pooling process were tested for Basta® resistance and for stress tolerance in the 3 surrogate drought screens.

To identify two independent events of 35S::cDNA 12334963 showing PEG, mannitol and ABA resistance, 36 seedlings from each of five events, ME01467-01, 02, 03, 04, and 05 were screened as previously described. Simultaneously, Basta segregation was assessed to identify events containing a single insert segregating in a 3:1 (R:S) ratio as calculated by a Chi-square test (Table 2-2). All of the lines segregated for a single functional insert.

TABLE 2-2

$Basta^R$ segregation for ME01467 individual events

| Event | Resistant | Sensitive | Total | Probability of Chi-test* |
|---|---|---|---|---|
| ME01467-01 | 28 | 8 | 36 | 0.70031 |
| ME01467-02 | 29 | 7 | 36 | 0.44142 |
| ME01467-03 | 24 | 12 | 36 | 0.24821 |
| ME01467-04 | 28 | 8 | 36 | 0.70031 |
| ME01467-05 | 27 | 9 | 36 | 1 |

*Chi-test to determine whether actual ratio of resistant to sensitive differs from the expected 3:1 ratio.

Events ME01467-03 and 05 were chosen as the two events because had the strongest and most consistent resistance to PEG, mannitol and ABA. Resistance was observed for ME01467-01, 02, and 04, although not in expected ratios in all three screens (data not shown). The controls were sown the same day and in the same plate as the individual events. The transgenic control in each of these plates is a segregant, from this ME line or another ME line being tested, that failed to show resistance to the particular osmotic stress. The PEG (Tables 2-3 and 2-4), mannitol (Tables 2-5 and 2-6) and ABA (Tables 2-7 and 2-8) segregation ratios observed for ME01467-03 and 05 are consistent with the presence of a single insert as demonstrated by Chi-Square. This result is similar to the observation for Basta® resistance (Table 2-2).

On 18% PEG, the resistant seedlings from these two events showed some root growth but they were also green with emergence of new leaves at day 14. The mannitol-resistant seedlings showed more root and shoot growth than the PEG resistant seedlings. The resistant seedlings on ABA show the least amount of growth, and very little root growth relative to the mannitol and PEG screens. The phenotype of the resistant seedlings is unique on each of the screens.

TABLE 2-3

Chi-square analysis assuming a 3:1 (R:S) ratio for progeny of ME01467-03 containing 35S::cDNA 12334963 on PEG.

| Event | Observed | Expected | $\chi^2$ | Probability of Chi-Test |
|---|---|---|---|---|
| PEG Resistant | 24 | 24 | 0 | 1.0 |
| PEG Sensitive | 8 | 8 | 0 | |
| | 32 | 32 | 0 | |

TABLE 2-4

Chi-square analysis assuming a 3:1 (R:S) ratio for progeny of ME01467-05 containing 35S::cDNA 12334963 on PEG.

| Event | Observed | Expected | $\chi^2$ | Probability of Chi-Test |
|---|---|---|---|---|
| PEG Resistant | 26 | 27 | 0.037 | 0.7 |
| PEG Sensitive | 10 | 9 | 0.111 | |
| | 36 | 36 | 0.148 | |

TABLE 2-5

Chi-square analysis assuming a 3:1 (R:S) ratio for progeny of ME01467-03 containing 35S::cDNA 12334963 on mannitol.

| Event | Observed | Expected | $\chi^2$ | Probability of Chi-Test |
|---|---|---|---|---|
| Mannitol Resistant | 29 | 27 | 0.148 | 0.4 |
| Mannitol Sensitive | 7 | 9 | 0.444 | |
| | 36 | 36 | 0.592 | |

TABLE 2-6

Chi-square analysis assuming a 3:1 (R:S) ratio for progeny of ME01467-05 containing 35S::cDNA 12334963 on mannitol.

| Event | Observed | Expected | $\chi^2$ | Probability of Chi-Test |
|---|---|---|---|---|
| Mannitol Resistant | 18 | 27 | 3 | 0.005 |
| Mannitol Sensitive | 18 | 9 | 9 | |
| | 36 | 36 | 12 | |

TABLE 2-7

Chi-square analysis assuming a 3:1 (R:S) ratio for progeny of ME01467-03 containing 35S::cDNA 12334963 on ABA.

| Event | Observed | Expected | $\chi^2$ | Probability of Chi-Test |
|---|---|---|---|---|
| ABA Resistant | 25 | 26.25 | 0.0595 | 0.626 |
| ABA Sensitive | 10 | 8.75 | 0.179 | |
| | 35 | 35 | 0.239 | |

TABLE 2-8

Chi-square analysis assuming a 3:1 (R:S) ratio for progeny of ME01467-05 containing 35S::cDNA 12334963 on ABA.

| Event | Observed | Expected | $\chi^2$ | Probability of Chi-Test |
|---|---|---|---|---|
| ABA Resistant | 22 | 27 | 0.926 | 0.054 |
| ABA Sensitive | 14 | 9 | 2.78 | |
| | 36 | 36 | 3.706 | |

Qualitative and Quantitative Analysis of Progeny of $T_2$ Plants Isolated on PEG, Mannitol and ABA Progeny of the $T_2$ plants that were recovered from the three screens and which contained cDNA 12334963 (SP1-A12, SP1-P9, and SP1-M4) were analyzed and found to be resistant to PEG, mannitol and ABA, indicating that resistance is transmitted to the next generation.

Taken together, 1) the isolation of resistant seedlings containing cDNA 12334963 from all three surrogate screens for drought, 2) the inheritance of this resistance in the next generation, and 3) the fact that the progeny from two or more events from the original transformation also segregated for resistance to these osmotic stresses, provides strong evidence that cDNA 12334963, when over-expressed, can provide tolerance to drought, freezing and other osmotic stresses.

FIG. 2 provides the results of the consensus sequence (SEQ ID NOs: 121-129) analysis based on Ceres cDNA 12334963.

Example 3—Ceres cDNA 12333678

Clone 26006, Ceres cDNA 12333678, encodes a full-length glycosyl hydrolase. Ectopic expression of Ceres cDNA 12333678 under the control of the CaMV35S promoter induces the following phenotypes:

Germination on high concentrations of polyethylene glycol (PEG), mannitol and abscissic acid (ABA).

Continued growth on high PEG, mannitol and ABA.

Generation and Phenotypic Evaluation of $T_1$ Lines Containing 35S::cDNA 12333678.

Wild-type *Arabidopsis* Wassilewskija (WS) plants were transformed with a Ti plasmid containing cDNA 12333678 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol and ABA) as described above. $T_3$ seeds were collected from the resistant plants and analyzed for resistance on all three surrogate drought screens.

Once cDNA 12333678 was identified in resistant plants from each of the three surrogate drought screens, the five individual $T_2$ events containing this cDNA (ME01334) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Results:

Qualitative Analysis of 13 Superpools on PEG, Mannitol and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed compared to unstressed plants, presumably because of the transient exposure to stress. The plants transferred to soil were sprayed with B Basta® to eliminate any false-positives, or any lines where the Basta® marker was suppressed. All of the Basta®-resistant candidates flowered and set seed. Resistant seedlings were recovered from Superpools 1, 7 and 11 on all screens (Table 3-1).

TABLE 3-1

| Number of stress-tolerant and Basta$^R$ seedlings identified on drought surrogate screens. | | | | |
|---|---|---|---|---|
| Superpool | Promoter | 18% PEG | 375 mM Mannitol | 1.5 uM ABA |
| SP1 | 35S | 10 | 13 | 11 |
| SP2 | 35S | 0 | 6 | 5 |
| SP3 | 35S | 0 | 2 | 10 |
| SP4 | 355 | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12333678 on PEG, Mannitol and ABA Seedlings that survived transfer to soil and which were Basta®-resistant were subjected to PCR and sequencing. At least one resistant plant in each of the three osmotic screens contained 35S::cDNA 12333678 (ME01334). $T_2$ seeds from the 5 independent transformants that contain this clone and that were used in the pooling process were tested for Basta® resistance and for stress tolerance in the 3 surrogate drought screens.

To identify two independent events of 35S::cDNA 12333678 showing PEG, mannitol, and ABA resistance, 36 seedlings from each of four events, ME01334-01, 02, 03, and 04 were screened as previously described. Simultaneously, Basta® segregation was assessed to identify events containing a single insert segregating in a 3:1 (R:S) ratio as calculated by a Chi-square test (Table 3-2). All of the events tested segregated for a single functional insert.

TABLE 3-2

| Basta$^R$ segregation for ME01334 individual events | | | | |
|---|---|---|---|---|
| Event | Resistant | Sensitive | Total | Probability of Chi-test* |
| ME01334-01 | 28 | 8 | 36 | 0.70031 |
| ME01334-02 | 22 | 14 | 36 | 0.05429 |
| ME01334-03 | 31 | 5 | 36 | 0.12366 |
| ME01334-04 | 24 | 12 | 36 | 0.24821 |
| ME01334-5 | | | Insufficient seeds to test | |

*Chi-test to determine whether actual ratio of resistant to sensitive differs from the expected 3:1 ratio.

Events ME01334-01 and 04 were chosen as the two events because they had the strongest and most consistent resistance to PEG, mannitol and ABA. Resistance was observed for ME01334-02 and 03 although not in expected ratios in all three screens (data not shown). The controls were sown the same day and in the same plate as the individual events. The transgenic control in each of these plates is a segregant, from this ME line or another ME line being tested, that failed to show resistance to the particular stress. The PEG (Tables 3-3 and 3-4), mannitol (Tables 3-5 and 3-6) and ABA (Tables 3-7 and 3-8) segregation ratios observed for ME01334-01 and 01 are consistent with the presence of a single insert as demonstrated by Chi-Square. This is similar to that observed for Basta® resistance (Table 3-2).

On 18% PEG, the resistant seedlings from these two events show some root growth but they are also green with new leaves emerging at day 14. The mannitol-resistant seedlings showed more root and shoot growth than the PEG resistant seedlings. The resistant seedlings on ABA show the least amount of growth, and very little root growth relative to the mannitol and PEG screens. The phenotype of the resistant seedlings is unique on each of the screens.

TABLE 3-3

| Chi-square analysis assuming a 3:1 (R:S) ratio for progeny of ME01334-01 containing 35S::cDNA 12333678 on PEG. | | | | |
|---|---|---|---|---|
| Event | Observed | Expected | $\chi^2$ | Probability of Chi-Test |
| PEG Resistant | 26 | 26.25 | 0.002 | 0.922 |
| PEG Sensitive | 9 | 8.75 | 0.007 | |
| | 35 | 35 | 0.009 | |

TABLE 3-4

| Chi-square analysis assuming a 3:1 (R:S) ratio for progeny of ME01334-04 containing 35S::cDNA 12333678 on PEG. | | | | |
|---|---|---|---|---|
| Event | Observed | Expected | $\chi^2$ | Probability of Chi-Test |
| PEG Resistant | 27 | 27 | 0 | 1.0 |
| PEG Sensitive | 9 | 9 | 0 | |
| | 36 | 36 | 0 | |

TABLE 3-5

| Chi-square analysis assuming a 3:1 (R:S) ratio for progeny of ME01334-01 containing 35S::cDNA 12333678 on mannitol. | | | | |
|---|---|---|---|---|
| Event | Observed | Expected | $\chi^2$ | Probability of Chi-Test |
| Mannitol Resistant | 14 | 23.25 | 3.68 | 0.0001 |
| Mannitol Sensitive | 17 | 7.75 | 11.04 | |
| | 31 | 31 | 14.72 | |

TABLE 3-6

| Chi-square analysis assuming a 3:1 (R:S) ratio for progeny of ME01334-04 containing 35S::cDNA 12333678 on mannitol. | | | | |
|---|---|---|---|---|
| Event | Observed | Expected | $\chi^2$ | Probability of Chi-Test |
| Mannitol Resistant | 16 | 22.5 | 1.88 | 0.006 |
| Mannitol Sensitive | 14 | 7.5 | 5.63 | |
| | 30 | 30 | 7.51 | |

TABLE 3-7

| Chi-square analysis assuming a 3:1 (R:S) ratio for progeny of ME01334-01 containing 35S::cDNA 12333678 on ABA. | | | | |
|---|---|---|---|---|
| Event | Observed | Expected | $\chi^2$ | Probability of Chi-Test |
| ABA Resistant | 24 | 24 | 0 | 1.0 |
| ABA Sensitive | 8 | 8 | 0 | |
| | 32 | 32 | 0 | |

TABLE 3-8

| Chi-square analysis assuming a 3:1 (R:S) ratio for progeny of ME01334-04 containing 35S::cDNA 12333678 on ABA. | | | | |
|---|---|---|---|---|
| Event | Observed | Expected | $\chi^2$ | Probability of Chi-Test |
| ABA Resistant | 19 | 25.5 | 1.657 | 0.01 |
| ABA Sensitive | 15 | 8.5 | 4.97 | |
| | 34 | 34 | 6.627 | |

Qualitative and Quantitative Analysis of Progeny of $T_2$ Plants Isolated on PEG, Mannitol and ABA Progeny from $T_2$ plants that were recovered from the three screens and contained cDNA 12333678 (SP1-A2, SP1-P3, and SP1-M19) were analyzed and also found to be resistant to PEG, mannitol and ABA indicating that resistance is transmitted to the next generation. Taken together, 1) the isolation of resistant seedlings containing cDNA 12333678 from all three surrogate screens for drought, 2) the inheritance of this resistance in the next generation, and 3) the fact that the progeny from two or more events from the original transformation also segregated for resistance to these osmotic stresses, provides strong evidence that cDNA 12333678 when over-expressed provides tolerance to osmotic stress.

This gene is annotated as an alpha/beta hydrolase, a probable acetone-cyanohydrin lyase. Acetone-cyanohydrin lyase is involved in the catabolism of cyanogenic glycosides.

Figure 3:
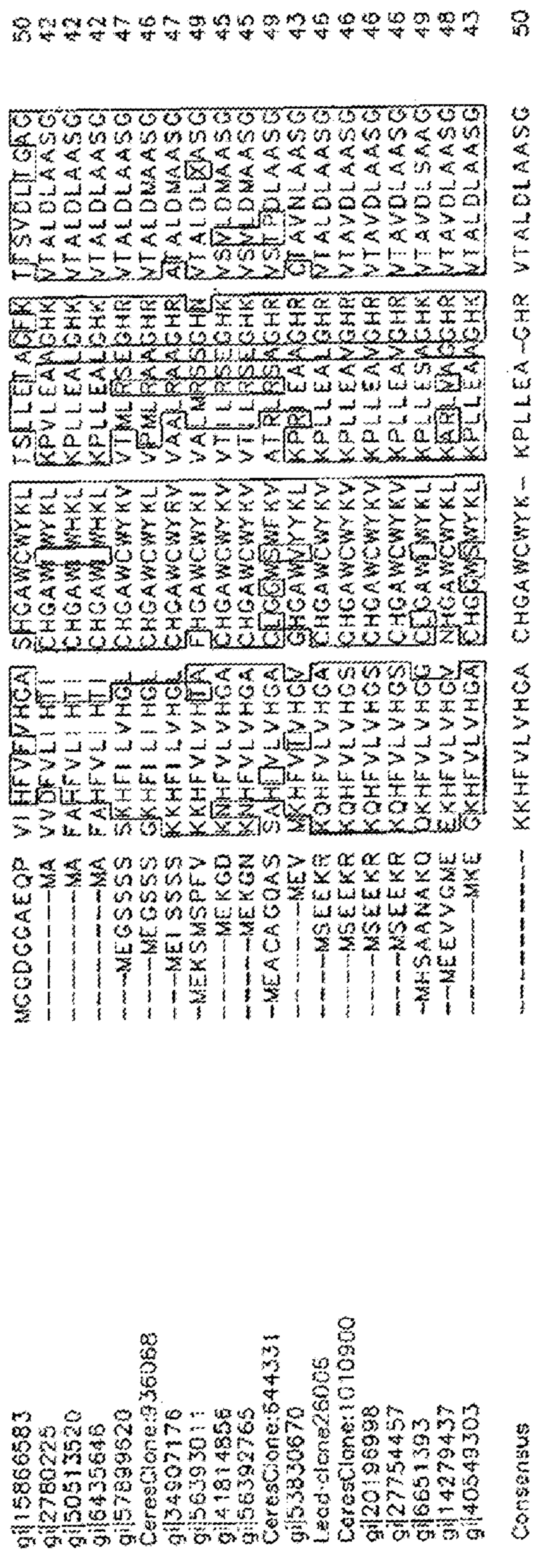
FIG. 3 provides the results of a consensus sequence (SEQ ID NOs: 130-146) analysis based on Ceres cDNA 12333678.

FIG. 3 provides the results of the consensus sequence (SEQ ID NOs: 130-146) analysis based on Ceres cDNA 12333678.

Example 4—Ceres cDNA 12384873

Clone 34419, Ceres cDNA 12384873, encodes a full-length strictosidine synthase. Ectopic expression of Ceres cDNA 12384873 under the control of the CaMV35S promoter induces the following phenotypes:

Germination on high concentrations of polyethylene glycol (PEG), mannitol, and abscissic acid (ABA).

Continued growth on high PEG, mannitol, and ABA.

Generation and Phenotypic Evaluation of $T_1$ Lines Containing 35S::cDNA 12384873

Wild-type *Arabidopsis* Wassilewskija (WS) plants were transformed with a $T_i$ plasmid containing cDNA 12384873 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12384873 was identified in resistant plants from each of the three surrogate drought screens, the five individual $T_2$ events containing this cDNA (ME01490) were screened on high PEG, mannitol and ABA to identify events with the resistance phenotype.

Superpools (SP) are referred to as SP1, SP2 and so on. The letter following the hyphen refers to the screen (P=PEG, M=mannitol and A=ABA) and the number following the letter refers to a number assigned to each plant obtained from that screen on that superpool. For example, SP1-M18 is the $18^{th}$ plant isolated from a mannitol screen of Superpool 1.

Qualitative Analysis of 13 Superpools on PEG, Mannitol, and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta® to eliminate any false-positives, or any lines where the Basta® marker was suppressed. All of the Basta®-resistant candidates flowered and set seed. Resistant seedlings were recovered from Superpools 1, 7 and 11 on all screens (Table 4-1).

TABLE 4-1

| Number of stress-tolerant and $Basta^R$ seedlings identified on drought surrogate screens. | | | | |
|---|---|---|---|---|
| Superpool | Promoter | 18% PEG | 375 mM Mannitol | 1.5 uM ABA |
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12384873 on PEG, Mannitol and ABA Seedlings that survived transfer to soil and which were Basta®-resistant were subjected to PCR and sequencing. At least one resistant plant in each of the three osmotic screens contained 35S::cDNA 12384873 (ME01490g. $T_2$ seeds from the 5 independent transformants that contain this clone and that were used in the pooling process were tested for Basta® resistance and for stress tolerance in the 3 surrogate drought screens.

To identify two independent events of 35S::cDNA 12384873 showing PEG, mannitol and ABA resistance, 36 seedlings from each of five events, ME01490-01, 02, 03, 04, and 05 were screened as previously described. Simultaneously, Basta® segregation was assessed to identify events containing a single insert segregating in a 3:1 (R:S) ratio as calculated by a Chi-square test (Table 4-2). Three of the events segregated for a single functional insert (-01, -02 and -04). For the other two events one segregated for two independent inserts (-03) and one segregated for a deficiency of Basta® seedlings (-05).

TABLE 4-2

Basta$^R$ segregation for ME01490 individual events

| Event | Resistant | Sensitive | Total | Probability of Chi-test* |
|---|---|---|---|---|
| ME01490-01* | 24 | 12 | 36 | 0.24821 |
| ME01490-02* | 26 | 10 | 36 | 0.70031 |
| ME01490-03 | 35 | 1 | 36 | 0.00208** |
| ME01490-04 | 28 | 8 | 36 | 0.70031 |
| ME01490-05 | 21 | 15 | 36 | 0.02092** |

*Chi-test to determine whether actual ratio of resistant to sensitive differs from the expected 3:1 ratio.

**Significantly different than a 3:1 (R:S) ratio

Events ME01490-01 and -02 were chosen as the two events because they had the strongest and most consistent resistance to PEG, mannitol and ABA. Resistance was observed for ME01490-03, -04, and -05 although not in expected ratios in all three screens (data not shown). The controls were sown the same day and in the same plate as the individual lines. The transgenic control in each of these plates is a segregant, from this ME line or another ME line being tested, that failed to show resistance to the particular stress. The PEG (Tables 4-3 and 4-4), mannitol (Tables 4-5 and 4-6) and ABA (Tables 4-7 and 4-8) segregation ratios observed for ME01490-01 and -02 are consistent with the presence of single insert, as demonstrated by Chi-square. This result is similar to that observed for Basta® resistance (Table 4-2).

TABLE 4-3

Chi-square analysis assuming a 3:1 (R:S) ratio for progeny of ME01490-01 containing 35S::cDNA 12384873 on PEG.

| Event | Observed | Expected | $\chi^2$ | Probability of Chi-Test |
|---|---|---|---|---|
| PEG Resistant | 29 | 27 | 0.148 | 0.441 |
| PEG Sensitive | 7 | 9 | 0.444 | |
| | 36 | 36 | 0.592 | |

TABLE 4-4

Chi-square analysis assuming a 3:1 (R:S) ratio for progeny of ME01490-02 containing 35S::cDNA 12384873 on PEG.

| Event | Observed | Expected | $\chi^2$ | Probability of Chi-Test |
|---|---|---|---|---|
| PEG Resistant | 24 | 24.75 | 0.0227 | 0.763 |
| PEG Sensitive | 9 | 8.25 | 0.068 | |
| | 33 | 33 | 0.0907 | |

TABLE 4-5

Chi-square analysis assuming a 3:1 (R:S) ratio for progeny of ME01498-01 containing 35S::cDNA 12384873 on mannitol.

| Event | Observed | Expected | $\chi^2$ | Probability of Chi-Test |
|---|---|---|---|---|
| Mannitol Resistant | 22 | 26.25 | 0.688 | 0.097 |
| Mannitol Sensitive | 13 | 8.75 | 2.06 | |
| | 35 | 35 | 2.748 | |

TABLE 4-6

Chi-square analysis assuming a 3:1 (R:S) ratio for progeny of ME01490-02 containing 35S::cDNA 12384873 on mannitol.

| Event | Observed | Expected | $\chi^2$ | Probability of Chi-Test |
|---|---|---|---|---|
| Mannitol Resistant | 20 | 23.25 | 0.454 | 0.178 |
| Mannitol Sensitive | 11 | 7.75 | 1.363 | |
| | 31 | 31 | 1.817 | |

TABLE 4-7

Chi-square analysis assuming a 3:1 (R:S) ratio for progeny of ME01490-01 containing 35S::cDNA 12384873 on ABA.

| Event | Observed | Expected | $\chi^2$ | Probability of Chi-Test |
|---|---|---|---|---|
| ABA Resistant | 28 | 27 | 0.037 | 0.7 |
| ABA Sensitive | 8 | 9 | 0.148 | |
| | 36 | 36 | 1.85 | |

TABLE 4-8

Chi-square analysis assuming a 3:1 (R:S) ratio for progeny of ME01490-02 containing 35S::cDNA 12384873 on ABA.

| Event | Observed | Expected | $\chi^2$ | Probability of Chi-Test |
|---|---|---|---|---|
| ABA Resistant | 23 | 27 | 0.593 | 0.124 |
| ABA Sensitive | 13 | 9 | 1.78 | |
| | 36 | 36 | 2.373 | |

Qualitative and Quantitative Analysis of Progeny of $T_2$ Plants Isolated on PEG, Mannitol and ABA Progeny of the $T_2$ plants that were recovered from the three screens and contained cDNA 12384873 (SP1-A18, SP1-P14, SP1-M5, SP1-M6 and SP1-M7) were analyzed and also found to be resistant to PEG, mannitol and ABA indicating that resistance is transmitted to the next generation. Taken together, 1) the isolation of resistant seedlings containing cDNA 12384873 from all three surrogate screens for drought, 2) the inheritance of this resistance in the next generation, and 3) the fact that the progeny from two or more events from the original transformation also segregated for resistance to these osmotic stresses, provides strong evidence that cDNA 12384873 when over-expressed can provide tolerance to osmotic stress.

Clone 34419 encodes the first 29 amino acids of a strictosidine synthase protein, and then a frame shift results in a novel stretch of 63 amino acids on the 3' end of the protein.

Example 5—Ceres cDNA 12659859

Ceres cDNA 12659859 encodes a FAD-linked oxidoreductase family, a probable berberine bridge enzyme from *Arabidopsis thaliana*. Ectopic expression of Ceres cDNA 12659859 under the control of the CaMV35S promoter induces the following phenotypes:

- Germination on high concentrations of polyethylene glycol (PEG), mannitol and abscissic acid (ABA).
- Continued growth on high concentration of PEG, mannitol and ABA.

Generation and Phenotypic Evaluation of $T_1$ Lines Containing 35S::cDNA 12659859.

Wild-type *Arabidopsis* Wassilewskija (WS) plants were transformed with a Ti plasmid containing cDNA 12659859 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12659859 was identified in resistant plants from each of the three surrogate drought screens, the five individual $T_2$ events containing this cDNA (SR01010) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the $18^{th}$ plant isolated from a mannitol screen of Superpool 1.

Qualitative and Quantitative Analysis of 2 Independent Events Representing 35S::cDNA 12659859 (SR01010) on PEG, Mannitol and ABA To identify two independent events of 35S::cDNA 12659859 showing PEG, mannitol, and ABA resistance, 36 seedlings from each of three events, SR01010-01, 02, and 03 were screened as previously described. Basta® segregation was assessed to identify lines containing a single insert segregating in a 3:1 (R:S) ratio as calculated by a Chi-square test (Table 5-1). Two of three $T_2$ generation events (01 and 03) segregated for a single insert although the segregation ratio for -01 is also not different than a 15:1 (R:S) ratio.

TABLE 5-1

Basta$^R$ segregation for SR01010 individual events

| Event | Resistant | Sensitive | Total | Probability of Chi-test* |
|---|---|---|---|---|
| SR01010-01 | 32 | 4 | 36 | 0.05429 |
| SR01010-02 | 32 | 3 | 35 | 0.0248** |
| SR01010-03 | 24 | 12 | 36 | 0.24821 |
| SR01010-01-1 | 27 | 9 | 36 | 1 |
| SR01010-03-1 | 20 | 13 | 33 | 0.05619 |

*Chi-test to determine whether actual ratio of resistant to sensitive differs from the expected 3:1 ratio.

**Significantly different than a 3:1 (R:S) ratio

Lines SR0101-01 and -03 were chosen as the two events because they had a strong and consistent resistance to PEG, mannitol and ABA. Resistance was observed for SR01010-02 although not in expected ratios in all three screens (data not shown). The controls were sown the same day and in the same plate as the individual lines. The PEG (Tables 5-2 and 5-3), mannitol (Tables 5-4 and 5-5) and ABA (Tables 5-6 and 5-7) segregation ratios observed for SR01010-01 and -03 are consistent with the presence of single insert as demonstrated by chi-square, similar to what we observed for Basta® resistance (Table 5-1).

The progeny from one resistant $T_2$ plant from each of these two events was tested in the $T_3$ generation in the same manner. Resistance to PEG, mannitol and ABA was also observed in the $T_3$ generation. Taken together, the segregation of resistant seedlings containing cDNA 12659859 from two events on all three drought surrogate screens and the inheritance of this resistance in a subsequent generation, provide strong evidence that cDNA 12659859 when over-expressed can provide tolerance to drought.

TABLE 5-2

Chi-square analysis assuming a 3:1 (R:S) ratio for progeny of SR01010-01$T_2$ containing 35S::cDNA 12659859 on PEG.

| Event | Observed | Expected | $\chi^2$ | Probability |
|---|---|---|---|---|
| PEG Resistant | 31 | 26.25 | .860 | .064 |
| PEG Sensitive | 4 | 8.75 | 2.579 | |
| | 35 | 35 | 3.438 | |

TABLE 5-3

Chi-square analysis assuming a 3:1 (R:S) ratio for progeny of SR01010-03 $T_2$ containing 35S::cDNA 12659859 on PEG.

| Event | Observed | Expected | $\chi^2$ | Probability |
|---|---|---|---|---|
| PEG Resistant | 28 | 27 | .037 | .700 |
| PEG Sensitive | 8 | 9 | .111 | |
| | 36 | 36 | .148 | |

TABLE 5-4

| Chi-square analysis assuming a 3:1 (R:S) ratio for progeny of SR01010-01$T_2$ containing 35S::cDNA 12659859 on mannitol. | | | | |
|---|---|---|---|---|
| Event | Observed | Expected | $\chi^2$ | Probability |
| Mannitol Resistant | 25 | 27 | .148 | .441 |
| Mannitol Sensitive | 11 | 9 | .444 | |
| | 36 | 36 | .593 | |

TABLE 5-5

| Chi-square analysis assuming a 3:1 (R:S) ratio for progeny of SR01010-3 $T_2$ containing 35S::cDNA 12659859 on mannitol. | | | | |
|---|---|---|---|---|
| Event | Observed | Expected | $\chi^2$ | Probability |
| Mannitol Resistant | 21 | 20.25 | .028 | .739 |
| Mannitol Sensitive | 6 | 6.75 | .083 | |
| | 27 | 27 | .111 | |

TABLE 5-6

| Chi-square analysis assuming a 3:1 (R:S) ratio for progeny of SR01010-01$T_2$ containing 35S::cDNA 12659859 on ABA. | | | | |
|---|---|---|---|---|
| Event | Observed | Expected | $\chi^2$ | Probability |
| ABA Resistant | 30 | 27 | .333 | .248 |
| ABA Sensitive | 6 | 9 | 1 | |
| | 36 | 36 | 1.333 | |

TABLE 5-7

| Chi-square analysis assuming a 3:1 (R:S) ratio for progeny of SR01010-03 $T_2$ containing 35S::cDNA 12659859 on ABA. | | | | |
|---|---|---|---|---|
| Event | Observed | Expected | $\chi^2$ | Probability |
| ABA Resistant | 27 | 27 | 0 | 1.0 |
| ABA Sensitive | 9 | 9 | 0 | |
| | 36 | 36 | 0 | |

Figure 4:
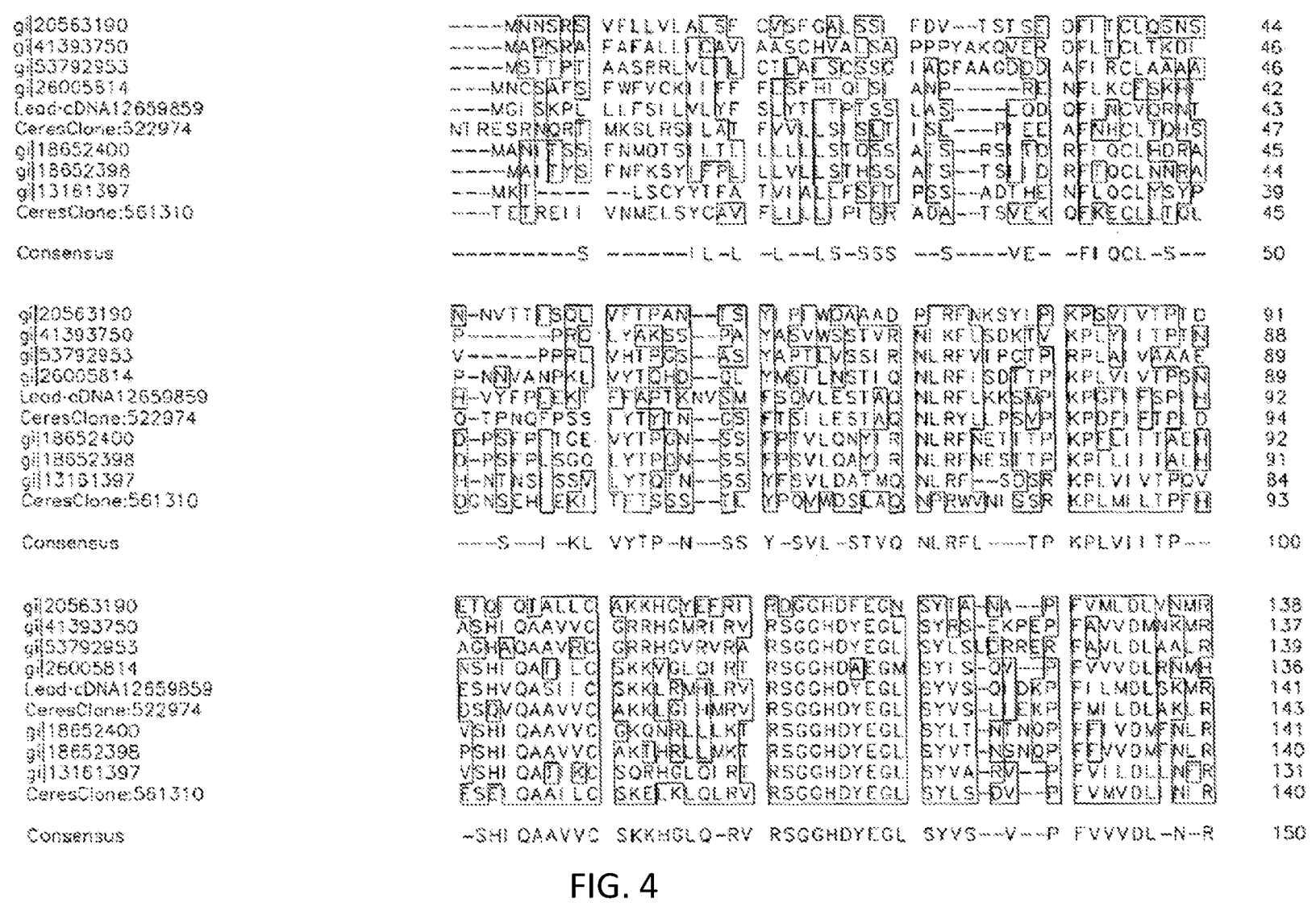
FIG. 4 provides the results of a consensus sequence (SEQ ID NOs: 147-177) analysis based on Ceres cDNA 12659859.

FIG. 4 provides the results of the consensus sequence (SEQ ID NOs: 147-177) analysis based on Ceres cDNA 12659859.

Example 6—Ceres cDNA 12723147

Ceres cDNA 12723147 encodes an *Arabidopsis* putative aldo/keto reductase. Ectopic expression of Ceres cDNA 12723147 under the control of the CaMV35S promoter induces the following phenotypes:

- Germination on high concentrations of polyethylene glycol (PEG), mannitol and abscissic acid (ABA).
- Continued growth on high concentration of PEG, mannitol and ABA.

Generation and Phenotypic Evaluation of $T_1$ Lines Containing 35S::cDNA 12723147.

Wild-type *Arabidopsis* Wassilewskija (WS) plants were transformed with a Ti plasmid containing cDNA 12723147 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12723147 was identified in resistant plants from each of the three surrogate drought screens, the five individual $T_2$ events containing this cDNA (SR01013) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative and Quantitative Analysis of 2 Independent Events Representing 35S::cDNA 12659859 (SR01010) on PEG, Mannitol and ABA To identify two independent events of 35S::cDNA 12659859 showing PEG, mannitol, and ABA resistance, 36 seedlings from each of two events, SR01013-01 and -02 were screened as previously described. Basta® segregation was assessed to verify that the lines contained a single insert segregating in a 3:1 (R:S) ratio as calculated by a chi-square test (Table 6-1). Both lines (01 and 02) segregated for a single insert in the $T_2$ generation (Table 1)

TABLE 6-1

| Basta$^R$ segregation for SR01013 individual events | | | | |
|---|---|---|---|---|
| Event | Resistant | Sensitive | Total | Probability Of Chi-test* |
| SR01013-01 | 30 | 5 | 35 | 0.14323 |
| SR01013-02 | 30 | 6 | 36 | 0.24821 |
| SR01013-01-3 | 34 | 1 | 36 | 0.00248** |
| SR01013-02-2 | 32 | 0 | 32 | 0.00109** |

*Chi-test to determine whether actual ratio of resistant to sensitive differs from the expected 3:1 ratio.
**Significantly different than a 3:1 (R:S) ratio Lines SR01013-01 and -02 were chosen as the two events because they had a strong and consistent resistance to PEG, mannitol and ABA. The controls were sown the same day and in the same plate as the individual lines. The PEG (Tables 6-2 and 6-3), mannitol (Tables 6-4 and 6-5) and ABA (Tables 6-6 and 6-7) segregation ratios observed for SR01013-01 and -02 are consistent with the presence of single insert as demonstrated by chi-square, similar to what we observed for Basta® resistance (Table 6-1).

The progeny from one resistant $T_2$ plant from each of these two events were tested in the same manner as the $T_2$. Resistance to PEG, mannitol and ABA was also observed in the $T_3$ generation. Taken together, the segregation of resistant seedlings containing cDNA 12723147 from two events on all three drought surrogate screens and the inheritance of this resistance in a subsequent generation, provide strong evidence that cDNA 12723147 when over-expressed can provide tolerance to drought.

TABLE 6-2

Chi-square analysis assuming a 3:1 (R:S) ratio for progeny of SR01013-01$T_2$ containing 35S::cDNA 12723147 on PEG.

| Event | Observed | Expected | $\chi^2$ | Probability of Chi-Test |
|---|---|---|---|---|
| PEG Resistant | 22 | 27 | 0.926 | 0.054 |
| PEG Sensitive | 14 | 9 | 2.778 | |
| | 36 | 36 | 3.704 | |

TABLE 6-3

Chi-square analysis assuming a 3:1 (R:S) ratio for progeny of SR01013-02 $T_2$ containing 35S::cDNA 12723147 on PEG.

| Event | Observed | Expected | $\chi^2$ | Probability of Chi-Test |
|---|---|---|---|---|
| PEG Resistant | 26 | 27 | 0.037 | .700 |
| PEG Sensitive | 10 | 9 | .111 | |
| | 36 | 36 | .148 | |

TABLE 6-4

Chi-square analysis assuming a 3:1 (R:S) ratio for progeny of SR01013-01 $T_2$ containing 35S::cDNA 12723147 on mannitol.

| Event | Observed | Expected | $\chi^2$ | Probability of Chi-Test |
|---|---|---|---|---|
| Mannitol Resistant | 28 | 27 | .037 | .700 |
| Mannitol Sensitive | 8 | 9 | .111 | |
| | 36 | 36 | .148 | |

TABLE 6-5

Chi-square analysis assuming a 3:1 (R:S) ratio for progeny of SR01013-02 $T_2$ containing 35S::cDNA 12723147 on mannitol.

| Event | Observed | Expected | $\chi^2$ | Probability of Chi-Test |
|---|---|---|---|---|
| Mannitol Resistant | 18 | 27 | 3 | .0005 |
| Mannitol Sensitive | 18 | 9 | 9 | |
| | 36 | 36 | 12 | |

TABLE 6-6

Chi-square analysis assuming a 3:1 (R:S) ratio for progeny of SR01013-02 $T_2$ containing 35S::cDNA 12723147 on ABA.

| Event | Observed | Expected | $\chi^2$ | Probability |
|---|---|---|---|---|
| ABA Resistant | 13 | 24 | 5.042 | 7.098 |
| ABA Sensitive | 19 | 8 | 15.125 | |
| | 32 | 32 | 20.167 | |

TABLE 6-7

Chi-square analysis assuming a 3:1 (R:S) ratio for progeny of SR01013-02 $T_2$ containing 35S::cDNA 12723147 on ABA.

| Event | Observed | Expected | $\chi^2$ | Probability |
|---|---|---|---|---|
| ABA Resistant | 13 | 24 | 5.042 | 7.098 |
| ABA Sensitive | 19 | 8 | 15.125 | |
| | 32 | 32 | 20.167 | |

Figure 5:
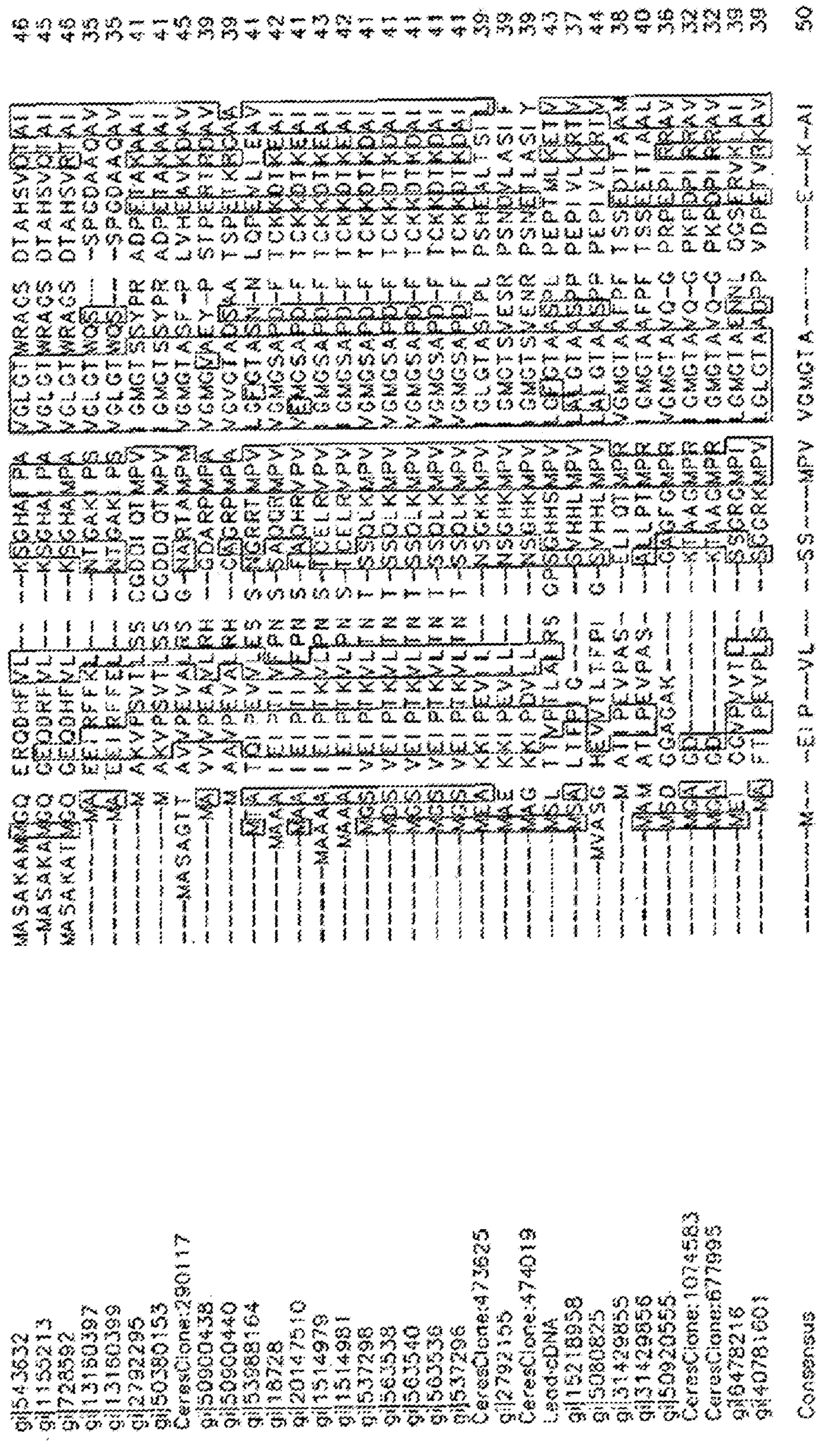
FIG. 5 provides the results of a consensus sequence (SEQ ID NOs: 178-200) analysis based on Ceres cDNA 12723147.

FIG. 5 provides the results of the consensus sequence (SEQ ID NOs: 178-200) analysis based on Ceres cDNA 12723147.

Example 7—Ceres cDNA 13488750

Clone 125039, Ceres cDNA 13488750, encodes a full-length putative adenylylsulfate (APS) kinase from *Arabidopsis thaliana*. Ectopic expression of Ceres cDNA 13488750 under the control of the CaMV35S promoter induces the following phenotypes:

Continued growth under high heat conditions.

Generation and Phenotypic Evaluation of $T_1$ Lines Containing 35S::cDNA 13488750.

Wild-type *Arabidopsis* Wassilewskija (WS) plants were transformed with a Ti plasmid containing cDNA 13488750 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No negative phenotypes were observed in the $T_1$ plants although three of the T1 lines produced a small rosette (ME02526-01, 02 and 05). $T_2$ and $T_3$ lines of events ME02526-01 and ME02526-05 did not show the small rosette phenotype.

Screens of Masterpools for Heat Tolerance Via Heat Shock In Vitro.

Seeds from 100 masterpools from the CaMV35S or 32449 over-expression lines were tested for heat tolerance in vitro as described above.

Once cDNA 13488750 was identified in tolerant plants from the screen, five individual $T_2$ events containing this cDNA (ME02526) were screened on soil as described above to identify events with the resistance phenotype.

Qualitative Analysis of the $T_2$ Masterpool of cDNA 13488750 Plants Heat Shocked on Plates Visual phenotyping of the masterpool containing cDNA 13488750 (ME02526) on agar or soil showed no visible alterations in phenotype (data not shown). After heat-shock at 15 days of age, the ME02526 masterpool showed greater heat recovery as compared to the wild-type control and other transgenic masterpools. Assessment was a measure of "greenness" as well as continued growth at 23° C. after heat shock at 45° C. for between 5 and 8 hours. Immediately after the heat shock stress, the extent of stress-induced damage in the control and ME02526 masterpool appeared comparable. The leaves and cotyledons were wilted and droopy although still green. However, after 4 days of recovery, 2 of 10 plants in the ME02526 masterpool had completely recovered and were growing again. Other seedlings showed some recovery as measured by greenness compared to the wild-type control.

Qualitative and Quantitative Analysis of Individual $T_2$ Events of cDNA 13488750 Under Continual Heat Treatment on Soil Five independent events of ME02526 were tested on soil as described above. Two of the events (ME02526-04 and -05) showed heat resistance after continual growth at 36° C. Heat resistance was noted as decreased chlorosis compared to wild-type. Segregation frequencies of the transgene under test suggest that these two events contain a single insert, as calculated by a chi-square test (Tables 7-1, 7-2 and 7-3). Ten and 11 plants from events 04 and 05, respectively, showed continued vigor and decreased chlorosis after continuous heat treatment compared to wild-type controls.

TABLE 7-1

Chi-square analysis assuming a 3:1 (R:S) ratio for progeny of ME02526-04 and -05 containing 35S::cDNA 13488750 on Finale.

| Event | Observed | Expected | $\chi^2$ | Probability of Chi-Test |
|---|---|---|---|---|
| ME02526-04 Finale Resistant | 29 | 27 | 0.593 | 0.44 |
| ME02526-04 Finale Sensitive | 7 | 9 | | |
| | 36 | 36 | | |
| ME02526-05 Finale Resistant | 27 | 27 | 0 | 1 |
| ME02526-05 Finale Sensitive | 9 | 9 | | |
| | 36 | 36 | | |

TABLE 7-2

Chi-square analysis assuming a 3:1 (R:S) ratio for progeny of ME02526-04 containing 35S::cDNA 13488750 for thermo tolerance (continual growth at 36° C. on soil).

| Event | Observed | Expected | $\chi^2$ | Probability of Chi-Test |
|---|---|---|---|---|
| Heat Tolerant | 10 | 11.25 | 0.556 | 0.456 |
| Heat Sensitive | 5 | 3.75 | | |
| | 15 | 15 | | |

TABLE 7-3

Chi-square analysis assuming a 3:1 (R:S) ratio for progeny of ME02526-05 containing 35S::cDNA 13488750 for thermo tolerance (continual growth at 36° C. on soil).

| Event | Observed | Expected | $\chi^2$ | Probability of Chi-Test |
|---|---|---|---|---|
| Heat Tolerant | 11 | 11.25 | 0.022 | 0.881 |
| Heat Sensitive | 4 | 3.75 | | |
| | 15 | 15 | | |

The plants that survive the heat treatment show premature bolting and reduced fecundity but much less so than the control plants. Control and ME02526 plants bolt after only 4 days of exposure to 36° C. (11-day old plants), but were more vigorous and less chlorotic than the controls and the height and branch number was comparable to those of wild-type (data not shown). Heat-tolerant lines all showed seed abortion and reduced fecundity (data not shown). Seed abortion and reduced silique size was also prevalent in all wild-type controls (data not shown). Events 04 and 05, which had a thermo tolerant phenotype in the $T_2$ generation, were evaluated in greater detail in the $T_3$ generation for heat resistance and fecundity after prolonged heat stress on MS plates.

Qualitative and Quantitative Analysis of Individual $T_3$ Events Under 36° C. Heat Treatment on Plates Seeds from five individuals of the $T_3$ generation for ME02526-04 and -05 lines and controls were sterilized, stratified and germinated for 7 days at 23° C. prior to exposure to 36° C. heat stress. The events were evaluated for heat resistance to prolonged heat stress.

The thermo tolerant phenotype became apparent after 15 days of 36° C. treatment. $T_3$ progeny from ME02526-04 (Table 7-4) and ME02526-05 (Table 7-5) were found to segregate in the expected 3:1 ratio for the thermo tolerant phenotype.

TABLE 7-4

Chi-square analysis assuming a 3:1 (R:S) ratio for progeny of ME02526-04 containing 35S::cDNA 13488750 for thermo tolerance (continual growth at 36° C.

| Event | Observed | Expected | $\chi^2$ | Probability of Chi-Test |
|---|---|---|---|---|
| Heat Tolerant | 14 | 14.25 | 0.017 | 0.89 |
| Heat Sensitive | 5 | 4.75 | | |
| | 19 | 19 | | |

TABLE 7-5

Chi-square analysis assuming a 3:1 (R:S) ratio for progeny of ME02526-05 containing 35S::cDNA 13488750 for thermo tolerance (continual growth at 36° C.

| Event | Observed | Expected | $\chi^2$ | Probability of Chi-Test |
|---|---|---|---|---|
| Heat Tolerant | 15 | 14.25 | 0.157 | 0.69 |
| Heat Sensitive | 4 | 4.75 | | |
| | 19 | 19 | | |

Qualitative Analysis of Individual $T_3$ Events Heat Shocked on Plates for Differentiation of Natural Acquired Thermo-tolerance Plants acquire thermotolerance to lethal high temperatures such as 45° C. if previously exposed to moderately high temperature or if the temperature is raised gradually to an otherwise lethal temperature (Vierling, 1991). To ascertain whether the thermotolerance observed in the $T_3$ generation is due to some naturally acquired thermotolerance imparted by heat exposure of the $T_2$ parent plant (ME2526-04 and 05), thermotolerance was assessed by comparing pre-heat treated wild-type and transgenic controls and unheated wild-type controls. $T_3$ events of ME02526-04 and 05 were heat shocked for 4 hours as described above. ME02526-04 and -05 were able to stay greener longer than both pre-heat treated controls and un-heat treated controls. However, both ME02526 lines and all controls (wild-type and transgenic) failed to elongate and thrive after heat treatment at 45° C. and eventually all died. Un-heat treated wild-type control became chlorotic faster (1-day after treatment) than pre-heat treated wildtype control and pre-heat treated transgenic control suggesting that there is some natural acquired thermotolerance that occurs that is not correlated with the over-expression of 35S::cDNA 13488750. Even with exposure to this lethal temperature, ME02526 was greener after 7 days than controls, indicating that ME02526 has a thermotolerance phenotype that is unrelated to the natural mechanisms of acquired thermotolerance.

Figure 6:
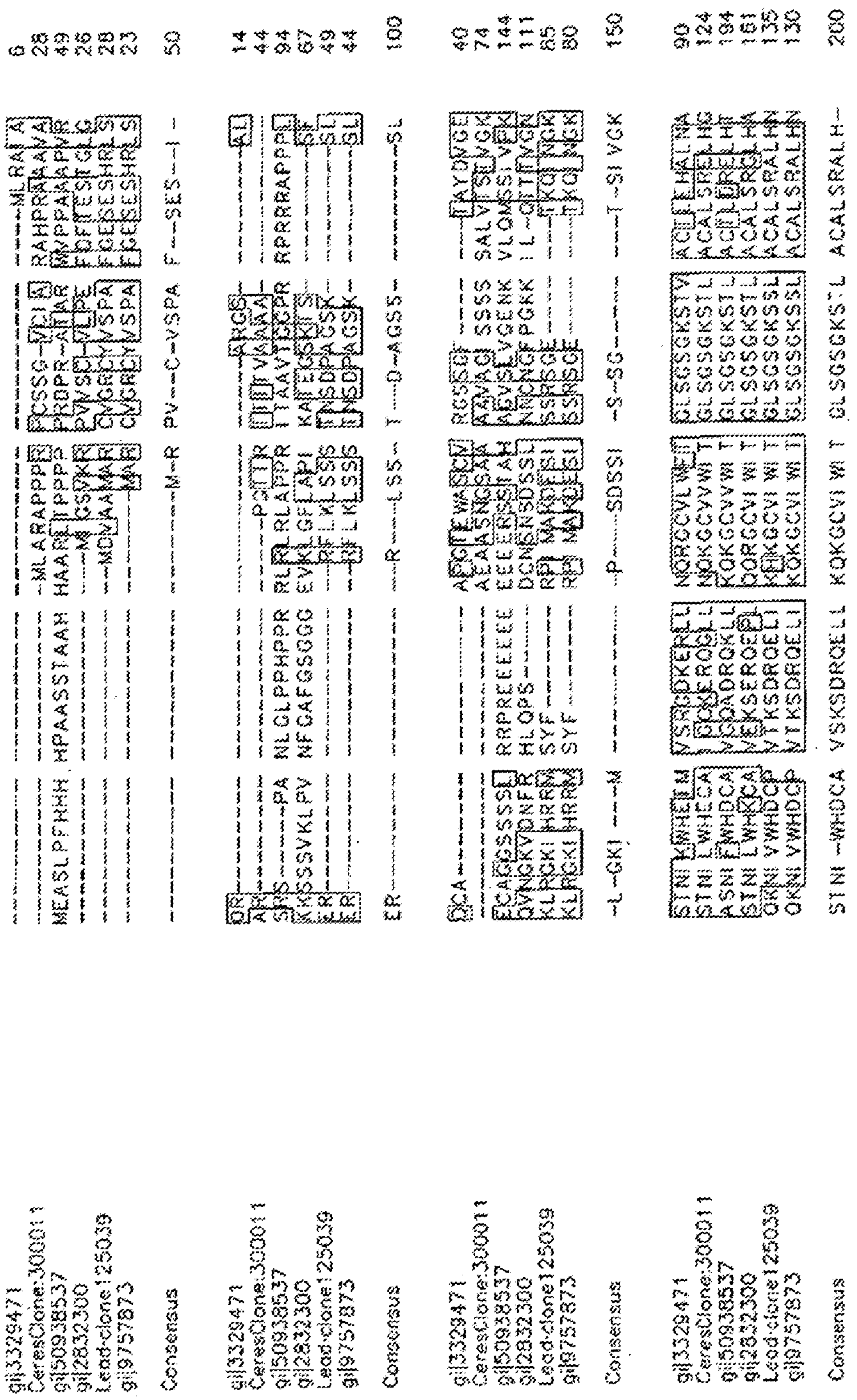
FIG. 6 provides the results of a consensus sequence (SEQ ID NOs: 201-214) analysis based on Ceres cDNA 13488750.

FIG. 6 provides the results of the consensus sequence (SEQ ID NOs: 201-214) analysis based on Ceres cDNA 13488750.

Example 8—Ceres cDNA 13489782

Clone 10044, Ceres cDNA 13489782, encodes a full-length putative 114-amino acid hypothetical protein from *Arabidopsis thaliana*. Ectopic expression of Ceres cDNA 13489782 under the control of the 32449 promoter induces the following phenotypes:

- Germination on high concentrations of polyethylene glycol (PEG) and abscissic acid (ABA) and
- Continued growth on high concentrations of PEG and ABA.

Generation and Phenotypic Evaluation of $T_1$ Lines Containing 32449::cDNA 13489782

Wild-type *Arabidopsis* Wassilewskija (WS) plants were transformed with a Ti plasmid containing cDNA 13489782 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13489782 was identified in resistant plants from each of the three surrogate drought screens, the five individual $T_2$ events containing this cDNA (ME00446) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative Analysis of Superpools on PEG, Mannitol, and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta to eliminate any false-positives, or any lines where the Basta® marker was suppressed. All of the Basta-resistant candidates flowered and set seed. Resistant seedlings were recovered from Superpools 1, 7 and 11 on all screens (Table 8-1).

TABLE 8-1

Number of stress-tolerant and $Basta^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

We obtained sequence from 3, 3, and 13 plants that were both Basta® and resistant to PEG, mannitol or ABA, respectively. For each of the three surrogate drought screens, one or more plants contained the 32449::clone 10044 (ME00446). The probability of finding a plant containing this cDNA at random in all three screens is 0.03×0.03×0.03.

Qualitative and Quantitative Analysis of 6 Independent Events Representing 32449::cDNA 13489782 on PEG, Mannitol and ABA To identify independent events of 32449::cDNA 13489782 showing PEG, mannitol and ABA resistance, 36 seedlings from each of six events, ME00446-01, 02, 03, 04, 05 and 06 were screened as previously described. Simultaneously, Basta® segregation was assessed to identify lines containing a single insert segregating in a 3:1 (R:S) ratio as calculated by a Chi-square test (Table 8-2). All of the lines segregated for a single functional insert.

TABLE 8-2

$Basta^R$ segregation for 6 events of ME00446

| ME Line | Assessment | Did Not Germinate | Resistant | Sensitive | Total | Probability of Chi-test |
|---|---|---|---|---|---|---|
| 00446-01 | Oct. 30, 2003 | 1 | 28 | 7 | 35 | 0.49452 |
| 00446-02 | Oct. 30, 2003 | 0 | 28 | 8 | 36 | 0.70031 |
| 00446-03 | Oct. 30, 2003 | 1 | 28 | 7 | 35 | 0.49452 |
| 00446-04 | Oct. 30, 2003 | 1 | 27 | 8 | 35 | 0.7697 |

TABLE 8-2-continued

| Basta[R] segregation for 6 events of ME00446 | | | | | | |
|---|---|---|---|---|---|---|
| ME Line | Assessment | Did Not Germinate | Resistant | Sensitive | Total | Probability of Chi-test |
| 00446-05 | Oct. 30, 2003 | 2 | 24 | 10 | 34 | 0.55245 |
| 00446-06 | Oct. 30, 2003 | 0 | 25 | 11 | 36 | 0.44142 |

*Chi-test to determine whether actual ratio of resistant to sensitive differs from the expected 3:1 ratio.

Events ME00446-02 and 04 were chosen as the two events for further analysis because they had the strongest and most consistent resistance to PEG and ABA. None of the lines showed mannitol resistance at 375 mM concentration. The controls were sown the same day and in the same plate as the individual lines. The PEG (Tables 8-3 and 8-4) and ABA (Tables 8-5 and 8-6) segregation ratios observed for ME00446-02 and 04 are consistent with the presence of single insert as demonstrated by the Chi-Square test. This is similar to that observed for Basta resistance (Table 8-2).

Despite the fact that this line was isolated from all three screens, it was subsequently concluded that it could not be considered mannitol resistant. This is likely due to an overly stringent mannitol concentration. In a superpool screen setting, the seedlings are more densely grown than in an individual line setting. This means that in a superpool screen, there is a lower effective concentration of mannitol. When putative tolerant plant from a superpool is tested as an individual line, the effective concentration it is grown on is actually higher. In the case of ME00446, this difference was enough to invalidate it as mannitol tolerant. In fact, a resistant plant to mannitol was isolated from superpool 11 that corresponds to clone 10044.

TABLE 8-3

| Chi-square analysis assuming a 3:1(R:S) ratio for progeny of ME00446-02 containing 32449::clone 10044 on PEG. | | | | |
|---|---|---|---|---|
| Event | Observed | Expected | $X^2$ | Probability of $X^2$ |
| PEG Resistant | 30 | 26.95 | 0.3452 | 0.2557 |
| PEG Sensitive | 5 | 7.7 | 0.9468 | |
| Total | 35 | 35 | 1.292 | |

TABLE 8-4

| Chi-square analysis assuming a 3:1(R:S) ratio for progeny of ME00446-04 containing 32449::clone 10044 on PEG. | | | | |
|---|---|---|---|---|
| Event | Observed | Expected | $X^2$ | Probability of $X^2$ |
| PEG Resistant | 26 | 27.77 | 0.113 | 0.482 |
| PEG Sensitive | 10 | 8.23 | 0.3813 | |
| Total | 36 | 36 | 0.4943 | |

TABLE 8-5

| Chi-square analysis assuming a 3:1(R:S) ratio for progeny of ME00446-02 containing 32449::clone 10044 on ABA. | | | | |
|---|---|---|---|---|
| Event | Observed | Expected | $X^2$ | Probability of $X^2$ |
| ABA Resistant | 31 | 27 | 0.5926 | 0.1237 |
| ABA Sensitive | 5 | 9 | 1.778 | |
| Total | 36 | 36 | 2.370 | |

TABLE 8-6

| Chi-square analysis assuming a 3:1(R:S) ratio for progeny of ME00446-04 containing 32449::clone 10044 on ABA. | | | | |
|---|---|---|---|---|
| Event | Observed | Expected | $X^2$ | Probability of $X^2$ |
| ABA Resistant | 31 | 27 | 0.5926 | 0.1237 |
| ABA Sensitive | 5 | 9 | 1.778 | |
| Total | 36 | 36 | 2.370 | |

Qualitative and Quantitative Analysis of Progeny of $T_2$ Plants Isolated on PEG, Mannitol and ABA Progeny from $T_2$ plants that were recovered from the three screens and containing clone 10044 (SP11-M13 and SP11-P5) were found to be resistant to PEG and ABA. Taken together, 1) the isolation of resistant seedlings containing clone 10044 from all three surrogate screens for drought, 2) the inheritance of this resistance in the next generation, and 3) the fact that the progeny from two or more events from the original transformation also segregated for resistance to these osmotic stresses, provide strong evidence that clone 10044 when over-expressed provides resistance to osmotic and dehydration stress.

Figure 7:
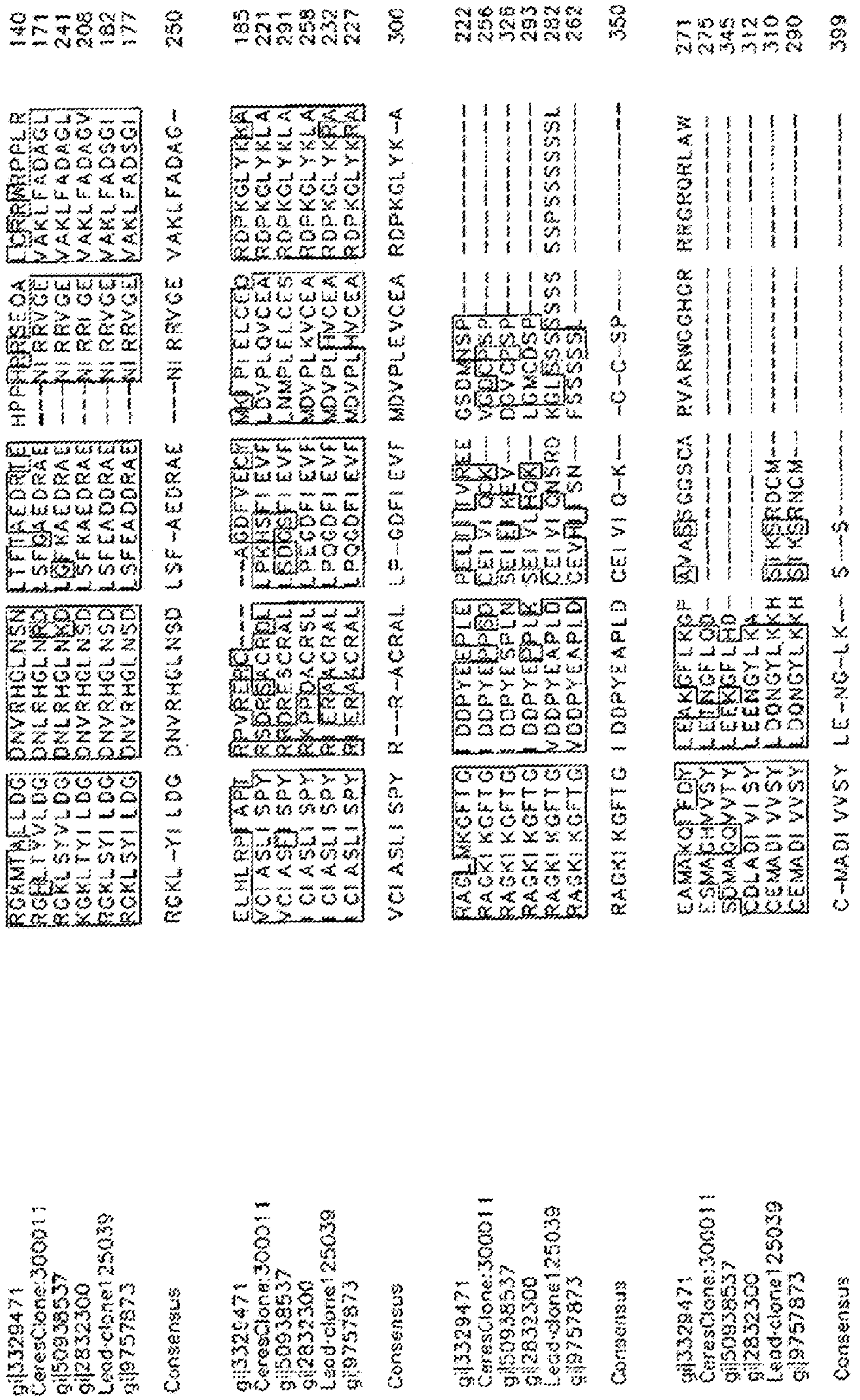
FIG. 7 provides the results of a consensus sequence (SEQ ID NOs: 215-222) analysis based on Ceres cDNA 13489782.

FIG. 7 provides the results of the consensus sequence (SEQ ID NOs: 215-222) analysis based on Ceres cDNA 13489782.

Example 9—Ceres cDNA 13486759

Clone 10987, corresponding Ceres cDNA 13486759, encodes an *Arabidopsis* 251-amino acid expressed protein. Ectopic expression of clone 10987 under the control of the CaMV35S promoter induces the following phenotypes:

- Germination on high concentrations of polyethylene glycol (PEG), mannitol, and abscissic acid (ABA), and
- Continued growth on high concentrations of PEG, mannitol, and ABA.

Generation and Phenotypic Evaluation of $T_1$ Lines Containing 35S::cDNA 13486759

Wild-type *Arabidopsis* Wassilewskija (WS) plants were transformed with a Ti plasmid containing cDNA 13486759 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13486759 was identified in resistant plants from each of the three surrogate drought screens, the five individual $T_2$ events containing this cDNA (ME03316) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative Analysis of 13 Superpools on PEG, Mannitol and ABA

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta to eliminate any false-positives, or any lines where the Basta® marker was suppressed. All of the Basta-resistant candidates flowered and set seed. Resistant seedlings were recovered from Superpools 1, 7 and 11 on all screens (Table 9-1).

TABLE 9-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

We obtained sequence from 3, 3, and 13 plants from Superpool 11 that were both Basta®-resistant and resistant to PEG, mannitol or ABA, respectively. For each of the three osmotic screens, one or more plants contained the 35S::clone 10987 (ME03316), which made it a good candidate for further testing. The probability of finding a plant containing this clone 10987 at random in all three screens is 0.03×0.03.

Qualitative and Quantitative Analysis of 5 Independent Events Representing 35S::cDNA 13486759 on PEG, Mannitol and ABA To identify independent events of 35S::cDNA 13486759 showing PEG, mannitol and ABA resistance, 36 seedlings from each of five events, ME03316-01, -02, -03, -04, and -05 were screened as previously described. Simultaneously, Basta® segregation was assessed to identify events containing a single insert segregating in a 3:1 (R:S) ratio as calculated by a chi-square test (Table 9-2). All of the events segregated for a single functional insert. ME03316-02 could be segregating for two linked or unlinked inserts but the ratios on the surrogate drought screens indicate it is likely to be a single insert.

TABLE 9-2

Basta$^R$ segregation for 5 individual events

| Event | Resistant | Sensitive | Total | Probability of Chi-test |
|---|---|---|---|---|
| ME03316-01 | 23 | 13 | 36 | 0.12366 |
| ME03316-02 | 32 | 4 | 36 | 0.05429 |
| ME03316-03 | 30 | 6 | 36 | 0.24821 |
| ME03316-04 | 25 | 11 | 36 | 0.44142 |
| ME03316-05 | 29 | 7 | 36 | 0.44142 |

*Chi-test to determine whether actual ratio of resistant to sensitive differs from the expected 3:1 ratio.

Lines ME03316-01 and 02 were chosen as the two events for further analysis because they had the strongest and most consistent resistance to PEG, mannitol and ABA. Resistance was observed for ME03316-03, 04, and 05 although not in expected ratios in all three screens (data not shown). The controls were sown the same day and on the same plate as the individual lines. The PEG (Tables 9-3 and 9-4), mannitol (Tables 9-5 and 9-6) and ABA (Table 9-7) segregation ratios observed are consistent with the presence of a single insert as demonstrated by chi-square. ME03316-02 seedlings on ABA (Table 9-8) appear to be segregating for two inserts which is still consistent with the ratio observed on Basta®. Both events segregate for a deficiency of resistant seedlings on mannitol.

TABLE 9-3

Chi-square analysis assuming a 3:1 (R:S) ratio for progeny of ME03316-01 containing 35S::clone 10987 on PEG.

| Event | Observed | Expected | $\chi^2$ | Probability of Chi-Test |
|---|---|---|---|---|
| PEG Resistant | 22 | 27 | 0.93 | 0.0543 |
| PEG Sensitive | 14 | 9 | 2.78 | |
| Total | 36 | 36 | 3.7 | |

TABLE 9-4

Chi-square analysis assuming a 3:1 (R:S) ratio for progeny of ME03316-02 containing 35S::clone 10987 on PEG.

| Event | Observed | Expected | $\chi^2$ | Probability of Chi-Test |
|---|---|---|---|---|
| PEG Resistant | 23 | 26.25 | 0.4024 | 0.2046 |
| PEG Sensitive | 12 | 8.75 | 1.2071 | |
| Total | 35 | 35 | 1.610 | |

TABLE 9-5

| Chi-square analysis assuming a 3:1 (R:S) ratio for progeny of ME03316-01 containing 35S::clone 10987 on Mannitol. | | | | |
|---|---|---|---|---|
| Event | Observed | Expected | $\chi^2$ | Probability of Chi-Test |
| Mannitol Resistant | 19 | 25.5 | 1.657 | 0.01 |
| Mannitol Sensitive | 15 | 8.5 | 4.971 | |
| Total | 34 | 34 | 6.63 | |

TABLE 9-6

| Chi-square analysis assuming a 3:1 (R:S) ratio for progeny of ME03316-02 containing 35S::clone 10987 on Mannitol. | | | | |
|---|---|---|---|---|
| Event | Observed | Expected | $\chi^2$ | Probability of Chi-Test |
| Mannitol Resistant | 18 | 26.25 | 2.593 | 0.0013 |
| Mannitol Sensitive | 17 | 8.75 | 7.779 | |
| Total | 35 | 35 | 10.371 | |

TABLE 9-7

| Chi-square analysis assuming a 3:1 (R:S) ratio for progeny of ME03316-01 containing 35S::clone 10987 on ABA. | | | | |
|---|---|---|---|---|
| Event | Observed | Expected | $\chi^2$ | Probability of Chi-Test |
| ABA Resistant | 27 | 25.5 | 0.0882 | 0.5525 |
| ABA Sensitive | 7 | 8.5 | 0.2647 | |
| Total | 34 | 34 | 0.3529 | |

TABLE 9-8

| Chi-square analysis assuming a 3:1 (R:S) ratio for progeny of ME03316-02 containing 35S::clone 10987 on ABA. | | | | |
|---|---|---|---|---|
| Event | Observed | Expected | $\chi^2$ | Probability of Chi-Test |
| ABA Resistant | 32 | 24.75 | 2.124 | 0.0036 |
| ABA Sensitive | 1 | 8.25 | 6.371 | |
| Total | 33 | 33 | 8.495 | |

Qualitative and Quantitative Analysis of Progeny of $T_2$ Plants Isolated on PEG, Mannitol and ABA Progeny from $T_2$ plants that were recovered from the three screens and containing clone 10987 (SP1 1-A15, SP11-A16, SP11-P2, and SP11-M10) were found to be resistant to PEG, mannitol and ABA.

On PEG, the progeny of SP11-M10 segregated for a deficiency of resistant seedlings similar to the deficiency that noted for the $T_2$ seedlings in Tables 9-5 and 9-6. A deficiency of resistant seedlings is also noted for the progeny of SP11P2 on PEG.

Taken together, 1) the isolation of resistant seedlings containing clone 10987 from all three surrogate screens for drought, 2) the inheritance of this resistance in the next generation, and 3) the fact that the progeny from two or more events from the original transformation also segregated for resistance to these osmotic stresses, these findings provide strong evidence that clone 10987 when over-expressed can provide tolerance to osmotic stresses.

Example 10—Ceres cDNA 13500101

Clone 17206, corresponding to Ceres cDNA 13500101, encodes a putative strictosidine synthase. Ectopic expression of cDNA 13500101 under the control of the CaMV35S promoter induces the following phenotypes:

- Germination on high concentrations of polyethylene glycol (PEG) and mannitol.
- Continued growth on high concentrations of PEG and mannitol.

Generation and Phenotypic Evaluation of $T_1$ Lines Containing 35S::cDNA 13500101.

Wild-type *Arabidopsis* Wassilewskija (WS) plants were transformed with a Ti plasmid containing cDNA 13500101 in the sense orientation relative to the CaMV35S constitutive promoter. The $T_1$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13500101 was identified in resistant plants from each of the three surrogate drought screens, the five individual $T_2$ events containing this cDNA (SR01000) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative and Quantitative Analysis of 2 Independent Events Representing 35S::cDNA 13500101 (SR01000) on PEG, Mannitol and ABA To identify two independent events of 35S::clone 17206 showing PEG, mannitol, and ABA resistance, 36 seedlings from each of three events, SR01000-01, 02 and 03 were screened as previously described. Basta segregation was assessed to verify that the lines contained a single insert segregating in a 3:1 (R:S) ratio as calculated by a chi-square test (Table 1). Two lines (-01 and -02) segregated for a single insert (Table 1).

TABLE 10-1

| $Basta^R$ segregation for SR01000 individual events | | | | |
|---|---|---|---|---|
| Event | Resistant | Sensitive | Total | Probability of Chi-test |
| SR01000-01 | 29 | 7 | 36 | 0.44142 |
| SR01000-02 | 23 | 13 | 36 | 0.12366 |
| SR01000-03 | 35 | 0 | 35 | 0.00064 |
| SR01000-01-01 | 35 | 0 | 35 | 0.00064 |

TABLE 10-1-continued

Basta[R] segregation for SR01000 individual events

| Event | Resistant | Sensitive | Total | Probability of Chi-test |
|---|---|---|---|---|
| SR01000-02-01 | 27 | 9 | 36 | 1 |
| SR01000-03-01 | 36 | 0 | 36 | 0.00053 |

*Chi-test to determine whether actual ratio of resistant to sensitive differs from the expected 3:1 ratio.

Testing of the progeny from the $T_2$ resistant plants on the 3 surrogate drought screens showed that lines SR01000-01 and 02 had a strong and consistent resistance to PEG, mannitol, but not to ABA. These were chosen as the two events for further analysis. The controls were sown the same day and in the same plate as the individual lines. The PEG (Tables 10-2 and 10-3), and mannitol (Tables 10-4 and 10-5) segregation ratios observed for SR01000-01 and 02 are consistent with the presence a of single insert as demonstrated by chi-square (Table 10-1).

TABLE 10-2

Chi-square analysis assuming a 3:1 (R:S) ratio for progeny of SR01000-01 $T_2$ containing 35S::cDNA 13500101 on PEG.

| Event | Observed | Expected | $\chi^2$ | Probability of Chi-Test |
|---|---|---|---|---|
| PEG Resistant | 26 | 26.25 | 0.002 | 0.922 |
| PEG Sensitive | 9 | 8.75 | 0.007 | |
| | 35 | 35 | 0.009 | |

TABLE 10-3

Chi-square analysis assuming a 3:1 (R:S) ratio for progeny of SR01000-02 $T_2$ containing 35S::cDNA 13500101 on PEG.

| Event | Observed | Expected | $\chi^2$ | Probability of Chi-Test |
|---|---|---|---|---|
| PEG Resistant | 27 | 24.75 | 0.205 | 0.366 |
| PEG Sensitive | 6 | 8.25 | 0.614 | |
| | 33 | 33 | 0.818 | |

TABLE 10-4

Chi-square analysis assuming a 3:1 (R:S) ratio for progeny of SR01000-01 $T_2$ containing 35S::cDNA 13500101 on mannitol.

| Event | Observed | Expected | $\chi^2$ | Probability of Chi-Test |
|---|---|---|---|---|
| Mannitol Resistant | 28 | 27 | 0.037 | 0.700 |
| Mannitol Sensitive | 8 | 9 | 0.111 | |
| | 36 | 36 | 0.148 | |

TABLE 10-5

Chi-square analysis assuming a 3:1 (R:S) ratio for progeny of SR01000-02 $T_2$ containing 35S::cDNA 13500101 on mannitol.

| Event | Observed | Expected | $\chi^2$ | Probability of Chi-Test |
|---|---|---|---|---|
| Mannitol Resistant | 30 | 27 | 0.333 | 0.248 |
| Mannitol Sensitive | 6 | 9 | 1.000 | |
| | 36 | 36 | 1.333 | |

Qualitative and Quantitative Analysis of Progeny of $T_2$ Plants Isolated on PEG, Mannitol and ABA The progeny from one resistant $T_2$ plant from each of these two events were tested in the same manner as the $T_2$. Resistance to PEG and mannitol persisted in the second generation. Taken together, 1) the isolation of resistant seedlings containing clone 17026 from two of the surrogate screens for drought (PEG and mannitol), 2) the inheritance of this resistance in the next generation, and 3) the fact that the progeny from two or more events from the original transformation also segregated for resistance to these osmotic stresses, these findings provide strong evidence that clone 17026 when over-expressed can provide tolerance to osmotic stresses.

Figure 8:
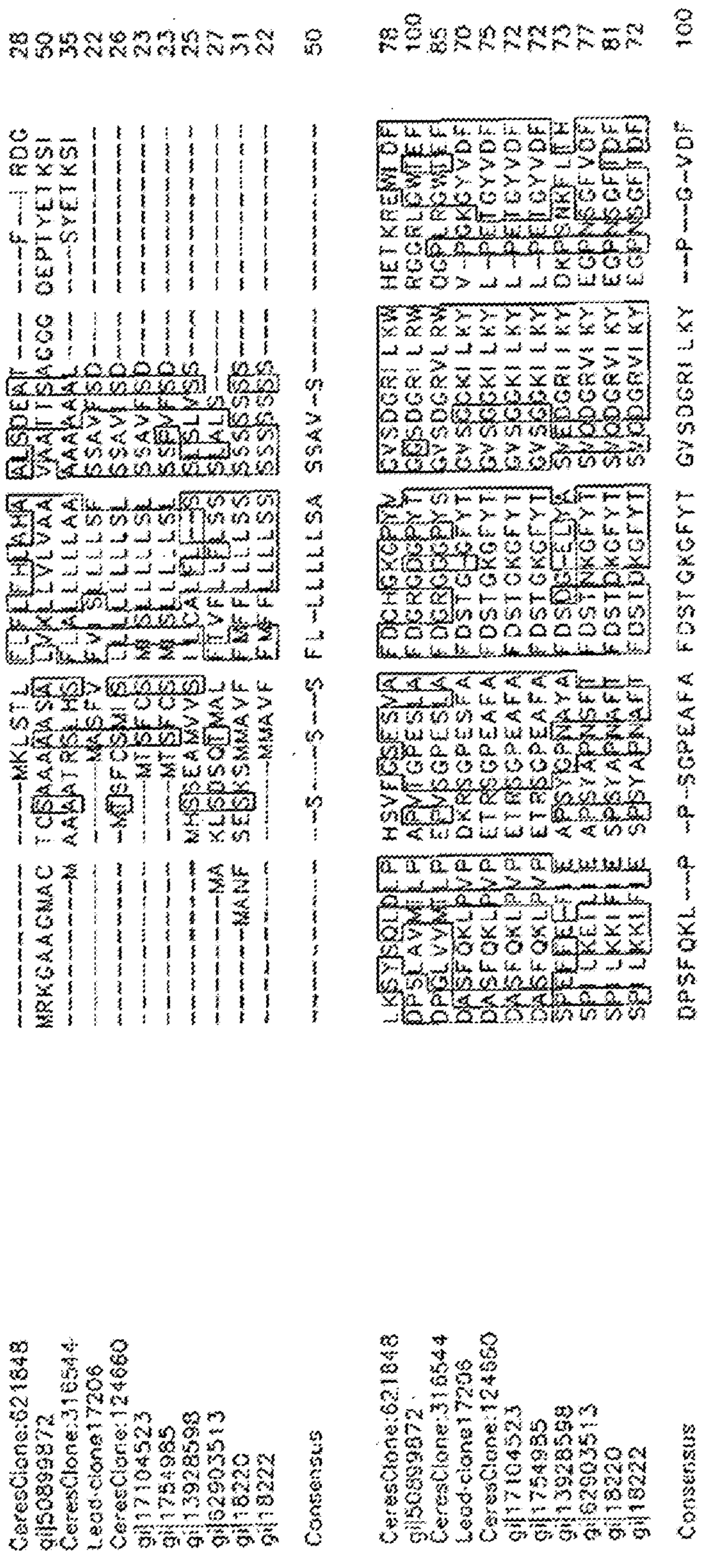
FIG. 8 provides the results of a consensus sequence (SEQ ID NOs: 223-240) analysis based on Ceres cDNA 13500101.

FIG. 8 provides the results of the consensus sequence (SEQ ID NOs: 223-240) analysis based on Ceres cDNA 13500101.

Example 11—Ceres cDNA 13509011 (12357529)

Clone 104691, corresponding to Ceres cDNA 13509011 (12357529), encodes a probable strictosidine synthase enzyme. Ectopic expression of cDNA 13509011 under the control of the CaMV35S promoter induces the following phenotypes:

- Germination on high concentrations of polyethylene glycol (PEG) and mannitol.
- Continued growth on high concentration of PEG and mannitol.

Generation and Phenotypic Evaluation of $T_1$ Lines Containing 35S::cDNA 13509011.

Wild-type *Arabidopsis* Wassilewskija (WS) plants were transformed with a Ti plasmid containing cDNA 12334963 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13509011 was identified in resistant plants from each of the three surrogate drought screens, the five individual $T_2$ events containing this cDNA (SR01002) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the $18^{th}$ plant isolated from a mannitol screen of Superpool 1.

Qualitative and Quantitative Analysis of 2 Independent Events Representing 35S::Clone 104691 (SR01002) on PEG, Mannitol and ABA To identify two independent events of 35S::clone 104691 showing PEG, mannitol and ABA resistance, 36 seedlings from each of three events, SR01002-01, 02, and 03 were screened as previously described. Simultaneously, Basta segregation was assessed to identify lines containing a single insert segregating in a 3:1 (R:S) ratio as calculated by a chi-square test (Table 1). Two lines (01 and 03) segregated for a single insert.

TABLE 11-1

Basta segregation for SR01002 individual events

| Event | Resistant | Sensitive | Total | Probability of Chi-test |
|---|---|---|---|---|
| SR01002-01 | 26 | 10 | 36 | 0.70031 |
| SR01002-02 | 23 | 8 | 31 | 0.91741 |
| SR01002-03 | 28 | 8 | 36 | 0.70031 |
| SR01002-01-1 | 36 | 0 | 36 | 0.00053 |
| SR01002-02-1 | 28 | 8 | 36 | 0.70031 |
| SR01002-03-1 | 25 | 11 | 36 | 0.44142 |

*Chi-test to determine whether actual ratio of resistant to sensitive differs from the expected 3:1 ratio.

Testing of the progeny from the resistant $T_2$ plants on the 3 surrogate drought screens showed that lines SR01002-01 and 03 had a strong and consistent resistance to PEG, mannitol, but not to ABA. These were chosen as the two events for further analysis. The controls were sown the same day and in the same plate as the individual lines. The PEG (Tables 11-2 and 11-3), and mannitol (Tables 11-4 and 11-5) segregation ratios observed for SR01002-01 and 03 are consistent with the presence of a single insert as demonstrated by chi-square. This is similar to that observed for Basta resistance (Table 11-1).

TABLE 11-2

Chi-square analysis assuming a 3:1 (R:S) ratio for progeny of SR01002-01 $T_2$ containing 35S::clone 104691 on PEG.

| Event | Observed | Expected | $\chi^2$ | Probability |
|---|---|---|---|---|
| PEG Resistant | 22 | 24.75 | 0.306 | 0.269 |
| PEG Sensitive | 11 | 8.25 | 0.917 | |
| | 33 | 33 | 1.222 | |

TABLE 11-3

Chi-square analysis assuming a 3:1 (R:S) ratio for progeny of SR01002-03 $T_2$ containing 35S::clone 104691 on PEG.

| Event | Observed | Expected | $\chi^2$ | Probability |
|---|---|---|---|---|
| PEG Resistant | 24 | 25.5 | 0.088 | 0.552 |
| PEG Sensitive | 10 | 8.5 | 0.265 | |
| | 34 | 34 | 0.353 | |

TABLE 11-4

Chi-square analysis assuming a 3:1 (R:S) ratio for progeny of SR01002-01 $T_2$ containing 35S::clone 104691 on mannitol.

| Event | Observed | Expected | $\chi^2$ | Probability |
|---|---|---|---|---|
| Mannitol Resistant | 30 | 27 | 0.333 | 0.248 |
| Mannitol Sensitive | 6 | 9 | 1.000 | |
| | 36 | 36 | 1.333 | |

TABLE 11-5

Chi-square analysis assuming a 3:1 (R:S) ratio for progeny of SR01002-03 $T_2$ containing 35S::clone 104691 on mannitol.

| Event | Observed | Expected | $\chi^2$ | Probability |
|---|---|---|---|---|
| Mannitol Resistant | 32 | 27 | 0.926 | 0.054 |
| Mannitol Sensitive | 4 | 9 | 2.78 | |
| | 36 | 36 | 3.70 | |

Qualitative and Quantitative Analysis of Progeny of $T_2$ Plants Isolated on PEG, Mannitol, and ABA Screens.

The progeny from one resistant $T_2$ plant from each of these two events was tested in the $T_3$ generation in the same manner. Resistance to PEG and mannitol persisted into the next generation. Taken together, 1) the isolation of resistant seedlings containing clone 104691 from two of the surrogate screens for drought (PEG and mannitol), 2) the inheritance of this resistance in the next generation, and 3) the fact that the progeny from two or more events from the original transformation also segregated for resistance to these surrogate drought conditions, these findings provide strong evidence that clone 104691 when over-expressed can provide tolerance to osmotic stresses.

Figure 9:
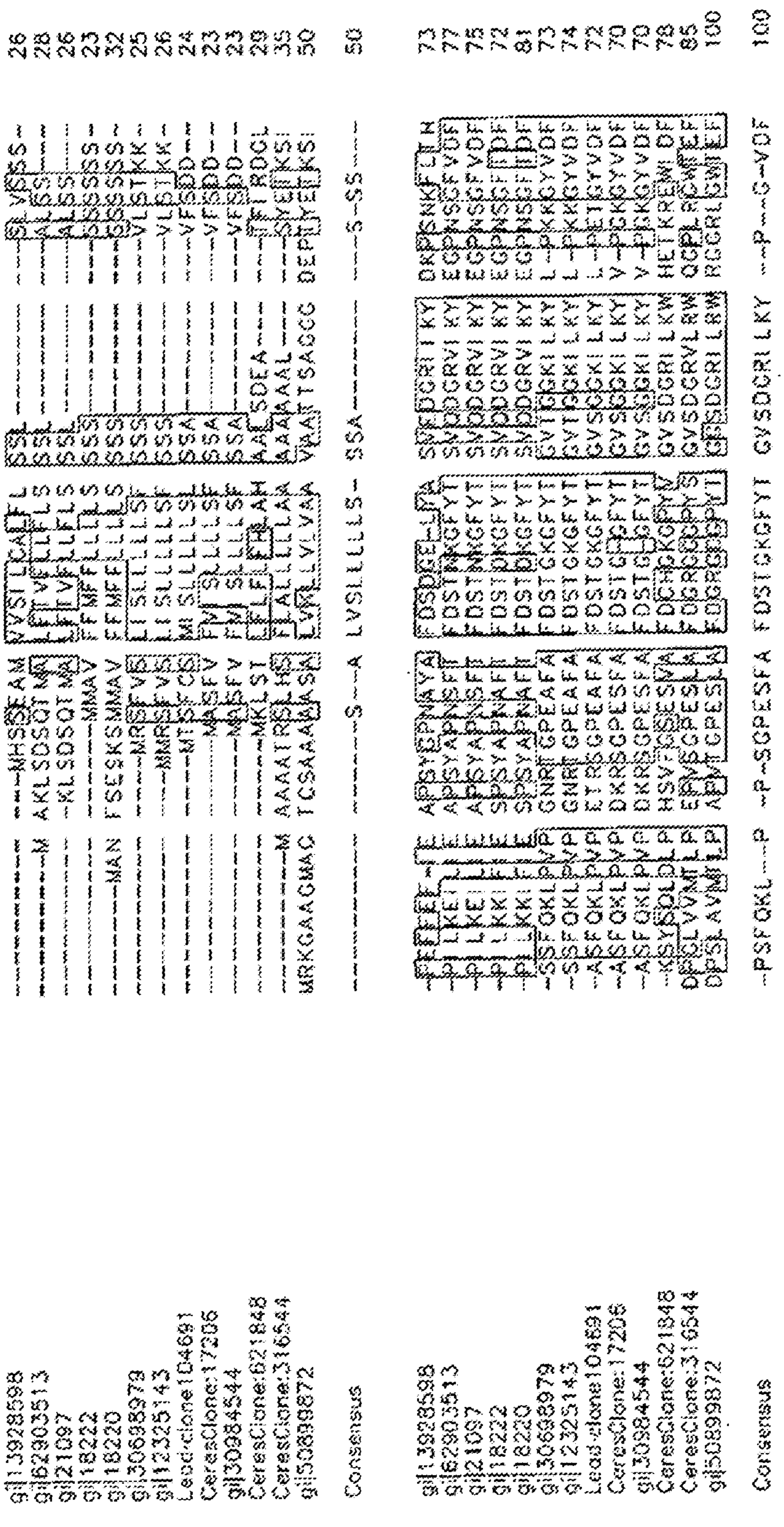
FIG. 9 provides the results of a consensus sequence (SEQ ID NOs: 241-262) analysis based on Ceres cDNA 13509011 (12357529).

FIG. 9 provides the results of the consensus sequence (SEQ ID NOs: 241-262) analysis based on Ceres cDNA 13509011 (12357529).

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. A method for producing a plant, the method comprising transforming a plant with a nucleic acid molecule, wherein the nucleic acid molecule comprises:

a) a first nucleic acid having a promoter sequence capable of causing transcription in a plant; and b) a second nucleic acid encoding a polypeptide, wherein the polypeptide comprises an amino acid sequence that exhibits at least 95% amino acid sequence identity to the amino acid sequence of SEQ ID NO: 44;

wherein said first and second nucleic acids are operably linked, wherein said second nucleic acid is heterologous to said first nucleic acid, and wherein expression of said second nucleic acid encoding said polypeptide in said transformed plant increases drought tolerance, thermo-tolerance, osmotic stress tolerance, or water use efficiency as compared to a control plant of the same species lacking said nucleic acid molecule, and grown under identical growth conditions.

2. The method of claim 1, wherein the second nucleic acid sequence comprises a polynucleotide sequence that exhibits at least 90% nucleic acid sequence identity to the polynucleotide sequence of SEQ ID NO: 43, and which encodes a polypeptide that exhibits at least 95% amino acid sequence identity to the amino acid sequence of SEQ ID NO: 44.

3. The method of claim 1, wherein the second nucleic acid sequence encodes a polypeptide comprising an amino acid sequence that exhibits at least 975% amino acid sequence identity to the amino acid sequence of SEQ ID NO: 44.

4. The method of claim 1, wherein the second nucleic acid sequence encodes a polypeptide comprising an amino acid sequence that exhibits at least 98% amino acid sequence identity to the amino acid sequence of SEQ ID NO: 44.

5. The method of claim 1, wherein the second nucleic acid sequence encodes a polypeptide comprising an amino acid sequence that exhibits at least 99% amino acid sequence identity to the amino acid sequence of SEQ ID NO: 44.

6. The method of claim 1, wherein the second nucleic acid sequence encodes a polypeptide comprising the amino acid sequence of SEQ ID NO: 44.

7. The method of claim 1, wherein the second nucleic acid sequence comprises a polynucleotide sequence that exhibits at least 95% nucleic acid sequence identity to the polynucleotide sequence of SEQ ID NO: 43, and which encodes a polypeptide that exhibits at least 95% amino acid sequence identity to the amino acid sequence of SEQ ID NO: 44.

8. The method of claim 1, wherein the second nucleic acid sequence comprises a polynucleotide sequence that exhibits at least 97% nucleic acid sequence identity to the polynucleotide sequence of SEQ ID NO: 43, and which encodes a polypeptide that exhibits at least 95% amino acid sequence identity to the amino acid sequence of SEQ ID NO: 44.

9. The method of claim 1, wherein the second nucleic acid sequence comprises a polynucleotide sequence that exhibits at least 98% nucleic acid sequence identity to the polynucleotide sequence of SEQ ID NO: 43, and which encodes a polypeptide that exhibits at least 95% amino acid sequence identity to the amino acid sequence of SEQ ID NO: 44.

10. The method of claim 1, wherein the second nucleic acid sequence comprises a polynucleotide sequence that exhibits at least 99% nucleic acid sequence identity to the polynucleotide sequence of SEQ ID NO: 43, and which encodes a polypeptide that exhibits at least 95% amino acid sequence identity to the amino acid sequence of SEQ ID NO: 44.

11. The method of claim 1, wherein the second nucleic acid sequence comprises a polynucleotide sequence that comprises the polynucleotide sequence of SEQ ID NO: 43, and which encodes the polypeptide having the amino acid sequence identity of SEQ ID NO: 44.

* * * * *